United States Patent
Cheung et al.

(10) Patent No.: US 11,672,799 B2
(45) Date of Patent: Jun. 13, 2023

(54) 1,4-DISUBSTITUTED PYRIDAZINE QUINOLNE ANALOGS THERE OF AND METHODS FOR TREATING SMN-DEFICIENCY-RELATED CONDITIONS

(71) Applicant: Novartis AG, Basel (CH)

(72) Inventors: Atwood Kim Cheung, Arlington, MA (US); Natalie Dales, Arlington, MA (US); Timothy Brian Hurley, Boston, MA (US)

(73) Assignee: NOVARTIS AG, Basel (CH)

( * ) Notice: Subject to any disclaimer, the term of this patent is extended or adjusted under 35 U.S.C. 154(b) by 266 days.

(21) Appl. No.: 16/259,441

(22) Filed: Jan. 28, 2019

(65) Prior Publication Data
US 2019/0160062 A1 May 30, 2019

Related U.S. Application Data

(63) Continuation of application No. 16/030,139, filed on Jul. 9, 2018, now abandoned, which is a continuation of application No. 14/909,052, filed as application No. PCT/US2014/048984 on Jul. 30, 2014, now abandoned.

(60) Provisional application No. 61/860,388, filed on Jul. 31, 2013.

(51) Int. Cl.
*A61K 31/501* (2006.01)
*C07D 401/14* (2006.01)
*C07D 401/04* (2006.01)
*A61K 31/502* (2006.01)
*A61K 31/517* (2006.01)
*C07D 487/10* (2006.01)
*C07D 405/14* (2006.01)
*C07D 413/14* (2006.01)
*C07D 487/04* (2006.01)
*A61K 31/5377* (2006.01)

(52) U.S. Cl.
CPC .......... *A61K 31/501* (2013.01); *A61K 31/502* (2013.01); *A61K 31/517* (2013.01); *A61K 31/5377* (2013.01); *C07D 401/04* (2013.01); *C07D 401/14* (2013.01); *C07D 405/14* (2013.01); *C07D 413/14* (2013.01); *C07D 487/04* (2013.01); *C07D 487/10* (2013.01)

(58) Field of Classification Search
CPC .. C07D 401/04; C07D 401/14; C07D 487/10; A61K 31/501; A61K 31/502; A61K 31/517
See application file for complete search history.

(56) References Cited

U.S. PATENT DOCUMENTS

| | | | |
|---|---|---|---|
| 4,026,891 A | 5/1977 | Volkhard et al. | |
| 6,376,508 B1 | 4/2002 | Li et al. | |
| 8,729,263 B2 * | 5/2014 | Cheung | C07D 403/10 544/238 |
| 9,545,404 B2 * | 1/2017 | Cheung | A61K 31/427 |
| 10,195,196 B2 * | 2/2019 | Cheung | A61P 21/00 |
| 10,758,533 B2 * | 9/2020 | Cheung | A61K 31/427 |
| 2008/0064703 A1 | 3/2008 | Stoner et al. | |
| 2008/0247964 A1 | 10/2008 | Xu et al. | |
| 2008/0275048 A1 | 11/2008 | Frost et al. | |
| 2010/0305089 A1 | 2/2010 | Ji et al. | |
| 2010/0267721 A1 | 10/2010 | Hohlweg et al. | |
| 2011/0059118 A1 | 3/2011 | Fidalgo et al. | |
| 2011/0142758 A1 | 6/2011 | Peters et al. | |
| 2012/0172346 A1 | 7/2012 | Di Paolo et al. | |
| 2012/0232078 A1 | 9/2012 | Hohlweg et al. | |
| 2013/0096160 A1 | 4/2013 | Marugan et al. | |
| 2013/0143862 A1 | 6/2013 | Ashcraft et al. | |
| 2014/0213570 A1 * | 7/2014 | Cheung | A61K 31/5377 514/210.2 |
| 2017/0290828 A1 * | 10/2017 | Cheung | C07D 417/14 |
| 2019/0358226 A1 * | 11/2019 | Cheung | A61P 21/00 |
| 2020/0345732 A1 * | 11/2020 | Cheung | A61K 31/502 |

FOREIGN PATENT DOCUMENTS

| | | |
|---|---|---|
| CN | 101466375 A | 6/2009 |
| DE | 2427943 A1 | 1/1976 |
| EP | 1637141 A1 | 3/2006 |
| EP | 2014656 A2 | 1/2009 |
| FR | 2868780 A1 | 10/2005 |
| JP | B-6461150 B2 | 1/2019 |
| WO | 1995014683 A1 | 6/1995 |

(Continued)

OTHER PUBLICATIONS

Xiao, Jingbo et al. "Discovery, Synthesis, and Biological Evaluation of Novel SMN Protein Modulators." Journal of Medicinal Chemistry. Aug. 5, 2011, 54, pp. 6215-6233.

Ohsawa, Akio et al., "Cross-Coupling Reaction of Chloropyridazines and Grignard Reagents with Nickel-phosphine Complexes: Alkylation and Arylation of Pyridazines," Chemical and Pharmaceutical Bulletin 26(8), Mar. 7, 9178. pp. 2550-2554.

(Continued)

*Primary Examiner* — Timothy P Thomas
(74) *Attorney, Agent, or Firm* — Adil R. Zhugralin

(57) ABSTRACT

The present invention provides a compound of formula IA or a pharmaceutically acceptable salt thereof;

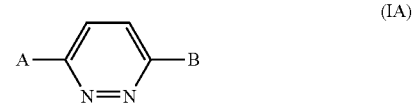

(IA)

a method for manufacturing the compounds of the invention, and its therapeutic uses. The present invention further provides a combination of pharmacologically active agents and a pharmaceutical composition.

9 Claims, No Drawings

(56) References Cited

FOREIGN PATENT DOCUMENTS

| WO | 2001/58891 A2 | 8/2001 |
| WO | 2001/66129 A1 | 9/2001 |
| WO | 2001/94351 A1 | 12/2001 |
| WO | 2003092678 A1 | 11/2003 |
| WO | 2004014370 A2 | 2/2004 |
| WO | 2004014881 A2 | 2/2004 |
| WO | 2004014902 A2 | 2/2004 |
| WO | 2004043960 A1 | 5/2004 |
| WO | 2004110351 A2 | 12/2004 |
| WO | 2005007644 A1 | 1/2005 |
| WO | 2005018547 A2 | 3/2005 |
| WO | 2005077368 A2 | 8/2005 |
| WO | 2005077373 A2 | 8/2005 |
| WO | 2006001958 A2 | 1/2006 |
| WO | 2006028545 A2 | 3/2006 |
| WO | 2006034341 A2 | 3/2006 |
| WO | 2006044860 A2 | 4/2006 |
| WO | 2007003604 A2 | 1/2007 |
| WO | 2007/022937 A1 | 3/2007 |
| WO | 2007133561 A2 | 11/2007 |
| WO | 2007137030 A2 | 11/2007 |
| WO | 2008/005368 A2 | 1/2008 |
| WO | 2008058064 A1 | 5/2008 |
| WO | 2008107677 A2 | 9/2008 |
| WO | 2008154126 A1 | 12/2008 |
| WO | 2009065131 A1 | 5/2009 |
| WO | 2009/108657 A2 | 9/2009 |
| WO | 2009/137503 A1 | 11/2009 |
| WO | 2009150240 A1 | 12/2009 |
| WO | WO 2009/150139 | 12/2009 |
| WO | 2010008739 A2 | 1/2010 |
| WO | 2010/028192 A1 | 3/2010 |
| WO | 2010045306 A2 | 4/2010 |
| WO | 10129053 A2 | 11/2010 |
| WO | 2011/009890 A2 | 1/2011 |
| WO | WO 2011/036167 | 3/2011 |
| WO | 2011/063159 A1 | 5/2011 |
| WO | 11078143 A1 | 6/2011 |
| WO | 2011107530 A2 | 9/2011 |
| WO | 2011130515 A1 | 10/2011 |
| WO | 2011133882 A1 | 10/2011 |
| WO | 2012/022467 A2 | 2/2012 |
| WO | 2012/127393 A1 | 9/2012 |
| WO | 2014/028459 A1 | 2/2014 |
| WO | WO-2014028459 A1 * | 2/2014 | .......... C07D 405/14 |
| WO | 2015/017589 A1 | 2/2015 |

OTHER PUBLICATIONS

Database Registry, Chemical Abstracts Service, Columbus, Ohio, US XP002716119, Database Accession No. 1330184-80-9 Abstract. Nov. 8, 2013, 4 pages.

Database Registry, Chemical Abstracts Service, Columbus, Ohio, US Petrenko et al., "Effect of an intramolecular hydrogen bond on the rate of nucleophilic substituion in a series of haloazines," XP002716255, Database Accession No. 1981:191211 abstract Compound with the Registry No. 77585-98-9. Nov. 11, 2013, 2 pages.

Wadman et al. "Drug Treatment for Spinal Muscular Atrophy Types II and III." The Cochrane Collaboration. Issue 4. John Wiley & Sons. 2012, pp. 1-53.

Wadman et al. "Drug Treatment for Spinal Muscular Atrophy Type I." The Cochrane Collaboration. Issue 12. John Wiley & Sons. 2011, pp. 1-22.

Bunnelle et al: Octahydropryrrolo(3,4-c)pyrrole: A Diamine Scaffold for Construction of Ether Alpha4Beta2 or alpha7-Selective Nictotinic Acetycholine Receptor (nAChR) Ligands. Substitutions that Switch Sybtype Selectivity; 2009; J. Med. Chem.; 52:4126-4141.

Li et al.: "Syntheses and structure-activity relationship (SAR) studies of 2,5-diazbicyclo[2.2.1]heptanes as novel alpha7 neuronal nictonic receptor (NNR) ligands, "Bioorg Med. Chem Lett., Jun. 15 2010, 20(12):3636-9.

Bitner et al.: "In vivo pharmacological characterization of a novel selective alpha7 neuronal nicotinic acetylcholine receptor agonist ABT-107: preclinical considerations in Alzheimer's disease," J. Pharmacol Exp. Ther., Sep. 1, 2010, 334(3): 875-86.

Li et al.: "Role of alpha7 nicotinic acetycholine receptors in regulating tumor necrosis factor-alpha (TNF-alpha) as revealed by subtype selective agonists," J Neuroimmunol., Oct. 2, 20118, 239(1-2):37-43.

International Search Report for International Application No. PCT/US2014/048984, dated Dec. 12, 2014 (7 pages).

* cited by examiner

1,4-DISUBSTITUTED PYRIDAZINE QUINOLNE ANALOGS THERE OF AND METHODS FOR TREATING SMN-DEFICIENCY-RELATED CONDITIONS

RELATED APPLICATIONS

This application is a continuation of U.S. patent application Ser. No. 16/030,139, filed on Jul. 9, 2018, which is a continuation of U.S. patent application Ser. No. 14/909,052, filed on Jan. 29, 2016, which is a national stage entry of PCT/US2014/048984, filed on Jul. 30, 2014, which claims priority to U.S. Provisional Patent Application No. 61/860,388 filed on Jul. 31, 2013. The contents of each of the foregoing applications are hereby incorporated by reference in their entireties.

BACKGROUND OF THE INVENTION

Proximal spinal muscular atrophy (SMA) is an inherited, clinically heterogeneous group of neuromuscular disorders characterized by degeneration of the anterior horn cells of the spinal cord.

Patients suffer from symmetrical weakness of trunk and limb muscles, the legs being more affected than the arms and the proximal muscles weaker than the distal ones; diaphragm, facial and ocular muscles are spared. There are three forms of childhood-onset SMA (types I, II and III), and a relatively recently categorized adult-onset form IV, all of which can be distinguished on the basis of age of onset and severity of the clinical course assessed by clinical examination, muscle biopsy and electromyography (EMG)(Munsat T L, Davies K E (1992)).

Type I (Werdnig-Hoffmann disease) is the most acute and severe form, with onset before six months and death usually before two years; children are never able to sit without support. Symptoms of the disease can be present in utero, as reduction of fetal movements; at birth; or more often, within the first four months of life. Affected children are particularly floppy, experience feeding difficulties and diaphragmatic breathing, and are characterized by a general weakness in the intercostals and accessory respiratory muscles. Affected children never sit or stand and usually die before the age of 2; death is generally due to respiratory insufficiency.

Type II (intermediate, chronic form) has onset between six and eighteen months of age; muscular fasciculations are common, and tendon reflexes progressively reduce. Children are unable to stand or walk without aid. Feeding and swallowing problems are not usually present in Type II SMA, although in some patients a feeding tube may become necessary. Most patients generally develop a progressive muscular scoliosis which can require surgical correction. Like patients with type I disease, clearing of tracheal secretions and coughing might become difficult because of poor bulbar function and weak intercostal muscles. These patients have profound hypotonia, symmetrical flaccid paralysis, and no control of head movement.

Type III (Kugelberg-Welander disease, or Juvenile Spinal Muscular Atrophy) is a mild, chronic form, with onset after the age of 18 months; motor milestones achievement is normal, and deambulation can be preserved until variable ages. These patients often develop scoliosis, and symptoms of joint overuse, generally caused by weakness, are frequently seen. Life expectancy is almost normal but quality of life is markedly compromised.

Types I, II and III progress over time, accompanied by deterioration of the patient's condition.

Adult-onset type IV is characterized by weakness in the second or third decade of life, with mild motor impairment not accompanied by respiratory or nutritional problems. Adult SMA is characterized by insidious onset and very slow progression. The bulbar muscles are rarely affected in Type IV. It is not clear that Type IV SMA is etiologically related to the Type I-III forms.

Other forms of spinal muscular atrophy include X-linked disease, spinal muscular atrophy with respiratory distress (SMARD), spinal and bulbar muscular atrophy (Kennedy's disease, or Bulbo-Spinal Muscular Atrophy), and distal spinal muscular atrophy.

SMA is due to mutations in the Survival of Motor Neuron (SMN) gene, which exists in two forms in humans (SMN1 and SMN2). Loss of SMN is deleterious to motor neurons and results in neuromuscular insufficiency, a hallmark of the disease. From a genetic point of view, SMA is an autosomal recessive condition, caused by disruption of SMN1 gene, located in 5q13 (Lefebvre S., et al. (1995) Cell 80: 155-165). More than 98% of patients with spinal muscular atrophy have a homozygous disruption of SMN1 by deletion, rearrangement, or mutation. All these patients, however, retain at least one copy of SMN2.

At the genomic level, only five nucleotides have been found that differentiate the SMN1 gene from the SMN2 gene. Furthermore, the two genes produce identical mRNAs, except for a silent nucleotide change in exon 7, i.e., a C-T change six base pairs inside exon 7 in SMN2. This mutation modulates the activity of an exon splicing enhancer (Lorson and Androphy (2000) Hum. Mol. Genet. 9:259-265). The result of this and the other nucleotide changes in the intronic and promoter regions is that most SMN2 are alternatively spliced, and their transcripts lack exons 3, 5, or 7. In contrast, the mRNA transcribed from the SMN1 gene is generally a full-length mRNA with only a small fraction of its transcripts spliced to remove exon 3, 5, or 7 (Gennarelli et al. (1995) Biochem. Biophys. Res. Commun. 213:342-348; Jong et al. (2000) J. Neurol. Sci. 173:147-153). All SMA subjects have at least one, and generally two to four copies of the SMN2 gene, which encodes the same protein as SMN1; however, the SMN2 gene produces only low levels of full-length SMN protein.

The SMN∆7 protein is non-functional and thought to be rapidly degraded. About 10% of SMN2 pre-mRNA is properly spliced and subsequently translated into full length SMN protein (FL-SMN), and the rest being the SMN∆7 copy. The efficiency of SMN2 splicing might be dependent on severity of disease, and production of a full length transcript of SMN2 could range from 10% to 50%. Furthermore, presence or absence of the SMN1 gene, roughly 90% of which becomes the FL-SMN gene product and protein, influences the severity of SMA by whether or not it can compensate for the truncated SMN∆7 copies. A low level of SMN protein allows embryonic development, but is not sufficient to sustain the survival of motor neurons of the spinal cord.

The clinical severity of SMA patients inversely correlates with the number of SMN2 genes and with the level of functional SMN protein produced (Lorson C L, et al. (1999) PNAS; 96:6307-6311) (Vitali T. et al. (1999) Hum Mol Genet; 8:2525-2532)(Brahe C. (2000) Neuromusc. Disord.; 10:274-275)(Feldkotter M, et al. (2002) Am J Hum Genet; 70:358-368)(Lefebvre S, et al. (1997) Nature Genet; 16:265-

269)(Coovert D D, et al. (1997) Hum Mol Genet; 6:1205-1214)(Patrizi A L, et al. (1999) Eur J Hum Genet; 7:301-309).

Current therapeutic strategies for SMA are mostly centered on elevating full length (wild type) SMN protein levels, modulating splicing towards exon 7 inclusion, stabilizing the wild type protein, and to a lesser extent, on restoring muscle function in SMA by providing trophic support or by inhibiting skeletal muscle atrophy.

The mechanism leading to motorneuron loss and to muscular atrophy still remains obscure, although the availability of animal models of the disease is rapidly increasing knowledge in this field (Frugier T, et al. (2000) Hum Mol. Genet. 9:849-58; Monani U R, et al. (2000) Hum Mol Genet 9:333-9; Hsieh-Li H M, et al. (2000) Nat Genet 24:66-70; Jablonka S, et al. (2000) Hum Mol. Genet. 9:341-6). Also the function of SMN protein is still partially unknown, and studies indicate that it can be involved in mRNA metabolism (Meister G, et al. (2002). Trends Cell Biol. 12:472-8; Pellizzoni L, et al. (2002). Science. 298: 1775-9), and probably in transport of proteins/mRNA to neuromuscular junctions (Ci-fuentes-Diaz C, et al. (2002) Hum Mol. Genet. 11: 1439-47; Chan Y B, et al. (2003) Hum Mol. Genet. 12:1367-76; McWhorter M L, et al. (2003) J. Cell Biol. 162:919-31; Rossoll W, et al. (2003) J. Cell Biol. 163:801-812).

In addition to the SMAs, a subclass of neurogenic-type arthrogryposis multiplex congenita (congenital AMC) has separately been reported to involve SMN1 gene deletion, suggesting that some degree of pathology in those afflicted is likely due to low levels of motor neuron SMN. (L. Burgien et al., (1996) J. Clin. Invest. 98(5):1130-32. Congenital AMC affects humans and animals, e.g., horses, cattle, sheep, goats, pigs, dogs, and cats. (M. Longeri et al., (2003) Genet. Sel. Evol. 35:S167-S175). Also, the risk of development or the severity of amyotrophic lateral sclerosis (ALS) has been found to be correlated with low levels of motor neuron SMN.

There is no cure for SMA available to date and therefore it would be advantageous to provide novel methods for modulating SMN in order to treat those afflicted with SMA, with neurogenic congenital AMC, ALS, or with other SMN-deficiency-related conditions. It would further be advantageous to provide novel drug targets that could be used as a basis for developing effective therapeutics or diagnostics for such neuronal conditions.

SUMMARY OF THE INVENTION

There remains a need for new treatments and therapies for Spinal Muscular Atrophy. The invention provides compounds, salts thereof, pharmaceutical formulations thereof and combinations thereof which compounds are Spinal Muscular Atrophy modulators. The invention further provides methods of treating, preventing, or ameliorating Spinal Muscular Atrophy, comprising administering to a subject in need thereof an effective amount of an SMN modulator (e.g., a compound of the invention).

Various embodiments of the invention are described herein. It will be recognized that features specified in each embodiment may be combined with other specified features to provide further embodiments.

Within certain aspects, SMN modulators provided herein are compounds of Formula IA and salts thereof:

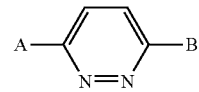
(IA)

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more therapeutically active.

One embodiment of the invention is to provide a method for treating, preventing, or ameliorating an SMN-deficiency-related condition, comprising administering to a subject in need thereof an effective amount of an SMN modulator, or a pharmaceutical composition comprising the same.

Another embodiment of the invention is a method of modulating SMN protein through the administration of an SMN modulator. In another embodiment, said SMN modulator is capable of increasing one or more of FL-SMN or SMNΔ7 levels. In still another embodiment, said SMN modulator is capable of preventing exon 7 from being spliced from the SMN transcript.

The present invention is based on the discovery that the SMN modulators of the invention (e.g., compounds of formula (I) and/or compounds of formula (I-A) are capable of modulating SMN proteins, e.g., through SMN promoter activation, splicing modulation (e.g., preventing exon7 from being spliced out of the SMN gene), and/or SMN protein stability modulation.

DETAILED DESCRIPTION OF THE INVENTION

As noted above, the present invention provides compounds that modulate SMN activity. Such compounds may be used in vitro or in vivo to modulate (preferably increase) SMN production and activity in a variety of contexts.

In a first embodiment, the invention provides compounds of Formula (IA) and pharmaceutically acceptable salts thereof, which modulate SMN activity. Compounds of Formula I are represented by the structure (IA):

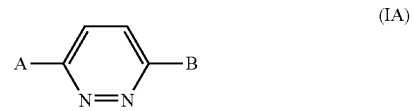
(IA)

wherein A is bicyclic heteroaryl or heterocyle having 9 or 10 ring atoms and 1 or 2 ring N atoms and 0 or 1 O atoms, which bicyclic heteroaryl or heterocycle is substituted with 0, 1, 2, 3, 4 or 5 substituents independently selected from —C(O)NH$_2$, —C(O)O—C$_1$-C$_4$alkyl, aryl, oxo, cyano, halogen, hydroxy, C$_1$-C$_4$alkyl, C$_2$-C$_4$alkenyl, C$_2$-C$_4$alkynyl, C$_1$-C$_4$alkoxy, C$_3$-C$_7$cycloalkyl, heterocyclyl, heteroaryl, heterocyclyl C$_1$-C$_4$alkyl, C$_1$-C$_4$alkyl aryl, C$_1$-C$_4$alkyl heterocyclyl, C$_1$-C$_4$alkyl heteroaryl, C$_1$-C$_4$alkoxy aryl, C$_1$-C$_4$alkoxy heterocyclyl, C$_1$-C$_4$alkoxy heteroaryl, $C_1$-$C_4$alkoxy substituted with hydroxy, $C_1$-$C_4$alkoxy, amino and mono- and di-$C_1$-$C_4$alkylamino; and B is a group of the formula:

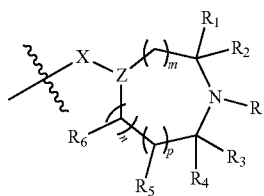

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$akylamino; $R_5$ and $R_6$ are independently selected from hydrogen and fluorine; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_AR_B$, O, $NR_7$ or a bond; $R_7$ is hydrogen, or $C_1$-$C_4$alkyl; $R_A$ and $R_B$ are independently selected from hydrogen and $C_1$-$C_4$alkyl, or $R_A$ and $R_B$, taken in combination, form a divalent $C_2$-$C_5$alkylene group; Z is $CR_8$ or N; when Z is N, X is a bond; $R_8$ is hydrogen or taken in combination with $R_6$ form a double bond; or B is a group of the formula:

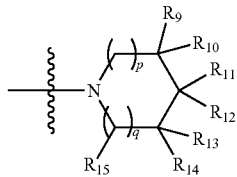

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$akylamino and $C_1$-$C_4$alkyl, which alkyl is optionally substituted with hydroxy, amino or mono- and di-$C_1$-$C_4$akylamino; $R_{11}$ is hydrogen, $C_1$-$C_4$alkyl, amino or mono- and di-$C_1$-$C_4$akylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a second embodiment the invention is a the compound, or salt thereof, according to the first embodiment wherein the compound is of Formula (I):

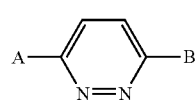

wherein A is bicyclic heteroaryl having 10 ring atoms and 1 or 2 ring N atoms, which bicyclic heteroaryl is substituted with 0, 1, or 2 substituents independently selected from oxo, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino; and B is a group of the formula:

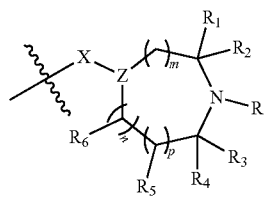

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$akylamino; $R_5$ and $R_6$ are independently selected from hydrogen and fluorine; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_AR_B$, O, $NR_7$ or a bond; $R_7$ is hydrogen, or $C_1$-$C_4$alkyl; $R_A$ and $R_B$ are independently selected from hydrogen and $C_1$-$C_4$alkyl, or $R_A$ and $R_B$, taken in combination, form a divalent $C_2$-$C_5$alkylene group; Z is $CR_8$ or N; when Z is N, X is a bond; $R_8$ is hydrogen or taken in combination with $R_6$ form a double bond; or B is a group of the formula:

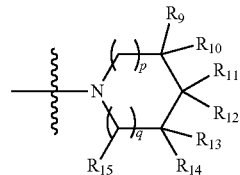

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$akylamino and $C_1$-$C_4$alkyl, which alkyl is optionally substituted with hydroxy, amino or mono- and di-$C_1$-$C_4$akylamino; $R_{11}$ is hydrogen, $C_1$-$C_4$alkyl, amino or mono- and di-$C_1$-$C_4$akylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a third embodiment, the invention is the compound according to any one the first or second embodiments, or salt thereof, wherein A is selected from:

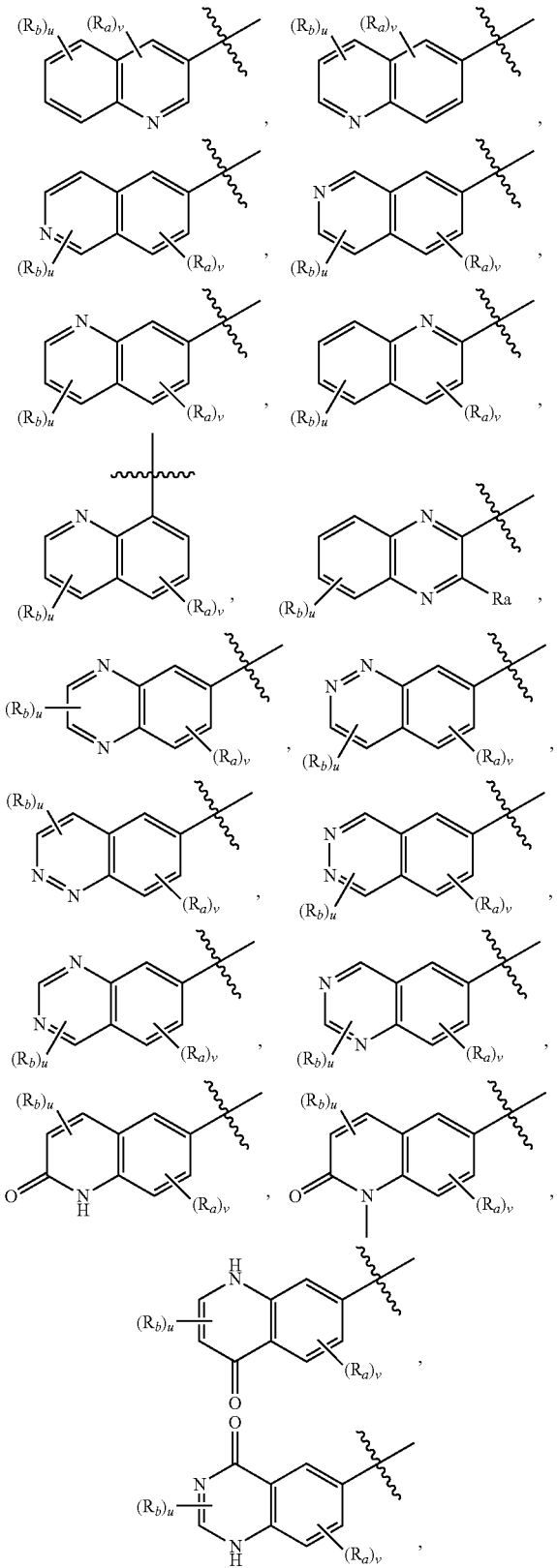

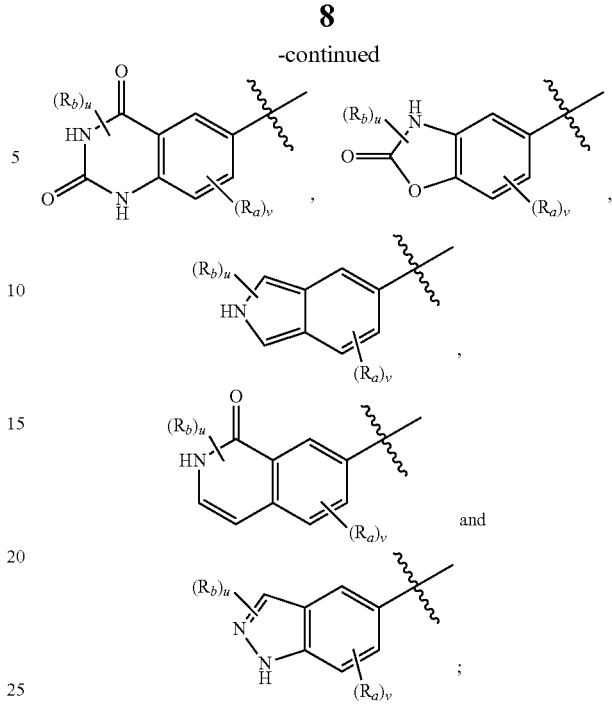

wherein u and v are each, independently, 0, 1, 2 or 3; and each $R_a$ and $R_b$ are, independently, selected from, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, and $C_1$-$C_4$alkoxy substituted with hydroxy, $C_1$-$C_4$alkoxy, amino and mono- and di-$C_1$-$C_4$alkylamino.

In a fourth embodiment, the invention is the compound of any one of the first through third embodiments, or salt thereof, wherein A is selected from:

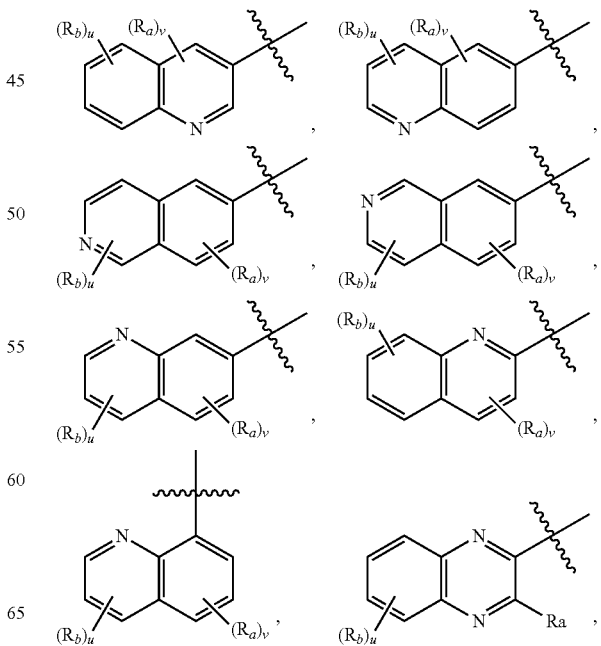

-continued

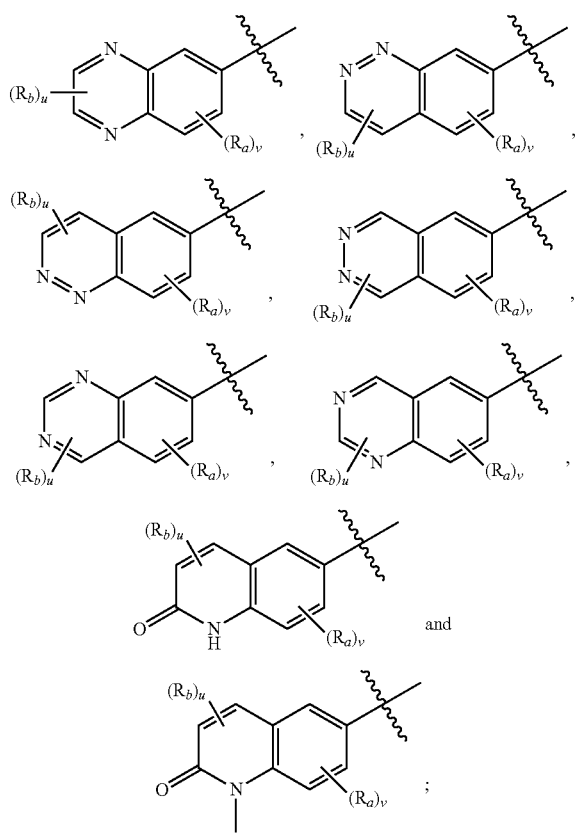

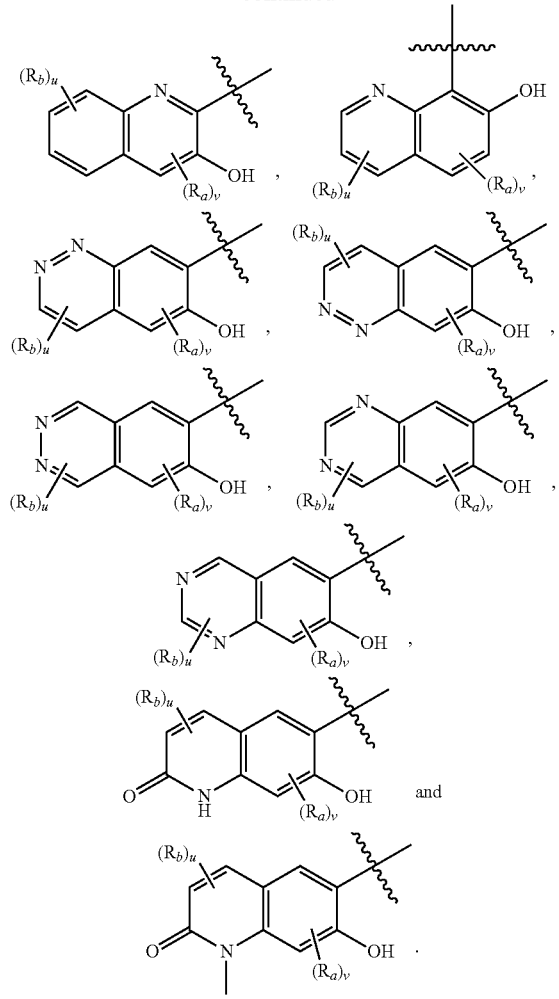

wherein u and v are each, independently, 0, 1, 2 or 3; and each $R_a$ and $R_b$ are, independently, selected from, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, and $C_1$-$C_4$alkoxy substituted with hydroxy, $C_1$-$C_4$alkoxy, amino and mono- and di-$C_1$-$C_4$alkylamino.

In another embodiment, the invention is the compound according to any one of the first through fourth embodiments, wherein A is substituted in the ortho position with a hydroxyl group.

In a fifth embodiment, the inveniotn is the compound according to any one of the first through fourth embodiments, or salt thereof, wherein A is selected from:

In a sixth embodiment, the invneiotn is the compound of any one of the first through fifth embodiments, or a salt thereof, wherein A has a single N atom In a seventh embodiment, the invention is the compound, according to any one of the first through sixth emebodiments, or salt thereof, wherein the compound is of formula II:

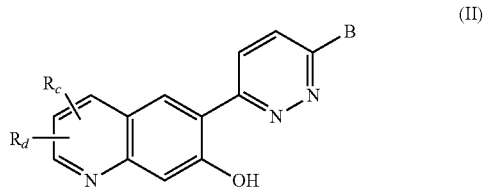

(II)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In an eighth embodiment, the invention is the compound, or salt thereof, according to any one of the first through sixth embodiments, wherein the compound is of formula III:

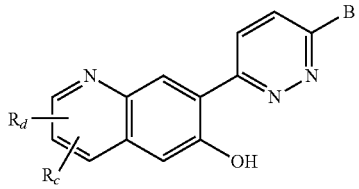

(III)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In a ninth embodiment, the invention is the compound, according to any one of the first through sixth embodiments, or salt thereof, wherein the compound is of formula IV:

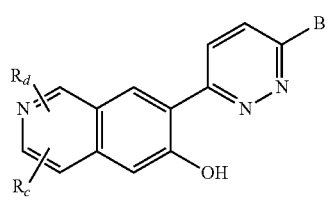

(IV)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In a tenth embodiment, the invention is the compound, according to any one of the first through sixth emebodiments, or salt thereof, wherein the compound is of formula V:

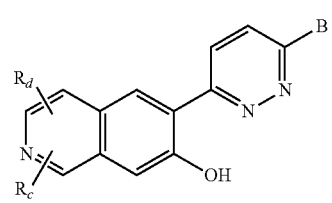

(V)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In an eleventh embodiment, the invention is the compound, according to any one of the first through sixth emebodiments, or salt thereof, wherein the compound is of formula VI:

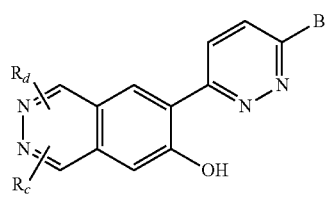

(VI)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In a twelfth embodiment, the invention is the compound, according to any one of the first through sixth embodiments, or salt thereof, wherein the compound is of formula VII:

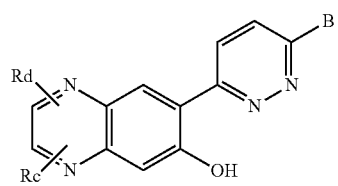

(VII)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In a thirteenth embodiment, the invention is the compound, according to any one of the first through sixth embodiments, or salt thereof, wherein the compound is of formula VIII:

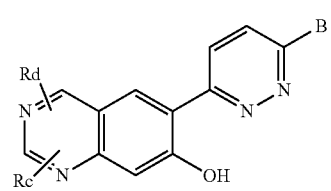

(VIII)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono- and di-$C_1$-$C_4$alkylamino.

In a fourteenth embodiment, the invention is the compound according to any one of the first through thirteenth embodiments, or a salt thereof, wherein B is a group of the formula:

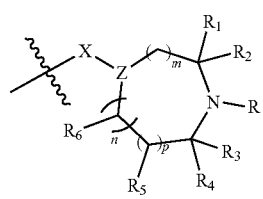

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$akylamino; $R_5$ and $R_6$ are hydrogen; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_AR_B$, O, $NR_7$ or a bond; $R_A$ and $R_B$ are independently selected from hydrogen and $C_1$-$C_4$alkyl, or $R_A$ and $R_B$, taken in combination, form a divalent $C_2$-$C_5$alkylene group; Z is $CR_8$ or N; when Z is N, X is a bond; $R_8$ is hydrogen or taken in combination with $R_6$ form a double bond.

In a fifteenth embodiment, the invention is the compound according to any one of the first through thirteenth embodiments, or a salt thereof, wherein B is a group of the formula:

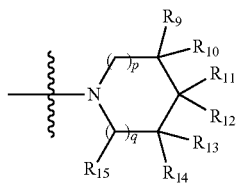

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$akylamino and $C_1$-$C_4$alkyl, which alkyl is optionally substituted with hydroxy, amino or mono- and di-$C_1$-$C_4$akylamino; $R_{11}$ is hydrogen, $C_1$-$C_4$alkyl, amino or mono- and di-$C_1$-$C_4$akylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a sixteenth embodiment, the invention is the compound of any one of the first through fifteenth embodiments, wherein B is selected from the group consisting of:

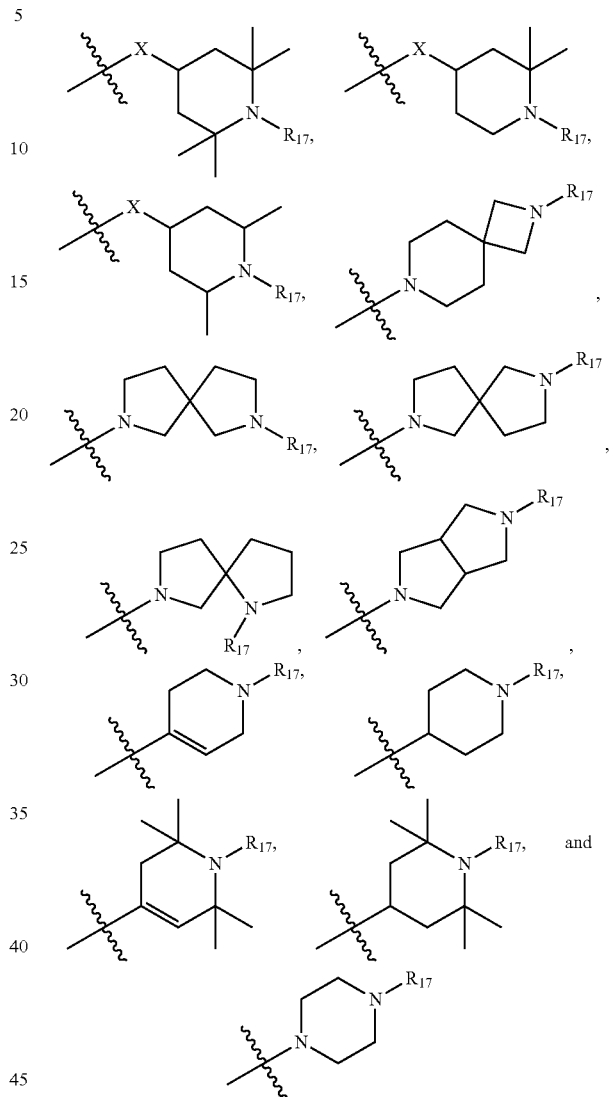

wherein X is O or N(Me) or NH; and $R_{17}$ is hydrogen or methyl.

In a seventeenth embodiment, the invention is the compound, or salt thereof, according to any one of the first through sixteenth embodiments, wherein B is:

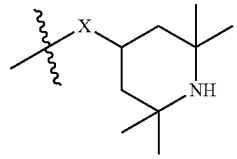

In an eighteenth embodiment, the invention is the compound, or salt thereof, according to any one of the first through seventeenth embodiments, wherein X is —O—.

In a nineteenth emebodiment, the invention is the compound, or salt thereof, according to any one of the first through eighteenth embodiments, wherein X is N(Me).

In a twentieth embodiment, the invention is a compound, or salt thereof, selected from the group consisting of:

7-hydroxy-6-(6-(methyl(2,2,6,6-tetramethylpiperidin-4-yl)amino)pyridazin-3-yl)quinolin-2(1H)-one;
6-(6-((3aR,6aS)-5-methylhexahydropyrrolo[3,4-c]pyrrol-2(1H)-yl)pyridazin-3-yl)quinolin-7-ol;
7-hydroxy-1-methyl-6-(6-(methyl(2,2,6,6-tetramethylpiperidin-4-yl)amino)pyridazin-3-yl)quinolin-2(1H)-one;
6-(6-(methyl(1,2,2,6,6-pentamethylpiperidin-4-yl)amino)pyridazin-3-yl)quinolin-7-ol;
2-methyl-6-(6-(methyl(2,2,6,6-tetramethylpiperidin-4-yl)amino)pyridazin-3-yl)-4-morpholinoquinolin-7-ol;
4-chloro-2-methyl-6-(6-(methyl(2,2,6,6-tetramethylpiperidin-4-yl)amino)pyridazin-3-yl)quinolin-7-ol;
3-bromo-6-(6-(methyl(2,2,6,6-tetramethylpiperidin-4-yl)amino)pyridazin-3-yl)quinolin-7-ol;
3-ethyl-6-(6-(methyl(2,2,6,6-tetramethylpiperidin-4-yl)amino)pyridazin-3-yl)quinolin-7-ol;
3-(1H-imidazol-1-yl)-6-(6-(methyl(2,2,6,6-tetramethylpiperidin-4-yl)amino)pyridazin-3-yl)quinolin-7-ol;
6-(6-(methyl(2,2,6,6-tetramethylpiperidin-4-yl)amino)pyridazin-3-yl)-3-(1-methyl-1H-imidazol-4-yl)quinolin-7-ol;
3-isopropyl-6-(6-(methyl(2,2,6,6-tetramethylpiperidin-4-yl)amino)pyridazin-3-yl)quinolin-7-ol;
6-(6-(methyl(2,2,6,6-tetramethylpiperidin-4-yl)amino)pyridazin-3-yl)quinoline-3,7-diol;
7-hydroxy-6-(6-(methyl(2,2,6,6-tetramethylpiperidin-4-yl)amino)pyridazin-3-yl)quinoline-3-carbonitrile;
6-(6-(methyl(2,2,6,6-tetramethylpiperidin-4-yl)amino)pyridazin-3-yl)quinolin-7-ol;
4-(dimethylamino)-2-methyl-6-(6-(methyl(2,2,6,6-tetramethylpiperidin-4-yl)amino)pyridazin-3-yl)quinolin-7-ol;
3-chloro-6-(6-(methyl(2,2,6,6-tetramethylpiperidin-4-yl)amino)pyridazin-3-yl)quinolin-7-ol;
4-methoxy-2-methyl-6-(6-(methyl(2,2,6,6-tetramethylpiperidin-4-yl)amino)pyridazin-3-yl)quinolin-7-ol;
6-(3-(benzyloxy)isoquinolin-6-yl)-N-methyl-N-(2,2,6,6-tetramethylpiperidin-4-yl)pyridazin-3-amine;
8-(6-(methyl(2,2,6,6-tetramethylpiperidin-4-yl)amino)pyridazin-3-yl)quinolin-7-ol;
7-(6-(methyl(2,2,6,6-tetramethylpiperidin-4-yl)amino)pyridazin-3-yl)isoquinoline-1,6-diol;
7-(6-(methyl(1,2,2,6,6-pentamethylpiperidin-4-yl)amino)pyridazin-3-yl)isoquinolin-6-ol;
1-cyclopropyl-7-(6-(methyl(2,2,6,6-tetramethylpiperidin-4-yl)amino)pyridazin-3-yl)isoquinalin-6-ol;
7-(6-(methyl(2,2,6,6-tetramethylpiperidin-4-yl)amino)pyridazin-3-yl)isoquinolin-6-ol;
6-(1-(benzyloxy)isoquinolin-7-yl)-N-methyl-N-(2,2,6,6-tetramethylpiperidin-4-yl)pyridazin-3-amine;
7-(6-(methyl(2,2,6,6-tetramethylpiperidin-4-yl)amino)pyridazin-3-yl)quinolin-6-ol;
2-methyl-7-(6-(methyl(2,2,6,6-tetramethylpiperidin-4-yl)amino)pyridazin-3-yl)quinlin-6-ol;
2-methyl-6-(6-(methyl(2,2,6,6-tetramethylpiperidin-4-yl)amino)pyridazin-3-yl)-4-(1-methyl-1H-pyrazol-4-yl)quinolin-7-ol;
2-methyl-6-(6-(methyl(2,2,6,6-tetramethylpiperidin-4-yl)amino)pyridazin-3-yl)quinlin-7-ol;
4-ethoxy-2-methyl-6-(6-(methyl(2,2,6,6-tetramethylpiperidin-4-yl)amino)pyridazin-3-yl)quinalin-7-ol;
4-chloro-7-(6-(methyl(2,2,6,6-tetramethylpiperidin-4-yl)amino)pyridazin-3-yl)quinolin-6-ol;
6-(6-(methyl(2,2,6,6-tetramethylpiperidin-4-yl)amino)pyridazin-3-yl)-3-(tetrahydro-2H-pyran-4-yl)quinolin-7-ol;
3-chloro-7-(6-(methyl(2,2,6,6-tetramethylpiperidin-4-yl)amino)pyridazin-3-yl)quinolin-6-ol;
3-bromo-7-(6-(methyl(2,2,6,6-tetramethyl piperidin-4-yl)amino)pyridazin-3-yl)quinolin-6-ol;
3-methyl-7-(6-(methyl(2,2,6,6-tetramethylpiperidin-4-yl)amino)pyridazin-3-yl)quinolin-6-ol;
5-bromo-3-methyl-7-(6-(methyl(2,2,6,6-tetramethylpiperidin-4-yl)amino)pyridazin-3-yl)quinolin-6-ol;
6-hydroxy-1-methyl-7-(6-(methyl(2,2,6,6-tetramethylpiperidin-4-yl)amino)pyridazin-3-yl)quinolin-4(1H)-one;
2,3-dimethyl-7-(6-(methyl(2,2,6,6-tetramethylpiperidin-4-yl)amino)pyridazin-3-yl)quinoxalin-6-ol;
2-methyl-7-(6-(methyl(2,2,6,6-tetramethylpiperidin-4-yl)amino)pyridazin-3-yl)quinoxalin-6-ol;
3-methyl-7-(6-(methyl(2,2,6,6-tetramethylpiperidin-4-yl)amino)pyridazin-3-yl)quinoxalin-6-ol;
4-methoxy-6-(6-(methyl(2,2,6,6-tetramethylpiperidin-4-yl)amino)pyridazin-3-yl)quinolin-7-ol;
4-(azetidin-1-yl)-2-methyl-6-(6-(methyl(2,2,6,6-tetramethylpiperidin-4-yl)amino)pyridazin-3-yl)quinolin-7-ol;
7-hydroxy-2-methyl-6-(6-(methyl(2,2,6,6-tetramethylpiperidin-4-yl)amino)pyridazin-3-yl)quinoline-4-carbonitrile;
4-cyclopropyl-2-methyl-6-(6-(methyl(2,2,6,6-tetramethylpiperidin-4-yl)amino)pyridazin-3-yl)quinolin-7-ol;
4-(3,6-dihydro-2H-pyran-4-yl)-2-methyl-6-(6-(methyl(2,2,6,6-tetramethylpiperidin-4-yl)amino)pyridazin-3-yl)quinolin-7-ol;
2-methyl-6-(6-(methyl(2,2,6,6-tetramethylpiperidin-4-yl)amino)pyridazin-3-yl)-4-(tetrahydro-2H-pyran-4-yl)quinolin-7-ol;
2-methyl-6-(6-(methyl(2,2,6,6-tetramethylpiperidin-4-yl)amino)pyridazin-3-yl)-4-(oxetan-3-yl)quinolin-7-ol;
4-(dimethylamino)-6-(6-(methyl(2,2,6,6-tetramethylpiperidin-4-yl)amino)pyridazin-3-yl)quinolin-7-ol;
7-hydroxy-6-(6-(methyl(2,2,6,6-tetramethylpiperidin-4-yl)amino)pyridazin-3-yl)quinazoin-4(1H)-one;
6-(6-(methyl(2,2,6,6-tetramethylpiperidin-4-yl)amino)pyridazin-3-yl)quinazolin-7-ol;
7-hydroxy-1-methyl-6-(6-(methyl(2,2,6,6-tetramethylpiperidin-4-yl)amino)pyridazin-3-yl)-3,4-dihydroquinolin-2(1H)-one;
7-hydroxy-1-methyl-6-(6-(methyl(2,2,6,6-tetramethylpiperidin-4-yl)amino)pyridazin-3-yl)-3,4-dihydroquinolin-2(1H)-one;
7-hydroxy-6-(6-(methyl(2,2,6,6-tetramethylpiperidin-4-yl)amino)pyridazin-3-yl)isoquinoline-1-carbonitrile;
7-hydroxy-6-(6-(methyl(2,2,6,6-tetramethylpiperidin-4-yl)amino)pyridazin-3-yl)quinoline-2-carbonitrile;
6-hydroxy-7-(6-(methyl(2,2,6,6-tetramethylpiperidin-4-yl)amino)pyridazin-3-yl)quinoline-2-carbonitrile;
6-hydroxy-7-(6-(methyl(2,2,6,6-tetramethylpiperidin-4-yl)amino)pyridazin-3-yl)isoquinoline-1-carboxamide;
7-hydroxy-6-(6-(methyl(2,2,6,6-tetramethylpiperidin-4-yl)amino)pyridazin-3-yl)quinoline-2-carboxamide;
6-hydroxy-7-(6-(methyl(2,2,6,6-tetramethylpiperidin-4-yl)amino)pyridazin-3-yl)quinoline-2-carboxamide;
methyl 6-hydroxy-7-(6-(methyl(2,2,6,6-tetramethylpiperidin-4-yl)amino)pyridazin-3-yl)quinoline-2-carboxylate;
6-hydroxy-7-(6-(piperazin-1-yl)pyridazin-3-yl)quinoline-2-carbonitrile;
7-hydroxy-6-(6-(piperazin-1-yl)pyridazin-3-yl)quinoline-2-carbonitrile;
7-(6-(piperazin-1-yl)pyridazin-3-yl)isoquinolin-6-ol;
7-(6-(1,2,3,6-tetrahydropyridin-4-yl)pyridazin-3-yl)quinolin-6-ol;

1-methyl-6-(6-(methyl(2,2,6,6-tetramethylpiperidin-4-yl)amino)pyridazin-3-yl)isoquinolin-7-ol;
1-methyl-7-(6-(methyl(2,2,6,6-tetramethylpiperidin-4-yl)amino)pyridazin-3-yl)isoquinolin-6-ol;
1,3-dimethyl-7-(6-(methyl(2,2,6,6-tetramethylpiperidin-4-yl)amino)pyridazin-3-yl)isoquinolin-6-ol;
7-hydroxy-3-methyl-6-(6-(methyl(2,2,6,6-tetramethylpiperidin-4-yl)amino)pyridazin-3-yl)isoquinoline-1-carbonitrile;
1-amino-7-(6-(methyl(2,2,6,6-tetramethylpiperidin-4-yl)amino)pyridazin-3-yl)isoquinolin-6-ol;
7-hydroxy-1,3-dimethyl-6-(6-(methyl(2,2,6,6-tetramethylpiperidin-4-yl)amino)pyridazin-3-yl)quinazoline-2,4(1H,3H)-dione;
6-hydroxy-5-(6-(methyl(2,2,6,6-tetramethylpiperidin-4-yl)amino)pyridazin-3-yl)benzo[d]oxazol-2(3H)-one;
2-methyl-5-(6-(methyl(2,2,6,6-tetramethylpiperidin-4-yl)amino)pyridazin-3-yl)-2H-indazol-6-ol;
1-methyl-5-(6-(methyl(2,2,6,6-tetramethylpiperidin-4-yl)amino)pyridazin-3-yl)-1H-indazol-6-ol;
6-hydroxy-2-methyl-7-(6-(methyl(2,2,6,6-tetramethylpiperidin-4-yl)amino)pyridazin-3-yl)isoquinolin-1(2H)-one;
2-ethyl-6-hydroxy-7-(6-((2,2,6,6-tetramethylpiperidin-4-yl)oxy)pyridazin-3-yl)isoquinolin-1(2H)-one;
1-ethoxy-7-(6-(methyl(2,2,6,6-tetramethylpiperidin-4-yl)amino)pyridazin-3-yl)isoquinolin-6-ol;
7-(6-((2,2,6,6-tetramethylpiperidin-4-yl)oxy)pyridazin-3-yl)isoquinoline-1,6-diol;
7-(6-(methyl(2,2,6,6-tetramethyl-piperidin-4-yl)amino)-pyridazin-3-yl)-3-phenylisoquinolin-6-ol;
3-methyl-7-(6-(methyl(2,2,6,6-tetramethylpiperidin-4-yl)amino)pyridazin-3-yl)isoquinolin-6-ol;
3-cyclopropyl-7-(6-(methyl(2,2,6,6-tetramethyl-piperidin-4-yl)amino)pyridazin-3-yl)isoquinolin-6-ol;
3-isopropyl-7-(6-(methyl(2,2,6,6-tetramethyl-piperidin-4-yl)amino)pyridazin-3-yl)isoquinolin-6-ol;
3-propyl-7-(6-((2,2,6,6-tetramethylpiperidin-4-yl)oxy)-pyridazin-3-yl)isoquinolin-6-ol;
3-isopropyl-7-(6-((2,2,6,6-tetramethylpiperidin-4-yl)oxy)-pyridazin-3-yl)isoquinolin-6-ol; and
3-methyl-7-(6-(piperazin-1-yl)pyridazin-3-yl)isoquinolin-6-ol;

In a twentyfirst embodiment, the invention is a compound, or salt thereof, selected from the group consisting of:
7-hydroxy-6-(6-(methyl(2,2,6,6-tetramethylpiperidin-4-yl)amino)pyridazin-3-yl)quinolin-2(1H)-one;
6-(6-((3aR,6aS)-5-methylhexahydropyrrolo[3,4-c]pyrrol-2(1H)-yl)pyridazin-3-yl)quinolin-7-ol;
7-hydroxy-1-methyl-6-(6-(methyl(2,2,6,6-tetramethylpiperidin-4-yl)amino)pyridazin-3-yl)quinolin-2(1H)-one;
6-(6-(methyl(1,2,2,6,6-pentamethylpiperidin-4-yl)amino)pyridazin-3-yl)quinolin-7-ol;
2-methyl-6-(6-(methyl(2,2,6,6-tetramethylpiperidin-4-yl)amino)pyridazin-3-yl)-4-morpholinoquinolin-7-ol;
4-chloro-2-methyl-6-(6-(methyl(2,2,6,6-tetramethylpiperidin-4-yl)amino)pyridazin-3-yl)quinolin-7-ol;
3-bromo-6-(6-(methyl(2,2,6,6-tetramethylpiperidin-4-yl)amino)pyridazin-3-yl)quinolin-7-ol;
3-ethyl-6-(6-(methyl(2,2,6,6-tetramethylpiperidin-4-yl)amino)pyridazin-3-yl)quinolin-7-ol;
3-(1H-imidazol-1-yl)-6-(6-(methyl(2,2,6,6-tetramethylpiperidin-4-yl)amino)pyridazin-3-yl)quinolin-7-ol;
6-(6-(methyl(2,2,6,6-tetramethylpiperidin-4-yl)amino)pyridazin-3-yl)-3-(1-methyl-1H-imidazol-4-yl)quinolin-7-ol;
3-isopropyl-6-(6-(methyl(2,2,6,6-tetramethylpiperidin-4-yl)amino)pyridazin-3-yl)quinolin-7-ol;
6-(6-(methyl(2,2,6,6-tetramethylpiperidin-4-yl)amino)pyridazin-3-yl)quinoline-3,7-diol;
7-hydroxy-6-(6-(methyl(2,2,6,6-tetramethylpiperidin-4-yl)amino)pyridazin-3-yl)quinoline-3-carbonitrile;
6-(6-(methyl(2,2,6,6-tetramethylpiperidin-4-yl)amino)pyridazin-3-yl)quinolin-7-ol;
4-(dimethylamino)-2-methyl-6-(6-(methyl(2,2,6,6-tetramethylpiperidin-4-yl)amino)pyridazin-3-yl)quinolin-7-ol;
3-chloro-6-(6-(methyl(2,2,6,6-tetramethylpiperidin-4-yl)amino)pyridazin-3-yl)quinolin-7-ol;
4-methoxy-2-methyl-6-(6-(methyl(2,2,6,6-tetramethylpiperidin-4-yl)amino)pyridazin-3-yl)quinolin-7-ol;
6-(3-(benzyloxy)isoquinolin-6-yl)-N-methyl-N-(2,2,6,6-tetramethylpiperidin-4-yl)pyridazin-3-amine;
8-(6-(methyl(2,2,6,6-tetramethylpiperidin-4-yl)amino)pyridazin-3-yl)quinolin-7-ol;
7-(6-(methyl(2,2,6,6-tetramethylpiperidin-4-yl)amino)pyridazin-3-yl)isoquinoline-1,6-diol;
7-(6-(methyl(1,2,2,6,6-pentamethylpiperidin-4-yl)amino)pyridazin-3-yl)isoquinolin-6-ol;
1-cyclopropyl-7-(6-(methyl(2,2,6,6-tetramethylpiperidin-4-yl)amino)pyridazin-3-yl)isoquinolin-6-ol;
7-(6-(methyl(2,2,6,6-tetramethylpiperidin-4-yl)amino)pyridazin-3-yl)isoquinolin-6-ol;
6-(1-(benzyloxy)isoquinolin-7-yl)-N-methyl-N-(2,2,6,6-tetramethylpiperidin-4-yl)pyridazin-3-amine;
7-(6-(methyl(2,2,6,6-tetramethylpiperidin-4-yl)amino)pyridazin-3-yl)quinolin-6-ol;
2-methyl-7-(6-(methyl(2,2,6,6-tetramethylpiperidin-4-yl)amino)pyridazin-3-yl)quinolin-6-ol;
2-methyl-6-(6-(methyl(2,2,6,6-tetramethylpiperidin-4-yl)amino)pyridazin-3-yl)-4-(1-methyl-1H-pyrazol-4-yl)quinolin-7-ol;
2-methyl-6-(6-(methyl(2,2,6,6-tetramethylpiperidin-4-yl)amino)pyridazin-3-yl)quinolin-7-ol;
4-ethoxy-2-methyl-6-(6-(methyl(2,2,6,6-tetramethylpiperidin-4-yl)amino)pyridazin-3-yl)quinolin-7-ol; and
4-chloro-7-(6-(methyl(2,2,6,6-tetramethylpiperidin-4-yl)amino)pyridazin-3-yl)quinolin-6-ol.

In a twentysecond embodiment, the invention is a compound, or salt thereof, selected from the group consisting of:
7-(6-(methyl(2,2,6,6-tetramethylpiperidin-4-yl)amino)pyridazin-3-yl)isoquinolin-6-ol;
2-methyl-7-(6-(methyl(2,2,6,6-tetramethylpiperidin-4-yl)amino)pyridazin-3-yl)quinoxalin-6-ol;
3-methyl-7-(6-(methyl(2,2,6,6-tetramethylpiperidin-4-yl)amino)pyridazin-3-yl)quinoxalin-6-ol;
6-(6-(methyl(2,2,6,6-tetramethylpiperidin-4-yl)amino)pyridazin-3-yl)quinazolin-7-ol;
7-hydroxy-6-(6-(methyl(2,2,6,6-tetramethylpiperidin-4-yl)amino)pyridazin-3-yl)quinoline-2-carbonitrile; and
1-amino-7-(6-(methyl(2,2,6,6-tetramethylpiperidin-4-yl)amino)pyridazin-3-yl)isoquinolin-6-ol.

In a twentythird embodiment, the inventiuon is a pharmaceutical composition comprising a therapeutically effective amount of a compound according to any one of the first through twentythird embodiments, or a pharmaceutically acceptable salt thereof and one or more pharmaceutically acceptable carriers.

In a twentyfourth embodiment, the invention is a combination comprising a therapeutically effective amount of a compound according to any one of the first through twentysecond embodiments, or a pharmaceutically acceptable salt thereof and one or more therapeutically active co-agents.

In a twentyfifth embodiment, the invention is a method to treat, prevent or ameliorate an SMN-deficiency-related condition, comprising administering to a subject in need thereof an effective amount of a compound or salt thereof of any one of the first through twentysecond embodiments.

In a twentysixth embodiment, the invention is the method of the twentyfifth embodiment, wherein said SMN-deficiency-related condition is Spinal Muscular Atrophy.

In a twentyseventh embodiment, the invention is a compound according to any one of the first through twentysecond embodiments, or a pharmaceutically acceptable salt thereof, for use as a medicament.

In a twentyeighth embodiment, the invention is a compound according to any one of the first through twentysecond embodiments, or a pharmaceutically acceptable salt thereof, for use in the treatment of an SMN-deficiency-related condition.

In a twentyninth embodiment, the invention is the compound according to the twentyeighth embodiment, or pharmaceutically acceptable salt thereof, for use in the treatment of spinal muscular atrophy.

In a thirtieth embodiment, the invention is the use of a compound according to any one of the first through twentysecond embodiments, or a pharmaceutically acceptable salt thereof in the manufacture of a medicament for the treatment of spinal muscular atrophy.

For purposes of interpreting this specification, the following definitions will apply and whenever appropriate, terms used in the singular will also include the plural and vice versa.

As used herein, the term "SMN modulator" includes agents, such as the compounds of the invention, which possess the ability to modulate, e.g., increase, SMN protein levels by at least one of multiple possible mechanisms. A non-limiting set of mechanisms includes SMN promoter activation, splicing modulation (e.g., preventing exon7 from being spliced out of the SMN gene), and SMN protein stability modulation. SMN modulators can modulate, e.g., increase FL-SMN and/or SMNΔ7 levels via any of said mechanisms, and/or can prevent SMNΔ7 from being degraded.

As used herein, the term "compounds of the invention" include but are not limited to the compounds of formula (I) and the compounds of formula (I-A)

As used herein, the term "SMN-deficiency-related conditions" includes but is not limited to Spinal Muscular Atrophy (SMA), neurogenic-type arthrogryposis multiplex congenita (congenital AMC), and amyotrophic lateral sclerosis (ALS).

As used herein, the term "Spinal Muscular Atrophy", "SMA," include three forms of childhood-onset SMA: Type I (Werdnig-Hoffmann disease); Type II (intermediate, chronic form), Type III (Kugelberg-Welander disease, or Juvenile Spinal Muscular Atrophy); Adult-onset type IV; as well as other forms of SMA, including X-linked disease, spinal muscular atrophy with respiratory distress (SMARD), spinal and bulbar muscular atrophy (Kennedy's disease, or Bulbo-Spinal Muscular Atrophy), and distal spinal muscular atrophy.

For purposes of interpreting this specification, the following definitions will apply and whenever appropriate, terms used in the singular will also include the plural and vice versa.

As used herein, the term "$C_{1-10}$alkyl" refers to a fully saturated branched or unbranched hydrocarbon moiety having 1 to 10 carbon atoms. The terms "$C_{1-6}$alkyl" and "$C_{1-4}$alkyl" are to be construed accordingly. Representative examples of $C_{1-10}$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

As used herein, the term "$C_{1-10}$alkylene" refers to divalent alkyl group as defined herein above having 1 to 10 carbon atoms. The terms "$C_{1-6}$alkylene" and "$C_{1-4}$alkylene" are to be construed accordingly. Representative examples of $C_{1-10}$alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

As used herein, the term "halo$C_{1-10}$alkyl" refers to a $C_{1-10}$alkyl group as defined herein, wherein at least one of the hydrogen atoms is replaced by a halo atom. The halo$C_{1-10}$alkyl group can be monohalo$C_{1-10}$alkyl, dihalo$C_{1-10}$alkyl or polyhalo$C_{1-10}$alkyl including perhalo$C_{1-10}$alkyl. A monohalo$C_{1-10}$alkyl can have one iodo, bromo, chloro or fluoro within the alkyl group. Dihalo$C_{1-10}$alkyl and polyhalo$C_{1-10}$alkyl groups can have two or more of the same halo atoms or a combination of different halo groups within the alkyl. Typically the polyhalo$C_{1-10}$alkyl group contains up to 12, or 10, or 8, or 6, or 4, or 3, or 2 halo groups. Non-limiting examples of halo$C_{1-10}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-10}$alkyl group refers to an $C_{1-10}$alkyl group having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

As used herein, the term "$C_{1-10}$alkoxy" refers to $C_{1-10}$alkyl-O—, wherein $C_{1-10}$alkyl is defined herein above. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy- and decyloxy-.

As used herein, the term "heterocyclyl" or "heterocyclo" refers to a saturated or unsaturated non-aromatic ring or ring system, which is a 4-, 5-, 6-, or 7-membered monocyclic ring containing 1, 2 or 3 heteroatoms selected from O, S and N, a 7-, 8-, 9-, 10-, 11-, or 12-membered bicyclic ring system containing 1, 2, 3, 4 or 5 heteroatoms selected from O, S and N, or a 10-, 11-, 12-, 13-, 14- or 15-membered tricyclic ring system and containing 1, 2, 3, 4, 5, 6 or 7 heteroatoms selected from O, S and N, where the N and S can also optionally be oxidized to various oxidation states. The heterocyclic group can be attached via a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane and thiomorpholine.

As used herein, the term "$C_{3-12}$cycloalkyl" refers to saturated or unsaturated monocyclic, bicyclic or tricyclic hydrocarbon groups of 3-12 carbon atoms. The term "$C_{3-18}$cycloalkyl" refers to a fully saturated or unsaturated monocyclic hydrocarbon group of 3-8 carbon atoms. Exemplary monocyclic hydrocarbon groups include, but are not limited to, cyclopropyl, cyclobutyl, cyclopentyl, cyclopentenyl, cyclohexyl and cyclohexenyl. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic hydrocarbon groups include, for example, adamantyl.

As used herein the term "$C_{3-12}$cycloalklyoxy" refers to $C_{3-12}$cycloalkyl-O—, wherein $C_{3-12}$cycloalkyl is defined herein above. Representative examples of $C_{3-12}$cycloalklyoxy include, but are not limited to monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

As used herein, the term "aryloxy" refers to both an —O-aryl and an —O-heteroaryl group, wherein aryl and heteroaryl are defined herein.

As used herein, the term "heteroaryl" refers to a 5-, 6-, or 7-membered monocyclic aromatic ring containing 1, 2, 3 or 4 heteroatoms selected from O, S and N, an 8-, 9-, or 10-membered fused bicyclic ring system containing 1, 2, 3, 4 or 5 heteroatoms selected from O, S and N, or an 11-, 12-, 13-, or 14-membered fused tricyclic ring system containing 1, 2, 3, 4, 5 or 6 heteroatoms selected from O, S and N, wherein at least one of the rings of the bicyclic or tricyclic ring systems is fully aromatic. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl, 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1—, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8- 5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein, the term "halogen" or "halo" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts." The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/di hydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Survival of Motor Neuron (SMN) gene or gene product, or by SMNΔ7 degradation, or by the relative levels of FL-SMN and SMNΔ7 (ii) associated with SMN activity, or (iii) characterized by activity (normal or abnormal) of SMN; or (2) reducing or inhibiting the activity of SMN; or (3) reducing or inhibiting the expression of SMN1 or SMN2.

In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SMN; or at least partially reducing or inhibiting the expression of SMN, in both cases by modulating the relative levels of FL-SMN and SMNΔ7.

The phrases "therapeutically effective amount" and "effective amount" are used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of an SMN-deficiency-related condition. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat", "treating" or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions).

The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with diluents, e.g., lactose, dextrose, sucrose, mannitol, sorbitol, cellulose and/or glycine;

lubricants, e.g., silica, talcum, stearic acid, its magnesium or calcium salt and/or polyethyleneglycol; for tablets also binders, e.g., magnesium aluminum silicate, starch paste, gelatin, tragacanth, methylcellulose, sodium carboxymethylcellulose and/or polyvinylpyrrolidone; if desired disintegrants, e.g., starches, agar, alginic acid or its sodium salt, or effervescent mixtures; and/or absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological properties, e.g. full length SMN protein production modulating properties, e.g. as indicated in in vitro and in vivo tests as provided in the next sections, and are therefore indicated for therapy or for use as research chemicals, e.g. as tool compounds.

Thus, as a further embodiment, the present invention provides the use of a compound of formula (I) or a salt thereof in therapy. In a further embodiment, the therapy is selected from a disease which may be treated by modulating full length SMN protein production. In another embodiment, the disease is selected from the afore-mentioned list, suitably spinal muscular atrophy.

In another embodiment, the invention provides a method of treating a disease which is treated by modulating full length SMN protein production comprising administration of a therapeutically acceptable amount of a compound of formula (I) or salt thereof to a patient in need of such therapy. In a further embodiment, the disease is selected from the afore-mentioned list, suitably spinal muscular atrophy.

Thus, as a further embodiment, the present invention provides the use of a compound of formula (I) or salt thereof for the manufacture of a medicament. In a further embodiment, the medicament is for treatment of a disease which may be treated by modulation of SMN protein production. In another embodiment, the disease is selected from the afore-mentioned list, suitably spinal muscular atrophy.

The pharmaceutical composition or combination of the present invention can be in unit dosage of about 0.01-1000 mg of active ingredient(s) for a subject of about 0.05-70 kg or about 1-20 kg, or about 1-500 mg or about 1-250 mg or about 1-150 mg or about 0.5-100 mg, or about 0.01-1 mg or about 0.01-0.1 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a spinal muscular atrophy. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Preparations of Compounds

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1999), 3rd Ed., Wiley. The protecting group may also be a polymer resin, such as a Wang resin or a 2-chlorotrityl-chloride resin.

It will also be appreciated by those skilled in the art, although such protected derivatives of compounds of this invention may not possess pharmacological activity as such, they may be administered to a subject and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this invention. A, B, X, R, $R^1$, $R^2$, $R^3$, $R^4$, are defined as in the Specification unless specifically defined.

In general, pyridazine compounds of Formula (I) of this invention can be synthesized following the general procedure described in Scheme 1.

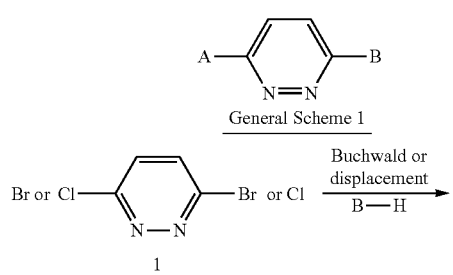

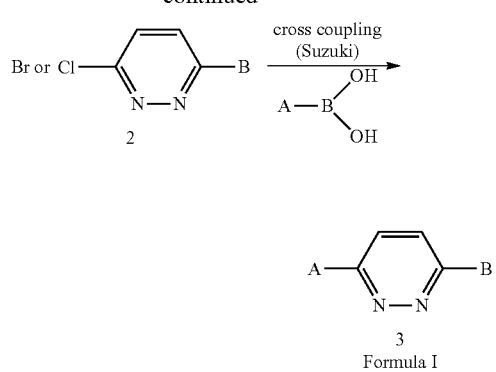

The starting materials for the above reaction scheme are commercially available or can be prepared according to methods known to one skilled in the art or by methods disclosed herein. In general, the compounds of the invention are prepared in the above reaction Scheme 1 as follows:

Di-halopyridazine (1) reacts in a displacement reaction or a metal-mediated cross coupling reaction (Buchwald) with an alcohol or an amine (B) to provide pyridazine intermediate (2). Transition metal-mediated cross coupling reaction, such as a Suzuki reaction, between halide compound (2) and a substituted aryl or heteroaryl compound A, such as a boronate acid or boronate ester, provides compound (3) of Formula (I) of the invention.

In a complementary manner, compounds of Formula (I) can be synthesized following the general procedure described in Scheme 2.

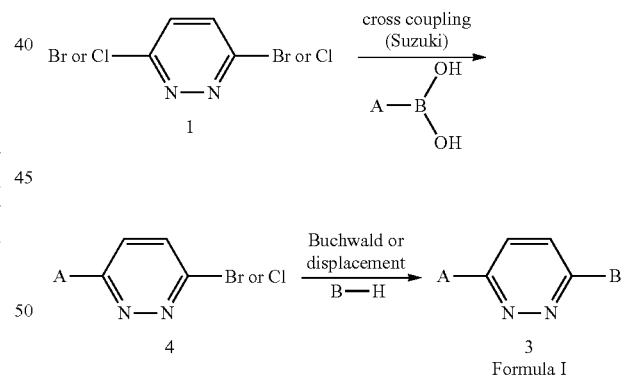

The starting materials for the above reaction scheme are commercially available or can be prepared according to methods known to one skilled in the art or by methods disclosed herein. In general, the compounds of the invention are prepared in the above reaction Scheme 2 as follows:

Di-halopyridazine (1) reacts in a transition metal-mediated cross coupling reaction, such as a Suzuki reaction, with a substituted aryl or heteroaryl compound A, such as a boronate acid or ester, to provide pyridazine intermediate (4). Pyridazine intermediate (4) reacts via a displacement reaction with an alcohol or an amine (B) to provide pyridazine (3) of Formula (I) of the invention.

Compounds of Formula (I) can also be prepared following the general procedure described in Scheme 3.

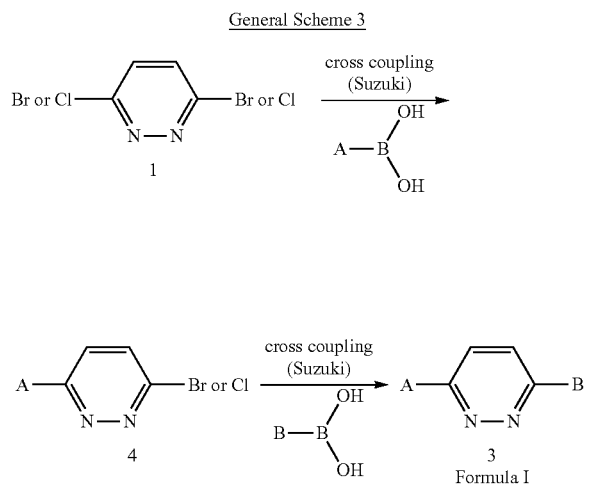

General Scheme 3

The starting materials for the above reaction scheme are commercially available or can be prepared according to methods known to one skilled in the art or by methods disclosed herein. In general, the compounds of the invention are prepared in the above reaction Scheme 3 as follows:

Di-halopyridazine (1) reacts in a transition metal-mediated cross coupling reaction, such as a Suzuki reaction, with a substituted aryl or heteroaryl compound A, such as a boronate acid or ester, to provide pyridazine intermediate (4). Pyridazine intermediate (4) reacts via second metal-mediated cross coupling, such as a Suzuki reaction, to provide pyridazine (3) of Formula (I) of the invention.

General Schemes 1, 2 and 3 can be followed for a variety of aromatic A groups such as substituted phenols, naphthyls, heteroaryls, and the like, and for a variety of amine or alcohol B groups such as substituted aminopiperdines, piperazines, homopiperazines, 4-hydroxy piperidines, and the like, to provide compounds of Formula (I) of the invention. Routine protecting group strategies may be required to achieve final compounds of Formula (I).

All starting materials, building blocks, reagents, acids, bases, dehydrating agents, solvents, catalysts and scavengers utilized to synthesize the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., LCMS, NMR, CHN. Abbreviations used are those conventional in the art, a list of which is provided at the end of the experimental section.

Preparation 1

Intermediate 1: Synthesis of 6-chloro-N-methyl-N-(2,2,6,6-tetramethylpiperidin-4-yl)pyridazin-3-amine

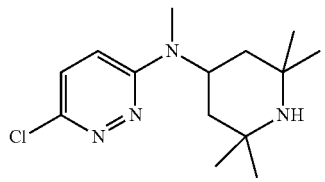 [SMILES: CN(c1ccc(Cl)nn1)C1CC(C)(C)NC(C)(C)C1]

A solution of 3,6-dichloropyridazine (4.00 g, 26.8 mmol) and N, 2,2,6,6-pentamethylpiperidin-4-amine (7.32 g, 43.0 mmol) in butan-1-ol (67 mL) was heated at 120° C. for 72 h. The solvent was removed via rotary evaporation and the residue was partitioned between water and DCM, then the water layer was further extracted with DCM. The combined organic layers were washed with water, brine, dried over $MgSO_4$, and concentrated in vacuo. The black crude material was stirred in small amount of EtOAc overnight, and the resulting off-white solid was collected to provide 6-chloro-N-methyl-N-(2,2,6,6-tetramethylpiperidin-4-yl)pyridazin-3-amine, Intermediate 1 (4.18 g). MS (M+1)=283.5. $^1$H NMR (400 MHz, METHANOL-$d_4$) δ 7.40 (d, J=9.60 Hz, 1H), 7.14 (d, J=9.60 Hz, 1H), 4.96-5.13 (m, 1H), 2.93 (s, 3H), 1.59-1.68 (m, 2H), 1.51 (t, J=12.38 Hz, 2H), 1.20 (s, 6H), 1.33 (s, 6H).

Preparation 2

Intermediate 2: Synthesis of 6-chloro-N-(2,2,6,6-tetramethylpiperidin-4-yl)pyridazin-3-amine

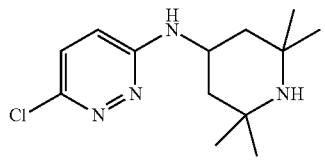

A mixture of 3,6-dichloropyridazine (6.26 g, 42.0 mmol) and 2,2,6,6-tetramethylpiperidin-4-amine (14.7 mL, 84 mmol) was stirred at 120° C. for 1 h, neat. To this mixture was added butan-1-ol (40 mL), and the reaction was stirred at 120° C. for 1 h. The mixture was cooled to room temperature and partitioned between water and DCM. The organic layer was dried over $MgSO_4$, filtered, and concentrated. The crude material was recrystallized from acetonitrile to provide 6-chloro-N-(2,2,6,6-tetramethylpiperidin-4-yl)pyridazin-3-amine, Intermediate 2 (7.3 g) as an off-white solid. MS (M+1)=269.2. $^1$H NMR (400 MHz, CHLOROFORM-d) δ 7.08 (d, J=9.3 Hz, 1H), 6.54 (d, J=9.3 Hz, 1H), 4.53 (d, J=7.6 Hz, 1H), 4.05-4.26 (m, 1H), 1.98 (dd, J=12.6, 3.8 Hz, 2H), 1.22 (s, 6H), 1.08 (s, 6H), 0.93 (apparent t, J=12.1 Hz, 2H).

Preparation 3

Intermediate 3: Synthesis of 3-chloro-6-(2,2,6,6-tetramethylpiperidin-4-yloxy)pyridazine

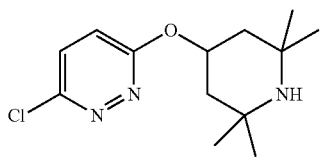 [SMILES: CC1(C)CC(Oc2ccc(Cl)nn2)CC(C)(C)N1]

To a solution of 2,2,6,6-tetramethylpiperidin-4-ol (106 mg, 0.67 mmol) in DMF (6.7 mL) was added NaH (60 wt %, 35 mg, 0.87 mmol). The solution was stirred at room temperature for 30 min, then 3,6-dichloropyridazine (100 mg, 0.67 mmol) was added and the reaction was stirred for 1 h. The crude reaction mixture was diluted with EtOAc. The organic layer was washed with water (5×), brine, dried over Na2SO4, filtered and concentrated under reduced pressure to provide 3-chloro-6-(2,2,6,6-tetramethylpiperidin-4-yloxy)pyridazine, Intermediate 3 (135 mg). MS (M+1)=270.2. $^1$H NMR (400 MHz, CHLOROFORM-d) δ 7.53 (s, 1H), 7.37 (d, J=9.1 Hz, 1H), 6.91 (d, J=9.1 Hz, 1H), 5.68-5.78 (m, 1H), 2.20 (dd, J=12.4, 4.0 Hz, 2H), 1.32 (s, 6H), 1.27-1.29 (m, 2H), 1.20 (s, 6H).

Preparation 4

Intermediate 4: Synthesis of 6-chloro-N-methyl-N-(1,2,2,6,6-pentamethylpiperidin-4-yl)pyridazin-3-amine

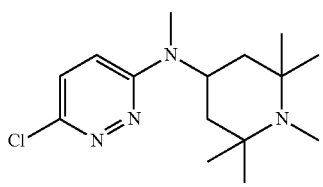 [SMILES: CN(c1ccc(Cl)nn1)C1CC(C)(C)N(C)C(C)(C)C1]

To a suspension of 6-chloro-N-(1,2,2,6,6-pentamethylpiperidin-4-yl)pyridazin-3-amine, Intermediate 2 (4.0 g, 14.1 mmol) in DMF (140 mL) cooled to 0° C. was added NaH (60 wt %, 735 mg, 18.39 mmol) portion-wise. The reaction was warmed to room temperature and stirred for 60 min. After 60 minutes, methyl iodide (0.88 mL, 14.1 mmol) was added and the reaction was stirred an additional 3 h, then slowly quenched with water at room temperature. The mixture was diluted with EtOAc. The organic layer was washed with water (5×), brine, dried over MgSO4, filtered and concentrated under reduced pressure to provide 6-chloro-N-methyl-N-(1,2,2,6,6-pentamethylpiperidin-4-yl)pyridazin-3-amine, Intermediate 4 (3.98 g). MS (M+1)=297.0. $^1$H NMR (400 MHz, CHLOROFORM-d) δ 7.10 (d, J=9.6 Hz, 1H), 6.69 (d, J=9.6 Hz, 1H), 4.79-5.00 (m, 1H), 2.86 (s, 3H), 2.22 (s, 3H), 1.61-1.73 (m, 2H), 1.48-1.57 (m, 2H), 1.14 (s, 6H), 1.10 (s, 6H).

Preparation 5

Intermediate 5: Synthesis of (3aR,6aS)-2-(6-chloropyridazin-3-yl)-5-methyloctahydropyrrolo[3,4-c]pyrrole

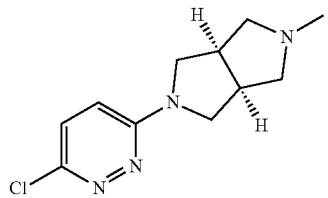 [SMILES: CN1C[C@@H]2CN(c3ccc(Cl)nn3)C[C@@H]2C1]

To a solution of 3,6-dichloropyridazine (0.596 g, 4.00 mmol) in butan-1-ol (10 mL) was added DIPEA (1.40 mL, 8.00 mmol) and 2-methyloctahydropyrrolo[3,4-c]pyrrole (0.505 g, 4.00 mmol). The solution was heated at 120° C. overnight. The reaction mixture was concentrated and the residue purified by silica gel chromatography (0-25% 2 N ammonia in MeOH gradient, in DCM) to provide (3aR,6aS)-2-(6-chloropyridazin-3-yl)-5-methyloctahydropyrrolo[3,4-c]pyrrole, Intermediate 5 (0.67 g), as an off-white solid. MS (M+1)=239.1. $^1$H NMR (400 MHz, METHANOL-d$_4$) δ 7.47 (d, J=9.6 Hz, 1H), 7.11 (d, J=9.6 Hz, 1H), 3.58-3.70 (m, 4H), 3.47 (dd, J=10.9, 7.3 Hz, 2H), 3.3 (2H, partially obscured by methanol residual solvent peak), 3.15 (d, J=11.1 Hz, 2H), 2.80 (s, 3H).

Preparation 6

Intermediate 6: Synthesis of (7-methoxyquinolin-6-yl)boronic acid

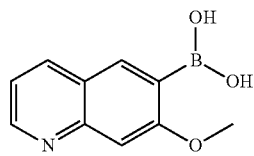

Step 1: 6-Bromo-7-methoxyquinoline

In a 100 mL round bottom flask, a solution of sulfuric acid (7.1 mL, 130 mmol) in water (6.5 mL) was treated with 3-nitrobenzenesulfonic acid (7.07 g, 34.8 mmol) and glycerol (8.7 mL, 120 mmol) to give a thick grey suspension. The suspension was heated to 110° C. and 4-bromo-3-methoxyaniline (6.7 g, 33 mmol) was added resulting in a slurry. Additional quantities of water (6 mL), glycerol (6 mL), sulfuric acid (6 mL) were added and the temperature increased to 140° C. After about 3 h the mixture became a homogeneous dark brown solution. The solution was cooled to room temperature, poured onto ice, and the pH adjusted to 8 by addition of concentrated ammonium hydroxide. The mixture was extracted with 1:1 EtOAc/diethyl ether (5×), dried over Mg$_2$SO$_4$ and concentrated to a brown liquid. Silica gel chromatography (0-20% EtOAc in DCM) provided the title compound which was further purified by silica gel chromatography (0-20% MeOH in DCM) to provide 6-bromo-7-methoxyquinoline (3.94 g) as an off-white solid.

MS (M+1)=240.1. ¹H NMR (400 MHz, CHLOROFORM-d) δ 8.86 (dd, J=4.0, 1.5 Hz, 1H), 8.01-8.12 (m, 2H), 7.53 (s, 1H), 7.34 (dd, J=8.1, 4.5 Hz, 1H), 4.07 (s, 3H).

Step 2: (7-Methoxyquinolin-6-yl)boronic acid

Butyllithium (1.6 M in heptane, 4.90 mL, 7.90 mmol) was added dropwise to a solution of 6-bromo-7-methoxyquinoline (1.71 g, 7.18 mmol) cooled to −78° C. The solution was stirred for 0.5 h after which time trimethyl borate (2.0 mL, 18 mmol) was added in a single portion. The reaction was allowed to warm to room temperature and stir overnight. The crude reaction was concentrated to dryness, then concentrated from heptane (2×). The resulting solids were passed through a plug of silica gel (80 mL, dry measure) eluting with 9:1 DCM/MeOH to provide (7-methoxyquinolin-6-yl)boronic acid, Intermediate 6, as an orange solid (778 mg). MS (M+1)=204.1

Preparation 7

Intermediate 7: Synthesis of (6-methoxyisoquinolin-7-yl)boronic acid

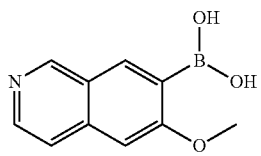

Step 1. 7-Bromo-6-methoxyisoquinoline

7-Bromo-6-methoxyisoquinoline was prepared as described in WO2007000240. MS (M+1)=240.3. ¹H NMR (400 MHz, CHLOROFORM-d) δ 9.08 (s, 1H), 8.49 (d, J=5.8 Hz, 1H), 8.20 (s, 1H), 7.56 (d, J=5.8 Hz, 1H), 7.11 (s, 1H), 4.05 (s, 3H).

Step 2. (6-Methoxyisoquinolin-7-yl)boronic acid

To a 50 mL round bottom flask was added 7-bromo-6-methoxyisoquinoline (300 mg, 1.26 mmol), bis(pinacolato)diboron (640 mg, 2.52 mmol), potassium acetate (742 mg, 7.56 mmol), and PdCl₂(dppf).CH₂Cl₂ (103 mg, 0.126 mmol). 1,4-Dioxane (0.2 M) was added and the flask was evacuated/purged with N₂ (3×). The reaction mixture was stirred at 100° C. for 2 h. The reaction was complete after 3 h as determined by LC/MS analysis; only the boronic acid was observed (no pinacol boronate ester). The mixture was diluted with EtOAc, filtered through Celite® and concentrated to provide (6-methoxyisoquinolin-7-yl)boronic acid, Intermediate 7, which was used without further purification. MS (M+1)=204.4

Preparation 8

Intermediate 8: Synthesis of (7-methoxyisoquinolin-6-yl)boronic acid

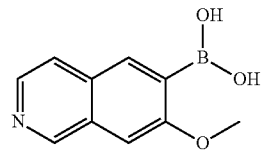

Step 1: (E)-N-(4-Bromo-3-methoxybenzylidene)-2,2-dimethoxyethanamine

In a 100 mL round-bottom flask fitted with a Dean-Stark trap and reflux condenser, 4-bromo-3-methoxybenzaldehyde (3.65 g, 17.0 mmol) and 2,2-dimethoxyethanamine (1.32 mL, 18.6 mmol) were refluxed in benzene (37 mL) overnight. The mixture was concentrated in vacuo to provide the title compound as an amber oil (3.65 g). ¹H NMR (400 MHz, CHLOROFORM-d) δ 8.20-8.26 (m, 1H), 7.58 (d, J=8.0 Hz, 1H), 7.40 (d, J=1.5 Hz, 1H), 7.10 (dd, J=1.76, 8.0 Hz, 1H), 4.69 (t, J=5.4 Hz, 1H), 3.96 (s, 3H), 3.78 (dd, J=1.3, 5.3 Hz, 2H), 3.43 (s, 6H).

Step 2: 6-Bromo-7-methoxyisoquinoline

A 100 mL round-bottom flask was charged with (E)-N-(4-bromo-3-methoxybenzylidene)-2,2-dimethoxyethanamine (3.65 g, 12.1 mmol) and THF (24 mL) to give a tan solution. Under N₂, the mixture was cooled to 0° C., and ethyl chloroformate (1.16 mL, 12.1 mmol) was added dropwise. After 5 min, triethyl phosphite (2.54 mL, 14.5 mmol) was added dropwise, and the mixture allowed to warm to room temperature and stir overnight. LC/MS analysis indicated consumption of the starting material, and the mixture was concentrated in vacuo. Toluene was added and removed in vacuo (2×). The crude residue was dissolved in chloroform (39 mL) and TiCl₄ (5.17 mL, 46.8 mmol) was added to give a brown solution. The solution was refluxed for two days under N₂. Product formation was confirmed by LC/MS analysis, and the solution was cooled to room temperature. The reaction mixture was poured into an ice/water bath (300 mL) and stirred for several hours. The pH was adjusted to neutral with aqueous ammonium hydroxide whereupon a brownish precipitate formed. EtOAc (200 mL) was added and the mixture stirred for 1 h, then filtered through Celite® to remove insoluble material. The aqueous layer was extracted with EtOAc (2×200 mL). The combined organic extracts were dried over MgSO₄, filtered, and concentrated in vacuo to provide the crude product. Silica gel chromatography (80 g column, 30-80% EtOAc/heptane) provided the title compound (1.64 g). MS (M+1)=238.3. ¹H NMR (400 MHz, CHLOROFORM-d) δ 9.16 (s, 1H), 8.45 (d, J=5.8 Hz, 1H), 8.08 (s, 1H), 7.52 (d, J=5.5 Hz, 1H), 7.25 (s, 1H), 4.05 (s, 3H).

Step 3: (7-Methoxyisoquinolin-6-yl)boronic acid

To a 50 mL round bottom flask was added 6-bromo-7-methoxyisoquinoline (400 mg, 1.68 mmol), bis(pinacolato)diboron (853 mg, 3.36 mmol), potassium acetate (989 mg, 10.1 mmol), PdCl₂(dppf).CH₂Cl₂ (137 mg, 0.168 mmol), and 1,4-dioxane (10 mL). The flask was vacuum/purged with $N_2$ (3×), then stirred at 100° C. for 2 h. The mixture was diluted with EtOAc and filtered through Celite® to provide (7-methoxyisoquinolin-6-yl)boronic acid, Intermediate 8, which was used without further purification. MS (M+1)=204.4

Preparation 9

Intermediate 9: Synthesis of 6-(7-methoxyquinolin-6-yl)-N-methyl-N-(2,2,6,6-tetramethylpiperidin-4-yl)pyridazin-3-amine

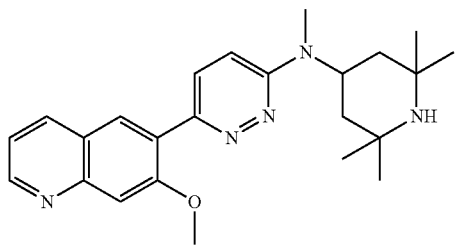 [SMILES: COc1cc2ncccc2cc1-c1ccc(N(C)C2CC(C)(C)NC(C)(C)C2)nn1]

6-Chloro-N-methyl-N-(2,2,6,6-tetramethylpiperidin-4-yl)pyridazin-3-amine, (Intermediate 1, 0.660 g, 2.334 mmol), was coupled with (7-methoxyquinolin-6-yl)boronic acid, (Intermediate 6, 0.771 g, 3.27 mmol), using GENERAL METHOD 1-2 for Suzuki coupling. The mixture was diluted with water, extracted with DCM (5×), and concentrated. The crude product was purified by silica gel chromatography as described in GENERAL METHOD 4-1 to provide 6-(7-methoxyquinolin-6-yl)-N-methyl-N-(2,2,6,6-tetramethylpiperidin-4-yl)pyridazin-3-amine, Intermediate 9 (0.857 g), as a yellow solid. MS (M+1)=406.2. $^1$H NMR (400 MHz, METHANOL-$d_4$) δ 8.80 (dd, J=4.3, 1.8 Hz, 1H), 8.37 (d, J=7.1 Hz, 1H), 8.16 (s, 1H), 7.84 (d, J=9.6 Hz, 1H), 7.53 (s, 1H), 7.44 (dd, J=8.1, 4.5 Hz, 1H), 7.15 (d, J=10.1 Hz, 1H), 5.25 (t, J=12.4 Hz, 1H), 4.03 (s, 3H), 3.01 (s, 3H), 1.66-1.74 (m, 2H), 1.51-1.63 (m, 2H), 1.37 (s, 6H), 1.23 (s, 6H).

Preparation 10

Intermediate 10: Synthesis of (2-amino-4-bromo-5-methoxyphenyl)methanol

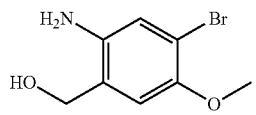

Step 1: 4-Bromo-5-fluoro-2-nitrobenzoic acid

According to the procedure of Beaulieu, P., et al, WO 2010037210, a mixture of 4-bromo-3-fluorobenzoic acid (10.0 g, 45.7 mmol) and concentrated sulfuric acid (75 mL) was stirred until a homogeneous solution formed (~15 min). Potassium nitrate (4.85 g, 47.9 mmol) was added portion-wise over 5 min and the reaction mixture was allowed to stir overnight. The mixture was poured into 500 mL crushed ice. After the ice melted, the mixture was extracted with 1:1 ethyl acetate/diethyl ether (3×). The extracts were washed with brine, dried over $MgSO_4$ and concentrated to provide 4-bromo-5-fluoro-2-nitrobenzoic acid as a dull yellow solid (12.14 g). $^1$H NMR (400 MHz, CHLOROFORM-d) δ ppm 8.18 (d, $J_{H-F}$=5.6 Hz, 1H), 7.61 (d, $J_{H-F}$=7.6 Hz, 1H).

Step 2: Methyl 4-bromo-5-fluoro-2-nitrobenzoate

Oxalyl chloride (4.18 ml, 47.7 mmol) was added drop-wise to a suspension of 4-bromo-5-fluoro-2-nitrobenzoic acid (11.46 g, 43.4 mmol) in DCM (175 mL) and catalytic DMF (100 uL). After 3 h the volatiles were removed via rotary evaporation. The remaining residue was redissolved into DCM (25 mL) and added portion-wise to rapidly stirring methanol (100 mL). The solvent was again removed and the residue concentrated from toluene (2×) to afford methyl 4-bromo-5-fluoro-2-nitrobenzoate as a yellow liquid (12.07 g) which was taken on without purification. $^1$H NMR (400 MHz, METHANOL-$d_4$) δ 8.39 (d, $J_{H-F}$=5.6 Hz, 1H), 7.71 (d, $J_{H-F}$=8.1 Hz, 1H), 3.91 (s, 3H).

Step 3: Methyl 4-bromo-5-methoxy-2-nitrobenzoate

Sodium methoxide (25 wt % solution in methanol, 10.9 mL, 47.7 mmol) was added to a solution of methyl 4-bromo-5-fluoro-2-nitrobenzoate (12.07 g, 43.4 mmol) in methanol (125 mL) and the solution was allowed to stir overnight during which time a thick precipitate formed. The mixture was diluted with water (400 mL) and the solids isolated by filtration, washing with water. The solids were dissolved into ethyl acetate, and the solution was washed with saturated $NaHCO_3$, brine, dried over $MgSO_4$ and concentrated to provide methyl 4-bromo-5-methoxy-2-nitrobenzoate (10.55 g) as an off-white solid. $^1$H NMR (400 MHz, CHLOROFORM-d) δ 8.27 (s, 1H), 7.07 (s, 1H), 4.03 (s, 3H), 3.95 (s, 3H).

Step 4: Methyl 2-amino-4-bromo-5-methoxybenzoate

Zinc powder (6.24 g, 95.4 mmol) was added portion-wise over 30 min (Caution! exotherm possible) to a solution of methyl 4-bromo-5-methoxy-2-nitrobenzoate (3.076 g, 10.60 mmol) in 3:1 DCM/AcOH (55 mL). The mixture was stirred at room temperature for three days. The mixture was filtered through Celite®, washing the filter pad with EtOAc, and concentrated. The crude product was redissolved into EtOAc, washed with saturated $NaHCO_3$, brine, dried over $MgSO_4$ and concentrated to a yellow oil. Concentration of the oil from toluene (2×) provided methyl 2-amino-4-bromo-5-methoxybenzoate as a yellow solid (2.737 g). MS (M+1)=262.1. $^1$H NMR (400 MHz, CHLOROFORM-d) δ 7.37 (s, 1H), 7.03 (s, 1H), 3.90 (s, 3H), 3.85 (s, 3H).

Step 5: (2-Amino-4-bromo-5-methoxyphenyl)methanol

To a solution of lithium aluminum hydride (1.0 M in THF, 11.5 mL, 11.5 mmol) in THF (52 mL) cooled to −78° C. was added 2-amino-4-bromo-5-methoxybenzoate (2.724 g, 10.47 mmol) as a solution in THF (30 mL) dropwise via syringe over 10 min. The cooling bath was allowed to warm to room temperature over 2 h. The reaction was quenched by slow addition of ethyl acetate. The solution was further diluted with ethyl acetate (100 mL) and stirred rapidly for two days with a saturated solution of Rochelle salt (potassium sodium tartrate). The layers were separated and the aqueous phase extracted with ethyl acetate (3×), and ether. The combined organics were dried over MgSO$_4$ and concentrated to provide (2-amino-4-bromo-5-methoxyphenyl)methanol, Intermediate 10 (2.358 g), as an orange solid which was used without further purification. MS (M+1)=232.1. $^1$H NMR (400 MHz, METHANOL-d$_4$) δ 6.97 (s, 1H), 6.88 (s, 1H), 4.53 (s, 2H), 3.78 (s, 3H).

Preparation 11

Intermediate 11: Synthesis of 4-chloro-2-methyl-6-(6-(methyl(2,2,6,6-tetramethylpiperidin-4-yl)amino)pyridazin-3-yl)quinolin-7-ol

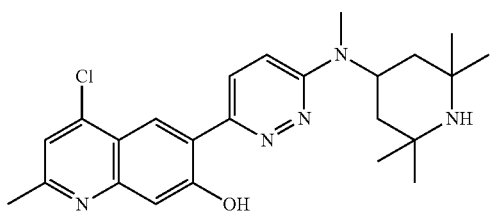

Step 1: (Z)-Ethyl 3-((4-bromo-3-methoxyphenyl)amino)but-2-enoate

To a mixture of 4-bromo-3-methoxyaniline (5.00 g, 24.8 mmol) and ethyl acetoacetate (3.1 mL, 25 mmol) was added 3 drops (~0.1 mL) of 1 M HCl. The mixture was stirred at room temperature overnight, then diluted with DCM, neutralized with aqueous NaHCO$_3$ and extracted with DCM. The extracts were dried over Na$_2$SO$_4$ and concentrated. The crude product was purified by silica gel column chromatography (0-20% EtOAc in heptane) to provide (Z)-ethyl 3-((4-bromo-3-methoxyphenyl)amino)but-2-enoate as a white solid (4.05 g). MS (M+1)=315.9. $^1$H NMR (CHLOROFORM-d) δ: 10.41 (br s, 1H), 7.46 (d, J=8.6 Hz, 1H), 6.61 (s, 1H), 6.56-6.60 (m, 1H), 4.73 (br s, 1H), 4.16 (q, J=7.1 Hz, 2H), 3.88 (s, 3H), 2.03 (s, 3H), 1.30 (t, J=7.1 Hz, 3H).

Step 2: 6-Bromo-7-methoxy-2-methylquinolin-4(1H)-one

A mixture of (Z)-ethyl 3-((4-bromo-3-methoxyphenyl)amino)but-2-enoate (4.0 g, 12 mmol) in diphenyl ether (12 mL) was heated at 190° C. for 1 hour. The brown reaction mixture was cooled to room temperature and diluted with diethyl ether. The solid was filtered, washed with ether and dried in a vaccum oven at 50° C. overnight to provide 6-bromo-7-methoxy-2-methylquinolin-4(1H)-one as a light brown solid (2.64 g). MS (M+1)=270.1. $^1$H NMR (DMSO-d$_6$) δ: 11.54 (br s, 1H), 8.11 (s, 1H), 6.99 (s, 1H), 5.86 (s, 1H), 3.93 (s, 3H), 2.30 (s, 3H).

Step 3: (7-Methoxy-2-methyl-4-oxo-1,4-dihydroquinolin-6-yl)boronic acid and 7-Methoxy-2-methyl-6-(4,4,5,5-tetramethyl-1,3,2-dioxaborolan-2-yl)quinolin-4(1H)-one To a mixture of 6-bromo-7-methoxy-2-methylquinolin-4(1H)-one (1.00 g, 3.73 mmol), bis(pinacolato) diboron (2.84 g, 11.2 mmol), dppf (207 mg, 0.37 mmol), PdCl$_2$(dppf).CH$_2$Cl$_2$ (304 mg, 0.37 mmol) and KOAc (2.20 g, 22.4 mmol) was added 1,4-dioxane (15 mL) and DMF (3.0 mL). The reaction mixture was evacuated and backfilled with nitrogen (4×), then heated at 90° C. overnight. The reaction mixture was cooled to room temperature, then filtered through Celite® washing with EtOAc, then 10% MeOH in DCM, and concentrated in vacuo to provide the crude product. A mixture of (7-methoxy-2-methyl-4-oxo-1,4-dihydroquinolin-6-yl)boronic acid (262 mg) and 7-methoxy-2-methyl-6-(4,4,5,5-tetramethyl-1,3,2-dioxaborolan-2-yl)quinolin-4(1H)-one (269 mg) was obtained as light brown solid after silica gel chromatography (0-15% MeOH in DCM). (7-Methoxy-2-methyl-4-oxo-1,4-dihydroquinolin-6-yl)boronic acid: MS (M+1)=234.1. $^1$H NMR (DMSO-d$_6$) δ 11.39 (br s, 1H), 8.28 (s, 1H), 7.72 (s, 2H), 6.76-6.88 (m, 1H), 5.76 (s, 1H), 3.86 (s, 3H), 2.29 (s, 3H). 7-Methoxy-2-methyl-6-(4,4,5,5-tetramethyl-1,3,2-dioxaborolan-2-yl)quinolin-4(1H)-one: MS (M+1)=316.0. $^1$H NMR (CHLOROFORM-d) δ 12.03 (br s, 1H), 8.68 (s, 1H), 6.98 (s, 1H), 6.10 (s, 1H), 3.73 (s, 3H), 2.42 (s, 3H), 1.28 (s, 12H).

Step 4: 7-Methoxy-2-methyl-6-(6-(methyl(2,2,6,6-tetramethylpiperidin-4-yl)amino)pyridazin-3-yl) quinolin-4(1H)-one (7-Methoxy-2-methyl-4-oxo-1,4-dihydroquinolin-6-yl)boronic acid (396 mg, 1.69 mmol), 6-chloro-N-methyl-N-(2,2,6,6-tetramethylpiperidin-4-yl)pyridazin-3-amine, (Intermediate 1, 400 mg, 1.41 mmol), Pd(PPh$_3$)$_4$(123 mg, 0.11 mmol) and Na$_2$CO$_3$ (375 mg, 3.54 mmol) were added to a microwave vial followed by addition of 4:1 1,4-dioxane/water (7.5 mL). The reaction mixture was sealed, then evacuated and back-filled with nitrogen (4×), and heated via microwave irradiation at 110° C. for 1 hour. The mixture was filtered through Celite® washing with EtOAc. The resulting filtrate was concentrated and acidified to pH 3 by 4 M HCl in 1,4-dioxane. SCX purification (GENERAL METHOD 3-1) followed by silica gel chromatography (0-30% MeOH in DCM) provided 7-methoxy-2-methyl-6-(6-(methyl(2,2,6,6-tetramethylpiperidin-4-yl)amino)-pyridazin-3-yl)quinolin-4(1H)-one (475 mg) as a dark purple solid. MS (M+1)=436.1. $^1$H NMR (METHANOL-d$_4$) δ 8.37 (s, 1H), 7.70 (d, J=9.6 Hz, 1H), 7.12 (d, J=9.6 Hz, 1H), 7.02 (s, 1H), 6.13 (s, 1H), 5.21 (t, J=12.1 Hz, 1H), 3.94 (s, 3H), 3.00 (s, 3H), 2.45 (s, 3H), 1.65-1.73 (m, 2H), 1.51-1.61 (m, 2H), 1.37 (s, 6H), 1.22 (s, 6H).

Step 5: 6-(4-Chloro-7-methoxy-2-methylquinolin-6-yl)-N-methyl-N-(2,2,6,6-tetramethylpiperidin-4-yl)pyridazin-3-amine A mixture of 7-methoxy-2-methyl-6-(6-(methyl(2,2,6,6-tetramethylpiperidin-4-yl)amino)pyridazin-3-yl)quinolin-4 (1H)-one (495 mg, 1.14 mmol) and phosphorous oxychloride (2.5 mL, 27 mmol) was sealed and heated via microwave irradiation at 110° C. for 1 hour. The reaction mixture was poured into 50 mL crushed ice then basified by slow addition of solid K$_2$CO$_3$. The mixture was extracted with DCM (3×). The combined organic extracts were dried over Na$_2$SO$_4$ and concentrated to afford the crude product. SCX purification (GENERAL METHOD 3-1, 5 g SiliaBond Propylsulfonic Acid® cartridge) provided 6-(4-chloro-7-methoxy-2-methylquinolin-6-yl)-N-methyl-N-(2,2,6,6-tetramethylpiperidin-4-yl)pyridazin-3-amine as a yellow solid (350 mg). MS (M+1)=454.0. $^1$H NMR (METHANOL-d$_4$) δ 8.60 (s, 1H), 8.12 (d, J=10.1 Hz, 1H), 7.78 (s, 1H), 7.63 (s, 1H), 7.53 (d, J=9.6 Hz, 1H), 5.36 (t, J=12.1 Hz, 1H), 4.12 (s, 3H), 3.12 (s, 3H), 2.85 (s, 3H), 1.95-2.14 (m, 4H), 1.66 (s, 6H), 1.57 (s, 6H).

Step 6: 4-Chloro-2-methyl-6-(6-(methyl(2,2,6,6-tetramethylpiperidin-4-yl)amino)pyridazin-3-yl)quinolin-7-ol 6-(4-Chloro-7-methoxy-2-methylquinolin-6-yl)-N-methyl-N-(2,2,6,6-tetramethylpiperidin-4-yl)pyridazin-3-amine (195 mg, 0.43 mmol) was subjected to methoxy deprotection conditions as described in GENERAL METHOD 2-3 using boron tribromide (1 M solution in DCM, 2.49 mL, 2.49 mmol). SCX purification (GENERAL METHOD 3-1, 2 g SiliaBond Propylsulfonic Acid® cartridge) provided 4-chloro-2-methyl-6-(6-(methyl(2,2,6,6-tetramethylpiperidin-4-yl)amino)pyridazin-3-yl)quinolin-7-ol, Intermediate 11, as a light orange solid (172 mg, 93% pure) which was used in subsequent reactions without further purification. LC/MS Rt=0.50 min. MS (M+1)=440.2. $^1$H NMR (METHANOL-$d_4$) δ 8.54 (s, 1H), 8.26 (d, J=9.6 Hz, 1H), 7.39 (s, 1H), 7.38 (s, 1H), 7.34 (d, J=9.6 Hz, 1H), 5.23 (t, J=12.0 Hz, 1H), 3.04 (s, 3H), 2.65 (s, 3H), 1.71-1.80 (m, 2H), 1.59-1.71 (m, 2H), 1.44 (s, 6H), 1.29 (s, 6H).

Preparation 12

Intermediate 12: Synthesis of 4-chloro-6-(6-(methyl(2,2,6,6-tetramethylpiperidin-4-yl)amino)pyridazin-3-yl)quinolin-7-ol

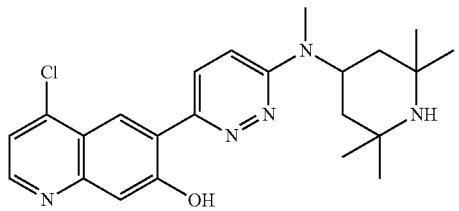 [SMILES: CN(c1ccc(-c2cc3c(Cl)ccnc3cc2O)nn1)C1CC(C)(C)NC(C)(C)C1]

Step 1: 5-(((4-Bromo-3-methoxyphenyl)amino)methylene)-2,2-dimethyl-1,3-dioxane-4,6-dione To a mixture of 4-bromo-3-methoxyaniline (5.10 g, 25.2 mmol) and 2,2-dimethyl-1,3-dioxane-4,6-dione (Meldrum's acid, 4.37 g, 30.3 mmol) in EtOH (30 mL) was added triethyl orthoformate (5.0 mL, 30 mmol). The reaction mixture was refluxed overnight. The mixture was cooled to room temperature and the solid was filtered, washed with EtOAc, and dried to provide 5-(((4-bromo-3-methoxyphenyl)amino)methylene)-2,2-dimethyl-1,3-dioxane-4,6-dione as a yellow solid (2.93 g). MS (M−1)=355.8. $^1$H NMR (CHLOROFORM-d) δ 11.25 (d, J=14.1 Hz, 1H), 8.62 (d, J=14.1 Hz, 1H), 7.59 (d, J=8.1 Hz, 1H), 6.72-6.78 (m, 2H), 3.96 (s, 3H), 1.77 (s, 6H).

Step 2: 6-Bromo-7-methoxyquinolin-4(1H)-one

A mixture of 5-(((4-bromo-3-methoxyphenyl)amino)methylene)-2,2-dimethyl-1,3-dioxane-4,6-dione (2.60 g, 7.30 mmol) in diphenyl ether (15 mL) was heated at 185° C. for 40 minutes. The brown mixture was cooled to room temperature and diluted with diethyl ether. The solid was filtered, washed with diethyl ether and dried in a vaccum oven at 50° C. overnight to provide 6-bromo-7-methoxyquinolin-4(1H)-one as a light brown solid (1.56 g). MS (M+1)=256.1. $^1$H NMR (DMSO-$d_6$) δ 11.67 (br s, 1H), 8.17 (s, 1H), 7.86 (dd, J=7.6, 5.6 Hz, 1H), 7.05 (s, 1H), 5.99 (d, J=7.6 Hz, 1H), 3.94 (s, 3H).

Step 3: 7-Methoxy-6-(4,4,5,5-tetramethyl-1,3,2-dioxaborolan-2-yl)quinolin-4(1H)-one and, (7-methoxy-4-oxo-1,4-dihydroquinolin-6-yl)boronic acid To a mixture of 6-bromo-7-methoxyquinolin-4(1H)-one (0.92 g, 2.72 mmol), dppf (151 mg, 0.272 mmol), PdCl$_2$(dppf).CH$_2$Cl$_2$ (222 mg, 0.272 mmol) and KOAc (1.33 g, 13.6 mmol) was added 1,4-dioxane (7 mL) and DMF (0.7 mL). The reaction mixture was evacuated and backfilled with nitrogen (4×), then heated at 80° C. for 0.5 hours. Bis(pinacolato) diboron (1.72 g, 6.79 mmol) was then added, and the mixture was heated at 90° C. overnight. The reaction mixture was cooled to room temperature, filtered through Celite®, washed with 9:1 MeOH/DCM, then 1:1 MeOH/DCM. The filtrates were concentrated in vacuo. 7-Methoxy-6-(4,4,5,5-tetramethyl-1,3,2-dioxaborolan-2-yl)quinolin-4(1H)-one (380 mg) and (7-methoxy-4-oxo-1,4-dihydroquinolin-6-yl)boronic acid (270 mg, ~50% pure) were obtained after silica gel chromatography (0-30% MeOH in DCM). MS (M+1)=302.0 and 220.2, respectively.

Step 4: 7-Methoxy-6-(6-(methyl(2,2,6,6-tetramethylpiperidin-4-yl)amino)pyridazin-3-yl)quinolin-4(1H)-one 7-Methoxy-6-(4,4,5,5-tetramethyl-1,3,2-dioxaborolan-2-yl)quinolin-4(1H)-one (380 mg, 1.69 mmol), 6-chloro-N-methyl-N-(2,2,6,6-tetramethylpiperidin-4-yl)pyridazin-3-amine, (Intermediate 1, 250 mg, 0.88 mmol), Pd(PPh$_3$)$_4$ (51 mg, 0.044 mmol), aqueous Na$_2$CO$_3$ (2.5 M, 1.1 mL, 2.2 mmol) and 1,4-dioxane (4 mL) were combined in a microwave vessel. The vessel was evacuated and back-filled with nitrogen (4×), and heated via microwave irradiation at 110° C. for 1.5 hour. The mixture was cooled to room temperature, diluted with MeOH (3 mL), filtered through Celite®, and washed with 9:1 MeOH/DCM and then with 1:1 MeOH/DCM. The resulting filtrate was concentrated and acidified to pH 3 with 1 M HCl in diethyl ether. SCX purification (GENERAL METHOD 3-1) followed by silica gel chromatography (0-20% 2 M NH$_3$/MeOH in DCM) provided 7-methoxy-6-(6-(methyl(2,2,6,6-tetramethylpiperidin-4-yl)amino)pyridazin-3-yl)quinolin-4(1H)-one (370 mg) as a light brown solid. MS (M+1)=422.1. $^1$H NMR (METHANOL-$d_4$) δ 8.45 (s, 1H), 7.91 (d, J=7.6 Hz, 1H), 7.76 (d, J=9.6 Hz, 1H), 7.16 (d, J=9.6 Hz, 1H), 7.10 (s, 1H), 6.28 (d, J=7.1 Hz, 1H), 5.39 (m, 1H), 3.96 (s, 3H), 3.01 (s, 3H), 1.78-1.90 (m, 4H), 1.54 (s, 6H), 1.41 (s, 6H).

Step 5: 6-(4-Chloro-7-methoxyquinolin-6-yl)-N-methyl-N-(2,2,6,6-tetramethylpiperidin-4-yl)pyridazin-3-amine A mixture of 7-methoxy-6-(6-(methyl(2,2,6,6-tetramethylpiperidin-4-yl)amino)pyridazin-3-yl)quinolin-4(1H)-one (59 mg, 0.14 mmol), phosphorous oxychloride (0.65 mL, 7.0 mmol) and acetonitrile (0.60 mL) was sealed and heated via microwave irradiation at 100° C. for 1 hour. The reaction mixture was poured into crushed ice and was basified by slow addition of solid K$_2$CO$_3$. The mixture was extracted with DCM (3×). The combined organic extracts were dried over Na$_2$SO$_4$ and concentrated to afford the crude product. SCX purification (GENERAL METHOD 3-1, 1 g SiliaBond Propylsulfonic Acid® cartridge) followed by silica gel chromatography (0-20% MeOH in DCM) provided 6-(4-chloro-7-methoxyquinolin-6-yl)-N-methyl-N-(2,2,6,6-tetramethylpiperidin-4-yl)pyridazin-3-amine as a brown solid (70 mg). MS (M+1)=440.1

Step 6: 4-chloro-6-(6-(methyl(2,2,6,6-tetramethylpiperidin-4-yl)amino)pyridazin-3-yl)quinolin-7-ol 6-(4-Chloro-7-methoxyquinolin-6-yl)-N-methyl-N-(2,2,6,6-tetramethylpiperidin-4-yl)pyridazin-3-amine (62 mg, 0.14 mmol) was subjected to methoxy deprotection conditions as described in GENERAL METHOD 2-3 using boron tribromide (1 M solution in DCM, 0.70 mL, 0.70 mmol). SCX purification (GENERAL METHOD 3-1, 1 g SiliaBond Propylsulfonic Acid® cartridge) followed by silica gel chromatography (0-20% 1.5 M NH$_3$/MeOH in DCM) provided 4-chloro-6-(6-(methyl(2,2,6,6-tetramethylpiperidin-4-yl)amino)pyridazin-3-yl)quinolin-7-ol, Intermediate 12, as a white solid (21 mg). LC/MS Rt=0.50 min. MS (M+1) =426.2. $^1$H NMR (METHANOL-d$_4$) δ 8.63 (d, J=5.1 Hz, 1H), 8.60 (s, 1H), 8.28 (d, J=9.6 Hz, 1H), 7.46 (s, 1H), 7.46 (d, J=4.0 Hz, 1H), 7.34 (d, J=9.6 Hz, 1H), 5.22 (t, J=11.9 Hz, 1H), 3.06 (s, 3H), 1.69-1.79 (m, 2H), 1.57-1.68 (m, 2H), 1.43 (s, 6H), 1.27 (s, 6H).

Preparation 13

Intermediate 13: Synthesis of 4-chloro-7-(6-(methyl (2,2,6,6-tetramethylpiperidin-4-yl)amino)pyridazin-3-yl)quinolin-6-ol

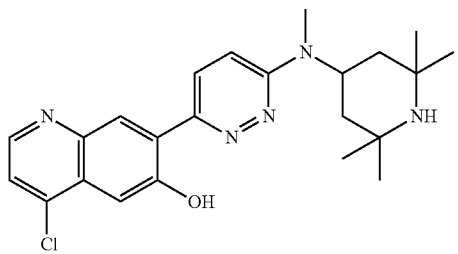 [SMILES: CN(c1ccc(-c2cc3nccc(Cl)c3cc2O)nn1)C1CC(C)(C)NC(C)(C)C1]

Step 1: 5-(((3-Chloro-4-methoxyphenyl)amino) methylene)-2,2-dimethyl-1,3-dioxane-4,6-dione Triethoxymethane (11 mL, 64 mmol) and 2,2-dimethyl-1,3-dioxane-4,6-dione (Meldrum's acid, 10.7 g, 74.2 mmol) were added to 3-chloro-4-methoxyaniline (10.0 g, 63.5 mmol) in ethanol (60 mL). The mixture was stirred at reflux overnight. An additional portion of triethoxymethane (2.1 mL, 13 mmol) and 2,2-dimethyl-1,3-dioxane-4,6-dione (2.74 g, 19.0 mmol) were added to the reaction and the mixture was stirred at reflux for 3 h. The mixture was cooled to room temperature and the precipitate was collected by filtration and washed with ethanol to provide 5-(((3-chloro-4-methoxyphenyl)amino)methylene)-2,2-dimethyl-1,3-dioxane-4,6-dione as a beige solid (18.5 g). MS (M−1)=310.2. $^1$H NMR (400 MHz, DMSO-d$_6$) δ 11.20 (d, J=14.4 Hz, 1H), 8.47 (d, J=14.5 Hz, 1H), 7.79 (d, J=2.8 Hz, 1H), 7.54 (dd, J=8.9, 2.8 Hz, 1H), 7.19 (d, J=9.0 Hz, 1H), 3.87 (s, 3H), 1.67 (s, 6H).

Step 2: 7-Chloro-6-methoxyquinolin-4(1H)-one and 5-chloro-6-methoxyquinolin-4(1H)-one 5-(((3-chloro-4-methoxyphenyl)amino)methylene)-2,2-dimethyl-1,3-dioxane-4,6-dione (12.9 g, 41.4 mmol) in diphenyl ether (100 mL) was heated at 190° C. for 2 hour. The reaction mixture was cooled to room temperature and diluted with diethyl ether (100 mL). The solid was filtered and washed with diethyl ether to provide a mixture of 7-chloro-6-methoxyquinolin-4(1H)-one and 5-chloro-6-methoxyquinolin-4(1H)-one (7.54 g) in a ratio of 4:1 (determined by $^1$H NMR). 7-Chloro-6-methoxyquinolin-4(1H)-one: MS (M+1)=210.1. $^1$H NMR (400 MHz, METHANOL-d$_4$) δ 7.95 (d, J=7.2 Hz, 1H), 7.77 (s, 1H), 7.69 (s, 1H), 6.33 (d, J=7.3 Hz, 1H), 4.01 (s, 3H). 5-Chloro-6-methoxyquinolin-4(1H)-one: MS (M+1)=210.1. $^1$H NMR (400 MHz, METHANOL-d$_4$) δ 7.81 (d, J=7.2 Hz, 1H), 7.57 (d, J=9.2 Hz, 1H), 7.52 (d, J=9.2 Hz, 1H), 6.22 (d, J=7.2 Hz, 1H), 3.97 (s, 3H).

Step 3: 6-Methoxy-7-(6-(methyl(2,2,6,6-tetramethylpiperidin-4-yl)amino)pyridazin-3-yl)quinolin-4 (1H)-one A mixture of 7-chloro-6-methoxyquinolin-4(1H)-one and 5-chloro-6-methoxyquinolin-4(1H)-one (1.42 g, 6.67 mmol), tetrahydroxydiboron (1.82 g, 20.3 mmol), 2$^{nd}$ Generation XPhos Precatalyst (0.27 g, 0.34 mmol), XPhos (0.32 g, 0.68 mmol) and potassium acetate (1.99 g, 20.3 mmol) were stirred in ethanol (70 mL) at 80° C. for 2 h. An aqueous solution of K$_2$CO$_3$ (1.8 M, 15 mL, 27 mmol) was added to the reaction at room temperature followed by Intermediate 1 (1.92 g, 6.77 mmol). The mixture was stirred at 80° C. overnight. The reaction mixture was cooled to room temperature, filtered and concentrated in vacuo. The residue was acidified to pH 1 using 1 M HCl (60 mL) and filtered. The filtrate was washed with DCM (2×), then basified to pH 11 with a saturated solution of K$_2$CO$_3$. The aqueous phase was extracted with 9:1 DCM/MeOH (3×). The combined organic phases were dried over anhydrous Na$_2$SO$_4$, filtered and concentrated under reduced pressure. The crude material was purified by silica gel chromatography (2-15% 7 M ammonia in MeOH gradient, in DCM) to afford 6-methoxy-7-(6-(methyl(2,2,6,6-tetramethylpiperidin-4-yl)amino) pyridazin-3-yl)quinolin-4(1H)-one (0.45 g) as a brown solid. MS (M+1)=422.4. $^1$H NMR (400 MHz, METHANOL-d$_4$) δ 7.99 (d, J=7.2 Hz, 1H), 7.95 (s, 1H), 7.93 (d, J=9.7 Hz, 1H), 7.83 (s, 1H), 7.16 (d, J=9.7 Hz, 1H), 6.38 (d, J=7.2 Hz, 1H), 5.21-5.33 (m, 1H), 4.00 (s, 3H), 3.03 (s, 3H), 1.72 (dd, J=12.7, 3.5 Hz, 2H), 1.60 (t, J=12.4 Hz, 2H), 1.40 (s, 6H), 1.25 (s, 6H).

Step 4: 6-(4-Chloro-6-methoxyquinolin-7-yl)-N-methyl-N-(2,2,6,6-tetramethylpiperidin-4-yl) pyridazin-3-amine 6-Methoxy-7-(6-(methyl(2,2,6,6-tetramethylpiperidin-4-yl)amino)pyridazin-3-yl)quinolin-4(1H)-one (0.22 g, 0.52 mmol) in phosphorous oxychloride (1.5 mL) was heated via microwave at 100° C. for 2 h. The reaction mixture was poured into crushed ice and was basified by slow addition of a saturated solution of K$_2$CO$_3$. The mixture was extracted with DCM (3×). The combined organic extracts were dried over Na$_2$SO$_4$ and concentrated under reduced pressure. The crude material was purified by silica gel chromatography (2-15% 7 M ammonia in MeOH gradient, in DCM) to afford 6-(4-chloro-6-methoxyquinolin-7-yl)-N-methyl-N-(2,2,6,6- tetramethylpiperidin-4-yl)pyridazin-3-amine (0.20 g) as a brown solid. MS (M+1)=440.5. $^1$H NMR (400 MHz, METHANOL-$d_4$) δ 8.66 (d, J=4.8 Hz, 1H), 8.33 (s, 1H), 7.87 (d, J=9.6 Hz, 1H), 7.68 (d, J=4.9 Hz, 1H), 7.66 (s, 1H), 7.16 (d, J=9.7 Hz, 1H), 5.26 (t, J=12.3 Hz, 1H), 4.06 (s, 3H), 3.03 (s, 3H), 1.72 (dd, J=12.6, 3.6 Hz, 2H), 1.59 (t, J=12.4 Hz, 2H), 1.39 (s, 6H), 1.24 (s, 6H).

Step 5: 4-Chloro-7-(6-(methyl(2,2,6,6-tetramethylpiperidin-4-yl)amino)pyridazin-3-yl)quinolin-6-ol A solution of $BBr_3$ in DCM (1 M, 0.7 mL, 0.7 mmol) was added to 6-(4-chloro-6-methoxyquinolin-7-yl)-N-methyl-N-(2,2,6,6-tetramethylpiperidin-4-yl)pyridazin-3-amine (0.10 g, 0.24 mmol) in DCM (2.2 mL) and the reaction was stirred at room temperature overnight. MeOH was added to the reaction and the solvent was concentrated under reduced pressure. The crude material was solubilized with 2 M ammonia in MeOH and DMSO and purified via preparative reverse-phase HPLC (15 to 45% acetonitrile in water, 5 mM ammonium hydroxide modifier) to afford 4-chloro-7-(6-(methyl(2,2,6,6-tetramethylpiperidin-4-yl)amino)pyridazin-3-yl)quinolin-6-ol (9 mg). LC/MS Rt=0.56 min. MS (M+1) =426.3. $^1$H NMR (400 MHz, METHANOL-$d_4$) δ 8.60 (d, J=4.8 Hz, 1H), 8.47 (s, 1H), 8.33 (d, J=9.8 Hz, 1H), 7.63 (s, 1H), 7.61 (d, J=4.8 Hz, 1H), 7.39 (d, J=9.9 Hz, 1H), 5.17-5.47 (m, 1H), 1.78 (dd, J=12.9, 3.7 Hz, 2H), 1.67 (t, J=12.4 Hz, 2H), 1.46 (s, 6H), 1.30 (s, 6H).

General Methods

General Method 1-1

Representative Procedure for Suzuki Coupling

A mixture of a chloropyridazine intermediate, such as Intermediate 1 (1.0 equivalents), potassium triphosphate (5.0 equivalents), and $2^{nd}$ generation XPhos precatalyst (0.07 equivalents), in DMF (0.3 M) is degassed via vacuum/$N_2$ purge (3×), and heated at 50° C. Next, a 50 or 100 mg/mL solution of a boronic acid, such as Intermediate 7 or Intermediate 8, in DMF is added in 1 mL aliquots every 2-3 h until Intermediate 1 is consumed. The reaction is cooled to room temperature, filtered through Celite® washing with EtOAc, and partially concentrated. The crude product is purified by SCX (GENERAL METHOD 3-1) and silica gel chromatography.

General Method 1-2

Representative Procedure for Suzuki Coupling

A mixture of a chloropyridazine intermediate, such as Intermediate 1 (1.0 equivalent), boronic acid reagent (1.5-2 equivalents), and $Na_2CO_3$ (3 equivalents) in 3:1 DME/water (0.12 M) in a microwave vial is degassed with a stream of dry nitrogen. $Pd(PPh_3)_4$ (0.1 equivalents) is added to the reaction mixture and the vial is sealed and heated in a Biotage® Initiator microwave reactor at 140° C. for 30 min. The mixture is diluted with water and extracted with DCM (4×). The organic extracts are dried over $MgSO_4$, filtered, and concentrated to afford the crude product. The crude product is purified via silica chromatography as described in GENERAL METHOD 4-1.

General Method 2-1

Representative Procedure for Methoxy Deprotection Using Pyridine HCl

The methoxy substrate (1 equivalent) and pyridine hydrochloride (20-30 equivalents) are heated at 160-190° C. for 15-120 min in a Biotage® Initiator microwave reactor. The reaction mixture is solubilized with MeOH/DMSO and purified via preparative reverse-phase HPLC (15 to 45% acetonitrile in water, 5 mM ammonium hydroxide modifier).

General Method 2-2

Representative Procedure for Methoxy Deprotection Using Pyridine HCl

The methoxy substrate (1 equivalent) and pyridine hydrochloride (20-25 equivalents) are heated at 160-190° C. for 15-120 min in a Biotage® Initiator microwave reactor. The reaction mixture is solubilized with MeOH and the solution loaded onto a mixture of solid sodium bicarbonate (30 equivalents) and silica gel (~6 g/mmol methoxy substrate), and concentrated to dryness. Column chromatography as described in GENERAL METHOD 4-1 provided the product.

General Method 2-3

Representative Procedure for Methoxy Deprotection Using Boron Tribromide ($BBr_3$)

The methoxy substrate (1.0 equivalent) is dissolved in DCM (0.03 M) and the solution cooled to 0° C. Boron tribromide (1 M solution in DCM, 3-10 equivalents) is added dropwise. The crude reaction mixture is stirred at room temperature overnight. If the reaction has not gone to completion, it can be heated at reflux for 4-24 h. The reaction mixture is diluted with DCM and water. The organic layer is diluted with EtOAc and washed with saturated $NaHCO_3$ (2×), water, brine and dried over $Na_2SO_4$ or $MgSO_4$. The crude product is purified via preparative reverse-phase HPLC, silica gel chromatography (GENERAL METHODS 4-1), or by recrystallization.

General Method 2-4

Representative Procedure for Methoxy Deprotection Using Thiophenol

Thiophenol (5.0 equivalents) and potassium carbonate (1.0 equivalent) are added to the methoxy substrate (1.0 equivalent) in NMP (0.2 M) and the reaction is heated at 190° C. for 15-30 min in a Biotage® Initiator microwave reactor. The reaction mixture is purified by catch and release as described in GENERAL METHOD 3-1, and the product is purified by reverse-phase preparative HPLC or silica gel chromatography.

General Method 3-1

Representative Procedure for Catch-and-Release (SCX) Purification/Free Basing

The crude product is dissolved in MeOH and loaded onto a SiliaBond Propylsulfonic Acid® cartridge (Silicycle, Inc.) or a Bond Elut SCX cartridge (Agilent Technologies, Inc.) preconditioned with MeOH or acetonitrile. The cartridge is flushed with MeOH or acetonitrile, and the product released by elution with 2-7 N ammonia in MeOH. Concentration of the eluent provides the purified product.

General Method 4-1

Representative Procedure for Silica Gel Chromatography Purification

The crude product (either neat, dissolved into DCM, or loaded onto a solid support such as silica gel or Celite®) is subjected to normal phase flash column chromatography using RediSep® Rf pre-packed silica gel cartridges (Teledyne Isco, Inc.) with an elution gradient of 1-20% ammonia in MeOH (1.5 N, or 3.5 N concentration), in DCM.

General Method 5-1

Representative Procedure for Iridium Catalyzed Borylation

To a degassed mixture of the substrate (1.0 equivalent), bis(pinacolato)diboron (1.50 equivalents) and 4,4'-di-tert-butyl bipyridine (0.1 equivalents) in 1,4-dioxane (0.3 M) is added [Ir(COD)(OMe)]$_2$ (0.05 equivalents). The mixture was heated at 85° C. overnight. The resulting boronic acid solution can be used directly in the subsequent reaction, or optionally the boronic acid is isolated and purified. The pinacol boronate ester is typically not observed as a reaction product.

General Method 6-1

Representative Procedure for Metal Scavenging

Residual palladium, and certain other metal contaminants, can be scavenged from reaction products by dissolution in an appropriate solvent (e.g., THF, DCM, or acetonitrile) and stirring with SiliaMetS® Dimercaptotriazine (DMT) resin (Silicycle, Inc.) for 4-24 h using 3-5 equivalents relative to the amount of the palladium catalyst (or other metal) used. Filtration, and washing of the resin, followed by concentration provides the purified product.

General Method 7-1

Representative Procedure for Boronate Ester Formation.

Bis(pinacolato) diboron (2.0 equivalents), KOAc (6.0 equivalents), and PdCl$_2$(dppf).CH$_2$Cl$_2$ (0.1 equivalents) were added to flask containing an aryl bromide (1.0 equivalent). DMSO (0.2 M) is added, and the reaction vessel is evacuated then filled with N$_2$ (2×), and heated at 100° C. overnight. The reaction mixture is cooled to room temperature, then filtered through Celite® (pre-packed filter funnel) using EtOAc, and concentrated in vacuo to provide the crude product, which is purified by silica gel chromatography (EtOAc/heptane).

EXAMPLES

The following compounds were prepared from chloro-pyridazine Intermediate 1, Intermediate 4, or Intermediate 5, and 7-methoxyquinolin-6-yl)boronic acid (Intermediate 6), according to GENERAL METHOD 1-2, followed by methoxy deprotection and purification as outlined in GENERAL METHOD 2-2. The hydrochloride salt was formed by dissolution of the free base in 1 M aqueous HCl (3 equivalents) followed by lyophilization.

| Example | Compound | MS (M + 1), LC/MS Rt | $^1$H NMR 400 MHz |
|---|---|---|---|
| 1-1 | 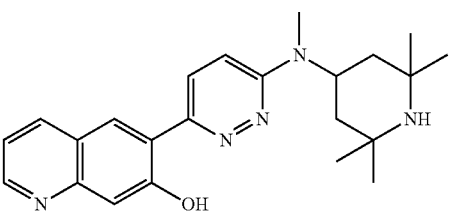 [SMILES: CN(c1ccc(-c2cc3cccnc3cc2O)nn1)C1CC(C)(C)NC(C)(C)C1]<br>6-(6-(Methyl(2,2,6,6-tetramethylpiperidin-4-yl)amino)pyridazin-3-yl)quinolin-7-ol | 392.3<br>0.40 min | METHANOL-d$_4$ δ 8.72 (dd, J = 4.5, 1.5 Hz, 1H), 8.39 (s, 1H), 8.33 (d, J = 8.1 Hz, 1H), 8.29 (d, J = 10.1 Hz, 1H), 7.43 (s, 1H), 7.31-7.38 (m, 2H), 5.16 (t, J = 11.6 Hz, 1H), 3.04 (s, 3H), 1.67-1.75 (m, 2H), 1.53-1.65 (m, 2H), 1.40 (s, 6H), 1.24 (s, 6H) |
| 1-2 | 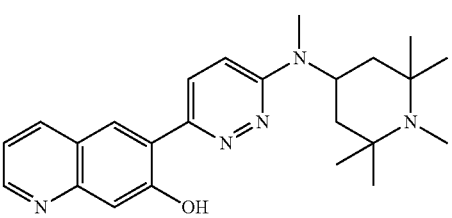 [SMILES: CN(c1ccc(-c2cc3cccnc3cc2O)nn1)C1CC(C)(C)N(C)C(C)(C)C1]<br>6-(6-(Methyl(1,2,2,6,6-entamethylpiperidin-4-yl)amino)pyridazin-3-yl)quinolin-7-ol hydrochloride salt | 406.3<br>0.39 min | METHANOL-d$_4$ δ 9.18 (d, J = 8.6 Hz, 1H), 9.09 (dd, J = 5.6, 1.5 Hz, 1H), 8.77 (s, 1H), 8.51 (d, J = 10.1 Hz, 1H), 7.96 (d, J = 10.1 Hz, 1H), 7.92 (dd, J = 8.3, 5.8 Hz, 1H), 7.67 (s, 1H), 5.05-5.17 (m, 1H), 3.25 (s, 3H), 2.93 (s, 3H), 2.40 (t, J = 13.1 Hz, 2H), 2.16 (dd, J = 13.9, 3.3 Hz, 2H), 1.66 (s, 6H), 1.64 (s, 6H) |

| Example | Compound | MS (M + 1), LC/MS Rt | ¹H NMR 400 MHz |
|---|---|---|---|
| 1-3 | 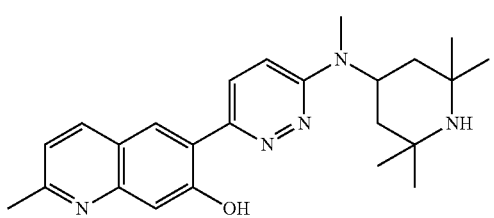<br>6-(6-((3aR,6aS)-5-Methylhexahydropyrrolo[3,4-c]pyrrol-2(1H)-yl)pyridazin-3-yl)quinolin-7-ol | 348.0<br>0.33 min | METHANOL-$d_4$ δ 8.73 (dd, J = 4.5, 1.5 Hz, 1H), 8.42 (s, 1H), 8.25-8.37 (m, 2H), 7.43 (s, 1H), 7.35 (dd, J = 8.3, 4.3 Hz, 1H), 7.25 (d, J = 9.6 Hz, 1H), 3.78 (dd, J = 11.1, 8.1 Hz, 2H), 3.59 (dd, J = 11.1, 3.0 Hz, 2H), 3.13 (d, J = 3.0 Hz, 2H), 2.82 (dd, J = 9.6, 7.1 Hz, 2H), 2.60 (dd, J = 10.1, 3.5 Hz, 2H), 2.37 (s, 3H) |

Example 2-1: Synthesis of 2-methyl-6-(6-(methyl(2,2,6,6-tetramethylpiperidin-4-yl)amino)pyridazin-3-yl)quinolin-7-ol

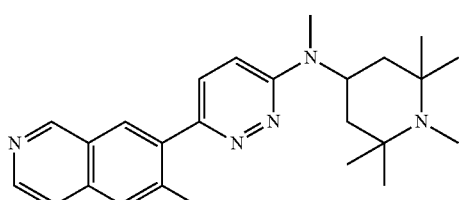

To a solution of Intermediate 11 (22 mg, 0.050 mmol) in MeOH (2 mL) under a nitrogen atmosphere was added palladium on carbon (10 wt %, 5.9 mg, 0.005 mmol) and a drop of concentrated HCl. The mixture was evacuated and back-filled with hydrogen (4×), and stirred rapidly overnight. The mixture was filtered through Celite®, rinsed with MeOH and concentrated. SCX purification (GENERAL METHOD 3-1, 1 g SiliaBond Propylsulfonic Acid® cartridge) and preparative reverse-phase HPLC purification provided 2-methyl-6-(6-(methyl(2,2,6,6-tetramethylpiperidin-4-yl)amino)pyridazin-3-yl)quinolin-7-ol as a light yellow solid (11.5 mg). LC/MS Rt=0.39 min. MS (M+1)=406.0. ¹H NMR (400 MHz, METHANOL-$d_4$) δ 8.20 (s, 1H), 8.16 (d, J=9.6 Hz, 1H), 8.12 (d, J=8.6 Hz, 1H), 7.32 (s, 1H), 7.26 (d, J=9.6 Hz, 1H), 7.17 (d, J=8.6 Hz, 1H), 5.09 (t, J=12.1 Hz, 1H), 2.98 (s, 3H), 2.64 (s, 3H), 1.62-1.72 (m, 2H), 1.50-1.60 (m, 2H), 1.38 (s, 6H), 1.22 (s, 6H).

Example 3-1: Synthesis of 7-(6-(methyl(1,2,2,6,6-pentamethylpiperidin-4-yl)amino)pyridazin-3-yl)isoquinolin-6-ol Step 1. 6-(6-Methoxyisoquinolin-7-yl)-N-methyl-N-(1,2,2,6,6-pentamethylpiperidin-4-yl)pyridazin-3-amine The title compound (63 mg, 0.15 mmol) was prepared following GENERAL METHOD 1-1 for Suzuki reaction of Intermediate 4 (75 mg, 0.25 mmol) and Intermediate 7 (77 mg, 0.38 mmol). MS (M+1)=420.1

Step 2. 7-(6-(Methyl(1,2,2,6,6-pentamethylpiperidin-4-yl)amino)pyridazin-3-yl)isoquinolin-6-ol The title compound (26 mg) was prepared from 6-(6-methoxyisoquinolin-7-yl)-N-methyl-N-(1,2,2,6,6-pentamethylpiperidin-4-yl)pyridazin-3-amine (63 mg, 0.150 mmol) following GENERAL METHOD 2-4 for demethylation using thiophenol. The crude residue was purified by preparative reverse-phase HPLC (25 to 50% acetonitrile in water, 5 mM ammonium hydroxide modifier). LC/MS Rt=0.38 min. MS (M+1)=406.2. ¹H NMR (400 MHz, METHANOL-$d_4$) δ 9.57 (s, 1H), 8.98 (s, 1H), 8.48 (d, J=10.0 Hz, 1H), 8.40 (d, J=6.8 Hz, 1H), 8.21 (d, J=6.8 Hz, 1H), 7.70 (d, J=9.8 Hz, 1H), 7.64 (s, 1H), 5.35 (br s, 1H), 3.18 (s, 3H), 2.94 (s, 3H), 2.24-2.36 (m, 2H), 2.10-2.19 (m, 2H), 1.66 (s, 6H), 1.61 (s, 6H).

Example 3-2: Synthesis of 7-(6-(methyl(2,2,6,6-tetramethylpiperidin-4-yl)amino)pyridazin-3-yl)isoquinolin-6-ol

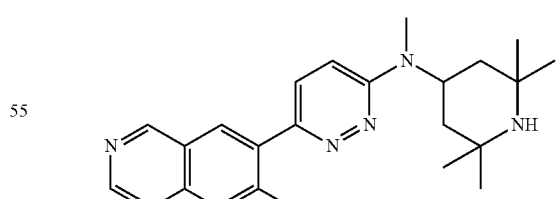

Step 1. 6-(6-Methoxyisoquinolin-7-yl)-N-methyl-N-(2,2,6,6-tetramethylpiperidin-4-yl)pyridazin-3-amine A 30 mL vial with a septum cap was charged with 6-chloro-N-methyl-N-(2,2,6,6-tetramethylpiperidin-4-yl)pyridazin-3-amine, Intermediate 1 (200 mg, 0.71 mmol), potassium triphosphate (751 mg, 3.54 mmol), and 2$^{nd}$ generation XPhos precatalyst (39 mg, 0.05 mmol), and DMF (2.5 mL). The mixture was degassed via vacuum/purge (3×), and heated at 50° C. A solution of Intermediate 7 in DMF (100 mg/mL) was added in 1 mL aliquots every 2-3 h until Intermediate 1 was consumed. The reaction was cooled to room temperature, filtered through a Celite® column washing with EtOAc, and partially concentrated. The mixture was diluted with MeOH and acidified to pH<4 with 1 M HCl. SCX purification (GENERAL METHOD 3-1) followed by elution through a silica gel plug (10-50% MeOH/DCM) provided the title compound (130 mg) which was taken on without further purification. MS (M+1)=406.7

Step 2. 7-(6-(Methyl(2,2,6,6-tetramethylpiperidin-4-yl)amino)pyridazin-3-yl)isoquinolin-6-ol 6-(6-Methoxyisoquinolin-7-yl)-N-methyl-N-(2,2,6,6-tetramethylpiperidin-4-yl)pyridazin-3-amine was deprotected following GENERAL METHOD 2-4 for demethylation using thiophenol. SCX purification (GENERAL METHOD 3-1) followed by preparative reverse phase HPLC (25 to 50% acetonitrile in water, 5 mM ammonium hydroxide modifier) provided the title compound (63 mg). LC/MS Rt=0.39 min. MS (M+1)=392.2. $^1$H NMR (400 MHz, METHANOL-d$_4$) δ 9.13 (s, 1H), 8.59 (s, 1H), 8.37 (d, J=10.0 Hz, 1H), 8.28 (d, J=5.8 Hz, 1H), 7.64 (d, J=6.0 Hz, 1H), 7.40 (d, J=10.0 Hz, 1H), 7.30 (s, 1H), 5.27 (br. s., 1H), 3.07 (s, 3H), 1.76-1.85 (m, 2H), 1.65-1.75 (m, 2H), 1.48 (s, 6H), 1.33 (s, 6H).

Example 3-3: Synthesis of 7-(6-((2,2,6,6-tetramethylpiperidin-4-yl)oxy)pyridazin-3-yl)isoquinolin-6-ol

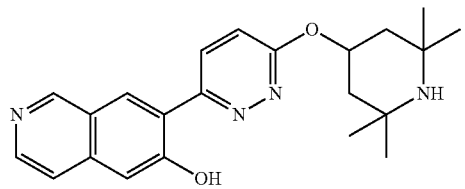 [SMILES: CC1(C)CC(Oc2ccc(-c3cc4cnccc4cc3O)nn2)CC(C)(C)N1]

Step 1. 6-Methoxy-7-(6-((2,2,6,6-tetramethylpiperidin-4-yl)oxy)pyridazin-3-yl)isoquinoline The title compound (product not isolated) was prepared following GENERAL METHOD 1-1 for Suzuki reaction from Intermediate 3 (200 mg, 0.741 mmol) and Intermediate 7 (256 mg, 1.26 mmol). MS (M+1)=393.0

Step 2. 7-(6-((2,2,6,6-Tetramethylpiperidin-4-yl)oxy)pyridazin-3-yl)isoquinolin-6-ol The title compound (66 mg) was prepared from 6-methoxy-7-(6-((2,2,6,6-tetramethylpiperidin-4-yl)oxy)pyridazin-3-yl)isoquinoline following GENERAL METHOD 2-4 for demethylation using thiophenol. LC/MS Rt=0.38 min. MS (M+1)=379.2. $^1$H NMR (400 MHz, METHANOL-d$_4$) δ 9.50 (s, 1H), 8.98 (s, 1H), 8.49 (d, J=9.5 Hz, 1H), 8.28-8.33 (m, 1H), 8.12 (d, J=6.8 Hz, 1H), 7.57 (s, 1H), 7.41 (d, J=9.3 Hz, 1H), 5.80 (tt, J=4.1, 10.7 Hz, 1H), 2.43 (dd, J=4.0, 13.8 Hz, 2H), 1.80 (dd, J=11.2, 13.4 Hz, 2H), 1.56 (s, 6H), 1.48 (s, 6H).

Example 3-4: Synthesis of 7-(6-((3aR,6aS)-5-methylhexahydropyrrolo[3,4-c]pyrrol-2(1H)-yl)pyridazin-3-yl)isoquinolin-6-ol

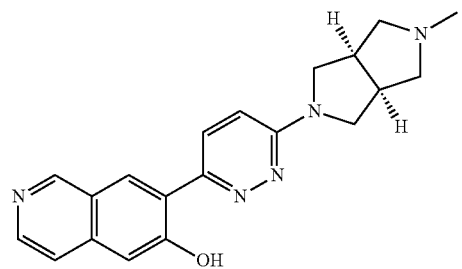 [SMILES: CN1C[C@@H]2CN(c3ccc(-c4cc5cnccc5cc4O)nn3)C[C@@H]2C1]

Step 1. 6-Methoxy-7-(6-((3aR,6aS)-5-methylhexahydropyrrolo[3,4-c]pyrrol-2(1H)-yl)pyridazin-3-yl)isoquinoline The title compound (product not isolated) was prepared following GENERAL METHOD 1-1 for Suzuki reaction from Intermediate 5 (75 mg, 0.314 mmol) and Intermediate 7 (108 mg, 0.534 mmol). MS (M+1)=362.5

Step 2. 7-(6-((3aR,6aS)-5-Methylhexahydropyrrolo[3,4-c]pyrrol-2(1H)-yl)pyridazin-3-yl)isoquinolin-6-ol The title compound (21 mg) was prepared from 6-methoxy-7-(6-((3aR,6aS)-5-methylhexahydropyrrolo[3,4-c]pyrrol-2(1H)-yl)pyridazin-3-yl)isoquinoline following GENERAL METHOD 2-4 for demethylation using thiophenol. LC/MS Rt=0.33 min. MS (M+1)=348.2. $^1$H NMR (400 MHz, METHANOL-d$_4$) δ 9.03 (s, 1H), 8.51 (s, 1H), 8.28 (d, J=9.8 Hz, 1H), 8.18 (d, J=6.0 Hz, 1H), 7.53 (d, J=6.0 Hz, 1H), 7.20 (t, J=4.9 Hz, 2H), 3.63-3.73 (m, 2H), 3.53-3.62 (m, 2H), 3.09-3.17 (m, 2H), 2.99-3.08 (m, 2H), 2.78 (dd, J=2.9, 10.2 Hz, 2H), 2.49 (s, 3H).

Example 3-5: Synthesis of 1-cyclopropyl-7-(6-(methyl(2,2,6,6-tetramethylpiperidin-4-yl)amino)pyridazin-3-yl)isoquinolin-6-ol

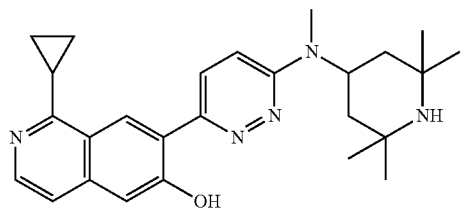 [SMILES: CN(c1ccc(-c2cc3c(C4CC4)nccc3cc2O)nn1)C1CC(C)(C)NC(C)(C)C1]

Step 1. 3-(Benzyloxy)-4-iodobenzoic acid

Benzyl bromide (7 mL, 57.8 mmol) was added to a mixture of 3-hydroxy-4-iodobenzoic acid (5.13 g, 18.9 mmol) and K$_2$CO$_3$ (8.0 g, 58 mmol) in acetone (200 mL). The mixture was then heated at reflux overnight. The mixture was cooled to room temperature then filtered through a small Celite® pad. The filtrate was concentrated in vacuo. MeOH (30 mL) was added to the residue followed by 1 M NaOH (94 mL, 94 mmol). The resulting mixture was heated in a 70° C. oil bath for 1 h. Next, the mixture was cooled to room temperature then concentrated in vacuo to approximately one half the starting volume to remove the MeOH. The resulting solution was diluted with water (20 mL) then extracted with Et$_2$O (2×100 mL). The organic layer was washed with 1 M NaOH (50 mL), and the combined aqueous layers were slowly acidified to pH 2 using concentrated HCl. Ethyl acetate (150 mL) was added to the resulting precipitate. After separation, the aqueous layer was extracted with EtOAc (3×150 mL). The combined organic layers were dried over MgSO$_4$, filtered, and concentrated in vacuo to afford the title compound as a white solid (6.6 g). MS (M+1)=353.5. $^1$H NMR (400 MHz, DMSO-d$_6$) δ 12.93 (br s, 1H), 7.93 (d, J=8.1 Hz, 1H), 7.48-7.57 (m, 3H), 7.41 (t, J=7.3 Hz, 2H), 7.28-7.35 (m, 2H), 5.26 (s, 2H).

Step 2. (3-(Benzyloxy)-4-iodophenyl) methanol

Borane tetrahydrofuran complex solution (1.0 M in THF, 7.83 ml, 7.83 mmol) was slowly added to a cooled solution (ice bath) of 3-(benzyloxy)-4-iodobenzoic acid (1.98 g, 5.59 mmol) in THF (50 mL). After complete addition, the reaction mixture was allowed to warm to room temperature overnight. The reaction mixture was cooled in an ice bath for 5 min then slowly quenched with 1 M HCl (10 mL). The reaction was then diluted with water (20 mL), and extracted with Et$_2$O (3×50 mL). The organic layer was washed successively with saturated aqueous NaHCO$_3$, and brine. The organics were dried over MgSO$_4$, filtered, and concentrated in vacuo affording the title compound as a thick colorless oil (1.9 g). MS (M-OH)=323.0

Step 3. 2-(3-(Benzyloxy)-4-iodobenzyloxy)tetrahydro-2H-pyran p-Toluenesulfonic acid monohydrate (0.215 g, 1.129 mmol) was added to a solution of (3-(benzyloxy)-4-iodophenyl)methanol (1.92 g, 5.64 mmol) and 3,4-dihydro-2H-pyran (0.64 mL, 6.8 mmol) in DCM (50 mL) at room temperature. After 2 h, the solution was diluted with DCM (30 mL), then washed with saturated aqueous NaHCO$_3$ solution (2×20 mL). The organic layer was washed with brine, dried over MgSO$_4$, filtered, and concentrated in vacuo. The resulting oil was stored under high vacuum overnight. The residue was purified by silica gel chromatography (80 g silica gel, 2-30% EtOAc/heptane) to afford the desired product as a thick colorless oil. (2.0 g, 4.7 mmol). MS (M+H$_2$O)=442.2. $^1$H NMR (400 MHz, CHLOROFORM-d) δ 7.76 (d, J=7.6 Hz, 1H), 7.51 (d, J=7.6 Hz, 2H), 7.39 (t, J=7.3 Hz, 2H), 7.29-7.35 (m, 1H), 6.92 (d, J=2.0 Hz, 1H), 6.74 (dd, J=8.1, 1.52 Hz, 1H), 5.18 (s, 2H), 4.71 (d, J=12.6 Hz, 1H), 4.66 (t, J=3.5 Hz, 1H), 4.47 (d, J=12.1 Hz, 1H), 3.82-3.93 (m, 1H), 3.46-3.58 (m, 1H), 1.80-1.94 (m, 1H), 1.68-1.79 (m, 1H), 1.50-1.68 (m, 4H).

Step 4. 2-(2-(Benzyloxy)-4-((tetrahydro-2H-pyran-2-yloxy)methyl)phenyl)-4,4,5,5-tetramethyl-1,3,2-dioxaborolane Following GENERAL METHOD 7-1 for boronate ester formation with 2-(3-(benzyloxy)-4-iodobenzyloxy)tetrahydro-2H-pyran (1.96 g, 4.62 mmol) afforded the title compound (1.96 g). MS (M+H$_2$O)=442.3. $^1$H NMR (400 MHz, CHLOROFORM-d) δ 7.68 (d, J=8.1 Hz, 1H), 7.61 (d, J=7.6 Hz, 2H), 7.36 (t, J=7.3 Hz, 2H), 7.30 (d, J=7.1 Hz, 1H), 6.94-7.00 (m, 2H), 5.14 (s, 2H), 4.77 (d, J=12.6 Hz, 1H), 4.68 (t, J=3.5 Hz, 1H), 4.54 (d, J=12.6 Hz, 1H), 3.85-3.95 (m, 1H), 3.48-3.57 (m, 1H), 1.82-1.94 (m, 1H), 1.50-1.78 (m, 5H), 1.37 (s, 12H).

Step 5. (3-(Benzyloxy)-4-(6-(methyl(2,2,6,6-tetramethylpiperidin-4-yl)amino)pyridazin-3-yl)phenyl) methanol 6-Chloro-N-methyl-N-(2,2,6,6-tetramethylpiperidin-4-yl)pyridazin-3-amine (Intermediate 1, 503 mg, 1.78 mmol), was added to a round bottom flask containing 2-(2-(benzyloxy)-4-((tetrahydro-2H-pyran-2-yloxy)methyl)phenyl)-4,4,5,5-tetramethyl-1,3,2-dioxaborolane (1.96 g, 3.23 mmol). Na$_2$CO$_3$ (566 mg, 5.34 mmol) and Pd(PPh$_3$)$_4$(230 mg, 0.20 mmol) were added followed by addition of 4:1 DME/water (15 mL). The reaction flask was equipped with a reflux condenser, and the flask evacuated and filled with N$_2$ (2×) then heated in a 100° C. oil bath overnight (18 h). The mixture was cooled to room temperature then filtered through Celite® with a MeOH wash. The filtrate was acidified to pH 2 using 1 M HCl then heated at 70° C. for 1 h. The mixture was cooled to room temperature then filtered through Celite® washing with MeOH. SCX purification (GENERAL METHOD 3-1, 20 g cartridge) afforded the title compound (750 mg) as a yellow amorphous solid after storing under high vacuum for several hours. MS (M+1)=461.4. $^1$H NMR (400 MHz, DMSO-d$_6$) δ ppm 7.74 (d, J=9.6 Hz, 1H), 7.68 (d, J=8.1 Hz, 1H), 7.41 (d, J=7.6 Hz, 1H), 7.36 (t, J=7.3 Hz, 2H), 7.27-7.33 (m, 1H), 7.19 (s, 1H), 6.94-7.06 (m, 2H), 5.16 (s, 2H), 5.09 (t, J=5.8 Hz, 2H), 4.54 (d, J=5.6 Hz, 2H), 2.90 (s, 3H), 1.38-1.63 (m, 5H), 1.28 (br s, 6H), 1.13 (br s, 6H).

Step 6. 3-(Benzyloxy)-4-(6-(methyl(2,2,6,6-tetramethylpiperidin-4-yl)amino)pyridazin-3-yl)benzaldehyde To a 50 mL round bottom flask containing (3-(benzyloxy)-4-(6-(methyl(2,2,6,6-tetramethylpiperidin-4-yl)amino)pyridazin-3-yl)phenyl)methanol (218 mg, 0.47 mmol) and DCM (2.4 mL) was added manganese dioxide (259 mg, 2.98 mmol). The reaction was stirred at room temperature for 18 h and additional manganese dioxide was added (123 mg, 1.42 mmol). The reaction was stirred at room temperature for 24 h then filtered through Celite® and concentrated in vacuo to afford 3-(benzyloxy)-4-(6-(methyl (2,2,6,6-tetramethylpiperidin-4-yl)amino)pyridazin-3-yl) benzaldehyde (217 mg). MS (M+1)=459.5

Step 7. 1-(3-(Benzyloxy)-4-(6-(methyl(2,2,6,6-tetramethylpiperidin-4-yl)amino)pyridazin-3-yl)phenyl)-2-nitroethanol To a 50 mL round bottom flask containing 3-(benzyloxy)-4-(6-(methyl(2,2,6,6-tetramethylpiperidin-4-yl)amino) pyridazin-3-yl)benzaldehyde (200 mg, 0.44 mmol) and MeOH (2.2 mL) was added nitromethane (0.47 mL, 0.87 mmol) and 1 M aqueous NaOH (1.3 mL, 1.31 mmol). The reaction was stirred at room temperature for 18 h then the pH was adjusted to 6-7 with 1 M aqueous HCl. SCX purification (GENERAL METHOD 3-1) and concentration of the product-containing fractions afforded 1-(3-(benzyloxy)-4-(6-(methyl(2,2,6,6-tetramethylpiperidin-4-yl)amino)pyridazin-3-yl)phenyl)-2-nitroethanol (176 mg). MS (M+1)=520.5

Step 8. 2-Amino-1-(3-methoxy-4-(6-(methyl(2,2,6,6-tetramethylpiperidin-4-yl)amino)pyridazin-3-yl)phenyl)ethanol To a 50 mL round bottom flask containing 1-(3-(benzyloxy)-4-(6-(methyl(2,2,6,6-tetramethylpiperidin-4-yl)amino)pyridazin-3-yl)phenyl)-2-nitroethanol (176 mg, 0.40 mmol) in MeOH (5.0 mL) was added 10% palladium on carbon (211 mg, 0.20 mmol). The resulting suspension was stirred under hydrogen at atmospheric pressure and room temperature for 18 h. The suspension was filtered through Celite® and the filter pad was washed with MeOH. SCX purification (GENERAL METHOD 3-1) and concentration of the product-containing fractions afforded 2-amino-1-(3-methoxy-4-(6-(methyl(2,2,6,6-tetramethylpiperidin-4-yl)amino)pyridazin-3-yl)phenyl)ethanol (164 mg). MS (M+1) =414.5

Step 9. N-(2-Hydroxy-2-(3-methoxy-4-(6-(methyl(2,2,6,6-tetramethylpiperidin-4-yl)amino)pyridazin-3-yl)phenyl)ethyl)cyclopropanecarboxamide In a 50 mL round bottom flask, 2-amino-1-(3-methoxy-4-(6-(methyl(2,2,6,6-tetramethylpiperidin-4-yl)amino)pyridazin-3-yl)phenyl)ethanol (250 mg, 0.61 mmol), cyclopropanecarboxylic acid (104 mg, 1.21 mmol), DIPEA (0.42 mL, 2.42 mmol), and HATU (230 mg, 0.61 mmol) in DCM (1.5 mL) and DMF (1.5 mL) were combined. The mixture was stirred at room temperature for 45 min, acidified with excess acetic acid and concentrated in vacuo. SCX purification (GENERAL METHOD 3-1) and concentration of the product-containing fractions afforded N-(2-hydroxy-2-(3-methoxy-4-(6-(methyl(2,2,6,6-tetramethylpiperidin-4-yl)amino)pyridazin-3-yl)phenyl)ethyl)cyclopropanecarboxamide (112 mg). MS (M+1)=482.6

Step 10. 6-(1-Cyclopropyl-6-methoxyisoquinolin-7-yl)-N-methyl-N-(2,2,6,6-tetramethylpiperidin-4-yl)pyridazin-3-amine To a 50 mL round bottom flask containing N-(2-hydroxy-2-(3-methoxy-4-(6-(methyl(2,2,6,6-tetramethylpiperidin-4-yl)amino)pyridazin-3-yl)phenyl)ethyl)cyclopropanecarboxamide (68 mg, 0.14 mmol) in acetonitrile (1.4 mL) was added phosphorus oxychloride (POCl$_3$, 0.66 mL, 0.71 mmol). The mixture was heated at 60° C. for 1 h then additional POCl$_3$ (0.66 mL, 0.71 mmol) was added and the reaction mixture was heated at 80° C. for 18 h. Additional POCl$_3$ (0.66 mL, 0.71 mmol) and toluene (1.4 mL) were added and the reaction heated at 90° C. for 1 h. The mixture was then cooled to room temperature, quenched with a minimal amount of water and concentrated in vacuo. SCX purification (GENERAL METHOD 3-1) and concentration of the product-containing fractions afforded 6-(1-cyclopropyl-6-methoxyisoquinolin-7-yl)-N-methyl-N-(2,2,6,6-tetramethylpiperidin-4-yl)pyridazin-3-amine (63 mg). MS (M+1)=446.1

Step 11. 1-Cyclopropyl-7-(6-(methyl(2,2,6,6-tetramethylpiperidin-4-yl)amino)pyridazin-3-yl)isoquinolin-6-ol Following standard GENERAL METHOD 2-3 for methoxy deprotection using boron tribromide, the title compound was afforded. LC/MS Rt=0.43 min. MS (M+1)=430.4 $^1$H NMR (400 MHz, METHANOL-d$_4$) δ 8.74 (s, 1H), 8.18 (d, J=10.0 Hz, 1H), 8.01 (d, J=5.8 Hz, 1H), 7.26 (d, J=6.0 Hz, 1H), 7.13-7.20 (m, 2H), 4.99-5.16 (m, 1H), 2.97 (s, 3H), 2.69-2.78 (m, 1H), 1.66-1.74 (m, 2H), 1.45-1.57 (m, 2H), 1.35 (s, 6H), 1.20 (s, 7H), 1.06-1.14 (m, 4H).

Example 3-6: Synthesis of 7-(6-(methyl(2,2,6,6-tetramethylpiperidin-4-yl)amino)pyridazin-3-yl)isoquinoline-1,6-diol

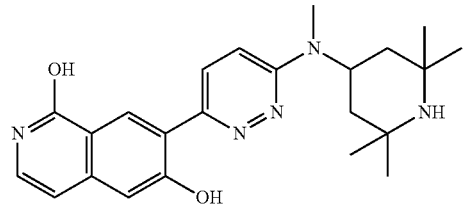 [SMILES: CN(c1ccc(-c2cc3c(O)nccc3cc2O)nn1)C1CC(C)(C)NC(C)(C)C1]

Step 1. 7-Bromo-1-ethoxy-6-methoxyisoquinoline

In a 30 mL vial, 7-bromo-1-chloro-6-methoxyisoquinoline (200 mg, 0.734 mmol) was partially dissolved in sodium ethoxide in ethanol (3 M, 2 mL, 6.00 mmol) and the mixture was heated for 18 h at 80° C. The mixture was cooled, and the solvent was removed under vacuum. The crude residue was purified by silica gel chromatography (5-30% EtOAc/heptane) to provide the title compound (157 mg). MS (M+1)=284.0. $^1$H NMR (400 MHz, CHLOROFORM-d) δ 8.46 (s, 1H), 7.95 (d, J=6.0 Hz, 1H), 7.09 (d, J=6.0 Hz, 1H), 7.03 (s, 1H), 4.53 (q, J=7.2 Hz, 2H), 4.02 (s, 3H), 1.50 (t, J=7.2 Hz, 3H).

Step 2: 1-Ethoxy-6-methoxy-7-(4,4,5,5-tetramethyl-1,3,2-dioxaborolan-2-yl)isoquinoline Following GENERAL METHOD 7-1 for boronate ester formation, 7-bromo-1-ethoxy-6-methoxyisoquinoline (53 mg, 0.188 mmol) afforded the title compound (60 mg). MS (M+1)=330.0

Step 3. 6-(1-Ethoxy-6-methoxyisoquinolin-7-yl)-N-methyl-N-(2,2,6,6-tetramethylpiperidin-4-yl)pyridazin-3-amine The title compound (product not isolated) was prepared following GENERAL METHOD 1-1 for Suzuki reaction from Intermediate 1 (35 mg, 0.12 mmol) and 1-ethoxy-6-methoxy-7-(4,4,5,5-tetramethyl-1,3,2-dioxaborolan-2-yl)isoquinoline (60 mg). MS (M+1)=450.2

Step 4. 7-(6-(Methyl(2,2,6,6-tetramethylpiperidin-4-yl)amino)pyridazin-3-yl)isoquinoline-1,6-diol The title compound (11 mg, 0.024 mmol) was prepared from 6-(1-ethoxy-6-methoxyisoquinolin-7-yl)-N-methyl-N-(2,2,6,6-tetramethylpiperidin-4-yl)pyridazin-3-amine following GENERAL METHOD 2-4 for deprotection using thiophenol. LC/MS Rt=0.50 min. MS (M+1)=408.3. $^1$H NMR (400 MHz, METHANOL-d$_4$) δ 8.57 (s, 1H), 8.48 (d, J=9.8 Hz, 1H), 8.08 (d, J=10.0 Hz, 1H), 7.25 (d, J=7.3 Hz, 1H), 7.17 (s, 1H), 6.60 (d, J=7.0 Hz, 1H), 4.8-5.1 (the methine signal is obscured by a broad H$_2$O peak), 3.21 (s, 3H), 2.12 (d, J=12.5 Hz, 2H), 1.99-2.07 (m, 2H), 1.66 (s, 6H), 1.59 (s, 6H)).

Example 3-7: Synthesis of 6-hydroxy-7-(6-(methyl (2,2,6,6-tetramethylpiperidin-4-yl)amino)pyridazin-3-yl)isoquinoline-1-carbonitrile

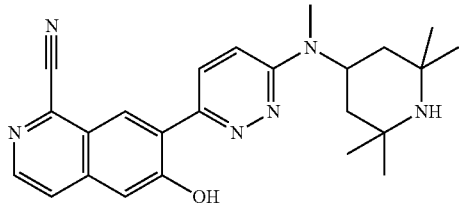 [SMILES: CN(c1ccc(-c2cc3c(C#N)nccc3cc2O)nn1)C1CC(C)(C)NC(C)(C)C1]

Step 1. 7-Bromo-6-methoxyisoquinoline 2-oxide

To a 50 mL round bottom flask containing 7-bromo-6-methoxyisoquinoline (prepared as described in WO2007000240) (200 mg, 0.84 mmol) in DCM (4.2 mL) was added m-chloroperoxybenzoic acid (mCPBA, 269 mg, 1.09 mmol). The mixture was stirred at room temperature for 18 h, diluted with DCM and washed with saturated aqueous sodium bicarbonate solution, then saturated aqueous sodium thiosulfate, and brine. The resulting organic layer was dried with sodium sulfate and concentrated in vacuo to afford 7-bromo-6-methoxyisoquinoline 2-oxide (213 mg). MS (M+1)=256.3

Step 2. 7-Bromo-6-methoxyisoquinoline-1-carbonitrile

To a 50 mL round bottom flask containing 7-bromo-6-methoxyisoquinoline 2-oxide (181 mg, 0.71 mmol) in acetonitrile (3.6 mL) was added TEA (0.20 mL, 1.43 mmol) and trimethylsilanecarbonitrile (0.29 mL, 2.14 mmol). The mixture was refluxed at 82° C. for 2 h, cooled, and concentrated in vacuo. The residue was basified with saturated aqueous Na$_2$CO$_3$, extracted with DCM, dried with MgSO$_4$, filtered and concentrated in vacuo. The residue was purified by silica gel chromatography (0-20% EtOAc/heptane) to afford 7-bromo-6-methoxyisoquinoline-1-carbonitrile (184 mg). MS (M+1)=265.0

Step 3. 6-Methoxy-7-(4,4,5,5-tetramethyl-1,3,2-dioxaborolan-2-yl)isoquinoline-1-carbonitrile Following GENERAL METHOD 7-1 for boronate ester formation, 7-bromo-6-methoxyisoquinoline-1-carbonitrile (184 mg, 0.70 mmol) afforded 6-methoxy-7-(4,4,5,5-tetramethyl-1,3,2-dioxaborolan-2-yl)isoquinoline-1-carbonitrile (217 mg). MS (M+1)=311.5

Step 4. 6-Methoxy-7-(6-(methyl(2,2,6,6-tetramethylpiperidin-4-yl)amino)pyridazin-3-yl)isoquinoline-1-carbonitrile Following GENERAL METHOD 1-1 for Suzuki coupling, 6-methoxy-7-(4,4,5,5-tetramethyl-1,3,2-dioxaborolan-2-yl)isoquinoline-1-carbonitrile (100 mg, 0.32 mmol) and 6-chloro-N-methyl-N-(2,2,6,6-tetramethylpiperidin-4-yl)pyridazin-3-amine, (Intermediate 1, 61 mg, 0.22 mmol), affords 6-methoxy-7-(6-(methyl(2,2,6,6-tetramethylpiperidin-4-yl)amino)pyridazin-3-yl)isoquinoline-1-carbonitrile (15 mg). MS (M+1)=431.6

Step 5. 6-Hydroxy-7-(6-(methyl(2,2,6,6-tetramethylpiperidin-4-yl)amino)pyridazin-3-yl)isoquinoline-1-carbonitrile Following standard GENERAL METHOD 2-1 for methoxy deprotection, the title compound was afforded. LC/MS Rt=0.51. MS (M+1)=417.2. $^1$H NMR (400 MHz, METHANOL-d$_4$) δ 8.63 (s, 1H), 8.55 (d, J=5.8 Hz, 1H), 8.50 (d, J=9.8 Hz, 1H), 7.89-8.04 (m, 2H), 7.49 (s, 1H), 5.05-5.24 (m, 1H), 3.23 (s, 3H), 2.01-2.21 (m, 4H), 1.69 (s, 6H), 1.59 (s, 6H).

Example 4-1: Synthesis of 6-(6-(methyl(2,2,6,6-tetramethylpiperidin-4-yl)amino)pyridazin-3-yl)isoquinolin-7-ol

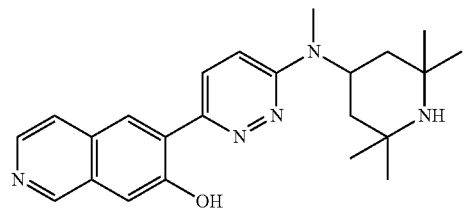 [SMILES: CN(c1ccc(-c2cc3ccncc3cc2O)nn1)C1CC(C)(C)NC(C)(C)C1]

Step 1. 6-(7-Methoxyisoquinolin-6-yl)-N-methyl-N-(2,2,6,6-tetramethylpiperidin-4-yl)pyridazin-3-amine The title compound (300 mg) was prepared from Intermediate 1 (240 mg, 0.849 mmol) and Intermediate 7 (350 mg, 1.724 mmol) following GENERAL METHOD 1-1 for Suzuki coupling. MS (M+1)=406.5

Step 2. 6-(6-(Methyl(2,2,6,6-tetramethylpiperidin-4-yl)amino)pyridazin-3-yl)isoquinolin-7-ol The title compound (72 mg) was prepared from 6-(7-methoxyisoquinolin-6-yl)-N-methyl-N-(2,2,6,6-tetramethylpiperidin-4-yl)pyridazin-3-amine (300 mg, 0.740 mmol) following GENERAL METHOD 2-4 for demethylation using thiophenol. LC/MS Rt=0.39 min. MS (M+1)=392.3. $^1$H NMR (400 MHz, METHANOL-d$_4$) δ 8.97 (s, 1H), 8.33 (s, 1H), 8.26 (d, J=9.8 Hz, 1H), 8.16 (d, J=5.8 Hz, 1H), 7.71 (d, J=5.8 Hz, 1H), 7.40 (s, 1H), 7.29 (d, J=10.0 Hz, 1H), 5.23 (br s, 1H), 2.97 (s, 3H), 1.59-1.79 (m, 4H), 1.41 (s, 6H), 1.26 (s, 6H).

Example 5-1: Synthesis of 8-(6-(methyl(2,2,6,6-tetramethylpiperidin-4-yl)amino)pyridazin-3-yl)quinolin-7-ol

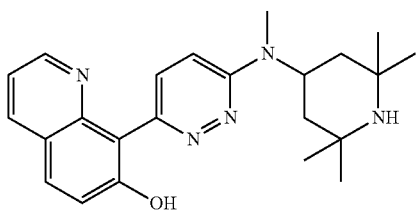 [SMILES: CN(c1ccc(-c2c(O)ccc3cccnc23)nn1)C1CC(C)(C)NC(C)(C)C1]

Step 1: 7-(Benzyloxy)-8-bromoquinoline

To a mixture of 8-bromoquinolin-7-ol (Chen, X., et al, WO 2010054006; 1257 mg, 5.61 mmol) and $K_2CO_3$ (2.32 g, 16.8 mmol) in DMF (12 mL) was added benzyl bromide (730 uL, 6.2 mmol), and the reaction mixture stirred overnight. The mixture was heated to 50° C. for 3 h to drive the reaction to completion. After cooling to room temperature, the mixture was diluted with 1:1 EtOAc/diethyl ether, washed with water (6×), brine, dried over $MgSO_4$, and concentrated to a brown liquid. Column chromatography (DCM elution, followed by 0-10% EtOAc in DCM) provided 7-(benzyloxy)-8-bromoquinoline (801 mg) as an off-white solid. MS (M+1)=314.1. $^1H$ NMR (400 MHz, CHLOROFORM-d) δ 9.05 (dd, J=1.8, 4.29 Hz, 1H), 8.13 (dd, J=1.8, 8.34 Hz, 1H), 7.77 (d, J=8.6 Hz, 1H), 7.56 (d, J=7.1 Hz, 2H), 7.31-7.47 (m, 5H), 5.39 (s, 2H).

Step 2: (7-(Benzyloxy)quinolin-8-yl)boronic acid

Butyllithium (2.5 M in heptane, 0.42 mL, 1.1 mmol) was added dropwise to a solution of 7-(benzyloxy)-8-bromoquinoline (300 mg, 0.95 mmol) cooled to −78° C. The solution was stirred for 0.5 h after which time trimethyl borate (0.270 mL, 2.4 mmol) was added and the solution slowly warmed to room temperature and stirred overnight. LC/MS analysis shows complete conversion of the bromide to the boronic acid. The solution was rotovapped to dryness and concentrated from heptane (2×) to provide the crude (7-(benzyloxy)quinolin-8-yl)boronic acid (276 mg) as an off-white solid. MS (M+1)=280.2. Based on LC/MS analysis, the yield of boronic acid was estimated to be near quantitative and this material was used directly in the subsequent Suzuki coupling.

Step 3: 6-(7-(Benzyloxy)quinolin-8-yl)-N-methyl-N-(2,6,6-tetramethylpiperidin-4-yl)pyridazin-3-amine A mixture of 6-chloro-N-methyl-N-(2,2,6,6-tetramethylpiperidin-4-yl)pyridazin-3-amine, (Intermediate 1, 200 mg, 0.707 mmol), the crude (7-(benzyloxy)quinolin-8-yl)boronic acid (estimated 0.95 mmol) and sodium carbonate (300 mg, 2.83 mmol) in 3:1 DME/water (8 mL) was degassed with a stream of dry nitrogen for 5 min. Tetrakis(triphenylphosphine)palladium(0) was added (123 mg, 0.106 mmol) and the mixture heated at 140° C. under microwave irradiation for 30 min. The reaction was diluted with DCM/water, and extracted with DCM (4×). The extracts were acidified with HCl (4 equivalents) in MeOH and concentrated. The crude material was subjected to catch and release purification as described in GENERAL METHOD 3-1, followed by silica gel chromatography as described in GENERAL METHOD 4-1 to provide 6-(7-(benzyloxy)quinolin-8-yl)-N-methyl-N-(2,2,6,6-tetramethylpiperidin-4-yl)pyridazin-3-amine as a light brown foam (214 mg). MS (M+1)=482.5

Step 4: 8-(6-(Methyl(2,2,6,6-tetramethylpiperidin-4-yl)amino)pyridazin-3-yl)quinolin-7-ol To a solution of 6-(7-(benzyloxy)quinolin-8-yl)-N-methyl-N-(2,2,6,6-tetramethylpiperidin-4-yl)pyridazin-3-amine (176 mg, 0.365 mmol) in 1:1 EtOAc/MeOH (3.6 mL) under a nitrogen atmosphere was added palladium on carbon (10 wt %, 39 mg, 0.037 mmol). The atmosphere was replaced with hydrogen (balloon) and the mixture stirred rapidly overnight. The flask was flushed with nitrogen, diluted with DCM, filtered through Celite®, and concentrated. Silica gel chromatography as described in GENERAL METHOD 4-1 provided 8-(6-(methyl(2,2,6,6-tetramethylpiperidin-4-yl)amino)pyridazin-3-yl)quinolin-7-ol as a yellow foam (100 mg). LC/MS Rt=0.41 min. MS (M+1)=392.3. $^1H$ NMR (400 MHz, METHANOL-$d_4$) δ 8.83 (d, J=10.1 Hz, 1H), 8.75 (dd, J=4.3, 1.8 Hz, 1H), 8.22 (dd, J=8.1, 1.5 Hz, 1H), 7.81 (d, J=9.1 Hz, 1H), 7.24-7.38 (m, 3H), 5.12 (t, J=12.4 Hz, 1H), 3.04 (s, 3H), 1.68-1.77 (m, 2H), 1.52-1.65 (m, 2H), 1.39 (s, 6H), 1.24 (s, 6H).

Example 6-1: Synthesis of 7-(6-(methyl(2,2,6,6-tetramethylpiperidin-4-yl)amino)pyridazin-3-yl)quinolin-6-ol

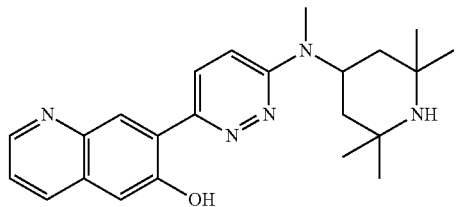 [SMILES: CN(c1ccc(-c2cc3ncccc3cc2O)nn1)C1CC(C)(C)NC(C)(C)C1]

Step 1: 7-Bromo-6-methoxyquinoline

According to the general procedure of Martinez, R., et al, J. Org. Chem. 2008, 73, 9778-9780, in a 100 mL round bottom flask, a mixture of (2-amino-4-bromo-5-methoxyphenyl)methanol (Intermediate 10, 2.36 g, 9.14 mmol), benzophenone (3.33 g, 18.3 mmol), KOtBu (2.05 g, 18.3 mmol), and ethanol (0.53 ml, 9.1 mmol) in 1,4-dioxane (30 mL) was heated at 80° C. for 2 h. The reaction was diluted with EtOAc and extracted with 1 M HCl (3×). The acidic extracts were washed with ether, basified to pH 10 and extracted with EtOAc (5×). The extracts were washed with brine, dried over $MgSO_4$ and concentrated to an orange oil. Silica gel chromatography (2-60% EtOAc in DCM) provided 7-bromo-6-methoxyquinoline (603 mg) as a yellow solid. MS (M+1)=238.1. $^1H$ NMR (400 MHz, CHLOROFORM-d) δ 8.80 (dd, J=4.5, 1.5 Hz, 1H), 8.44 (s, 1H), 8.12 (d, J=8.1 Hz, 1H), 7.43 (dd, J=8.3, 4.3 Hz, 1H), 7.12 (s, 1H), 4.04 (s, 3H).

Step 2: (6-Methoxyquinolin-7-yl)boronic acid

Butyllithium (1.6 M in heptane, 1.90 mL, 3.04 mmol) was added drop-wise over the course of one hour to a solution of 7-bromo-6-methoxyquinoline (0.603 g, 2.53 mmol) and triisopropyl borate (0.823 ml, 3.55 mmol) in THF (12.6 mL) cooled to −78° C. After the addition was complete, the cooling bath was removed and the slurry allowed to warm to room temperature. LC/MS analysis shows near quantitative conversion to the boronic acid. The mixture was concentrated, then the residue was concentrated sequentially from toluene and from heptane, to provide (6-methoxyquinolin-7-yl)boronic acid as an orange foam which was used immediately without purification. MS (M+1)=204.2

Step 3. 6-(6-Methoxyquinolin-7-yl)-N-methyl-N-(2,2,6,6-tetramethylpiperidin-4-yl)pyridazin-3-amine Suzuki coupling between 6-chloro-N-methyl-N-(2,2,6,6-tetramethylpiperidin-4-yl)pyridazin-3-amine, (Intermediate 1, 100 mg, 0.354 mmol) and the crude (6-methoxyquinolin-7-yl)boronic acid (0.530 mmol) using GENERAL METHOD 1-2, SCX purification (GENERAL METHOD 3-1, 2 g SiliaBond Propylsulfonic Acid® cartridge), silica gel chromatography (GENERAL METHOD 4-1), and palladium scavenging (GENERAL METHOD 6-1, SiliaMetS® DMT (232 mg, 0.141 mmol)) provided 6-(6-methoxyquinolin-7-yl)-N-methyl-N-(2,2,6,6-tetramethylpiperidin-4-yl)pyridazin-3-amine as a light yellow solid (105 mg). MS (M+1)=406.3. $^1$H NMR (400 MHz, METHANOL-$d_4$) δ 8.73 (dd, J=4.5, 1.5 Hz, 1H), 8.34 (d, J=7.6 Hz, 1H), 8.25 (s, 1H), 7.83 (d, J=9.6 Hz, 1H), 7.49-7.55 (m, 1H), 7.48 (s, 1H), 7.15 (d, J=9.6 Hz, 1H), 5.25 (t, J=12.4 Hz, 1H), 4.01 (s, 3H), 3.02 (s, 3H), 1.66-1.76 (m, 2H), 1.51-1.64 (m, 2H), 1.38 (s, 6H), 1.23 (s, 6H).

Step 4. 7-(6-(Methyl(2,2,6,6-tetramethylpiperidin-4-yl)amino)pyridazin-3-yl)quinolin-6-ol 6-(6-Methoxyquinolin-7-yl)-N-methyl-N-(2,2,6,6-tetramethylpiperidin-4-yl)pyridazin-3-amine was subjected to methoxy deprotection conditions as described in GENERAL METHOD 2-1. The crude material was subjected to silica gel chromatography (GENERAL METHOD 4-1) two times, to provide 7-(6-(methyl(2,2,6,6-tetramethylpiperidin-4-yl)amino)pyridazin-3-yl)quinolin-6-ol as a light yellow solid (35 mg). LC/MS Rt=0.47 min. MS (M+1)=392.3. $^1$H NMR (400 MHz, METHANOL-$d_4$) δ 8.67 (dd, J=4.0, 1.5 Hz, 1H), 8.40 (s, 1H), 8.30 (d, J=10.1 Hz, 1H), 8.18 (d, J=8.1 Hz, 1H), 7.45 (dd, J=8.3, 4.3 Hz, 1H), 7.37 (d, J=10.1 Hz, 1H), 7.33 (s, 1H), 5.09-5.24 (m, 1H), 3.05 (s, 3H), 1.67-1.76 (m, 2H), 1.53-1.65 (m, 2H), 1.40 (s, 6H), 1.24 (s, 6H).

Example 6-2: Synthesis of 2-methyl-7-(6-(methyl(2,2,6,6-tetramethylpiperidin-4-yl)amino)pyridazin-3-yl)quinolin-6-ol

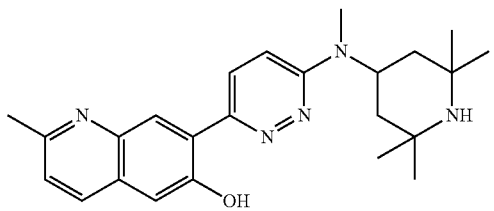

Step 1. 7-Bromo-6-methoxy-2-methylquinoline

According to the general procedure of Matsugi, M, et al, *Tetrahedron Lett.*, 2000, 41, 8523, to a solution of 3-bromo-4-methoxyaniline (1.00 g, 4.95 mmol) in 6 M HCl (25 mL) and toluene (6 mL) heated to 100° C. was added dropwise crotonaldehyde (0.407 mL, 4.95 mmol). Stirring was continued for 2 h at 100° C. and the mixture then allowed to cool to room temperature. The toluene layer was removed and the aqueous layer basified to pH 7 by slow addition of 2 M NaOH. The aqueous phase was extracted with DCM (6×) and concentrated to a green residue. Following the general procedure for quinoline purification described by Leir, C. M. *J. Org. Chem.*, 1977, 42, 911, the residue was dissolved into 1 M HCl (75 mL) and zinc chloride (1.349 g, 9.90 mmol) was added resulting in immediate formation of a dark gummy solid. Sonication and stirring of the mixture transformed the gummy solid to a light brown precipitate. The solids were isolated by filtration, washing with 1 M HCl, 2-propanol, then water. The solids were partitioned between 1:1 EtOAc/diethyl ether and 1:1 water/concentrated ammonium hydroxide. The organic phase was washed with water, brine, dried over MgSO$_4$ and concentrated to a dark brown residue consisting of a mixture of the two possible cyclization regioisomers. Silica gel chromatography (3-40% gradient of EtOAc in DCM) provided the more mobile title compound, 7-bromo-6-methoxy-2-methylquinoline (365 mg), TLC (4:1 DCM/EtOAc) R$_f$ 0.6, MS (M+1)=254.0, $^1$H NMR (400 MHz, METHANOL-$d_4$) δ 8.10-8.18 (m, 1H), 7.38 (d, J=8.6 Hz, 1H), 7.32 (s, 1H), 3.99 (s, 3H), 2.66 (s, 3H), and the less mobile 5-bromo-6-methoxy-2-methylquinoline (70 mg), TLC (4:1 DCM/EtOAc) R$_f$ 0.4, MS (M+1)=254.0, $^1$H NMR (400 MHz, METHANOL-$d_4$) δ 8.49 (d, J=8.6 Hz, 1H), 7.98 (d, J=9.1 Hz, 1H), 7.67 (d, J=9.1 Hz, 1H), 7.48 (d, J=8.6 Hz, 1H), 4.03 (s, 3H), 2.71 (s, 3H).

Step 2. (6-Methoxy-2-methylquinolin-7-yl)boronic acid

Butyllithium (1.6 M in heptane, 0.41 mL, 0.65 mmol) was added dropwise over the course of 1 h to a solution of 7-bromo-6-methoxy-2-methylquinoline (150 mg, 0.60 mmol) and triisopropyl borate (0.180 mL, 0.77 mmol) cooled to −78° C. After addition was complete, the reaction was stirred at −78° C. for one hour and then allowed to warm to room temperature and stir overnight. LC/MS analysis shows a 9:1 ratio of the title boronic acid to the debrominated side product (6-methoxy-2-methylquinoline). Solvent was removed via rotary evaporation, and the resulting solid concentrated from heptane (2×) to provide the crude (6-methoxy-2-methylquinolin-7-yl)boronic acid (MS (M+1)=218.1) which was used directly in the subsequent Suzuki coupling estimating 90% yield based on LC/MS analysis.

Step 3: 6-(6-Methoxy-2-methylquinolin-7-yl)-N-methyl-N-(2,2,6,6-tetramethylpiperidin-4-yl)pyridazin-3-amine 6-Chloro-N-methyl-N-(2,2,6,6-tetramethylpiperidin-4-yl)pyridazin-3-amine, Intermediate 1 (107 mg, 0.38 mmol) and the crude (6-methoxy-2-methylquinolin-7-yl)boronic acid were subjected to Suzuki coupling using GENERAL METHOD 1-2. The reaction was partitioned between DCM/water, extracted with DCM (3×), dried over MgSO$_4$ and concentrated. The crude material was subjected to silica gel chromatography (GENERAL METHOD 4-1) to provide 6-(6-methoxy-2-methylquinolin-7-yl)-N-methyl-N-(2,2,6,6-tetramethylpiperidin-4-yl)pyridazin-3-amine (149 mg) as an off-white solid. MS (M+1)=420.1. $^1$H NMR (400 MHz, METHANOL-$d_4$) δ 8.21 (d, J=8.6 Hz, 1H), 8.17 (s, 1H), 7.81 (d, J=9.6 Hz, 1H), 7.38-7.46 (m, 2H), 7.15 (d, J=9.6 Hz, 1H), 5.25 (t, J=12.4 Hz, 1H), 3.98 (s, 3H), 3.02 (s, 3H), 2.69 (s, 3H), 1.67-1.76 (m, 2H), 1.54-1.64 (m, 2H), 1.39 (s, 6H), 1.24 (s, 6H).

Step 4. 2-Methyl-7-(6-(methyl(2,2,6,6-tetramethypiperidin-4-yl)methylpiperidin-4-yl)amino)pyridazin-3-yl)quinolin-6-ol 6-(6-Methoxy-2-methylquinolin-7-yl)-N-methyl-N-(2,2,6,6-tetramethylpiperidin-4-yl)pyridazin-3-amine (140 mg, 0.317 mmol) was subjected to methoxy deprotection conditions as described in GENERAL METHOD 2-2. The crude material was subjected to silica gel chromatography (GENERAL METHOD 4-1) to provide 2-methyl-7-(6-

(methyl(2,2,6,6-tetramethylpiperidin-4-yl)amino)pyridazin-3-yl)quinolin-6-ol (97 mg) as a light yellow solid. LC/MS Rt=0.47 min. MS (M+1)=406.1. $^1$H NMR (400 MHz, METHANOL-$d_4$) δ 8.31 (s, 1H), 8.28 (d, J=10.1 Hz, 1H), 8.07 (d, J=8.6 Hz, 1H), 7.38 (d, J=9.6 Hz, 1H), 7.35 (d, J=8.6 Hz, 1H), 7.29 (s, 1H), 5.09-5.25 (m, 1H), 3.05 (s, 3H), 2.68 (s, 3H), 1.67-1.77 (m, 2H), 1.54-1.65 (m, 2H), 1.40 (s, 6H), 1.24 (s, 6H).

Example 7-1: Synthesis of 3-chloro-6-(6-(methyl(2,2,6,6-tetramethylpiperidin-4-yl)amino)pyridazin-3-yl)quinolin-7-ol hydrochloride salt

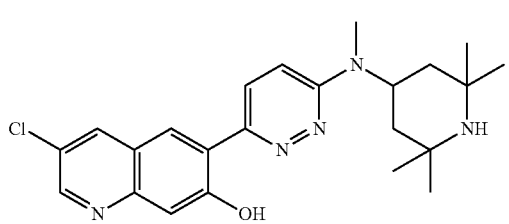 [SMILES: CN(c1ccc(-c2cc3cc(Cl)cnc3cc2O)nn1)C1CC(C)(C)NC(C)(C)C1]

Step 1: 6-(3-Chloro-7-methoxyquinolin-6-yl)-N-methyl-N-(2,2,6,6-tetramethylpiperidin-4-yl)pyridazin-3-amine 6-(7-Methoxyquinolin-6-yl)-N-methyl-N-(2,2,6,6-tetramethylpiperidin-4-yl)pyridazin-3-amine, (Intermediate 9, 50 mg, 0.123 mmol), was borylated according to GENERAL METHOD 5-1, with the exception that the reaction was heated at 65° C. overnight. To the crude boronic acid solution was added water (400 uL) and CuCl$_2$ (49.7 mg, 0.370 mmol). The mixture was heated at 65° C. for 1 h, then allowed to stir at room temperature overnight. The mixture was partitioned between DCM/water, and was washed with DCM (6×). The aqueous phase was acidified to pH 1 and concentrated to dryness. SCX purification of the resulting solids (GENERAL METHOD 3-1) followed by silica gel chromatography (GENERAL METHOD 4-1) provided 6-(3-chloro-7-methoxyquinolin-6-yl)-N-methyl-N-(2,2,6,6-tetramethylpiperidin-4-yl)pyridazin-3-amine (18 mg) as a light yellow solid. MS (M+1)=440.3

Step 2: 3-Chloro-6-(6-(methyl(2,2,6,6-tetramethylpiperidin-4-yl)amino)pyridazin-3-yl)quinolin-7-ol 6-(3-Chloro-7-methoxyquinolin-6-yl)-N-methyl-N-(2,2,6,6-tetramethylpiperidin-4-yl)pyridazin-3-amine (18 mg) was subjected to methoxy deprotection conditions as described in GENERAL METHOD 2-2. The crude material was subjected to silica gel chromatography (GENERAL METHOD 4-1) to provide the title compound. The solid was dissolved into aqueous HCl (1.0 M, 0.21 mL, 0.205 mmol)/water (300 uL) and the solution was lyophilized overnight to provide 3-chloro-6-(6-(methyl(2,2,6,6-tetramethylpiperidin-4-yl)amino)pyridazin-3-yl)quinolin-7-ol hydrochloride salt (14 mg) as a yellow/orange solid. LC/MS Rt=0.53 min. MS (M+1)=426.3. Free base: $^1$H NMR (400 MHz, METHANOL-$d_4$) δ 8.68 (d, J=2.5 Hz, 1H), 8.33-8.39 (m, 2H), 8.27 (d, J=10.1 Hz, 1H), 7.44 (s, 1H), 7.35 (d, J=10.1 Hz, 1H), 5.14-5.25 (m, 1H), 3.05 (s, 3H), 1.68-1.77 (m, 2H), 1.54-1.66 (m, 2H), 1.41 (s, 6H), 1.25 (s, 6H).

Example 7-2: Synthesis of 3-bromo-6-(6-(methyl(2,2,6,6-tetramethylpiperidin-4-yl)amino)pyridazin-3-yl)quinolin-7-ol

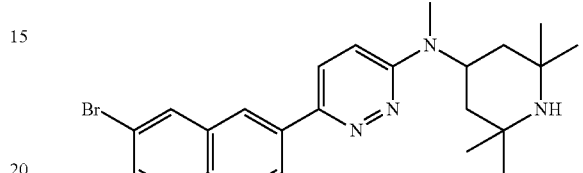

Step 1: 6-(3-Bromo-7-methoxyquinolin-6-yl)-N-methyl-N-(2,2,6,6-tetramethylpiperidin-4-yl)pyridazin-3-amine 6-(7-methoxyquinolin-6-yl)-N-methyl-N-(2,2,6,6-tetramethylpiperidin-4-yl)pyridazin-3-amine (Intermediate 9, 100 mg, 0.247 mmol), was borylated according to GENERAL METHOD 5-1. To the crude boronic acid solution was added water (800 uL) and CuBr$_2$ (165 mg, 0.740 mmol). The resulting mixture was stirred at room temperature overnight. The mixture was partitioned between DCM/water. The aqueous phase was extracted with EtOAc (5×), DCM (2×), and the combined organic extracts were concentrated. Silica gel chromatography (GENERAL METHOD 4-1) provided 6-(3-bromo-7-methoxyquinolin-6-yl)-N-methyl-N-(2,2,6,6-tetramethylpiperidin-4-yl)pyridazin-3-amine (73 mg) as a light yellow solid. MS (M+1)=484.3. $^1$H NMR (400 MHz, METHANOL-$d_4$) δ 8.84 (d, J=2.5 Hz, 1H), 8.57 (d, J=2.0 Hz, 1H), 8.11 (s, 1H), 7.84 (d, J=9.6 Hz, 1H), 7.53 (s, 1H), 7.15 (d, J=9.6 Hz, 1H), 5.27 (t, J=12.1 Hz, 1H), 4.03 (s, 3H), 3.02 (s, 3H), 1.66-1.75 (m, 2H), 1.52-1.63 (m, 2H), 1.38 (s, 6H), 1.23 (s, 6H).

Step 2. 3-Bromo-6-(6-(methyl(2,2,6,6-tetramethylpiperidin-4-yl)amino)pyridazin-3-yl)quinolin-7-ol 6-(3-Bromo-7-methoxyquinolin-6-yl)-N-methyl-N-(2,2,6,6-tetramethylpiperidin-4-yl)pyridazin-3-amine (73 mg) was subjected to methoxy deprotection conditions as described in GENERAL METHOD 2-2. The crude material was subjected to silica gel chromatography (GENERAL METHOD 4-1) to provide 3-bromo-6-(6-(methyl(2,2,6,6-tetramethylpiperidin-4-yl)amino)pyridazin-3-yl)quinolin-7-ol (36 mg) as a bright yellow solid. LC/MS Rt=0.53 min. MS (M+1)=472.2. $^1$H NMR (400 MHz, METHANOL-$d_4$) δ ppm 8.74 (d, J=2.0 Hz, 1H), 8.51 (s, 1H), 8.32 (s, 1H), 8.26 (d, J=10.1 Hz, 1H), 7.41 (s, 1H), 7.34 (d, J=10.1 Hz, 1H), 5.13-5.27 (m, 1H), 3.04 (s, 3H), 1.69-1.78 (m, 2H), 1.55-1.67 (m, 2H), 1.41 (s, 6H), 1.26 (s, 6H).

Example 7-3: Synthesis of 7-hydroxy-6-(6-(methyl (2,2,6,6-tetramethylpiperidin-4-yl)amino)pyridazin-3-yl)quinoline-3-carbonitrile

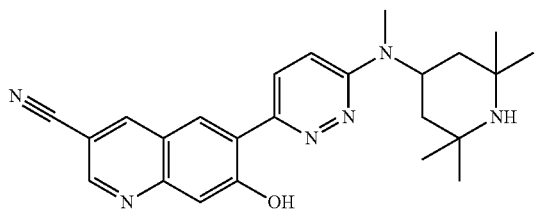 [SMILES: CN(c1ccc(-c2cc3cc(C#N)cnc3cc2O)nn1)C1CC(C)(C)NC(C)(C)C1]

To a vial containing 3-bromo-6-(6-(methyl(2,2,6,6-tetramethylpiperidin-4-yl)amino)pyridazin-3-yl)quinolin-7-ol (Example 7-2, 52 mg, 0.11 mmol), Pd(PPh$_3$)$_4$ (13 mg, 0.01 mmol), and zinc cyanide (26 mg, 0.22 mmol) was added DMF (1 mL). The mixture was sealed and heated in a Biotage® Initiator microwave reactor at 120° C. for 1 h. Copper iodide (4 mg, 0.02 mmol) was added and the reaction mixture was heated under microwave irradiation at 120° C. for 1 h. The crude reaction mixture was cooled to room temperature, filtered through Celite® and purified via reverse phase preparative HPLC (15 to 45% acetonitrile in water, 5 mM ammonium hydroxide modifier). The product-containing fractions were concentrated in vacuo to afford 7-hydroxy-6-(6-(methyl(2,2,6,6-tetramethylpiperidin-4-yl) amino)pyridazin-3-yl)quinoline-3-carbonitrile as a brown solid (5 mg). LC/MS Rt=0.51 min. MS (M+1)=417.2. $^1$H NMR (400 MHz, DMSO-d$_6$) δ 9.01 (d, J=2.0 Hz, 1H), 8.87 (d, J=2.0 Hz, 1H), 8.64 (s, 1H), 8.20-8.36 (m, 2H), 7.38-7.46 (m, 2H), 5.10 (br s, 1H), 2.99 (s, 3H), 1.44-1.74 (m, 4H), 1.32 (s, 6H), 1.17 (s, 6H).

Example 7-4: Synthesis of 6-(6-(methyl(2,2,6,6-tetramethylpiperidin-4-yl)amino)pyridazin-3-yl)-3-(1-methyl-1H-imidazol-4-yl)quinolin-7-ol

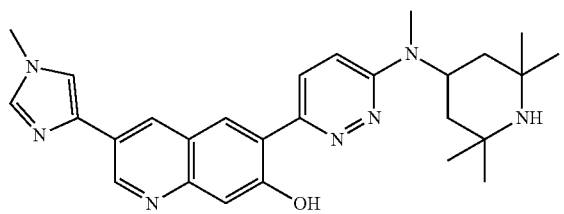 [SMILES: CN(c1ccc(-c2cc3cc(-c4cn(C)cn4)cnc3cc2O)nn1)C1CC(C)(C)NC(C)(C)C1]

Step 1. (7-Methoxy-6-(6-(methyl(2,2,6,6-tetramethylpiperidin-4-yl)amino)pyridazin-3-yl)quinolin-3-yl) boronic acid The title compound was synthesized from 6-(7-methoxyquinolin-6-yl)-N-methyl-N-(2,2,6,6-tetramethylpiperidin-4-yl)pyridazin-3-amine (Intermediate 9), following GENERAL METHOD 5-1 for borylation, and purified following GENERAL METHOD 3-1 to afford (7-methoxy-6-(6-(methyl(2,2,6,6-tetramethylpiperidin-4-yl)amino)pyridazin-3-yl)quinolin-3-yl)boronic acid. MS (M+1)=450.5

Step 2. 6-(7-Methoxy-3-(1-methyl-1H-imidazol-4-yl)quinolin-6-yl)-N-methyl-N-(2,2,6,6-tetramethylpiperidin-4-yl)pyridazin-3-amine 7-Methoxy-6-(6-(methyl(2,2,6,6-tetramethylpiperidin-4-yl)amino)pyridazin-3-yl)quinolin-3-yl)boronic acid (0.24 g, 0.53 mmol), 4-bromo-1-methyl-1H-imidazole (0.26 g, 1.6 mmol), and Na$_2$CO$_3$ (0.20 g, 1.9 mmol) were added to a microwave vial. Pd(PPh$_3$)$_4$ (0.05 g, 0.04 mmol) was then added followed by addition of 1,4-dioxane (2.2 mL) and water (0.6 mL). The reaction mixture was sealed and heated in a Biotage® Initiator microwave reactor at 130° C. for 1 h. A solution of NaHCO$_3$ was added to the reaction and the aqueous phase was extracted with DCM (3×). The combined organic phases were dried over anhydrous Na$_2$SO$_4$, filtered and concentrated under reduced pressure. The crude material was purified by silica gel chromatography (1-10% 7 M ammonia in MeOH gradient, in DCM) to give 6-(7-methoxy-3-(1-methyl-1H-imidazol-4-yl)quinolin-6-yl)-N-methyl-N-(2,2,6,6-tetramethylpiperidin-4-yl)pyridazin-3-amine as a yellow solid (25 mg). MS (M+1)=486.6

Step 3. 6-(6-(Methyl(2,2,6,6-tetramethylpiperidin-4-yl)amino)pyridazin-3-yl)-3-(1-methyl-1H-imidazol-4-yl)quinolin-7-ol Following GENERAL METHOD 2-1, methoxy deprotection of 6-(7-methoxy-3-(1-methyl-1H-imidazol-4-yl)quinolin-6-yl)-N-methyl-N-(2,2,6,6-tetramethylpiperidin-4-yl) pyridazin-3-amine (0.05 g, 0.10 mmol) afforded 6-(6-(methyl(2,2,6,6-tetramethylpiperidin-4-yl)amino)pyridazin-3-yl)-3-(1-methyl-1H-imidazol-4-yl)quinolin-7-ol as a brown solid (5 mg). LC/MS Rt=0.44 min. MS (M+1)=472.3. $^1$H NMR (400 MHz, DMSO-d$_6$) δ 13.52 (br s, 1H), 9.19 (d, J=2.0 Hz, 1H), 8.55 (s, 1H), 8.54 (d, J=2.0 Hz, 2H), 8.34 (d, J=10.0 Hz, 1H), 7.80 (d, J=1.0 Hz, 1H), 7.73 (d, J=1.0 Hz, 1H), 7.43 (d, J=10.0 Hz, 1H), 7.35 (s, 1H), 5.02 (brs, 1H), 3.74 (s, 3H), 2.99 (s, 3H), 1.55 (dd, J=12.0, 3.5 Hz, 2H), 1.45 (t, J=12.0 Hz, 2H), 1.27 (s, 6H), 1.10 (s, 6H).

Example 7-5: Synthesis of 3-(1H-imidazol-1-yl)-6-(6-(methyl(2,2,6,6-tetramethylpiperidin-4-yl)amino) pyridazin-3-yl)quinolin-7-ol hydrochloride salt

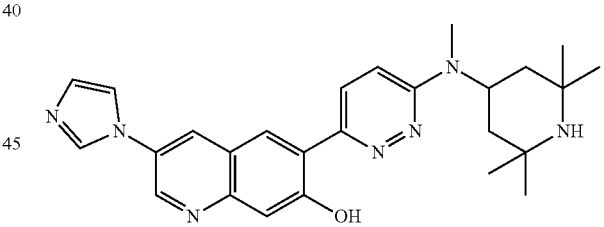

Step 1. 6-(3-(1H-Imidazol-1-yl)-7-methoxyquinolin-6-yl)-N-methyl-N-(2,2,6,6-tetramethylpiperidin-4-yl)pyridazin-3-amine 7-Methoxy-6-(6-(methyl(2,2,6,6-tetramethylpiperidin-4-yl)amino)pyridazin-3-yl)quinolin-3-yl)boronic acid (Example 7-4 Step 1, 0.06 g, 0.14 mmol), imidazole (0.06 g, 0.8 mmol) and copper(II) nitrate hemi(pentahydrate) (0.04 g, 0.2 mmol) were added to tetramethylethylenediamine (0.03 mL, 0.20 mmol) in methanol (2 mL). The reaction mixture was heated at 40° C. overnight. A 28% ammonium hydroxide solution was added to the reaction and the aqueous phase was extracted with DCM (3×). The combined organic phases were dried over anhydrous Na$_2$SO$_4$, filtered and concentrated under reduced pressure. The crude material was purified by silica gel chromatography (1-10% 7 M ammonia in MeOH gradient, in DCM) to provide 6-(3-(1H-imidazol- 1-yl)-7-methoxyquinolin-6-yl)-N-methyl-N-(2,2,6,6-tetramethylpiperidin-4-yl)pyridazin-3-amine. MS (M+1)=472.5. $^1$H NMR (400 MHz, METHANOL-d$_4$) δ 9.13 (d, J=2.6 Hz, 1H), 8.60 (d, J=2.6 Hz, 1H), 8.36 (s, 1H), 8.28 (s, 1H), 7.89 (d, J=9.7 Hz, 1H), 7.79 (s, 1H), 7.65 (s, 1H), 7.27 (s, 1H), 7.19 (d, J=9.6 Hz, 1H), 5.31 (br s, 1H), 4.08 (s, 3H), 3.05 (s, 3H), 1.75 (dd, J=12.3, 2.9 Hz, 2H), 1.56-1.70 (m, 2H), 1.42 (s, 6H), 1.27 (s, 6H).

Step 2. 3-(1H-Imidazol-1-yl)-6-(6-(methyl(2,2,6,6-tetramethylpiperidin-4-yl)amino)pyridazin-3-yl) quinolin-7-ol hydrochloride salt and 7-Methoxy-6-(6-(methyl(2,2,6,6-tetramethylpiperidin-4-yl)amino)pyridazin-3-yl)quinolin-3-ol Following GENERAL METHOD 2-1, methoxy deprotection of 6-(7-methoxy-3-(1-methyl-1H-imidazol-4-yl)quinolin-6-yl)-N-methyl-N-(2,2,6,6-tetramethylpiperidin-4-yl)pyridazin-3-amine (0.04 g, 0.07 mmol) afforded a mixture of 7-methoxy-6-(6-(methyl(2,2,6,6-tetramethylpiperidin-4-yl)amino)pyridazin-3-yl)quinolin-3-ol (25 mg, MS (M+1)=422.5), and 6-(6-(methyl(2,2,6,6-tetramethylpiperidin-4-yl)amino)pyridazin-3-yl)-3-(1-methyl-1H-imidazol-4-yl)quinolin-7-ol which were separated by preparative reverse-phase HPLC. 6-(6-(Methyl(2,2,6,6-tetramethylpiperidin-4-yl)amino)pyridazin-3-yl)-3-(1-methyl-1H-imidazol-4-yl)quinolin-7-ol was suspended in acetonitrile/H$_2$O (3/1 mL). 1 M Aqueous HCl (3 equivalents) was then added and solvent was concentrated in vacuo to afford 6-(6-(methyl(2,2,6,6-tetramethylpiperidin-4-yl)amino)pyridazin-3-yl)-3-(1-methyl-1H-imidazol-4-yl)quinolin-7-ol hydrochloride salt as a yellow solid (9.1 mg). LC/MS Rt=0.42 min. MS (M+1)=458.4. $^1$H NMR (400 MHz, DMSO-d$_6$) δ 9.74 (s, 1H), 9.19 (d, J=2.5 Hz, 1H), 9.10-9.19 (m, 1H), 8.74 (d, J=2.5 Hz, 1H), 8.62 (s, 1H), 8.36 (s, 1H), 8.33 (d, J=10.0 Hz, 1H), 8.17-8.26 (m, 1H), 7.96 (s, 1H), 7.52-7.65 (m, 2H), 5.08-5.24 (m, 1H), 3.04 (s, 3H), 2.04 (t, J=12.5 Hz, 2H), 1.80 (d, J=12.5 Hz, 2H), 1.55 (s, 6H), 1.49 (s, 6H).

Example 7-6: Synthesis of 6-(6-(methyl(2,2,6,6-tetramethylpiperidin-4-yl)amino)pyridazin-3-yl)quinoline-3,7-diol formate salt

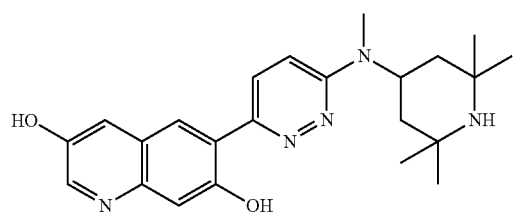 [SMILES: CN(c1ccc(-c2cc3cc(O)cnc3cc2O)nn1)C1CC(C)(C)NC(C)(C)C1]

A 1 M solution of BBr$_3$ in DCM (1.2 mL, 1.2 mmol) was added to 7-methoxy-6-(6-(methyl(2,2,6,6-tetramethylpiperidin-4-yl)amino)pyridazin-3-yl)quinolin-3-ol (Example 7-5 Step 2, 50 mg, 0.12 mmol) in DCM (0.6 mL) and the reaction was stirred at room temperature for 3 h. MeOH was added to the reaction and the solvent was concentrated under reduced pressure. The crude material was purified via preparative reverse-phase HPLC (5 to 20% acetonitrile in water, 0.1% formic acid modifier). The solvent was concentrated in vacuo to afford the formate salt of 6-(6-(methyl(2,2,6,6-tetramethylpiperidin-4-yl)amino)pyridazin-3-yl)quinoline-3,7-diol (3 mg). LC/MS Rt=0.42 min. MS (M+1)=408.3. $^1$H NMR (400 MHz, DMSO-d$_6$) δ 13.07 (br s, 1H), 8.49 (d, J=2.5 Hz, 1H), 8.37 (s, 1H), 8.32 (d, J=10.0 Hz, 1H), 8.29 (s, 2H), 7.50 (d, J=2.5 Hz, 1H), 7.41 (d, J=10.0 Hz, 1H), 7.29 (s, 1H), 4.91-5.18 (m, 1H), 2.99 (s, 3H), 1.62 (d, J=7.5 Hz, 4H), 1.35 (s, 6H), 1.20 (s, 6H).

Example 8-1: Synthesis of 3-ethyl-6-(6-(methyl(2,2,6,6-tetramethylpiperidin-4-yl)amino)pyridazin-3-yl) quinolin-7-ol

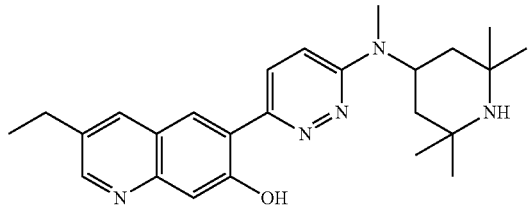 [SMILES: CCc1cnc2cc(O)c(-c3ccc(N(C)C4CC(C)(C)NC(C)(C)C4)nn3)cc2c1]

Step 1: 6-Bromo-3-ethyl-7-methoxyquinoline

Following the general procedure of Mierde, V. and Verpoort, et al, Tetrahedron Lett., 2009, 50, 201, a solution of (2-amino-5-bromo-4-methoxyphenyl)methanol (Ramurthy, S., et al, WO 2008079988; 0.886 g, 3.82 mmol) and butyraldehyde (0.344 ml, 3.82 mmol) was heated at 80° C. in 1,4-dioxane (9 mL) for 2 h. Benzophenone (0.765 g, 4.20 mmol) and potassium tert-butoxide (0.514 g, 4.58 mmol) were added and the mixture heated at 120° C. for 0.5 h. The mixture was cooled to room temperature, diluted with EtOAc, washed with saturated aqueous sodium bicarbonate and brine. The organic phase was extracted with 1 M HCl (3×). The acidic extracts were basified to pH 12 by addition of 2 M NaOH and extracted with EtOAc (3×) and diethyl ether (2×). The organic extracts were concentrated to a yellow residue which was subjected to silica gel chromatography (2-30% EtOAc in DCM) providing 6-bromo-3-ethyl-7-methoxyquinoline (433 mg) as a yellow solid. MS (M+1)=267.9. $^1$H NMR (400 MHz, METHANOL-d$_4$) δ ppm 8.69 (d, J=2.0 Hz, 1H), 8.14 (s, 1H), 8.04 (d, J=1.0 Hz, 1H), 7.40 (s, 1H), 4.03 (s, 3H), 2.84 (q, J=7.6 Hz, 2H), 1.34 (t, J=7.6 Hz, 3H).

Step 2: (3-Ethyl-7-methoxyquinolin-6-yl)boronic acid

From 6-bromo-3-ethyl-7-methoxyquinoline (150 mg, 0.564 mmol), 3-ethyl-7-methoxyquinolin-6-yl)boronic acid (0.564 mmol, estimated quantitative conversion based on LC/MS analysis. MS (M+1)=232.1), was produced in a manner similar to that outlined in Example 5-1, Step 2. This material was used directly in the subsequent Suzuki coupling.

Step 3: 6-(3-Ethyl-7-methoxyquinolin-6-yl)-N-methyl-N-(2,2,6,6-tetramethylpiperidin-4-yl) pyridazin-3-amine 6-Chloro-N-methyl-N-(2,2,6,6-tetramethylpiperidin-4-yl)pyridazin-3-amine (Intermediate 1, 115 mg, 0.407 mmol), and the crude 3-ethyl-7-methoxyquinolin-6-yl)boronic acid (132 mg, 0.564 mmol) were subjected to Suzuki coupling using GENERAL METHOD 1-2. The reaction was partitioned between DCM/water, extracted with DCM (3×), dried over MgSO₄ and concentrated to a light yellow solid. The crude material was subjected to silica gel chromatography (GENERAL METHOD 4-1) to provide 6-(3-ethyl-7-methoxyquinolin-6-yl)-N-methyl-N-(2,2,6,6-tetramethylpiperidin-4-yl)pyridazin-3-amine (100 mg). MS (M+1)=434.2. ¹H NMR (400 MHz, METHANOL-d₄) δ 8.70 (d, J=2.0 Hz, 1H), 8.17 (d, J=1.5 Hz, 1H), 8.10 (s, 1H), 7.83 (d, J=9.6 Hz, 1H), 7.49 (s, 1H), 7.15 (d, J=9.6 Hz, 1H), 5.26 (t, J=12.4 Hz, 1H), 4.01 (s, 3H), 3.01 (s, 3H), 2.81-2.92 (m, 2H), 1.66-1.75 (m, 2H), 1.51-1.62 (m, 2H), 1.32-1.42 (m, 9H), 1.23 (s, 6H).

Step 4. 3-Ethyl-6-(6-(methyl(2,2,6,6-tetramethypiperidin-4-yl)methylpiperidin-4-yl)amino)pyridazin-3-yl)quinolin-7-ol 6-(3-Ethyl-7-methoxyquinolin-6-yl)-N-methyl-N-(2,2,6,6-tetramethylpiperidin-4-yl)pyridazin-3-amine (100 mg, 0.231 mmol) was subjected to methoxy deprotection conditions as described in GENERAL METHOD 2-2. The crude material was subjected to silica gel chromatography (GENERAL METHOD 4-1) to provide 3-ethyl-6-(6-(methyl(2,2,6,6-tetramethylpiperidin-4-yl)amino)pyridazin-3-yl)quinolin-7-ol as a yellow solid (81 mg). LC/MS Rt=0.44 min. MS (M+1)=420.2. ¹H NMR (400 MHz, METHANOL-d₄) δ 8.63 (d, J=2.0 Hz, 1H), 8.33 (s, 1H), 8.27 (d, J=9.6 Hz, 1H), 8.13 (s, 1H), 7.41 (s, 1H), 7.35 (d, J=9.6 Hz, 1H), 5.10-5.23 (m, 1H), 3.04 (s, 3H), 2.84 (q, J=7.6 Hz, 2H), 1.67-1.75 (m, 2H), 1.54-1.65 (m, 2H), 1.40 (s, 6H), 1.36 (t, J=7.6 Hz, 3H), 1.24 (s, 6H).

Example 8-2: Synthesis of 3-isopropyl-6-(6-(methyl (2,2,6,6-tetramethylpiperidin-4-yl)amino)pyridazin-3-yl)quinolin-7-ol

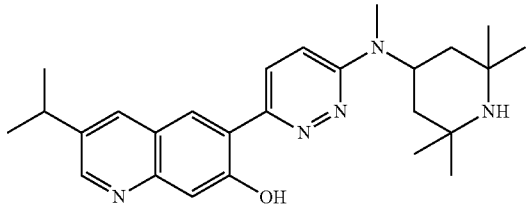 [SMILES: CC(C)c1cnc2cc(O)c(-c3ccc(N(C)C4CC(C)(C)NC(C)(C)C4)nn3)cc2c1]

Using procedures described in Example 8-1, Steps 1-4, beginning with 3-methyl butanal and (2-amino-5-bromo-4-methoxyphenyl)methanol, 3-isopropyl-6-(6-(methyl(2,2,6,6-tetramethyl-piperidin-4-yl)amino)pyridazin-3-yl)quinolin-7-ol was produced as a light yellow solid. LC/MS Rt=0.47 min. MS (M+1)=434.5. ¹H NMR (400 MHz, METHANOL-d₄) δ 8.66 (d, J=2.0 Hz, 1H), 8.34 (s, 1H), 8.27 (d, J=10.1 Hz, 1H), 8.15 (d, J=2.0 Hz, 1H), 7.40 (s, 1H), 7.34 (d, J=10.1 Hz, 1H), 5.15 (t, J=12.4 Hz, 1H), 3.13 (m, 1H), 3.04 (s, 3H), 1.67-1.75 (m, 2H), 1.53-1.64 (m, 2H), 1.36-1.42 (m, 12H), 1.23 (s, 6H).

Example 9-1: Synthesis of 7-hydroxy-6-(6-(methyl (2,2,6,6-tetramethylpiperidin-4-yl)amino)pyridazin-3-yl)quinolin-2(1H)-one

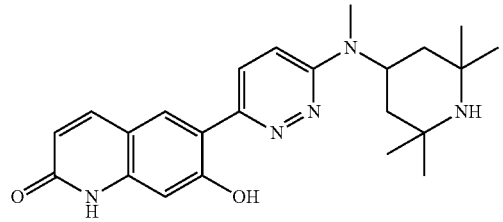 [SMILES: CN(c1ccc(-c2cc3ccc(=O)[nH]c3cc2O)nn1)C1CC(C)(C)NC(C)(C)C1]

Step 1: 6-Bromo-7-methoxyquinoline 1-oxide

To a solution of 6-bromo-7-methoxyquinoline (PREPARATION 6 Step 1, 2 g, 8.40 mmol) in DCM (42 mL) was added methyltrioxorhenium(VII) (0.209 g, 0.840 mmol). The solution was stirred for 5 min after which time hydrogen peroxide (30 wt % in water, 1.03 mL, 10.1 mmol) was added. The solution was allowed to stir overnight during which time a thick precipitate formed. The mixture was diluted with heptane and the solids were isolated by filtration, washing with heptane. Drying of the solids in vacuo provided 6-bromo-7-methoxyquinoline 1-oxide (1.76 g). MS (M+1)=255.9. ¹H NMR (400 MHz, METHANOL-d₄) δ 8.57 (dd, J=6.1, 1.0 Hz, 1H), 8.28 (s, 1H), 7.95 (d, J=8.6 Hz, 1H), 7.93 (s, 1H), 7.34 (dd, J=8.3, 6.3 Hz, 1H), 4.01 (s, 3H).

Step 2: 6-Bromo-7-methoxyquinolin-2(1H)-one

Trifluoroacetic anhydride (1.4 mL, 9.9 mmol) was added dropwise to 6-bromo-7-methoxyquinoline 1-oxide (0.26 g, 1.03 mmol) in DMF (7 mL) and the mixture was stirred at room temperature overnight. Water (20 mL) was added to the reaction and the resulting solid was collected by filtration. The solid was triturated with hot acetonitrile and filtered to afford 6-bromo-7-methoxyquinolin-2(1H)-one (0.17 g). MS (M+1)=256.0. ¹H NMR (400 MHz, DMSO-d₆) δ 8.60 (d, J=6.1 Hz, 1H), 8.49 (s, 1H), 7.98 (s, 1H), 7.86 (d, J=8.4 Hz, 1H), 7.38 (dd, J=8.4, 6.1 Hz, 1H), 4.05 (s, 3H).

Step 3: (7-Methoxy-2-oxo-1,2-dihydroquinolin-6-yl) boronic acid and 7-methoxy-6-(4,4,5,5-tetramethyl-1,3,2-dioxaborolan-2-yl)quinolin-2(1H)-one Bis(pinacolato)diboron (0.33 g, 1.31 mmol), KOAc (0.19 g, 2.0 mmol), PdCl₂(dppf).CH₂Cl₂ (0.03 g, 0.03 mmol) and 6-bromo-7-methoxyquinolin-2(1H)-one (0.17 g, 0.65 mmol) in DMSO (3.3 mL) were heated to 80° C. for 3 h. Additional portions of bis(pinacolato)diboron (0.17 g, 0.66 mmol) and KOAc (0.19 g, 2.0 mmol) were added and the mixture was heated at 80° C. overnight. The mixture was cooled to room temperature and the precipitate was collected by filtration to afford 7-methoxy-6-(4,4,5,5-tetramethyl-1,3,2-dioxaborolan-2-yl)quinolin-2(1H)-one. The filtrate was diluted with water and the aqueous phase was extracted with 3:1 chloroform/propan-2-ol (2×). To the combined organic phases was added to the previously collected 7-methoxy-6-(4,4,5,5-tetramethyl-1,3,2-dioxaborolan-2-yl)quinolin-2(1H)-one, and the solvent was concentrated in vacuo to afford a mixture (0.18 g) of 7-methoxy-6-(4,4,5,5-tetramethyl-1,3,2- dioxaborolan-2-yl)quinolin-2(1H)-one (MS (M+1)=302.2) and (7-methoxy-2-oxo-1,2-dihydroquinolin-6-yl)boronic acid (MS (M+1)=220.1).

Step 4: 7-Methoxy-6-(6-(methyl(2,2,6,6-tetramethylpiperidin-4-yl)amino)pyridazin-3-yl)quinolin-2(1H)-one The mixture of (7-methoxy-2-oxo-1,2-dihydroquinolin-6-yl)boronic acid and 7-methoxy-6-(4,4,5,5-tetramethyl-1,3,2-dioxaborolan-2-yl)quinolin-2(1H)-one (0.18 g), (Intermediate 1, 0.17 g, 0.60 mmol), Na$_2$CO$_3$ (0.19 g, 1.8 mmol) and Pd(PPh$_3$)$_4$(0.07 g, 0.06 mmol) in 6:1 1,4-dioxane/water (3 mL) were heated in a Biotage® Initiator microwave reactor at 130° C. for 1 h. Dichloromethane and 1 M HCl were added. The aqueous phase was washed with DCM (2×), then basified to pH 9 with a saturated solution of K$_2$CO$_3$. The aqueous phase was extracted with DCM (3×). The combined organic phases were dried over anhydrous Na$_2$SO$_4$, filtered and concentrated under reduced pressure. The crude material was purified by silica gel chromatography (2-10% 7 M ammonia in MeOH gradient, in DCM) to afford 7-methoxy-6-(6-(methyl(2,2,6,6-tetramethylpiperidin-4-yl)amino) pyridazin-3-yl)quinolin-2(1H)-one (16 mg). MS (M+1)=422.3

Step 5: 7-Hydroxy-6-(6-(methyl(2,2,6,6-tetramethylpiperidin-4-yl)amino)pyridazin-3-yl)quinolin-2(1H)-one Following GENERAL METHOD 2-1, methoxy deprotection of 7-methoxy-6-(6-(methyl(2,2,6,6-tetramethylpiperidin-4-yl)amino)pyridazin-3-yl)quinolin-2(1H)-one (16 mg, 0.038 mmol) afforded 7-hydroxy-6-(6-(methyl(2,2,6,6-tetramethylpiperidin-4-yl)amino)pyridazin-3-yl)quinolin-2(1H)-one (3.6 mg). LC/MS Rt=0.44 min. MS (M+1)=408.2. $^1$H NMR (400 MHz, METHANOL-d$_4$) δ 8.21 (d, J=10.0 Hz, 1H), 8.14 (s, 1H), 7.95 (d, J=9.5 Hz, 1H), 7.36 (d, J=10.0 Hz, 1H), 6.87 (s, 1H), 6.44 (d, J=9.5 Hz, 1H), 5.09-5.23 (m, 1H), 3.04 (s, 3H), 1.76 (dd, J=12.5, 3.5 Hz, 2H), 1.65 (t, J=12.5 Hz, 2H), 1.44 (s, 6H), 1.29 (s, 6H).

Example 9-2: Synthesis of 7-hydroxy-1-methyl-6-(6-(methyl(2,2,6,6-tetramethylpiperidin-4-yl)amino)pyridazin-3-yl)quinolin-2(1H)-one hydrochloride salt

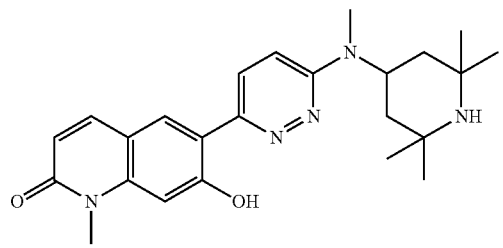 [SMILES: CN(c1ccc(-c2cc3ccc(=O)n(C)c3cc2O)nn1)C1CC(C)(C)NC(C)(C)C1]

Step 1. 6-Chloro-7-methoxyquinoline

The title compound was synthesized from 4-chloro-3-methoxyaniline in a manner analogous to PREPARATION 6 Step 1. MS (M+1)=194.0. $^1$H NMR (400 MHz, METHANOL-d$_4$) δ 8.80 (dd, J=4.5, 1.5 Hz, 1H), 8.26 (dd, J=8.5, 1.5 Hz, 1H), 8.02 (s, 1H), 7.49 (s, 1H), 7.45 (dd, J=8.5, 4.5 Hz, 1H), 4.07 (s, 3H).

Step 2. 6-Chloro-7-methoxyquinoline 1-oxide

Methyltrioxorhenium (0.03 g, 0.12 mmol) was added to 6-chloro-7-methoxyquinoline (1.69 g, 8.73 mmol) in DCM (40 mL). A solution of hydrogen peroxide (50 wt % in water, 1.0 mL, 17 mmol) was then added at 5° C. and the mixture was stirred at room temperature overnight. An additional portion of methyltrioxorhenium (0.03 g, 0.12 mmol) was added followed by hydrogen peroxide (50 wt % in water, 1.0 mL, 17 mmol) and the reaction was stirred for 4 h. The precipitate was collected by filtration to afford 6-chloro-7-methoxyquinoline 1-oxide as a beige solid (1.8 g). MS (M+1)=210.0. $^1$H NMR (400 MHz, DMSO-d$_6$) δ 8.59 (d, J=6.0 Hz, 1H), 8.32 (s, 1H), 8.03 (s, 1H), 7.85 (d, J=8.5 Hz, 1H), 7.39 (dd, J=8.5, 6.0 Hz, 1H), 4.05 (s, 3H).

Step 3. 6-Chloro-7-methoxyquinolin-2(1H)-one

Trifluoroacetic anhydride (6.0 mL, 42 mmol) was added dropwise to 6-chloro-7-methoxyquinoline 1-oxide (1.18 g, 5.63 mmol) in DMF (8.0 mL) at 5° C. The reaction mixture was heated in a Biotage® Initiator microwave reactor at 100° C. for 30 min. Water (20 mL) was added to the reaction and the resulting solid was collected by filtration. The solid was triturated with hot acetonitrile and filtered to afford 6-chloro-7-methoxyquinolin-2(1H)-one (0.39 g). MS (M+1)=210.1. $^1$H NMR (400 MHz, DMSO-d$_6$) δ 11.70 (br s, 1H), 7.79 (d, J=9.5 Hz, 1H), 7.79 (s, 1H), 6.95 (s, 1H), 6.37 (dd, J=9.5, 2.0 Hz, 1H), 3.89 (s, 3H).

Step 4. 6-Chloro-7-methoxy-1-methylquinolin-2(1H)-one

Potassium bis(trimethylsilyl)amide (0.5 M in toluene, 2.7 mL, 1.4 mmol) was added to 6-chloro-7-methoxyquinolin-2(1H)-one (0.20 g, 0.95 mmol) in toluene (5 mL) and the mixture was stirred for 10 min at room temperature. Iodomethane (0.07 mL, 1 mmol) was added to the reaction and the mixture was stirred 2 h at 50° C. An additional portion of potassium bis(trimethylsilyl)amide (0.5 M in toluene, 2.7 mL, 1.4 mmol) was added and the mixture was stirred for 10 min at room temperature. Iodomethane (0.08 mL, 1 mmol) was added to the reaction and the mixture was stirred at 50° C. overnight. Water was added to the reaction and the aqueous phase was extracted with DCM (3×). The combined organic phases were concentrated under reduced pressure. The crude material was purified by silica gel chromatography (gradient of 50-100% 3:1 EtOAc/EtOH, in heptane) to give 6-chloro-7-methoxy-1-methylquinolin-2(1H)-one (0.14 g). MS (M+1)=224.1. $^1$H NMR (400 MHz, METHANOL-d$_4$) δ 7.82 (d, J=9.3 Hz, 1H), 7.75 (s, 1H), 7.11 (s, 1H), 6.58 (d, J=9.4 Hz, 1H), 4.08 (s, 3H), 3.78 (s, 3H).

Step 5. 7-Methoxy-1-methyl-6-(6-(methyl(2,2,6,6-tetramethylpiperidin-4-yl)amino)pyridazin-3-yl) quinolin-2(1H)-one 6-Chloro-7-methoxy-1-methylquinolin-2(1H)-one (0.14 g, 0.62 mmol), tetrahydroxydiboron (0.22 g, 2.5 mmol), 2$^{nd}$ Generation XPhos Precatalyst (0.01 g, 0.02 mmol), XPhos (0.02 g, 0.04 mmol) and potassium acetate (0.24 g, 2.47 mmol) were stirred in ethanol (6.5 mL) at 80° C. for 30 min.

An aqueous solution of K₂CO₃ (1.8 M, 1.1 mL, 2.0 mmol) was added to the reaction at room temperature followed by Intermediate 1 (0.23 g, 0.80 mmol). The mixture was stirred at 80° C. for 2 h, then a 4% solution of Na₂CO₃ was added to the reaction and the aqueous phase was extracted with DCM (3×). The combined organic phases were extracted with 2 M HCl (3×). The combined acidic aqueous phases were basified to pH 11 with 6 M NaOH then extracted with DCM (3×). The combined organic phases were dried over anhydrous Na₂SO₄, filtered and concentrated under reduced pressure. The crude material was purified by silica gel chromatography (2-15% 7 N ammonia in MeOH gradient, in DCM) to give an inseparable mixture of 7-methoxy-1-methyl-6-(6-(methyl(2,2,6,6-tetramethylpiperidin-4-yl)amino)pyridazin-3-yl)quinolin-2(1H)-one and Intermediate 1 (0.26 g). MS (M+1)=436.5

Step 6. 7-Hydroxy-1-methyl-6-(6-(methyl(2,2,6,6-tetramethylpiperidin-4-yl)amino)pyridazin-3-yl)quinolin-2(1H)-one hydrochloride salt A 1 M solution of BBr₃ in DCM (0.2 mL, 3 mmol) was added to the mixture of 7-methoxy-1-methyl-6-(6-(methyl(2,2,6,6-tetramethylpiperidin-4-yl)amino)pyridazin-3-yl)quinolin-2(1H)-one and Intermediate 1 (0.03 g) in DCM (0.6 mL) at 5° C. and the reaction was stirred at 5° C. for 2 h. The solvent was concentrated under reduced pressure. The crude material was purified via preparative reverse-phase HPLC (5 to 20% acetonitrile in water, 7.5% formic acid modifier). The product-containing fractions were free based following GENERAL METHOD 3-1. The resulting solid was suspended in acetonitrile/H₂O (3/1 mL). 1 M aqueous HCl (3 equivalents) was added and solvent was concentrated in vacuo to afford 7-hydroxy-1-methyl-6-(6-(methyl(2,2,6,6-tetramethyl piperidin-4-yl)amino)pyridazin-3-yl)quinolin-2(1H)-one hydrochloride as a yellow solid (5 mg). LC/MS Rt=0.48 min. MS (M+1)=422.2. ¹H NMR (400 MHz, DMSO-d₆) δ 8.95-9.08 (m, 1H), 8.21-8.41 (m, 2H), 7.99-8.16 (m, 1H), 7.84 (d, J=9.5 Hz, 1H), 7.49-7.74 (m, 1H), 6.99 (s, 1H), 6.45 (d, J=9.5 Hz, 1H), 5.00-5.20 (m, 1H), 3.57 (s, 3H), 3.01 (s, 3H), 1.99 (t, J=13.0 Hz, 2H), 1.80 (d, J=13.0 Hz, 2H), 1.53 (s, 6H), 1.46 (s, 6H).

Example 10-1: Synthesis of 4-methoxy-2-methyl-6-(6-(methyl(2,2,6,6-tetramethylpiperidin-4-yl)amino)pyridazin-3-yl)quinolin-7-ol

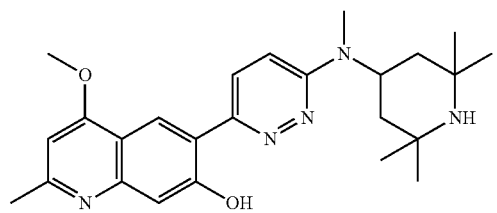

To a mixture of Intermediate 11 (150 mg, 0.32 mmol) in MeOH (1.5 mL) was added NaOMe (25 wt % in methanol, 0.36 mL, 1.6 mmol). The mixture was heated at 120° C. under microwave irradiation for 1 h. An additional portion of NaOMe (25 wt % in methanol, 0.2 mL) was added and the mixture was then heated at 130° C. for 2 h. The mixture was diluted with aqueous NaHCO₃ solution and extracted with DCM. The combined organic extracts were dried over Na₂SO₄, and concentrated in vacuo to give a light brown solid. The crude product was purified by silica gel chromatography (0-10% 2 M NH₃ in MeOH/DCM), then by preparative reverse-phase HPLC to obtain the title compound as a white solid (82 mg). LC/MS Rt=0.41 min. MS (M+1)=436.3. ¹H NMR (METHANOL-d₄) δ 8.39 (s, 1H), 8.11 (d, J=10.1 Hz, 1H), 7.27 (d, J=10.1 Hz, 1H), 7.24 (s, 1H), 6.66 (s, 1H), 5.09 (t, J=12.1 Hz, 1H), 4.06 (s, 3H), 3.00 (s, 3H), 2.59 (s, 3H), 1.64-1.74 (m, 2H), 1.51-1.62 (m, 2H), 1.39 (s, 6H), 1.23 (s, 6H).

Example 10-2: Synthesis of 2-methyl-6-(6-(methyl(2,2,6,6-tetramethylpiperidin-4-yl)amino)pyridazin-3-yl)-4-(pyrrolidin-1-yl)quinolin-7-ol

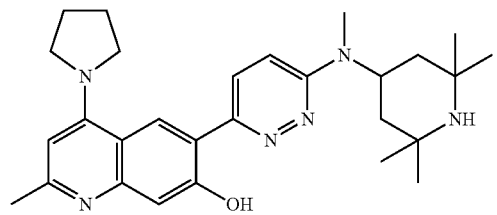

To a mixture of Intermediate 11 (22 mg, 0.046 mmol) in NMP (0.8 mL) was added pyrrolidine (26.3 mg, 0.370 mmol). The mixture was heated at 130° C. under microwave irradiation for 2 h. The mixture was cooled to room temperature, acidified by addition of 1 M HCl in ether and subjected to SCX purification (GENERAL METHOD 3-1, 1 g SiliaBond Propylsulfonic Acid® cartridge). The crude product was further purified by preparative reverse-phase HPLC to obtain 2-methyl-6-(6-(methyl(2,2,6,6-tetramethylpiperidin-4-yl)amino)pyridazin-3-yl)-4-(pyrrolidin-1-yl)quinolin-7-ol as a light yellow solid (7.5 mg). LC/MS Rt=0.44 min. MS (M+1)=475.2. ¹H NMR (METHANOL-d₄) δ 8.59 (s, 1H), 8.14 (d, J=9.6 Hz, 1H), 7.14 (d, J=9.6 Hz, 1H), 6.77 (s, 1H), 6.23 (s, 1H), 5.20 (t, J=12.4 Hz, 1H), 3.91 (br s, 4H), 2.99 (s, 3H), 2.48 (s, 3H), 2.03-2.17 (m, 4H), 1.71 (d, J=3.5 Hz, 2H), 1.51-1.64 (m, 2H), 1.39 (s, 6H), 1.24 (s, 6H).

The following example compounds were prepared from the Intermediate 11 and the appropriate sodium alkoxide or amine according to the preparations of Example 10-1 or Example 10-2.

| Example | Compound | MS (M + 1), LC/MS Rt | $^1$H NMR 400 MHz |
|---|---|---|---|
| 10-3 | 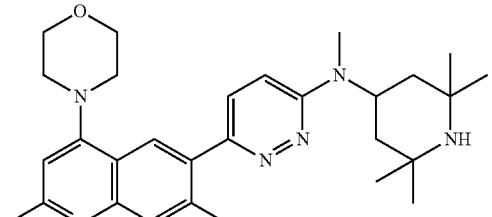<br>2-Methyl-6-(6-(methyl(2,2,6,6-tetramethylpiperidin-4-yl)amino)pyridazin-3-yl)-4-morpholinoquinolin-7-ol | 491.3<br>0.41 min | METHANOL-d$_4$ δ 8.27 (s, 1H), 8.05 (d, J = 10.1 Hz, 1H), 7.28 (d, J = 10.1 Hz, 1H), 7.26 (s, 1H), 6.72 (s, 1H), 5.12 (t, J = 11.6 Hz, 1H), 3.92-4.06 (m, 4H), 3.19-3.29 (m, 4H), 3.01 (s, 3H), 2.58 (s, 3H), 1.65-1.76 (m, 2H), 1.52-1.65 (m, 2H), 1.40 (s, 6H), 1.24 (s, 6H) |
| 10-4 | 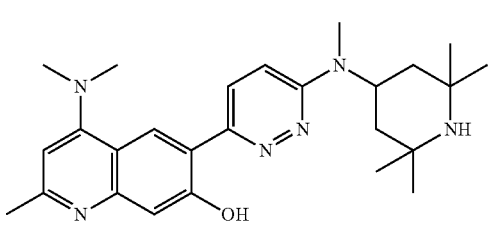<br>4-(Dimethylamino)-2-methyl-6-(6-(methyl(2,2,6,6-tetramethylpiperidin-4-yl)amino)pyridazin-3-yl)quinolin-7-ol | 449.3<br>0.42 min | METHANOL-d$_4$ δ 8.38 (s, 1H), 8.15 (d, J = 9.6 Hz, 1H), 7.24 (d, J = 9.6 Hz, 1H), 7.09 (s, 1H), 6.55 (s, 1H), 5.18 (t, J = 12.0 Hz, 1H), 3.19 (s, 6H), 3.01 (s, 3H), 2.55 (s, 3H), 1.68-1.78 (m, 2H), 1.57-1.68 (m, 2H), 1.42 (s, 6H), 1.27 (s, 6H) |
| 10-5 | 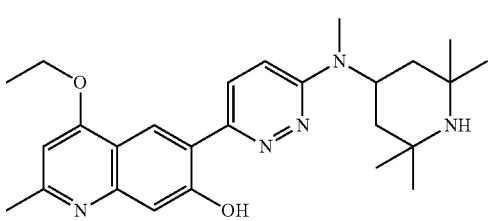<br>4-Ethoxy-2-methyl-6-(6-(methyl(2,2,6,6-tetramethylpiperidin-4-yl)amino)pyridazin-3-yl)quinolin-7-ol | 450.1<br>0.43 min | METHANOL-d$_4$ δ 8.46 (s, 1H), 8.14 (d, J = 9.6 Hz, 1H), 7.30 (d, J = 9.6 Hz, 1H), 7.26 (s, 1H), 6.67 (s, 1H), 5.13 (t, J = 12.6 Hz, 1H), 4.32 (q, J = 7.1 Hz, 2H), 3.02 (s, 3H), 2.59 (s, 3H), 1.67-1.74 (m, 2H), 1.62 (m, 5H), 1.39 (s, 6H), 1.24 (s, 6H) |

Example 11-1: Synthesis of 2-methyl-6-(6-(methyl (2,2,6,6-tetramethylpiperidin-4-yl)amino)pyridazin-3-yl)-4-(1-methyl-1H-pyrazol-4-yl)quinolin-7-ol

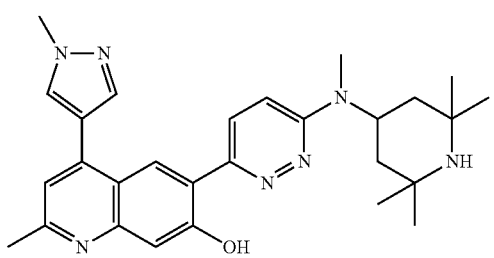

Step 1: 6-(7-Methoxy-2-methyl-4-(1-methyl-1H-pyrazol-4-yl) quinolin-6-yl)-N-methyl-N-(2,2,6,6-tetramethylpiperidin-4-yl)pyridazin-3-amine A mixture of 6-(4-chloro-7-methoxy-2-methylquinolin-6-yl)-N-methyl-N-(2,2,6,6-tetramethylpiperidin-4-yl)pyridazin-3-amine (35 mg, 0.077 mmol) from PREPARATION 11 Step 5, 4-(4,4,5,5-tetramethyl-1,3,2-dioxaborolan-2-yl)-1-methyl-pyrazole (48.1 mg, 0.231 mmol), XPhos Precatalyst (CAS No. 1028206-56-5, 5.70 mg, 7.71 umol) and cesium carbonate (100 mg, 0.308 mmol) in 1,4-dioxane (1 mL) and water (0.25 mL) was evacuated, filled with N$_2$ (4×) and heated under microwave irradiation at 120° C. for 1 h. The reaction mixture was concentrated and acidified to pH 3 by addition of 4 M HCl in 1,4-dioxane. SCX purification (GENERAL METHOD 3-1, 1 g SiliaBond Propylsulfonic Acid® cartridge) provided the crude product as a ~2:1 mixture (23 mg) of 6-(7-methoxy-2-methyl-4-(1-methyl-1H-pyrazol-4-yl)quinolin-6-yl)-N-methyl-N-(2,2,6,6-tetramethylpiperidin-4-yl)pyridazin-3-amine (MS (M+1)=500.2) and 7-methoxy-2-methyl-6-(6-(methyl(2,2,6,6-tetramethylpiperidin-4-yl)amino)-pyridazin-3-yl)quinolin-4(1H)-one.

Step 2: 2-Methyl-6-(6-(methyl(2,2,6,6-tetramethylpiperidin-4-yl)amino)pyridazin-3-yl)-4-(1-methyl-1H-pyrazol-4-yl)quinolin-7-ol The mixture of 6-(7-methoxy-2-methyl-4-(1-methyl-1H-pyrazol-4-yl)quinolin-6-yl)-N-methyl-N-(2,2,6,6-tetramethylpiperidin-4-yl)pyridazin-3-amine and 7-methoxy-2-methyl-6-(6-(methyl(2,2,6,6-tetramethylpiperidin-4-yl)amino)-pyridazin-3-yl)quinolin-4(1H)-one (21 mg) was subjected to methoxy deprotection conditions as described in GENERAL METHOD 2-1 using pyridine HCl. Preparative reverse-phase HPLC purification provided 2-methyl-6-(6-(methyl(2,2,6,6-tetramethylpiperidin-4-yl)amino)

pyridazin-3-yl)-4-(1-methyl-1H-pyrazol-4-yl)quinolin-7-ol as a yellow solid (4.6 mg). LC/MS Rt=0.42 min. MS (M+1)=486.3. $^1$H NMR (METHANOL-d$_4$) δ 8.43 (s, 1H), 8.14 (s, 1H), 8.02 (d, J=9.6 Hz, 1H), 7.92 (s, 1H), 7.36 (s, 1H), 7.24 (d, J=9.6 Hz, 1H), 7.20 (s, 1H), 5.14 (t, J=12.1 Hz, 1H), 4.04 (s, 3H), 2.99 (s, 3H), 2.64 (s, 3H), 1.66-1.79 (m, 2H), 1.53-1.66 (m, 2H), 1.41 (s, 6H), 1.26 (s, 6H).

Example 12-1: Synthesis of 4-methoxy-7-(6-(methyl(2,2,6,6-tetramethylpiperidin-4-yl)amino)pyridazin-3-yl)quinolin-6-ol formate salt

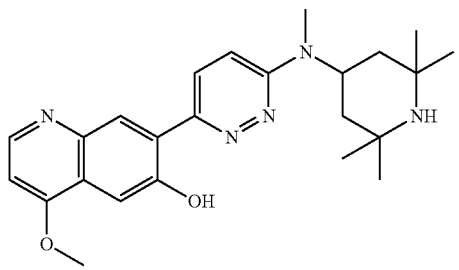 [SMILES: COc1ccnc2cc(-c3ccc(N(C)C4CC(C)(C)NC(C)(C)C4)nn3)c(O)cc12]

To 4-chloro-7-(6-(methyl(2,2,6,6-tetramethypiperidin-4-yl)amino)pyridazin-3-yl)quinolin-6-ol (Intermediate 13, 0.05 g, 0.12 mmol) in MeOH (0.2 mL) was added NaOMe (25 wt % in methanol, 0.3 mL, 10 mmol). The mixture was heated at 165° C. under microwave irradiation for 1 h. The reaction mixture was diluted with DMSO (5 mL), acidified with formic acid (0.5 mL) and purified via preparative reverse-phase HPLC (5 to 20% acetonitrile in water, 7.5% formic acid as modifier) to afford 4-methoxy-7-(6-(methyl (2,2,6,6-tetramethylpiperidin-4-yl)amino)pyridazin-3-yl) quinolin-6-ol formate salt (6 mg) as a yellow solid. LC/MS Rt=0.42 min. MS (M+1)=422.5. $^1$H NMR (METHANOL-d$_4$) δ 8.57 (d, J=5.5 Hz, 1H), 8.40 (br s, 2H), 8.35 (s, 1H), 8.33 (d, J=10.0 Hz, 1H), 7.61 (s, 1H), 7.42 (d, J=10.0 Hz, 1H), 6.96 (d, J=5.5 Hz, 1H), 5.48 (m, 1H), 4.12 (s, 3H), 3.08 (s, 3H), 2.05-1.94 (m, 4H), 1.68 (s, 6H), 1.53 (s, 6H).

Example 13-1: Synthesis of 7-(6-(methyl(2,2,6,6-tetramethylpiperidin-4-yl)amino)pyridazin-3-yl)quinoxalin-6-ol hydrochloride salt

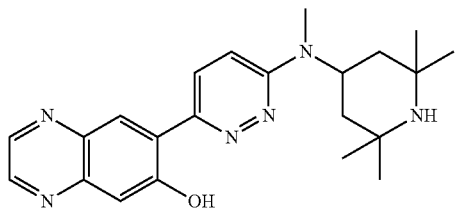 [SMILES: CN(c1ccc(-c2cc3nccnc3cc2O)nn1)C1CC(C)(C)NC(C)(C)C1]

Step 1: 4-Bromo-5-ethoxybenzene-1,2-diamine

Acetic acid (2 mL) was added drop-wise to 4-bromo-5-ethoxy-2-nitroaniline (5.00 g, 19.2 mmol) and zinc (6.47 g, 99.0 mmol) in CH$_2$Cl$_2$ (100 mL) at 4° C. (Caution! Reaction is exothermic). After the exotherm, an additional portion of AcOH (2 mL) was added at 4° C. and the reaction was stirred at room temperature for three days. The reaction mixture was filtered and the filtrate was concentrated in vacuo to provide 4-bromo-5-ethoxybenzene-1,2-diamine (8.41 g). MS (M+1)=231.2

Step 2: 6-Bromo-7-ethoxyquinoxaline

Glyoxal (8.8 M in water, 1.7 mL, 15.0 mmol) was added to 4-bromo-5-ethoxybenzene-1,2-diamine (1.16 g, 5.00 mmol) in THF (50 mL) and the reaction mixture was stirred for 3 h. Silica gel (6 g) was added to the reaction and solvent was concentrated in vacuo. The material was purified by silica gel chromatography (gradient of 10-50% 3:1 EtOAc/EtOH, in heptane) to give 6-bromo-7-ethoxyquinoxaline (0.94 g). MS (M+1)=255.2, $^1$H NMR (400 MHz, DMSO-d$_6$) δ 8.91 (d, J=2.0 Hz, 1H), 8.81 (d, J=2.0 Hz, 1H), 8.38 (s, 1H), 7.57 (s, 1H), 4.32 (q, J=7.0 Hz, 2H), 1.46 (t, J=7.0 Hz, 3H).

Step 3: 6-(7-Ethoxyquinoxalin-6-yl)-N-methyl-N-(2,2,6,6-tetramethylpiperidin-4-yl)pyridazin-3-amine Following the general procedure of Bernhardt, S.; Manolikakes, G.; Kunz, T.; Knochel, P. *Angew. Chem. Int. Ed.* 2011, 50, 9205-9209, Zn(OPiv)$_2$·2 LiCl (1.64 g, 4.64 mmol) was placed in a Schlenk-flask equipped with a magnetic stir bar and a septum, and dried for 5 min under vaccum with a heat gun. The zinc salt was dissolved in dry THF (10 mL). 6-Bromo-7-ethoxyquinoxaline (0.94 g, 3.71 mmol) was added and the mixture was stirred for 5 min at room temperature. Magnesium turnings (0.23 g, 9.28 mmol) were added. The reaction mixture was stirred at 50° C. for 4 h. The solution was transferred, via canula, to another reaction flask. Intermediate 1 (0.88 g, 3.09 mmol) and [1,3-bis(2,6-diisopropylphenyl)imidazol-2-ylidene](3-chloropyridyl) palladium(II) dichloride (0.21 g, 0.31 mmol) were added and the reaction mixture was heated at 50° C. for 5 days. The reaction mixture was cooled to room temperature and the volatiles were removed under vacuum. 2 M aqueous HCl was added to the crude material and the aqueous phase was washed with DCM and basified to pH 11 with 6 M aqueous NaOH. The precipitate was collected by filtration and the filtrate was extracted with 9:1 DCM/MeOH (3×). The organic extracts and the collected precipitate were mixed and volatiles were removed under vacuum. The crude material was purified by silica gel chromatography (2-15% 7 M ammonia in MeOH gradient, in DCM) followed by a second purification via reverse-phase preparative HPLC (25-50% acetonitrile in water, 5 mM NH$_4$OH as modifier). 6-(7-Ethoxyquinoxalin-6-yl)-N-methyl-N-(2,2,6,6-tetramethylpiperidin-4-yl)pyridazin-3-amine (0.05 g) was provided as a brown solid. MS (M+1)=421.2. $^1$H NMR (400 MHz, METHANOL-d$_4$) δ 8.84 (d, J=2.0 Hz, 1H), 8.78 (d, J=2.0 Hz, 1H), 8.34 (s, 1H), 7.95 (d, J=9.5 Hz, 1H), 7.58 (s, 1H), 7.20 (d, J=9.5 Hz, 1H), 5.24-5.49 (m, 1H), 4.35 (q, J=7.0 Hz, 2H), 3.05 (s, 3H), 1.76 (dd, J=12.5, 3.5 Hz, 2H), 1.64 (t, J=12.5 Hz, 2H), 1.51 (t, J=7.0 Hz, 3H), 1.43 (s, 6H), 1.28 (s, 6H).

Step 4: 7-(6-(Methyl(2,2,6,6-tetramethylpiperidin-4-yl)amino)pyridazin-3-yl)quinoxalin-6-ol hydrochloride salt A solution of BBr$_3$ in DCM (1 M, 1.0 mL, 1 mmol) was rapidly added to 6-(7-ethoxyquinoxalin-6-yl)-N-methyl-N-(2,2,6,6-tetramethylpiperidin-4-yl)pyridazin-3-amine (0.04 mg, 0.10 mmol) in DCM (1 mL). The reaction mixture was stirred at 40° C. for 4 days. MeOH was added to the reaction at 0° C. and the solvent was concentrated under reduced pressure. The crude material was dissolved with 2:1 DMSO/7 N ammonia in MeOH (6 mL) and was purified via reverse-phase preparative HPLC (15-40% acetonitrile in water, 5 mM ammonium hydroxide as modifier). The product-containing fractions were concentrated in vacuo and the resulting solid was dissolved in 4:1 acetonitrile/H$_2$O (5 mL). 1 M aqueous HCl (3 equivalents) was added and solvent was concentrated in vacuo to afford 7-(6-(methyl(2,2,6,6-tetramethylpiperidin-4-yl)amino)pyridazin-3-yl)quinoxalin-6-ol hydrochloride as a brown solid (26 mg). LC/MS Rt=0.48 min. MS (M+1)=393.2. $^1$H NMR (400 MHz, METHANOL-d$_4$) δ 8.89 (d, J=2.0 Hz, 1H), 8.83 (d, J=2.0 Hz, 1H), 8.54 (d, J=10.0 Hz, 1H), 8.44 (s, 1H), 8.11 (d, J=10.0 Hz, 1H), 7.58 (s, 1H), 4.97 (br s, 1H), 3.25 (s, 3H), 1.95-2.29 (m, 4H), 1.67 (s, 6H), 1.59 (s, 6H).

Preparation 14

Intermediate 14: Synthesis of 7-bromo-6-methoxyisoquinolin-1-ol

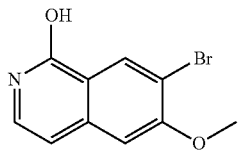

In a 10 mL microwave vial, 7-bromo-1-chloro-6-methoxyisoquinoline (240 mg, 0.881 mmol) was dissolved in acetic acid (5041 μl, 88 mmol). The mixture was heated to 150° C. for 180 min in microwave. Water was then added to the reaction vessel. The resulting precipitate was collected, washed with water, and then allowed to dry under vacuum to provide 7-bromo-6-methoxyisoquinolin-1-ol, Intermediate 14 (171 mg, 0.660 mmol, 74.9% yield). MS (M+1)=256.3. $^1$H NMR (400 MHz, DMSO-d$_6$) δ 11.27 (d, J=3.26 Hz, 1H), 8.26 (s, 1H), 7.30 (s, 1H), 7.20 (dd, J=5.77, 7.03 Hz, 1H), 6.52 (d, J=7.03 Hz, 1H), 3.96 (s, 3H).

Preparation 15

Intermediate 15: Synthesis of 2-hydroxy-4-methoxy-5-(4,4,5,5-tetramethyl-1,3,2-dioxaborolan-2-yl)benzaldehyde

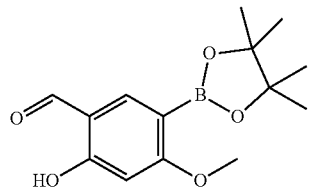 [SMILES: COc1cc(O)c(C=O)cc1B1OC(C)(C)C(C)(C)O1]

Step 1: 5-Bromo-2-hydroxy-4-methoxybenzaldehyde

In a 250 mL flask, 2-hydroxy-4-methoxybenzaldehyde (5 g, 32.9 mmol) was dissolved in acetic acid (65.7 mL), and cooled to 0° C., then Br$_2$ (1.862 ml, 36.1 mmol) in 10 mL acetic acid was added slowly. Upon complete addition, the reaction mixture was allowed to warm to room temperature, and stirred for 2 h. 100 mL of water was added to reaction flask, and the resulting white precipitate was filtered and washed with water. Drying under vacuum afforded the title compound (6.8 g, 29.4 mmol, 90% yield). MS (M+1)=233.3. $^1$H NMR (400 MHz, CHLOROFORM-d) δ 11.45 (s, 1H), 9.70 (s, 1H), 7.69 (s, 1H), 6.49 (s, 1H), 3.96 (s, 3H).

Step 2: 2-Hydroxy-4-methoxy-5-(4,4,5,5-tetramethyl-1,3,2-dioxaborolan-2-yl)benzaldehyde The title compound (4.9 g, 17.6 mmol, 82% yield) was prepared following GENERAL METHOD 7-1 for boronate ester formation from 5-bromo-2-hydroxy-4-methoxybenzaldehyde (5.0 g, 21.64 mmol) and purified by silica gel chromatography (0-5% MeOH/DCM). MS (M+1)=279.3.

Preparation 16

Intermediate 16: Synthesis of 2-formyl-5-methoxy-4-(6-(methyl(2,2,6,6-tetramethylpiperidin-4-yl)amino)pyridazin-3-yl)phenyl trifluoromethanesulfonate

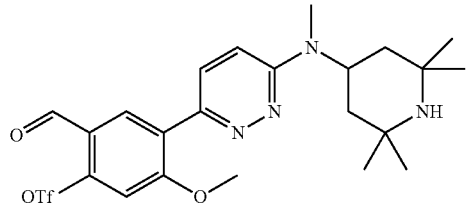 [SMILES: COc1cc(OS(=O)(=O)C(F)(F)F)c(C=O)cc1-c1ccc(N(C)C2CC(C)(C)NC(C)(C)C2)nn1]

Step 1: 2-Hydroxy-4-methoxy-5-(6-(methyl(2,2,6,6-tetramethylpiperidin-4-yl)amino)pyridazin-3-yl)benzaldehyde The title compound (3.5 g, 8.78 mmol, 53%) was prepared following GENERAL METHOD 9-1 for Suzuki reaction of Intermediate 1 (4.7 g, 16.62 mmol) and Intermediate 15 (7.86 g, 28.3 mmol). MS (M+1)=399.2.

Step 2: 2-Formyl-5-methoxy-4-(6-(methyl(2,2,6,6-tetramethylpiperidin-4-yl)amino)pyridazin-3-yl)phenyl trifluoromethanesulfonate In a 100 mL flask, 2-hydroxy-4-methoxy-5-(6-(methyl(2,2,6,6-tetramethylpiperidin-4-yl)amino)pyridazin-3-yl)benzaldehyde (2.07 g, 5.19 mmol) and N-phenyltrifluoromethane sulfonimide (3.71 g, 10.39 mmol) were dissolved in DCM (26.0 mL) under N$_2$. TEA (2.90 ml, 20.78 mmol) was added, and the heterogenous mixture was stirred for several hours at RT until complete dissolution was observed. The reaction was stirred overnight, then taken up in minimum amount of DCM and purified by silica gel chromatography (1-20% MeOH/DCM, elutes at 5% MeOH, column pretreated with TEA). The collected fractions were concentrated, and placed under high vacuum for several days to provide the title compound, (2.3 g, 4.03 mmol, 78% yield). MS (M+1)=399.2.

Preparation 17

Intermediate 17: Synthesis of 2-formyl-5-methoxy-4-(6-((2,2,6,6-tetramethylpiperidin-4-yl)oxy)pyridazin-3-yl)phenyl trifluoromethanesulfonate

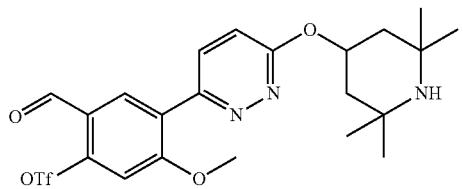 [SMILES: COc1cc(OS(=O)(=O)C(F)(F)F)c(C=O)cc1-c1ccc(OC2CC(C)(C)NC(C)(C)C2)nn1]

Step 1: 2-Hydroxy-4-methoxy-5-(6-((2,2,6,6-tetramethylpiperidin-4-yl)oxy)pyridazin-3-yl)benzaldehyde The title compound (3.5 g, 8.78 mmol, 53%) was prepared following GENERAL METHOD 9-1 for Suzuki reaction of Intermediate 15 (2.63 g, 9.45 mmol) and Intermediate 3 (1.5 g, 5.56 mmol). MS (M+1)=386.5. $^1$H NMR (400 MHz, CHLOROFORM-d) δ 9.82 (s, 1H), 8.20 (s, 1H), 7.85 (d, J=9.35 Hz, 1H), 6.92 (d, J=9.09 Hz, 1H), 6.56 (s, 1H), 5.76-5.90 (m, 1H), 3.93 (s, 3H), 2.24 (dd, J=4.04, 12.38 Hz, 2H), 1.35 (m, 8H), 1.14-1.27 (s, 6H).

Step 2. 2-Formyl-5-methoxy-4-(6-((2,2,6,6-tetramethylpiperidin-4-yl)oxy)pyridazin-3-yl)phenyl trifluoromethanesulfonate 2-Hydroxy-4-methoxy-5-(6-((2,2,6,6-tetramethylpiperidin-4-yl)oxy)pyridazin-3-yl)benzaldehyde (500 mg, 1.297 mmol) and N-phenyltrifluoromethane sulfonimide (927 mg, 2.59 mmol) were dissolved in DCM (6486 µl) under N$_2$. Triethylamine (723 µl, 5.19 mmol) was added, and the heterogenous mixture was stirred for several hour at room temperature until complete dissolution was observed. After stirring overnight, the reaction was taken up in a minimum amount of dichloromethane, and purified by silica gel chromatography (1-20% MeOH/DCM, elutes at 5% MeOH, column pretreated with TEA) to provide the title compound (650 mg, 1.256 mmol, 97% yield). MS (M+1)=518.1.

General Method 8-1

Representative Procedure for MP-Carbonate Free Basing

The trifluoroacetic acid salt of the product from preparatory reverse phase HPLC purification is dissolved in MeOH and loaded onto PL-HCO$_3$ MP® cartridge (Agilent Technologies) preconditionsed with MeOH. The cartridge is then flushed with excess MeOH to provided the product as a free base. MP-carbonate, a resin-bound base, is also available from Biotage (part number 800267 for 10 grams). The chemical name for MP-carbonate is macroporous triethylammonium methyl polystyrene carbonate.

General Method 9-1 for Suzuki Reaction

Representative Procedure for Suzuki Coupling with Pd$_2$(Dba)$_3$ and SPhos

A mixture of a chloropyridazine intermediate, such as Intermediate 1 (1.0 equivalent), a boronic acid reagent (1.5-2 equivalents), SPhos (0.2 equivalents), Pd$_2$(dba)$_3$ (0.05 equivalents), and K$_3$PO$_4$ (3 equivalents) in 4:1 dioxane/water (0.2 M) was heated in an oil bath at 100° C. for 18 h. The mixture was concentrated in vacuo and the crude residue was purified via silica gel chromatography (1-30% MeOH/DCM, column pretreated with TEA).

General Method 10-1 for Sonogashira Reaction

Representative Procedure for Sonogashira Reaction

Intermediate 16 or Intermediate 17 (1 equivalent) was dissolved in dry acetonitrile (5A MS) and TEA (0.1 M, Ratio: 3:1). Acetylene (4 equivalents), CuI (0.6 equivalent), and Pd(PPh$_3$)$_2$Cl$_2$ (0.3 equivalents) were added. The vessel was purged with N$_2$, and stirred at room temperature for 6 h. The mixture was concentrated in vacuo. The crude residue was taken up in dichloromethane, and purified by silica gel chromatography (1-20% MeOH/DCM, elutes at 10% MeOH, column pretreated with TEA), and used in next step without further purification.

General Method 11-1 for Isoquinoline Formation

Representative Procedure for Aldehyde Cyclization

In a microwave vial, the product from Sonogashira reaction (1 equivalent) and NH$_3$ (2M in MeOH) (2-5 mL) were combined and heated in the microwave for 30 min at 150° C. The crude product was concentrated, diluted with a minimum amount of MeOH, and purified by prep-HPLC (0.1% TFA/MeCN/H$_2$O) or taken on without further purification.

Example 14-1: Synthesis of 6-(6-(methyl(2,2,6,6-tetramethylpiperidin-4-yl)amino)pyridazin-3-yl)-3-(tetrahydro-2H-pyran-4-yl)quinolin-7-ol

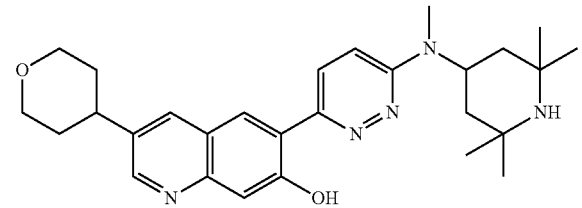 [SMILES: CN(c1ccc(-c2cc3cc(C4CCOCC4)cnc3cc2O)nn1)C1CC(C)(C)NC(C)(C)C1]

Using procedures described in Example 8-1, Steps 1-4, beginning with 2-(tetrahydro-2H-pyran-4-yl)acetaldehyde and (2-amino-5-bromo-4-methoxyphenyl)methanol, 6-(6-(methyl(2,2,6,6-tetramethylpiperidin-4-yl)amino)pyridazin-3-yl)-3-(tetrahydro-2H-pyran-4-yl)quinolin-7-ol was produced as a light yellow solid. LC/MS Rt=0.48 min. MS (M+1)=476.5. $^1$H NMR (400 MHz, METHANOL-d$_4$) δ ppm 8.71 (d, J=2.0 Hz, 1H), 8.40 (s, 1H), 8.31 (d, J=9.6 Hz, 1H), 8.20 (d, J=2.0 Hz, 1H), 7.43 (s, 1H), 7.38 (d, J=9.6 Hz, 1H), 5.15-5.29 (m, 1H), 4.12 (d, J=11.1 Hz, 2H), 3.57-3.73 (m, 2H), 3.07 (m, 4H), 1.87-2.00 (m, 4H), 1.72-1.81 (m, 2H), 1.60-1.71 (m, 2H), 1.45 (s, 6H), 1.29 (s, 6H).

Example 15-1: Synthesis of 3-chloro-7-(6-(methyl (2,2,6,6-tetramethylpiperidin-4-yl)amino)pyridazin-3-yl)quinolin-6-ol

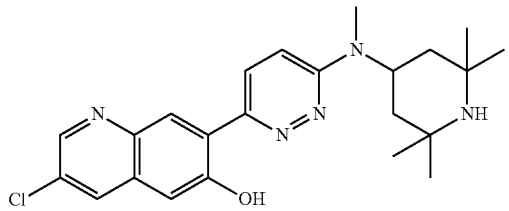

Using procedures described in Example 7-1, Steps 1-2, beginning with 6-(6-methoxyquinolin-7-yl)-N-methyl-N-(2,2,6,6-tetramethylpiperidin-4-yl)pyridazin-3-amine (Example 6-1 Step 3, 50 mg, 0.123 mmol), 3-chloro-7-(6-(methyl(2,2,6,6-tetramethylpiperidin-4-yl)amino)pyridazin-3-yl)quinolin-6-ol (6 mg) was obtained as a light yellow solid. LC/MS Rt=0.57 min. MS (M+1)=426.2.

Example 15-2: Synthesis of 3-bromo-7-(6-(methyl (2,2,6,6-tetramethylpiperidin-4-yl)amino)pyridazin-3-yl)quinolin-6-ol

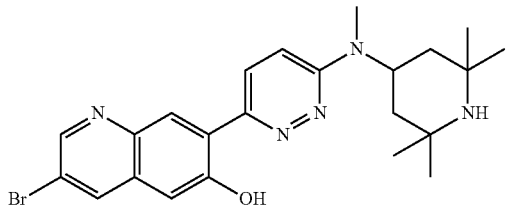 [SMILES: CN(c1ccc(-c2cc3ncc(Cl)cc3cc2O)nn1)C1CC(C)(C)NC(C)(C)C1]

Using procedures described in Example 7-2, Steps 1-2, beginning with 6-(6-methoxyquinolin-7-yl)-N-methyl-N-(2,2,6,6-tetramethylpiperidin-4-yl)pyridazin-3-amine (Example 6-1 Step 3, 200 mg, 0.493 mmol), 3-bromo-7-(6-(methyl(2,2,6,6-tetramethylpiperidin-4-yl)amino)pyridazin-3-yl)quinolin-6-ol (48 mg) was obtained as a light yellow solid. LC/MS Rt=0.60 min. MS (M+1)=472.1. $^1$H NMR (400 MHz, METHANOL-$d_4$) δ 8.71 (d, J=2.3 Hz, 1H), 8.44 (s, 1H), 8.42 (d, J=2.2 Hz, 1H), 8.34 (d, J=9.9 Hz, 1H), 7.40 (d, J=9.9 Hz, 1H), 7.30 (s, 1H), 5.37-5.17 (m, 1H), 3.08 (s, 3H), 1.75 (dd, J=36.1, 12.5 Hz, 4H), 1.47 (s, 6H), 1.32 (s, 6H).

Example 15-3: Synthesis of 3-methyl-7-(6-(methyl (2,2,6,6-tetramethylpiperidin-4-yl)amino)pyridazin-3-yl)quinolin-6-ol

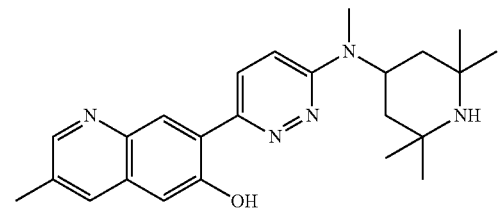

Step 1. 7-Bromo-6-methoxy-3-methylquinoline

According to the general procedure of Matsugi, M, et al, *Tetrahedron Lett.*, 2000, 41, 8523, to a solution of 3-bromo-4-methoxyaniline (1.00 g, 4.95 mmol) in 6 M HCl (25 mL) and toluene (6 mL) heated to 100° C. was added dropwise methacrolein (0.408 mL, 4.95 mmol). Heating was continued for two hours. The reaction was cooled to room temperature and the phases separated. The aqueous phase was basified to pH 12 by addition of 2 M NaOH, extracted with DCM (5×), and ethyl acetate (2×). The combined organics were dried over MgSO$_4$ and concentrated to provide a green residue. Silica gel chromatography (3-40% gradient of EtOAc in DCM) provided the more mobile title compound, 7-bromo-6-methoxy-3-methylquinoline (373 mg) as an off-white solid, TLC (9:1 DCM/EtOAc) R$_f$ 0.6, MS (M+1)=254.2, $^1$H NMR (400 MHz, METHANOL-$d_4$) δ ppm 8.57 (d, J=2.0 Hz, 1H), 8.18 (s, 1H), 8.07 (s, 1H), 7.32 (s, 1H), 4.01 (s, 3H), 2.50 (s, 3H), and the less mobile isomer, 5-bromo-6-methoxy-3-methylquinoline, (245 mg) as a brown solid, TLC (9:1 DCM/EtOAc) R$_f$ 0.6, MS (M+1)=254.2, $^1$H NMR (400 MHz, METHANOL-$d_4$) δ ppm 8.63 (d, J=2.0 Hz, 1H), 8.35-8.43 (m, 1H), 8.03 (d, J=8.6 Hz, 1H), 7.66 (d, J=9.1 Hz, 1H), 4.06 (s, 3H), 2.59 (s, 3H).

Step 2. (6-Methoxy-3-methylquinolin-7-yl)boronic acid

Using procedures described in Example 6-2, Step 2, starting with 7-bromo-6-methoxy-3-methylquinoline (373 mg), (6-methoxy-3-methylquinolin-7-yl)boronic acid was obtained as an off-white solid (176 mg) after purification of the crude product by silica gel chromatography (12 g silica gel, 2-30% MeOH in DCM over 30 column volumes). MS (M+1)=218.3. $^1$H NMR (400 MHz, METHANOL-$d_4$) δ ppm 8.54 (d, J=2.0 Hz, 1H), 8.04 (s, 1H), 7.83 (s, 1H), 7.21 (s, 1H), 3.95 (s, 3H), 2.52 (s, 3H).

Step 3. 6-(6-Methoxy-3-methylquinolin-7-yl)-N-methyl-N-(2,2,6,6-tetramethylpiperidin-4-yl)pyridazin-3-amine Using procedures described in Example 6-2, Step 3, starting with (6-methoxy-3-methylquinolin-7-yl)boronic acid (172 mg, 0.79 mmol), 6-(6-methoxy-3-methylquinolin-7-yl)-N-methyl-N-(2,2,6,6-tetramethylpiperidin-4-yl)pyridazin-3-amine (144 mg) was obtained as a light yellow solid. MS (M+1)=420.6. $^1$H NMR (400 MHz, METHANOL-$d_4$) δ ppm 8.59 (d, J=2.0 Hz, 1H), 8.19 (s, 1H), 8.10 (s, 1H), 7.81 (d, J=9.6 Hz, 1H), 7.38 (s, 1H), 7.14 (d, J=9.6 Hz, 1H), 5.23 (t, J=12.4 Hz, 1H), 3.99 (s, 3H), 3.01 (s, 3H), 2.54 (s, 3H), 1.66-1.74 (m, 2H), 1.51-1.62 (m, 2H), 1.38 (s, 6H), 1.23 (s, 6H).

Step 4. 3-Methyl-7-(6-(methyl(2,2,6,6-tetramethylpiperidin-4-yl)amino)pyridazin-3-yl)quinolin-6-ol 6-(6-Methoxy-3-methylquinolin-7-yl)-N-methyl-N-(2,2,6,6-tetramethylpiperidin-4-yl)pyridazin-3-amine (144 mg, 0.34 mmol) was subjected to methoxy deprotection conditions as described in GENERAL METHOD 2-2. The crude material was subjected to silica gel chromatography (GENERAL METHOD 4-1) to provide 3-methyl-7-(6-(methyl(2,2,6,6-tetramethylpiperidin-4-yl)amino)pyridazin-3-yl)quinolin-6-ol as a yellow solid (107 mg). LC/MS Rt=0.49 min MS (M+1)=406.6. $^1$H NMR (400 MHz, METHANOL-$d_4$) δ ppm 8.54 (d, J=2.0 Hz, 1H), 8.35 (s, 1H), 8.28 (d, J=10.1 Hz, 1H), 7.95 (br. s., 1H), 7.37 (d, J=9.6 Hz, 1H), 7.24 (s, 1H), 5.08-5.24 (m, 1H), 3.04 (s, 3H), 2.51 (s, 3H), 1.68-1.77 (m, 2H), 1.54-1.66 (m, 2H), 1.40 (s, 6H), 1.24 (s, 6H).

Example 16-1: Synthesis of 5-bromo-3-methyl-7-(6-(methyl(2,2,6,6-tetramethylpiperidin-4-yl)amino) pyridazin-3-yl)quinolin-6-ol

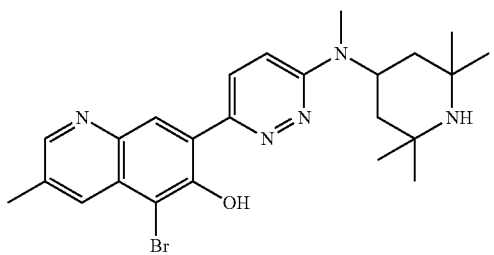

To a solution of 3-methyl-7-(6-(methyl(2,2,6,6-tetramethylpiperidin-4-yl)amino)pyridazin-3-yl)quinolin-6-ol (Example 15-3, 36 mg, 0.089 mmol) in DCM (1 mL) was added N-bromosuccinimide (19 mg, 0.11 mmol). After stirring for one hour, the mixture was diluted with ethyl acetate, washed with saturated sodium bisulfite, brine, dried over magnesium sulfate and concentrated under reduced pressure. The crude material was purified by silica gel chromatography according to GENERAL METHOD 4-1 to provide 5-bromo-3-methyl-7-(6-(methyl(2,2,6,6-tetramethylpiperidin-4-yl)amino)pyridazin-3-yl)quinolin-6-ol (20 mg) as a yellow solid. LC/MS Rt=0.58 min. MS (M+1)=486.4. $^1$H NMR (400 MHz, METHANOL-$d_4$) δ ppm 8.58 (d, J=2.0 Hz, 1H), 8.38 (s, 1H), 8.34 (d, J=10.1 Hz, 1H), 8.32 (s, 1H), 7.40 (d, J=10.1 Hz, 1H), 5.22 (m, 1H), 3.07 (s, 3H), 2.59 (s, 3H), 1.73-1.82 (m, 2H), 1.60-1.72 (m, 2H), 1.46 (s, 6H), 1.30 (s, 6H).

Example 17-1: Synthesis of 6-hydroxy-1-methyl-7-(6-(methyl(2,2,6,6-tetramethylpiperidin-4-yl)amino) pyridazin-3-yl)quinolin-4(1H)-one

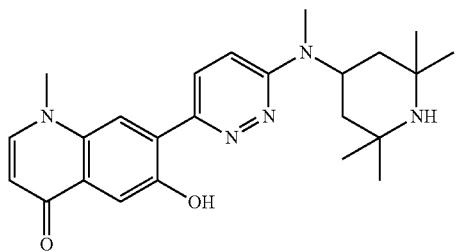 [SMILES: CN(c1ccc(-c2cc3c(cc2O)c(=O)ccn3C)nn1)C1CC(C)(C)NC(C)(C)C1]

Step 1: 6-methoxy-1-methyl-7-(6-(methyl(2,2,6,6-tetramethylpiperidin-4-yl)amino)pyridazin-3-yl) quinolin-4(1H)-one 6-Methoxy-7-(6-(methyl(2,2,6,6-tetramethylpiperidin-4-yl)amino)pyridazin-3-yl)quinolin-4(1H)-one (PREPARATION 13, Step 3) (0.07 g, 0.17 mmol), iodomethane (0.05 g, 0.32 mmol) and KH (50% by weight in paraffin, 0.02 g, 0.03 mmol) were stirred in dry THF (2.0 mL) and DMF (0.6 mL) at room temperature under dry nitrogen for 1 h. A solution of sodium bicarbonate was added to the reaction mixture. The aqueous phase was extracted with 9:1 DCM/MeOH (3×). The combined organic phases were dried over anhydrous $Na_2SO_4$, filtered and concentrated under reduced pressure. The crude material was purified by silica gel chromatography (2-15% 7 M ammonia in MeOH gradient, in DCM) to afford 6-methoxy-1-methyl-7-(6-(methyl(2,2,6,6-tetramethylpiperidin-4-yl)amino)pyridazin-3-yl)quinolin-4(1H)-one as a brown solid (90 mg). MS (M+1)=436.5. $^1$H NMR (400 MHz, METHANOL-$d_4$) δ 8.10 (s, 1H), 8.02 (d, J=7.4 Hz, 1H), 7.98 (d, J=9.8 Hz, 1H), 7.92 (s, 1H), 7.18 (d, J=9.7 Hz, 1H), 6.33 (d, J=7.4 Hz, 1H), 5.47-5.30 (m, 1H), 4.01 (s, 3H), 4.01 (s, 3H), 3.03 (s, 3H), 1.79 (d, J=13.1 Hz, 2H), 1.70 (t, J=12.9 Hz, 2H), 1.47 (s, 6H), 1.32 (s, 6H).

Step 2: 6-Hydroxy-1-methyl-7-(6-(methyl(2,2,6,6-tetramethylpiperidin-4-yl)amino)pyridazin-3-yl) quinolin-4(1H)-one A solution of $BBr_3$ (1.0 M in DCM, 1.0 mL, 1.0 mmol) was added to 6-methoxy-1-methyl-7-(6-(methyl(2,2,6,6-tetramethylpiperidin-4-yl)amino)pyridazin-3-yl)quinolin-4 (1H)-one (0.09 g, 0.20 mmol) in DCM (2.0 mL) and the reaction was stirred at reflux for 5 h. The reaction mixture was then added dropwise to MeOH (10 mL) and the solvent was concentrated under reduced pressure. The crude material was purified via preparative reverse-phase HPLC (15 to 40% acetonitrile in water, 5 mM ammonium hydroxide modifier) and the product-containing fractions were concentrated in vacuo. The resulting solid was suspended in acetonitrile/water (3/1 mL) and 1 M aqueous HCl (3 equivalents) was then added. The solvent was concentrated in vacuo to afford 6-hydroxy-1-methyl-7-(6-(methyl(2,2,6,6-tetramethylpiperidin-4-yl)amino)pyridazin-3-yl)quinolin-4 (1H)-one hydrochloride salt as a yellow solid (28 mg). LC/MS Rt=0.43 min. MS (M+1)=422.2. $^1$H NMR (400 MHz, METHANOL-$d_4$) δ 8.80 (d, J=7.0 Hz, 1H), 8.58 (d, J=10.2 Hz, 1H), 8.57 (s, 1H), 8.06 (d, J=10.0 Hz, 1H), 7.94 (s, 1H), 7.13 (d, J=6.7 Hz, 1H), 5.02 (br.s, 1H), 4.43 (s, 3H), 3.26 (s, 3H), 2.27-2.02 (m, 4H), 1.68 (s, 6H), 1.59 (s, 6H).

Example 18-1: Synthesis of 2,3-dimethyl-7-(6-(methyl(2,2,6,6-tetramethylpiperidin-4-yl)amino) pyridazin-3-yl)quinoxalin-6-ol

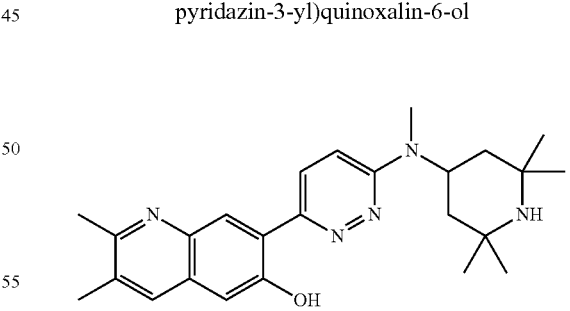

Step 1: 6-Bromo-7-ethoxy-2,3-dimethylquinoxaline

Biacetyl (0.51 mL, 5.85 mmol) was added to 4-bromo-5-ethoxybenzene-1,2-diamine (Example 13-1, Step 1) (1.04 g, 4.50 mmol) and ammonium chloride (0.24 g, 4.50 mmol) in MeOH (45 mL) and the reaction was stirred at reflux for 3 h. Silica gel (6 g) was added and the solvent was removed in vacuo. Silica gel chromatography (gradient of 5-40% 3:1 EtOAc/EtOH, in heptane) provided 6-bromo-7-ethoxy-2,3- dimethylquinoxaline as an orange solid (1.04 g). MS=281.2. ¹H NMR (400 MHz, METHANOL-d₄) δ 8.15 (s, 1H), 7.34 (s, 1H), 4.28 (q, J=7.0 Hz, 2H), 2.70 (s, 3H), 2.70 (s, 3H), 1.55 (t, J=7.0 Hz, 3H).

Step 2:
(7-Ethoxy-2,3-dimethylquinoxalin-6-yl)boronic acid

Bis(pinacolato) diboron (0.50 g, 2.0 mmol), KOAc (0.29 g, 3.0 mmol), and PdCl₂(dppf).CH₂Cl₂ (0.06 g, 0.07 mmol) were added to 6-bromo-7-ethoxy-2,3-dimethylquinoxaline (0.28 g, 0.99 mmol) in dioxane (5 mL). The mixture heated at 80° C. overnight under an atmosphere of nitrogen. The reaction mixture was cooled to RT, filtered through Celite® (pre-packed filter funnel) washing with EtOAc, and concentrated in vacuo to afford (7-ethoxy-2,3-dimethylquinoxalin-6-yl)boronic acid as a black solid. MS (M+1)=247.1.

Step 3: 6-(7-Ethoxy-2,3-dimethylquinoxalin-6-yl)-N-methyl-N-(2,2,6,6-tetramethylpiperidin-4-yl) pyridazin-3-amine (7-Ethoxy-2,3-dimethylquinoxalin-6-yl)boronic acid (0.49 g, 1.98 mmol), 6-chloro-N-methyl-N-(2,2,6,6-tetramethylpiperidin-4-yl)pyridazin-3-amine (0.85 g, 3.00 mmol), and Na₂CO₃ (0.81 g, 3.9 mmol) were added to a microwave vial. Pd(PPh₃)₄(0.23 g, 0.20 mmol) was then added followed by addition of 1,4-dioxane (8.5 mL) and water (1.4 mL). The reaction mixture was sealed and heated in a Biotage® Initiator microwave reactor at 130° C. for 1 h. A solution of NaHCO₃ was added to the reaction and the aqueous phase was extracted with DCM (3×). The combined organic phases were dried over anhydrous Na₂SO₄ filtered, and concentrated under reduced pressure. The crude material was purified by silica gel chromatography (1-15% 7 M ammonia in MeOH gradient, in DCM) followed by a second purification via reverse-phase preparative HPLC (5-20% acetonitrile in water, 7.5% formic acid modifier). The product-containing fractions were free-based by catch and release using SiliaBond Propylsulphonic Acid® (4 eq, acetonitrile as eluent and a 2 N ammonia solution in MeOH to release the material). The solvent was concentrated in vacuo to give 6-(7-ethoxy-2,3-dimethylquinoxalin-6-yl)-N-methyl-N-(2,2,6,6-tetramethylpiperidin-4-yl)pyridazin-3-amine as a yellow solid (0.35 g). MS (M+1)=449.5. ¹H NMR (400 MHz, METHANOL-d₄) δ 8.23 (s, 1H), 7.93 (d, J=9.6 Hz, 1H), 7.47 (s, 1H), 7.20 (d, J=9.7 Hz, 1H), 5.31 (t, J=12.6 Hz, 1H), 4.32 (q, J=7.0 Hz, 2H), 3.06 (s, 3H), 2.77 (s, 3H), 2.75 (s, 3H), 1.77 (dd, J=12.6, 3.5 Hz, 2H), 1.64 (t, J=12.4 Hz, 2H), 1.50 (t, J=7.0 Hz, 3H), 1.44 (s, 6H), 1.29 (s, 6H).

Step 4: 2,3-Dimethyl-7-(6-(methyl(2,2,6,6-tetramethylpiperidin-4-yl)amino)pyridazin-3-yl)quinoxalin-6-ol A solution of BBr₃ (1.0 M in DCM, 7.7 mL, 7.7 mmol) was added to 6-(7-ethoxy-2,3-dimethylquinoxalin-6-yl)-N-methyl-N-(2,2,6,6-tetramethylpiperidin-4-yl)pyridazin-3-amine (0.35 g, 0.77 mmol) in DCM (7 mL). The reaction mixture was stirred at 40° C. overnight. The reaction mixture was added to MeOH (50 mL) at 0° C. and the solvent was concentrated under reduced pressure. The crude material was purified by silica gel chromatography (1-15% 7 M ammonia in MeOH gradient, in DCM). The product-containing fractions were concentrated in vacuo and the resulting solid was dissolved in 4:1 acetonitrile/water (15 mL). 1 M aqueous HCl (3 equivalents) was added and solvent was concentrated in vacuo to afford the hydrochloride salt of 2,3-dimethyl-7-(6-(methyl(2,2,6,6-tetramethylpiperidin-4-yl)amino)pyridazin-3-yl)quinoxalin-6-ol as a yellow solid (0.26 g). LC/MS Rt=0.53 min. MS (M+1)=421.3. ¹H NMR (400 MHz, METHANOL-d₄) δ 8.52 (d, J=8.2 Hz, 1H), 8.43 (s, 1H), 8.11 (br.s, 1H), 7.56 (s, 1H), 4.92 (partially obscured by residual water peak, 1H), 3.25 (s, 3H), 2.86 (s, 3H), 2.81 (s, 3H), 2.36-1.95 (m, 4H), 1.66 (s, 6H), 1.58 (s, 6H).

Examples 18-2 and 18-3: Synthesis of 2-methyl-7-(6-(methyl(2,2,6,6-tetramethylpiperidin-4-yl)amino) pyridazin-3-yl)quinoxalin-6-ol and 3-methyl-7-(6-(methyl(2,2,6,6-tetramethylpiperidin-4-yl)amino) pyridazin-3-yl)quinoxalin-6-ol

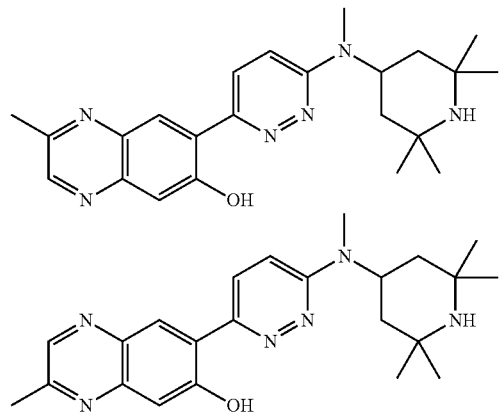

Step 1: 6-Bromo-7-ethoxy-2-methylquinoxaline and 7-bromo-6-ethoxy-2-methylquinoxaline 2-Oxopropanal (8.26 g, 45.8 mmol) was added dropwise to 4-bromo-5-ethoxybenzene-1,2-diamine (Example 13-1 Step 1) (8.41 g, 36.4 mmol) in THF (360 mL) and the reaction was stirred overnight. The solvent was removed in vacuo and the crude material purified by silica gel chromatography (gradient of 25-50% 3:1 EtOAc/EtOH, in heptane) to give a mixture of 6-bromo-7-ethoxy-2-methylquinoxaline and 7-bromo-6-ethoxy-2-methylquinoxaline (2.04 g). MS (M+1)=269.1. ¹H NMR (400 MHz, CHLOROFORM-d) as a 1.7:1.0 mixture of regioisomers δ 8.67 (s) and 8.60 (s) (1H), 8.30 (s) and 8.26 (s) (1H), 7.36 (s) and 7.35 (s) (1H), 4.26 (q, J=7.0 Hz) and 4.26 (q, J=7.0 Hz) (2H), 2.71 (s, 3H), 1.57 (t, J=6.9 Hz) and 1.54 (t, 7.0 Hz) (3H).

Step 2: 6-Ethoxy-2-methyl-7-(4,4,5,5-tetramethyl-1,3,2-dioxaborolan-2-yl) quinoxaline, (7-ethoxy-3-methylquinoxalin-6-yl)boronic acid, and 7-ethoxy-2-methyl-6-(4,4,5,5-tetramethyl-1,3,2-dioxaborolan-2-yl)quinoxaline and (7-ethoxy-2-methylquinoxalin-6-yl)boronic acid Bis(pinacolato)diboron (4.85 g, 19.1 mmol), KOAc (2.25 g, 22.3 mmol), PdCl₂(dppf).CH₂Cl₂ (0.47 g, 0.08 mmol), 6-bromo-7-ethoxy-2-methylquinoxaline and 7-bromo-6-ethoxy-2-methylquinoxaline (2.04 g, 7.64 mmol) in dioxane (75 mL) were heated at 80° C. overnight. The reaction mixture was cooled to RT, filtered through Celite® (pre-packed filter funnel) washing with EtOAc, and concentrated in vacuo. Silica gel chromatography (gradient of 5-30%

MeOH in DCM) afforded a 2.1:1.0 mixture of (7-ethoxy-3-methylquinoxalin-6-yl)boronic acid, (7-ethoxy-2-methylquinoxalin-6-yl)boronic acid and 6-ethoxy-2-methyl-7-(4,4,5,5-tetramethyl-1,3,2-dioxaborolan-2-yl)quinoxaline, 7-ethoxy-2-methyl-6-(4,4,5,5-tetramethyl-1,3,2-dioxaborolan-2-yl)quinoxaline as a dark oil. (M+1)=233.3 and 315.3.

Step 3: 6-(7-Ethoxy-3-methylquinoxalin-6-yl)-N-methyl-N-(2,2,6,6-tetramethylpiperidin-4-yl)pyridazin-3-amine, and 6-(7-ethoxy-2-methylquinoxalin-6-yl)-N-methyl-N-(2,2,6,6-tetramethylpiperidin-4-yl)pyridazin-3-amine A mixture of 6-ethoxy-2-methyl-7-(4,4,5,5-tetramethyl-1,3,2-dioxaborolan-2-yl)quinoxaline, (7-ethoxy-3-methylquinoxalin-6-yl)boronic acid, 7-ethoxy-2-methyl-6-(4,4,5,5-tetramethyl-1,3,2-dioxaborolan-2-yl)quinoxaline and (7-ethoxy-2-methylquinoxalin-6-yl)boronic acid, 6-chloro-N-methyl-N-(2,2,6,6-tetramethylpiperidin-4-yl)pyridazin-3-amine (Intermediate 1, 2.52 g, 8.90 mmol), aqueous tripotassium phosphate (0.5 M, 36 mL, 18 mmol), $2^{nd}$ generation XPhos precatalyst (0.21 g, 0.27 mmol) and XPhos (0.12 g, 0.27 mmol) in 1:1 THF/water (64 mL) was stirred at 50° C. overnight. The reaction mixture was concentrated in vacuo and diluted with water. The aqueous phase was extracted with 9:1 DCM/MeOH (3×). The combined organic phases were dried over anhydrous $Na_2SO_4$, filtered and concentrated under reduced pressure. Silica gel chromatography (1-15% 7 M ammonia in MeOH gradient, in DCM) provided 6-(7-ethoxy-3-methylquinoxalin-6-yl)-N-methyl-N-(2,2,6,6-tetramethylpiperidin-4-yl)pyridazin-3-amine and 6-(7-ethoxy-2-methylquinoxalin-6-yl)-N-methyl-N-(2,2,6,6-tetramethylpiperidin-4-yl)pyridazin-3-amine (2.60 g) as a 2:1 mixture of regioisomers. MS (M+1)=435.5. $^1$H NMR (400 MHz, METHANOL-$d_4$) δ 8.75 (s) and 8.68 (s) (1H), 8.27 (s) and 8.23 (s) (1H), 7.91 (d, J=9.7 Hz) and 7.90 (d, J=9.7 Hz) (1H), 7.52 (s) and 7.46 (s) (1H), 7.20-7.10 (m, 1H), 5.27 (t, J=12.6 Hz, 1H), 4.31 (q, J=7.0 Hz) and 4.30 (q, J=6.9 Hz) (2H), 3.02 (s) and 2.93 (s) (3H), 2.75 (s) and 2.74 (s) (3H), 1.72 (dd, J=12.5, 3.5 Hz) and 1.68-1.50 (m) (4H), 1.48 (t, J=7.0 Hz) and 1.48 (t, J=7.0 Hz) (3H), 1.39 (s) and 1.33 (s) (6H), 1.24 (s) and 1.20 (s) (6H).

Step 4: 2-Methyl-7-(6-(methyl(2,2,6,6-tetramethylpiperidin-4-yl)amino)pyridazin-3-yl)quinoxalin-6-ol, and 3-methyl-7-(6-(methyl(2,2,6,6-tetramethylpiperidin-4-yl)amino)pyridazin-3-yl)quinoxalin-6-ol A solution of $BBr_3$ (1.0 M in DCM, 16 mL, 16 mmol) was added to 6-(7-ethoxy-2-methylquinoxalin-6-yl)-N-methyl-N-(2,2,6,6-tetramethylpiperidin-4-yl)pyridazin-3-amine and 6-(7-ethoxy-3-methylquinoxalin-6-yl)-N-methyl-N-(2,2,6,6-tetramethylpiperidin-4-yl)pyridazin-3-amine (0.70 g, 1.61 mmol) in DCM (16 mL) and the reaction was stirred at reflux overnight. The mixture was then added dropwise to MeOH (50 mL) at 0° C. and the solvent concentrated under reduced pressure. The crude material was purified via preparative reverse-phase HPLC (15 to 40% acetonitrile in water, 5 mM ammonium hydroxide modifier) and the regioisomers were separated via preparative SFC (AS-H 21×250 mm column, 15% MeOH 10 mM $NH_4OH$ in $CO_2$). Residual palladium was scavenged from each using GENERAL METHOD 6-1. The two solids were separately suspended in 3:1 acetonitrile/water (8 mL). 1 M aqueous HCl (3 equivalents) was added and the solvent concentrated in vacuo to afford two yellow solids, the major regioisomer (56 mg) and the minor regioisomer (19 mg). NMR structure determination attempts were not able to conclusively distinguish the two regioisomers.

Major regioisomer, 18-3 LC/MS Rt=0.49 min. MS (M+1)=407.2. $^1$H NMR (400 MHz, METHANOL-$d_4$) δ 8.80 (s, 1H), 8.53 (d, J=9.9 Hz, 1H), 8.43 (s, 1H), 8.08 (d, J=10.0 Hz, 1H), 7.50 (s, 1H), 5.00 (partially obscured by residual water peak, 1H) 3.23 (s, 3H), 2.80 (s, 3H), 2.19-1.99 (m, 4H), 1.66 (s, 6H), 1.58 (s, 6H).

Minor regioisomer, 18-2 LC/MS Rt=0.50 min; MS (M+1)=407.3. $^1$H NMR (400 MHz, METHANOL-$d_4$) δ 8.86 (s, 1H), 8.54 (d, J=9.9 Hz, 1H), 8.34 (s, 1H), 8.10 (d, J=9.9 Hz, 1H), 7.56 (s, 1H), 4.97 (partially obscured by residual water peak, 1H), 3.24 (s, 3H), 2.77 (s, 3H), 2.23-1.98 (m, 4H), 1.66 (s, 6H), 1.58 (s, 6H).

Example 19-1: Synthesis of 4-methoxy-6-(6-(methyl(2,2,6,6-tetramethylpiperidin-4-yl)amino)pyridazin-3-yl)quinolin-7-ol

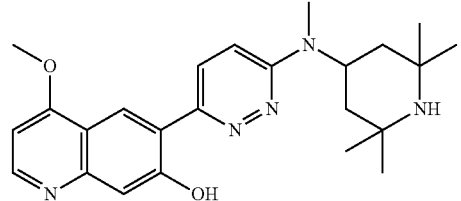 [SMILES: COc1ccnc2cc(O)c(-c3ccc(N(C)C4CC(C)(C)NC(C)(C)C4)nn3)cc12]

To a mixture of Intermediate 12 (19.5 mg, 0.046 mmol) in MeOH (0.8 mL) was added NaOMe (25 wt % in methanol, 0.084 mL, 0.37 mmol). The mixture was heated at 120° C. under microwave irradiation for 1 h. An additional portion of NaOMe (25 wt % in methanol, 0.08 mL) was added and the mixture was then heated at 130° C. for 2 h. The mixture was cooled to room temperature, acidified by addition of 1 M HCl in ether and subjected to SCX purification (GENERAL METHOD 3-1, 1 g SiliaBond Propylsulfonic Acid® cartridge). The crude product was further purified by preparative reverse-phase HPLC to obtain the title compound as a white solid (8 mg). LC/MS Rt=0.39 min. MS (M+1)=422.3. $^1$H NMR (METHANOL-$d_4$) δ 8.50 (s, 1H), 8.47 (d, J=5.6 Hz, 1H), 8.14 (d, J=10.1 Hz, 1H), 7.25 (s, 1H), 7.24 (d, J=10.1 Hz, 1H), 6.74 (d, J=5.6 Hz, 1H), 5.07 (t, J=12.1 Hz, 1H), 4.02 (s, 3H), 2.94 (s, 3H), 1.58-1.70 (m, 2H), 1.46-1.58 (m, 2H), 1.32 (s, 6H), 1.16 (s, 6H).

Example 20-1: Synthesis of 4-(azetidin-1-yl)-2-methyl-6-(6-(methyl(2,2,6,6-tetramethylpiperidin-4-yl)amino)pyridazin-3-yl)quinolin-7-ol

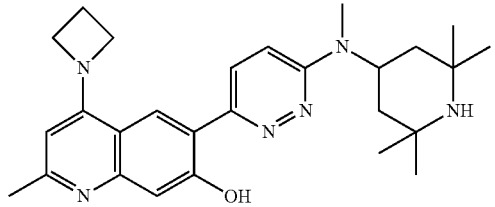

To a mixture of Intermediate 11 (31 mg, 0.070 mmol) in NMP (0.8 mL) was added azetidine (0.047 mL, 0.70 mmol).

The mixture was heated at 130° C. under microwave irradiation for 2 h. The mixture was cooled to room temperature, acidified by addition of 1 M HCl in ether and subjected to SCX purification (GENERAL METHOD 3-1, 1 g SiliaBond Propylsulfonic Acid® cartridge). The crude product was further purified by preparative reverse-phase HPLC to obtain 4-(azetidin-1-yl)-2-methyl-6-(6-(methyl(2,2,6,6-tetramethylpiperidin-4-yl)amino)pyridazin-3-yl)quinolin-7-ol as a light yellow solid (16 mg). LC/MS Rt=0.48 min. MS (M+1)=461.3. $^1$H NMR (METHANOL-$d_4$) δ 8.17 (s, 1H), 8.11 (d, J=9.6 Hz, 1H), 7.14 (d, J=9.6 Hz, 1H), 6.74 (s, 1H), 5.81 (s, 1H), 5.22 (t, J=12.4 Hz, 1H), 4.62 (t, J=7.6 Hz, 4H), 2.99 (s, 3H), 2.56 (dt, J=15.5, 7.6 Hz, 2H), 2.44 (s, 3H), 1.66-1.75 (m, 2H), 1.54-1.66 (m, 2H), 1.40 (s, 6H), 1.25 (s, 6H).

Example 20-2: Synthesis of 7-hydroxy-2-methyl-6-(6-(methyl(2,2,6,6-tetramethylpiperidin-4-yl)amino)pyridazin-3-yl)quinoline-4-carbonitrile

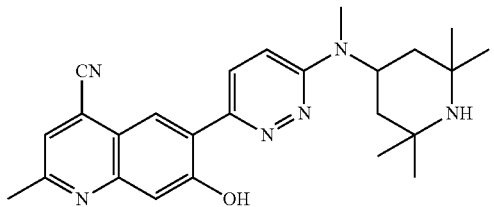

A mixture of Intermediate 11 (40 mg, 0.091 mmol), zinc cyanide (21 mg, 0.18 mmol) and tetrakis(triphenylphosphine)palladium(0) (11 mg, 9.1 µmol) in NMP (1 mL) was evacuated, filled with $N_2$ (4×) and heated under microwave irradiation at 150° C. for 1.5 h. The reaction mixture was filtered through celite, washed with MeOH, concentrated, and subjected to SCX purification (GENERAL METHOD 3-1, 1 g SiliaBond Propylsulfonic Acid® cartridge). The crude product was purified by preparative reverse-phase HPLC to obtain 7-hydroxy-2-methyl-6-(6-(methyl(2,2,6,6-tetramethylpiperidin-4-yl)amino)pyridazin-3-yl)quinoline-4-carbonitrile as a yellow solid (22 mg). LC/MS Rt=0.54 min. MS (M+1)=431.3. $^1$H NMR (METHANOL-$d_4$) δ 8.37 (s, 1H), 8.24 (d, J=9.6 Hz, 1H), 7.60 (s, 1H), 7.42 (s, 1H), 7.33 (d, J=9.6 Hz, 1H), 5.23 (t, J=11.9 Hz, 1H), 3.05 (s, 3H), 2.71 (s, 3H), 1.70-1.81 (m, 2H), 1.58-1.69 (m, 2H), 1.43 (s, 6H), 1.27 (s, 6H).

Example 20-3: Synthesis of 4-cyclopropyl-2-methyl-6-(6-(methyl(2,2,6,6-tetramethylpiperidin-4-yl)amino)pyridazin-3-yl)quinolin-7-ol

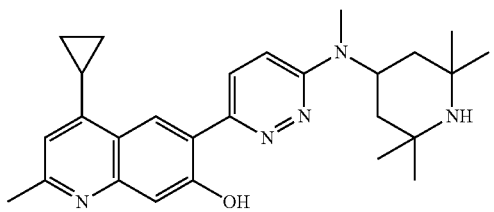

Step 1: 6-(4-Cyclopropyl-7-methoxy-2-methylquinolin-6-yl)-N-methyl-N-(2,2,6,6-tetramethylpiperidin-4-yl)pyridazin-3-amine A flask containing a mixture of 6-(4-chloro-7-methoxy-2-methylquinolin-6-yl)-N-methyl-N-(2,2,6,6-tetramethylpiperidin-4-yl)pyridazin-3-amine (PREPARATION 11 Step 5, 48 mg, 0.11 mmol), cyclopropyltrifluoroborate (24 mg, 0.16 mmol), n-butyl di-1-adamantylphosphine (5 mg, 0.013 mmol) and cesium carbonate (103 mg, 0.32 mmol) in toluene (1 mL) and water (0.1 mL) was evacuated, filled with $N_2$ (4×) and heated at 100° C. for 7 h. The reaction mixture was concentrated and acidified by addition of 1 M HCl in ether. SCX purification (GENERAL METHOD 3-1, 2 g SiliaBond Propylsulfonic Acid® cartridge) provided the crude product as a light brown solid (50 mg, 93% pure).

Step 2: 4-Cyclopropyl-2-methyl-6-(6-(methyl(2,2,6,6-tetramethylpiperidin-4-yl)amino)pyridazin-3-yl)quinolin-7-ol 6-(4-Cyclopropyl-7-methoxy-2-methylquinolin-6-yl)-N-methyl-N-(2,2,6,6-tetramethylpiperidin-4-yl)pyridazin-3-amine (50 mg, 0.10 mmol) was subjected to methoxy deprotection conditions as described in GENERAL METHOD 2-3 using $BBr_3$. Preparative reverse-phase HPLC purification provided 4-cyclopropyl-2-methyl-6-(6-(methyl(2,2,6,6-tetramethylpiperidin-4-yl)amino)pyridazin-3-yl)quinolin-7-ol as a beige solid (28 mg). LC/MS Rt=0.46 min. MS (M+1)=446.3. $^1$H NMR (METHANOL-$d_4$) δ 8.70 (s, 1H), 8.29 (d, J=9.6 Hz, 1H), 7.36 (s, 1H), 7.32 (d, J=9.6 Hz, 1H), 6.86 (s, 1H), 5.17 (t, J=12.4 Hz, 1H), 3.04 (s, 3H), 2.60 (s, 3H), 2.53-2.65 (m, 1H), 1.67-1.80 (m, 2H), 1.54-1.67 (m, 2H), 1.41 (s, 6H), 1.26 (s, 6H), 1.21-1.24 (m, 2H), 0.88-0.95 (m, 2H).

Example 20-4: Synthesis of 4-(3,6-dihydro-2H-pyran-4-yl)-2-methyl-6-(6-(methyl(2,2,6,6-tetramethylpiperidin-4-yl)amino)pyridazin-3-yl)quinolin-7-ol

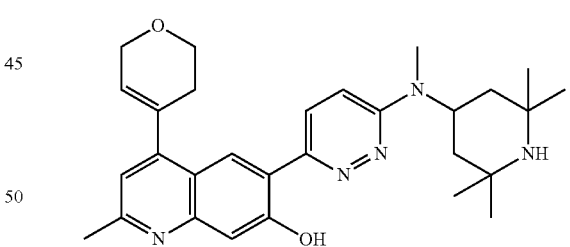

A mixture of Intermediate 11 (27 mg, 0.061 mmol), 3,6-dihydro-2H-pyran-4-boronic acid pinacol ester (38.7 mg, 0.18 mmol), tetrakis(triphenylphosphine)palladium(0) (7 mg, 6 µmol) and $NaHCO_3$ (1 M aqueous solution, 0.18 ml, 0.18 mmol) in 1,4-dioxane (0.8 mL) was evacuated, filled with $N_2$ (4×) and heated under microwave irradiation at 120° C. for 1 h. The reaction mixture was filtered through Celite®, washed with MeOH, concentrated, and subjected to SCX purification (GENERAL METHOD 3-1, 1 g SiliaBond Propylsulfonic Acid® cartridge). The crude product was further purified by Silica Gel Chromatography (GENERAL METHOD 4-1) to obtain 4-(3,6-dihydro-2H-pyran-4-yl)-2-methyl-6-(6-(methyl(2,2,6,6-tetramethylpiperidin-4-yl)amino)pyridazin-3-yl)quinolin-7-ol as a yellow solid (27 mg). LC/MS Rt=0.43 min. MS (M+1)=488.3. $^1$H NMR (METHANOL-$d_4$) δ 8.36 (s, 1H), 8.12 (d, J=10.1 Hz, 1H), 7.38 (s, 1H), 7.30 (d, J=10.1 Hz, 1H), 7.08 (s, 1H), 6.01 (t, J=1.5 Hz, 1H), 5.14 (t, J=12.1 Hz, 1H), 4.41 (q, J=2.5 Hz, 2H), 4.04 (t, J=5.3 Hz, 2H), 3.03 (s, 3H), 2.65 (s, 3H), 2.56 (dd, J=4.5, 2.5 Hz, 2H), 1.67-1.74 (m, 2H), 1.52-1.64 (m, 2H), 1.39 (s, 6H), 1.20-1.27 (m, 6H).

Example 20-5: Synthesis of 2-methyl-6-(6-(methyl (2,2,6,6-tetramethylpiperidin-4-yl)amino)pyridazin-3-yl)-4-(tetrahydro-2H-pyran-4-yl)quinolin-7-ol formate salt

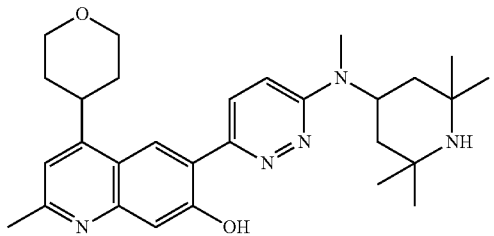

A mixture of Example 20-4 (14 mg, 0.029 mmol), Pd—C (3 mg, 10 wt % on carbon, 3 μmol), Pd(OH)$_2$ (2.0 mg, 20 wt % on carbon, 3 μmol) and one drop of concentrated HCl aqueous solution in methanol (10 mL) was evacuated, filled with H$_2$ (4×) and shaken under H$_2$ (50 psi) on a Parr shaker hydrogenator at room temperature overnight. The reaction mixture was filtered through Celite®, washed with MeOH, concentrated, and subjected to SCX purification (GENERAL METHOD 3-1, 1 g SiliaBond Propylsulfonic Acid® cartridge). The crude product was further purified by preparative reverse-phase HPLC to obtain 2-methyl-6-(6-(methyl(2,2,6,6-tetramethylpiperidin-4-yl)amino)pyridazin-3-yl)-4-(tetrahydro-2H-pyran-4-yl)quinolin-7-ol formate salt as a yellow solid (6 mg). LC/MS Rt=0.42 min. MS (M+1)=490.4. $^1$H NMR (METHANOL-$d_4$) δ 8.42 (s, 1H), 8.40 (s, 1H), 8.23 (d, J=9.8 Hz, 1H), 7.30 (s, 1H), 7.25 (d, J=9.8 Hz, 1H), 7.11 (s, 1H), 5.40 (p, J=8.0 Hz, 1H), 4.07-3.97 (m, 2H), 3.68 (m, 3H), 2.97 (s, 3H), 2.57 (s, 3H), 1.94-1.75 (m, 8H), 1.57 (s, 6H), 1.42 (s, 6H).

Example 20-6: Synthesis of 2-methyl-6-(6-(methyl (2,2,6,6-tetramethylpiperidin-4-yl)amino)pyridazin-3-yl)-4-(oxetan-3-yl)quinolin-7-ol

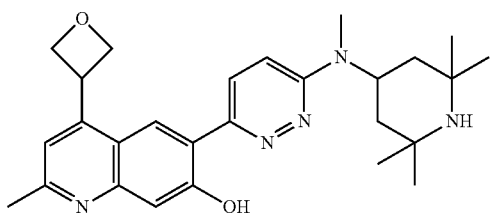

To a mixture of Intermediate 11 (46 mg, 0.11 mmol), 3-iodooxetane (27 mg, 0.15 mmol), FeSO$_4$.7H$_2$O (10 mg, 0.034 mmol) and H$_2$SO$_4$ (0.024 mL, 0.45 mmol, ~1 drop) in DMSO (0.5 mL) was added H$_2$O$_2$(30% aqueous solution, 0.035 mL, 0.34 mmol) at room temperature. After 30 min, another portion of FeSO$_4$.7H$_2$O (9.5 mg, 0.034 mmol) was added and the mixture was stirred at room temperature for 40 min. Further FeSO$_4$.7H$_2$O (9.5 mg, 0.034 mmol) and H$_2$O$_2$(30% aqueous solution, 0.035 mL, 0.34 mmol) was added and the mixture was stirred at room temperature for 60 min, treated with Na$_2$S$_2$O$_3$ (0.5 mL, 20% aqueous solution), and subjected to SCX purification (GENERAL METHOD 3-1, 2 g SiliaBond Propylsulfonic Acid® cartridge). The crude product was further purified by preparative reverse-phase HPLC to obtain 2-methyl-6-(6-(methyl (2,2,6,6-tetramethylpiperidin-4-yl)amino)pyridazin-3-yl)-4-(oxetan-3-yl)quinolin-7-ol (5 mg) as a yellow solid. MS (M+1)=462.3. $^1$H NMR (METHANOL-$d_4$) δ 8.22 (d, J=10.1 Hz, 1H), 8.05 (s, 1H), 7.39 (s, 1H), 7.26-7.35 (m, 2H), 5.29 (dd, J=8.1, 5.6 Hz, 2H), 5.08 (q, J=7.9, 1H), 4.97 (dd, J=7.1, 5.7 Hz, 2H), 3.03 (s, 3H), 2.69 (s, 3H), 1.71 (dd, J=12.6, 3.6 Hz, 2H), 1.59 (t, J=12.4 Hz, 2H), 1.40 (s, 6H), 1.24 (s, 6H).

Example 21-1: Synthesis of 4-(dimethylamino)-6-(6-(methyl(2,2,6,6-tetramethylpiperidin-4-yl)amino) pyridazin-3-yl)quinolin-7-ol di-formate salt

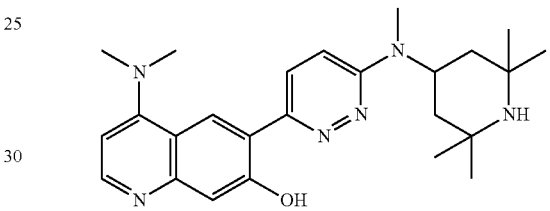

To a mixture of Intermediate 12 (45 mg, 0.094 mmol) in NMP (1 mL) was added dimethylamine (2 M in THF, 0.25 mL, 0.50 mmol). The mixture was heated at 140° C. under microwave irradiation for 1.5 h. The mixture was cooled to room temperature, acidified by addition of 1 M HCl in ether and subjected to SCX purification (GENERAL METHOD 3-1, 1 g SiliaBond Propylsulfonic Acid® cartridge). The crude product was further purified by preparative reverse-phase HPLC to obtain 4-(dimethylamino)-6-(6-(methyl(2,2,6,6-tetramethylpiperidin-4-yl)amino)pyridazin-3-yl)quinolin-7-ol di-formate as a light yellow solid (25 mg). LC/MS Rt=0.43 min. MS (M+1)=435.3. $^1$H NMR (METHANOL-$d_4$) 8.71 (s, 1H), 8.46 (s, 2H), 8.28 (d, J=9.9 Hz, 1H), 8.21 (d, J=7.1 Hz, 1H), 7.39 (d, J=9.8 Hz, 1H), 7.23 (s, 1H), 6.82 (d, J=7.1 Hz, 1H), 5.49 (tt, J=11.0, 5.0 Hz, 1H), 3.54 (s, 6H), 3.08 (s, 3H), 2.05-1.93 (m, 5H), 1.66 (s, 6H), 1.52 (s, 6H).

Example 22-1: Synthesis of 7-hydroxy-6-(6-(methyl (2,2,6,6-tetramethylpiperidin-4-yl)amino)pyridazin-3-yl)quinazolin-4(1H)-one

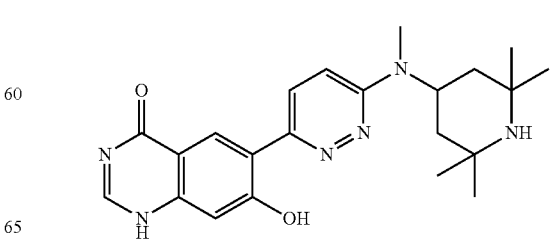

Step 1: 2-Amino-5-bromo-4-methoxybenzoic acid

To a mixture of 4-methoxyanthranilic acid (0.67 g, 4.0 mmol) in DCM (10 mL) and DMF (3 mL) was added NBS (0.71 g, 4.0 mmol) at 0° C. The mixture was stirred at room temperature for 4 h, then concentrated and subjected to silica gel chromatography (5-100% EtOAc/Heptane) to provide 2-amino-5-bromo-4-methoxybenzoic acid as a beige solid (1.30 g, containing 1 equivalent succinamide). MS (M−1)=244.3/246.3. $^1$H NMR (DMSO-$d_6$) δ 7.76 (s, 1H), 6.42 (s, 1H), 3.79 (s, 3H). This material was used without further purification.

Step 2: 6-Bromo-7-methoxyquinazolin-4(1H)-one

A mixture of 2-amino-5-bromo-4-methoxybenzoic acid (1.25 g, 3.6 mmol) and formimidamide acetate (0.75 g, 7.2 mmol) in EtOH (15 mL) was refluxed for 24 h. The mixture was cooled to room temperature and the solid was filtered, washed with water, and dried to provide 6-bromo-7-methoxyquinazolin-4(1H)-one as a white solid (0.858 g). MS (M+1)=255.0/257.0. $^1$H NMR (DMSO-$d_6$) δ 12.30 (br. s, 1H), 8.21 (s, 1H), 8.12 (s, 1H), 7.25 (s, 1H), 4.00 (s, 3H).

Step 3: 7-Methoxy-6-(4,4,5,5-tetramethyl-1,3,2-dioxaborolan-2-yl)quinazolin-4(1H)-one A mixture of 6-bromo-7-methoxyquinazolin-4(1H)-one (385 mg, 1.51 mmol), dppf (84 mg, 0.15 mmol), PdCl$_2$(dppf).CH$_2$Cl$_2$ (123 mg, 0.15 mmol), and KOAc (899 mg, 9.1 mmol) in 1,4-dioxane (6 mL) and DMF (1 mL) was evacuated and backfilled with nitrogen (4×), then heated at 90° C. for 45 min. Bis(pinacolato) diboron (1.15 g, 4.5 mmol) was then added, and the mixture was heated at 100° C. for 21 h. The reaction mixture was cooled to room temperature and concentrated in vacuo. After silica gel chromatography (0-20% MeOH in DCM) 7-methoxy-6-(4,4,5,5-tetramethyl-1,3,2-dioxaborolan-2-yl)quinazolin-4(1H)-one (305 mg, ~61% pure) was obtained as a brown solid. MS (M+1)=303.1.

Step 4: 7-Methoxy-6-(6-(methyl(2,2,6,6-tetramethylpiperidin-4-yl)amino)pyridazin-3-yl)quinazolin-4(1H)-one 7-Methoxy-6-(4,4,5,5-tetramethyl-1,3,2-dioxaborolan-2-yl)quinazolin-4(1H)-one (305 mg, ~61% pure, 0.62 mmol), 6-chloro-N-methyl-N-(2,2,6,6-tetramethylpiperidin-4-yl)pyridazin-3-amine, (Intermediate 1, 145 mg, 0.51 mmol), Pd(PPh$_3$)$_4$ (47 mg, 0.041 mmol), aqueous Na$_2$CO$_3$ (2.0 M, 0.64 mL, 1.3 mmol) and 1,4-dioxane (2.4 mL) were combined in a microwave vessel. The vessel was evacuated and back-filled with nitrogen (4×), and heated via microwave irradiation at 110° C. for 1 h. The mixture was cooled to room temperature and acidified to pH 2 with 4 M HCl in 1,4-dioxane. SCX purification (GENERAL METHOD 3-1) followed by silica gel chromatography (0-20% MeOH in DCM) provided 7-methoxy-6-(6-(methyl(2,2,6,6-tetramethylpiperidin-4-yl)amino)pyridazin-3-yl)quinazolin-4(1H)-one (137 mg) as a light brown solid. MS (M+1)=423.1. $^1$H NMR (METHANOL-$d_4$) δ 8.47 (s, 1H), 8.14 (s, 1H), 7.81 (d, J=9.6 Hz, 1H), 7.29 (s, 1H), 7.15 (d, J=9.6 Hz, 1H), 5.25 (t, J=12.4 Hz, 1H), 4.02 (s, 3H), 3.03 (s, 3H), 1.72 (m, 2H), 1.60 (m, 2H), 1.41 (s, 6H), 1.26 (s, 6H).

Step 5: 7-Hydroxy-6-(6-(methyl(2,2,6,6-tetramethylpiperidin-4-yl)amino)pyridazin-3-yl)quinazolin-4(1H)-one 7-Methoxy-6-(6-(methyl(2,2,6,6-tetramethylpiperidin-4-yl)amino)pyridazin-3-yl)quinazolin-4(1H)-one (32 mg, 0.076 mmol) was subjected to methoxy deprotection conditions as described in GENERAL METHOD 2-3 using boron tribromide (1.0 M solution in DCM, 0.38 mL, 0.38 mmol). SCX purification (GENERAL METHOD 3-1, 1 g SiliaBond Propylsulfonic Acid® cartridge) followed by preparative reverse-phase HPLC provided 7-hydroxy-6-(6-(methyl(2,2,6,6-tetramethylpiperidin-4-yl)amino)pyridazin-3-yl)quinazolin-4(1H)-one as a white solid (10 mg). LC/MS Rt=0.45 min. MS (M+1)=409.2. $^1$H NMR (METHANOL-$d_4$) δ 8.63 (s, 1H), 8.22 (d, J=9.6 Hz, 1H), 8.05 (s, 1H), 7.37 (d, J=9.6 Hz, 1H), 7.12 (s, 1H), 5.19 (t, J=12.0 Hz, 1H), 3.03 (s, 3H), 1.71-1.81 (m, 2H), 1.59-1.71 (m, 2H), 1.44 (s, 6H), 1.29 (s, 6H).

Example 23-1: Synthesis of 6-(6-(methyl(2,2,6,6-tetramethylpiperidin-4-yl)amino)pyridazin-3-yl)quinazolin-7-ol

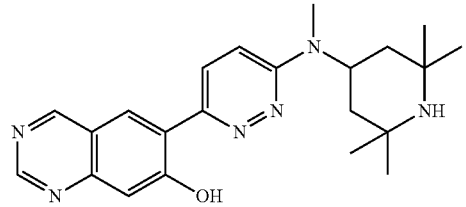 [SMILES: CN(c1ccc(-c2cc3cncnc3cc2O)nn1)C1CC(C)(C)NC(C)(C)C1]

Step 1: 2-Amino-4-methoxybenzaldehyde

To a suspension of 2-amino-4-methoxybenzyl alcohol (2 g, 13.1 mmol) in DCM (30 mL) and was added MnO$_2$ (6.81 g, 78 mmol) at room temperature. After stirring overnight, the mixture was filtered through Celite®, rinsed with DCM, concentrated and purified by silica gel chromatography (5-50% EtOAc/Heptane) to provide 2-amino-4-methoxybenzaldehyde (0.99 g) as a yellow solid. MS (M+1)=152.2. $^1$H NMR (Chloroform-d) δ9.74 (s, 1H), 7.40 (d, J=8.6 Hz, 1H), 6.35 (dd, J=8.7, 2.4 Hz, 1H), 6.23 (s, 2H), 6.09 (d, J=2.3 Hz, 1H), 3.84 (d, J=4.1 Hz, 3H).

Step 2: 2-Amino-5-bromo-4-methoxybenzaldehyde

To a solution of 2-amino-4-methoxybenzaldehyde (0.99 g, 6.6 mmol) in THF (20 mL) was added NBS (1.17 g, 6.6 mmol) at 0° C. The mixture was stirred at room temperature for 3 h, then quenched with Na$_2$S$_2$O$_3$ (5 mL, 20% aqueous solution). After stirring for 5 min, the mixture was diluted with an aqueous NaHCO$_3$ solution and extracted with EtOAc. The combined organic extracts were washed with brine, dried over Na$_2$SO$_4$, concentrated in vacuo, and subjected to silica gel chromatography (5-50% EtOAc/Heptane) to provide 2-amino-5-bromo-4-methoxybenzaldehyde (0.79 g) as a yellow solid. MS (M+1)=230.1/232.1. $^1$H NMR (Chloroform-d) δ 9.59 (s, 1H), 7.52 (s, 1H), 6.21 (s, 2H), 6.03 (s, 1H), 3.83 (s, 3H).

Step 3: 6-Bromo-7-methoxyquinazoline

A mixture of 2-amino-5-bromo-4-methoxybenzaldehyde (350 mg, 1.52 mmol) and formimidamide acetate (238 mg, 2.28 mmol) in EtOH (10 mL) was refluxed for 16 h. The mixture was cooled to room temperature and concentrated. The residue was basified with an aqueous $NaHCO_3$ solution and extracted with DCM. The combined organic extracts were dried over $Na_2SO_4$, concentrated in vacuo, and subjected to silica gel chromatography (0-30% EtOAc/Heptane) to provide 6-bromo-7-methoxyquinazoline (253 mg) as a yellow solid. MS (M+1)=239.0/241.0. $^1$H NMR (Chloroform-d) δ 9.28 (s, 1H), 9.23 (s, 1H), 8.18 (s, 1H), 7.39 (s, 1H), 4.11 (s, 3H).

Step 4: 7-Methoxy-6-(4,4,5,5-tetramethyl-1,3,2-dioxaborolan-2-yl)quinazoline To a mixture of 6-bromo-7-methoxyquinazoline (253 mg, 0.95 mmol), dppf (53 mg, 0.095 mmol), $PdCl_2(dppf).CH_2Cl_2$ (78 mg, 0.095 mmol), and KOAc (561 mg, 5.7 mmol) was added 1,4-dioxane (5 mL). The reaction mixture was evacuated and backfilled with nitrogen (4×), then heated at 90° C. for 30 min. Bis(pinacolato) diboron (726 mg, 2.9 mmol) was then added, and the mixture was heated at 90° C. for 16 hr. Further bis(pinacolato) diboron (242 mg, 0.95 mmol), dppf (26.4 mg, 0.048 mmol) and $PdCl_2(dppf).CH_2Cl_2$ (39 mg, 0.048 mmol) were added and the mixture was heated at 95° C. for 23 h. The mixture was cooled to room temperature and filtered through Celite® washing with 9:1 MeOH/DCM. The filtrates were concentrated in vacuo. After silica gel chromatography (0-20% MeOH in DCM), 7-methoxy-6-(4,4,5,5-tetramethyl-1,3,2-dioxaborolan-2-yl)quinazoline (180 mg, ~67% pure) was obtained as a brown solid. MS (M+1)=287.2.

Step 5: 6-(7-Methoxyquinazolin-6-yl)-N-methyl-N-(2,2,6,6-tetramethylpiperidin-4-yl)pyridazin-3-amine 7-Methoxy-6-(4,4,5,5-tetramethyl-1,3,2-dioxaborolan-2-yl)quinazoline (180 mg, ~67% pure, 0.42 mmol) was coupled with 6-chloro-N-methyl-N-(2,2,6,6-tetramethylpiperidin-4-yl)pyridazin-3-amine (Intermediate 1, 100 mg, 0.35 mmol), using the same method as Example Example 20-6 Step 4 for Suzuki coupling. The crude product was purified by SCX purification (GENERAL METHOD 3-1) followed by silica gel chromatography as described in GENERAL METHOD 4-1 to provide 6-(7-methoxyquinazolin-6-yl)-N-methyl-N-(2,2,6,6-tetramethylpiperidin-4-yl)pyridazin-3-amine (28.9 mg) as a light brown solid. MS (M+1)= 407.3. $^1$H NMR (METHANOL-$d_4$) δ 9.41 (s, 1H), 9.14 (s, 1H), 8.29 (s, 1H), 7.82 (d, J=9.6 Hz, 1H), 7.47 (s, 1H), 7.12 (d, J=9.6 Hz, 1H), 5.24 (t, J=12.1 Hz, 1H), 4.07 (s, 3H), 3.00 (s, 3H), 1.62-1.73 (m, 2H), 1.48-1.60 (m, 2H), 1.36 (s, 6H), 1.17-1.26 (m, 6H).

Step 6: 6-(6-(Methyl(2,2,6,6-tetramethylpiperidin-4-yl)amino)pyridazin-3-yl)quinazolin-7-ol 6-(7-Methoxyquinazolin-6-yl)-N-methyl-N-(2,2,6,6-tetramethylpiperidin-4-yl)pyridazin-3-amine (28 mg, 0.069 mmol) was subjected to methoxy deprotection conditions as described in GENERAL METHOD 2-3 using boron tribromide (1.0 M solution in DCM, 0.41 mL, 0.41 mmol). SCX purification (GENERAL METHOD 3-1, 1 g SiliaBond Propylsulfonic Acid® cartridge) followed by preparative reverse-phase HPLC provided 6-(6-(methyl(2,2,6,6-tetramethylpiperidin-4-yl)amino)pyridazin-3-yl)quinazolin-7-ol as a yellow solid (16 mg). LC/MS Rt=0.46 min. MS (M+1)=393.2. $^1$H NMR (METHANOL-$d_4$) δ 9.20 (s, 1H), 8.91 (s, 1H), 8.40 (s, 1H), 8.25 (d, J=9.6 Hz, 1H), 7.29 (d, J=9.6 Hz, 1H), 7.20 (s, 1H), 5.18-5.36 (m, 1H), 3.03 (s, 3H), 1.75-1.83 (m, 2H), 1.64-1.74 (m, 2H), 1.46 (s, 6H), 1.31 (s, 6H).

Example 24-1: Synthesis of 7-hydroxy-1-methyl-6-(6-(methyl(2,2,6,6-tetramethylpiperidin-4-yl)amino)pyridazin-3-yl)-3,4-dihydroquinolin-2(1H)-one

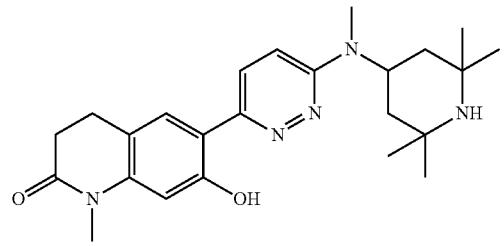 [SMILES: CN1C(=O)CCc2cc(-c3ccc(N(C)C4CC(C)(C)NC(C)(C)C4)nn3)c(O)cc21]

Step 1: 6-Bromo-7-hydroxy-3,4-dihydroquinolin-2(1H)-one

To a solution of 7-hydroxy-3,4-dihydroquinolin-2(1H)-one (590 mg, 3.5 mmol) in DMF (3 mL) was added NBS (655 mg, 3.7 mmol) at 0° C. in three portions over 30 min. The mixture was stirred at room temperature overnight, then quenched with $Na_2S_2O_3$ (5 mL, 20% aqueous solution). After stirring for 5 min, the mixture was diluted with aqueous $NaHCO_3$ and extracted with EtOAc. The combined organic extracts were washed with brine, dried over $Na_2SO_4$, concentrated in vacuo, and purified by silica gel chromatography (5-50% EtOAc/Heptane) to provide 6-bromo-7-hydroxy-3,4-dihydroquinolin-2(1H)-one (0.82 g) as a yellow solid. MS (M+1)=241.9/243.9. $^1$H NMR (Methanol-$d_4$) δ 7.24 (s, 1H), 6.47 (s, 1H), 2.84 (t, J=7.6 Hz, 2H), 2.47-2.56 (m, 2H).

Step 2: 6-Bromo-7-methoxy-1-methyl-3,4-dihydroquinolin-2(1H)-one

To a solution of 6-bromo-7-hydroxy-3,4-dihydroquinolin-2(1H)-one (650 mg, 2.7 mmol) in DMF (3 mL) was added $K_2CO_3$ (557 mg, 4.0 mmol) at room temperature. After 5 min, MeI (0.185 ml, 2.9 mmol) was added and the mixture was stirred overnight. The mixture was quenched with water and extracted with EtOAc (3×). The combined organic extracts were washed with brine, dried over $Na_2SO_4$ and concentrated to afford the crude product. 6-Bromo-7-methoxy-1-methyl-3,4-dihydroquinolin-2(1H)-one (174 mg) and 6-bromo-7-methoxy-3,4-dihydroquinolin-2(1H)-one (396 mg) were obtained after silica gel chromatography purification (5-50% EtOAc/Heptane). MS (M+1)=269.9/271.9 and 255.9/257.9, respectively.

Step 3: 7-Methoxy-1-methyl-6-(4,4,5,5-tetramethyl-1,3,2-dioxaborolan-2-yl)-3,4-dihydroquinolin-2(1H)-one To a mixture of 6-bromo-7-methoxy-1-methyl-3,4-dihydroquinolin-2(1H)-one (170 mg, 0.63 mmol), dppf (34.9 mg, 0.063 mmol), PdCl₂(dppf).CH₂Cl₂ (51.4 mg, 0.063 mmol), and KOAc (371 mg, 3.78 mmol) was added 1,4-dioxane (2 mL). The reaction mixture was evacuated and backfilled with nitrogen (4×), then heated at 90° C. for 20 min. Bis(pinacolato) diboron (479 mg, 1.89 mmol) was then added, and the mixture was heated at 98° C. for 16 h. The reaction mixture was cooled to room temperature and filtered through Celite® washing with 9:1 MeOH/DCM. The filtrates were concentrated in vacuo. After silica gel chromatography (0-10% MeOH in DCM) 7-methoxy-1-methyl-6-(4,4,5,5-tetramethyl-1,3,2-dioxaborolan-2-yl)-3,4-dihydroquinolin-2(1H)-one (500 mg, ~38% pure) was obtained as a brown solid. MS (M+1)=318.4.

Step 4: 7-Methoxy-1-methyl-6-(6-(methyl(2,2,6,6-tetramethylpiperidin-4-yl)amino)pyridazin-3-yl)-3,4-dihydroquinolin-2(1H)-one 7-Methoxy-1-methyl-6-(4,4,5,5-tetramethyl-1,3,2-dioxaborolan-2-yl)-3,4-dihydroquinolin-2(1H)-one (470 mg, ~38% pure, 0.56 mmol) was coupled with 6-chloro-N-methyl-N-(2,2,6,6-tetramethylpiperidin-4-yl)pyridazin-3-amine (Intermediate 1, 110 mg, 0.39 mmol), using the same method as Example 20-6 Step 4 for Suzuki coupling. The crude product was purified by SCX purification (GENERAL METHOD 3-1) followed by silica gel chromatography as described in GENERAL METHOD 4-1 to provide 7-methoxy-1-methyl-6-(6-(methyl(2,2,6,6-tetramethylpiperidin-4-yl)amino)pyridazin-3-yl)-3,4-dihydroquinolin-2(1H)-one (92 mg) as a white solid. MS (M+1)=438.2. ¹H NMR (METHANOL-d₄) δ 7.84 (d, J=9.6 Hz, 1H), 7.49 (s, 1H), 7.16 (d, J=9.6 Hz, 1H), 6.85 (s, 1H), 5.42-5.55 (m, 1H), 3.91 (s, 3H), 3.43 (s, 3H), 3.01 (s, 3H), 2.92 (t, J=7.3 Hz, 2H), 2.60-2.70 (m, 2H), 1.90-2.02 (m, 4H), 1.64 (s, 6H), 1.52 (s, 6H).

Step 5: 7-Hydroxy-1-methyl-6-(6-(methyl(2,2,6,6-tetramethylpiperidin-4-yl)amino)pyridazin-3-yl)-3,4-dihydroquinolin-2(1H)-one 7-Methoxy-1-methyl-6-(6-(methyl(2,2,6,6-tetramethylpiperidin-4-yl)amino)pyridazin-3-yl)-3,4-dihydroquinolin-2(1H)-one (91 mg, 0.21 mmol) was subjected to methoxy deprotection conditions as described in GENERAL METHOD 2-3 using boron tribromide (1.0 M solution in DCM, 1.04 mL, 1.04 mmol). SCX purification (GENERAL METHOD 3-1, 2 g SiliaBond Propylsulfonic Acid® cartridge) followed by preparative reverse-phase HPLC provided 7-hydroxy-1-methyl-6-(6-(methyl(2,2,6,6-tetramethylpiperidin-4-yl)amino)pyridazin-3-yl)-3,4-dihydroquinolin-2(1H)-one as a yellow solid (69 mg). LC/MS Rt=0.51 min. MS (M+1)=424.4. ¹H NMR (METHANOL-d₄) δ 8.04 (d, J=9.6 Hz, 1H), 7.57 (s, 1H), 7.28 (d, J=9.6 Hz, 1H), 6.69 (s, 1H), 5.03 (t, J=12.4 Hz, 1H), 3.34 (s, 3H), 2.99 (s, 3H), 2.90 (t, J=7.1 Hz, 2H), 2.63 (t, J=7.1 Hz, 2H), 1.63-1.72 (m, 2H), 1.50-1.61 (m, 2H), 1.38 (s, 6H), 1.22 (s, 6H).

Example 25-1: Synthesis of 7-hydroxy-1-methyl-6-(6-(methyl(2,2,6,6-tetramethylpiperidin-4-yl)amino)pyridazin-3-yl)-3,4-dihydroquinolin-2(1H)-one

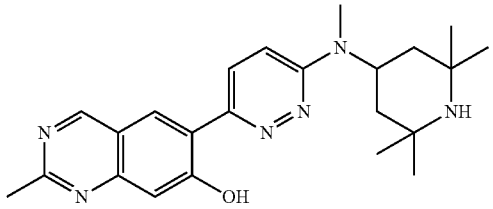

Step 1: N-(4-Bromo-2-formyl-5-methoxyphenyl)acetamide

To a mixture of 2-amino-5-bromo-4-methoxybenzaldehyde (1.1 g, 4.2 mmol) in DCM (30 mL) and was added pyridine (1.68 mL, 20.8 mmol) at room temperature. The mixture was cooled to 0° C., and acetyl chloride (1.48 mL, 20.8 mmol) was added. The mixture was stirred at room temperature overnight, quenched with water, and extracted with DCM (3×). The combined organic extracts were dried over Na₂SO₄ and concentrated to afford the crude product. Silica gel chromatography (5-50% EtOAc/Heptane) provided N-(4-bromo-2-formyl-5-methoxyphenyl)acetamide (498 mg). MS (M+1)=271.9/273.9. ¹H NMR (Chloroform-d) δ 11.37 (s, 1H), 9.73 (s, 1H), 8.52 (s, 1H), 7.79 (s, 1H), 4.02 (s, 3H), 2.28 (s, 3H).

Step 2: 6-Bromo-7-methoxy-2-methylquinazoline

The mixture of N-(4-bromo-2-formyl-5-methoxyphenyl)acetamide (138 mg, 0.41 mmol) and ammonia (2.0 M methanol solution, 4.1 mL, 8.1 mmol) was heated at 75° C. for 4 h in a sealed vial vented with a 22 gauge needle. The mixture was cooled to room temperature, concentrated, and subjected to silica gel chromatography (5-60% EtOAc/Heptane) to provide 6-bromo-7-methoxy-2-methylquinazoline (103 mg) as a yellow solid. MS (M+1)=252.9/254.9. ¹H NMR (Chloroform-d) δ 9.04 (s, 1H), 8.02 (d, J=3.1 Hz, 1H), 7.21 (s, 1H), 3.99 (d, J=3.2 Hz, 3H), 2.78 (s, 3H).

Step 3: 7-Methoxy-2-methyl-6-(4,4,5,5-tetramethyl-1,3,2-dioxaborolan-2-yl)quinazoline To a mixture of 6-bromo-7-methoxy-2-methylquinazoline (103 mg, 0.41 mmol), dppf (23 mg, 0.041 mmol), PdCl₂(dppf).CH₂Cl₂ (33 mg, 0.041 mmol), and KOAc (240 mg, 2.44 mmol) was added 1,4-dioxane (2.5 mL). The reaction mixture was evacuated and backfilled with nitrogen (4×), then heated at 90° C. for 20 min. Bis(pinacolato) diboron (310 mg, 1.22 mmol) was then added, and the mixture was heated at 98° C. for 16 h. Further bis(pinacolato) diboron (207 mg, 0.81 mmol), dppf (23 mg, 0.041 mmol) and PdCl₂(dppf).CH₂Cl₂ (33 mg, 0.041 mmol) were added and the mixture was heated at 98° C. for 16 h. The reaction mixture was cooled to room temperature and filtered through Celite®, washing with 9:1 MeOH/DCM. The filtrates were concentrated in vacuo. After silica gel chromatography (0-10% MeOH in DCM) 7-methoxy-2-methyl-6-(4,4,5,5-tetramethyl-1,3,2-dioxaborolan-2-yl)quinazoline (157 mg, ~72% pure) was obtained as a brown solid. MS (M+1)=301.0.

Step 4: 6-(7-Methoxy-2-methylquinazolin-6-yl)-N-methyl-N-(2,2,6,6-tetramethylpiperidin-4-yl)pyridazin-3-amine 7-Methoxy-2-methyl-6-(4,4,5,5-tetramethyl-1,3,2-dioxaborolan-2-yl)quinazoline (180 mg, ~72% pure, 0.37 mmol) was coupled with 6-chloro-N-methyl-N-(2,2,6,6-tetramethylpiperidin-4-yl)pyridazin-3-amine (Intermediate 1, 80 mg, 0.283 mmol), using the same method as Example 20-6 Step 4 for Suzuki coupling. The crude product was purified by SCX purification (GENERAL METHOD 3-1) followed by silica gel chromatography as described in GENERAL METHOD 4-1 to provide 6-(7-methoxy-2-methylquinazolin-6-yl)-N-methyl-N-(2,2,6,6-tetramethylpiperidin-4-yl)pyridazin-3-amine (90 mg) as a yellow solid. MS (M+1)=421.1. $^1$H NMR (METHANOL-$d_4$) δ 9.34 (s, 1H), 8.26 (s, 1H), 7.82 (d, J=9.6 Hz, 1H), 7.40 (s, 1H), 7.15 (d, J=9.6 Hz, 1H), 5.25 (t, J=12.9 Hz, 1H), 4.06 (s, 3H), 3.01 (s, 3H), 2.82 (s, 3H), 1.70 (dd, J=12.5, 3.6 Hz, 2H), 1.58 (t, J=12.4 Hz, 2H), 1.38 (s, 6H), 1.23 (s, 6H).

Step 5: 6-(6-(Methyl(2,2,6,6-tetramethylpiperidin-4-yl)amino)pyridazin-3-yl)quinazolin-7-ol 6-(7-Methoxy-2-methylquinazolin-6-yl)-N-methyl-N-(2,2,6,6-tetramethylpiperidin-4-yl)pyridazin-3-amine (92 mg, 0.21 mmol) was subjected to methoxy deprotection conditions as described in GENERAL METHOD 2-4 using thiophenol (0.028 mL, 0.27 mmol). SCX purification (GENERAL METHOD 3-1, 2 g SiliaBond Propylsulfonic Acid® cartridge) followed by preparative reverse-phase HPLC provided 6-(6-(methyl(2,2,6,6-tetramethylpiperidin-4-yl)amino)pyridazin-3-yl)quinazolin-7-ol as a yellow solid (27 mg). LC/MS Rt=0.47 min. MS (M+1)=407.2. $^1$H NMR (METHANOL-$d_4$) δ 9.17 (s, 1H), 8.41 (s, 1H), 8.25 (d, J=9.7 Hz, 1H), 7.32 (d, J=9.8 Hz, 1H), 7.17 (s, 1H), 5.25 (t, J=13.1 Hz, 1H), 3.03 (s, 3H), 2.74 (s, 3H), 1.79 (dd, J=12.9, 3.7 Hz, 2H), 1.69 (t, J=12.5 Hz, 2H), 1.47 (s, 6H), 1.32 (s, 6H).

Example 26-1: Synthesis of 7-hydroxy-6-(6-(methyl(2,2,6,6-tetramethylpiperidin-4-yl)amino)pyridazin-3-yl)isoquinoline-1-carbonitrile

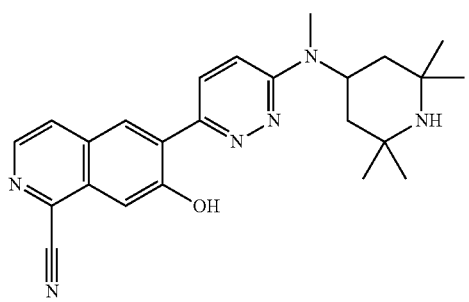 [SMILES: CN(c1ccc(-c2cc3ccnc(C#N)c3cc2O)nn1)C1CC(C)(C)NC(C)(C)C1]

Step 1: 6-Bromo-7-methoxyisoquinoline 2-oxide

To a 50 mL round bottom flask containing 6-bromo-7-methoxyisoquinoline (prepared as described in in Example 3-7 (100 mg, 0.42 mmol) in DCM (2.1 mL) was added methyltrioxorhenium (MTO, 4.2 mg, 0.02 mmol). The mixture cooled to 00° C. and 50% aqueous hydrogen peroxide (57 mg, 0.84 mmol) was added dropwise. The reaction mixture was stirred at room temperature for 18 h. Then 5-10 mg managanese dioxide was added and the reaction stirred for 2 h then filtered through celite. The filtrate was concentrated in vacuo to afford 6-bromo-7-methoxyisoquinoline 2-oxide (213 mg). MS (M+1)=256.3

Step 2: 7-Hydroxy-6-(6-(methyl(2,2,6,6-tetramethylpiperidin-4-yl)amino)pyridazin-3-yl)isoquinoline-1-carbonitrile 7-Hydroxy-6-(6-(methyl(2,2,6,6-tetramethylpiperidin-4-yl)amino)pyridazin-3-yl)isoquinoline-1-carbonitrile was prepared from 6-bromo-7-methoxyisoquinoline 2-oxide according to the synthesis of 6-methoxy-7-(6-(methyl(2,2,6,6-tetramethylpiperidin-4-yl)amino)pyridazin-3-yl)isoquinoline-1-carbonitrile (as described in Example 3-7) LC/MS Rt=0.54 MS (M+1)=417.2 $^1$H NMR (400 MHz, Methanol-$d_4$) δ 8.44 (d, J=5.4 Hz, 2H), 8.25 (d, J=9.9 Hz, 1H), 8.00 (d, J=5.5 Hz, 1H), 7.70 (s, 1H), 7.25 (d, J=9.9 Hz, 1H), 5.34-5.04 (m, 1H), 3.06 (s, 3H), 1.78 (dd, J=12.7, 3.5 Hz, 2H), 1.58 (t, J=12.5 Hz, 2H), 1.43 (s, 6H), 1.27 (s, 6H).

Example 26-2: Synthesis of 7-hydroxy-6-(6-(methyl(2,2,6,6-tetramethylpiperidin-4-yl)amino)pyridazin-3-yl)quinoline-2-carbonitrile

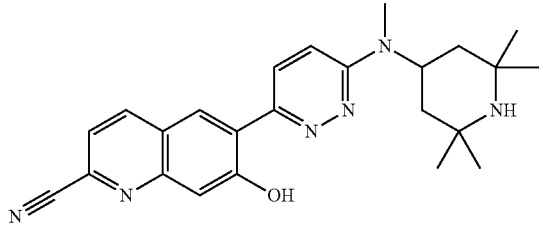 [SMILES: CN(c1ccc(-c2cc3ccc(C#N)nc3cc2O)nn1)C1CC(C)(C)NC(C)(C)C1]

7-Hydroxy-6-(6-(methyl(2,2,6,6-tetramethylpiperidin-4-yl)amino)pyridazin-3-yl)quinoline-2-carbonitrile was prepared from 6-chloro-7-methoxyquinoline according to the synthesis of Example 26-1. LC/MS Rt=0.51. MS (M+1)=417.2 $^1$H NMR (400 MHz, DMSO-$d_6$) δ 8.70 (s, 1H), 8.54 (dd, J=8.5, 0.8 Hz, 1H), 8.33 (d, J=9.9 Hz, 1H), 7.82 (d, J=8.3 Hz, 1H), 7.51-7.37 (m, 2H), 5.21-4.94 (m, 1H), 2.99 (s, 3H), 1.68-1.42 (m, 4H), 1.30 (s, 6H), 1.14 (s, 6H).

Example 26-3: Synthesis of 6-hydroxy-7-(6-(methyl(2,2,6,6-tetramethylpiperidin-4-yl)amino)pyridazin-3-yl)quinoline-2-carbonitrile

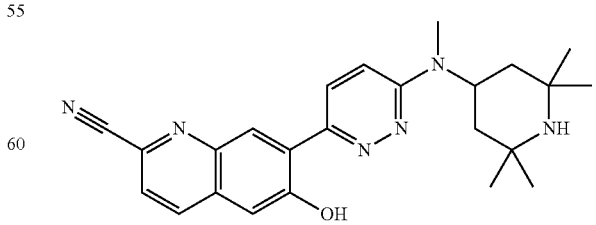

6-Hydroxy-7-(6-(methyl(2,2,6,6-tetramethylpiperidin-4-yl)amino)pyridazin-3-yl)quinoline-2-carbonitrile was prepared from 7-Bromo-6-methoxyquinoline according to the synthesis of Example 26-1. LC/MS Rt=0.54. MS (M+1)=417.2 ¹H NMR (400 MHz, DMSO-d6) δ 8.71 (s, 1H), 8.50 (d, J=9.9 Hz, 1H), 8.41 (d, J=8.5 Hz, 1H), 7.90 (d, J=8.5 Hz, 1H), 7.48-7.39 (m, 2H), 5.26-4.78 (m, 1H), 3.00 (s, 3H), 1.66-1.41 (m, 5H), 1.29 (s, 6H), 1.12 (s, 6H).

Example 26-4: Synthesis of 6-hydroxy-7-(6-(methyl (2,2,6,6-tetramethylpiperidin-4-yl)amino)pyridazin-3-yl)isoquinoline-1-carboxamide

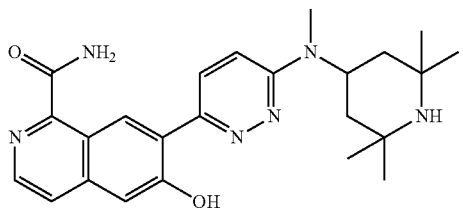 [SMILES: CN(c1ccc(-c2cc3c(C(N)=O)nccc3cc2O)nn1)C1CC(C)(C)NC(C)(C)C1]

Step 1: 6-Methoxy-7-(6-(methyl(2,2,6,6-tetramethylpiperidin-4-yl)amino)pyridazin-3-yl)isoquinoline-1-carboxamide A mixture of 6-methoxy-7-(6-(methyl(2,2,6,6-tetramethylpiperidin-4-yl)amino)pyridazin-3-yl)isoquinoline-1-carbonitrile (87 mg, 0.202 mmol), potassium hydroxide (10% aqueous, 0.15 mL, 0.263 mmol) and hydrogen peroxide (33% aqueous, 0.08 mL, 0.909 mmol) was heated at 40° C. for 1 h. SCX purification (GENERAL METHOD 3-1) afforded 6-methoxy-7-(6-(methyl(2,2,6,6-tetramethylpiperidin-4-yl)amino)pyridazin-3-yl)isoquinoline-1-carboxamide (91 mg). MS (M+1)=449.5

Step 2: 6-Hydroxy-7-(6-(methyl(2,2,6,6-tetramethylpiperidin-4-yl)amino)pyridazin-3-yl)isoquinoline-1-carboxamide 6-Methoxy-7-(6-(methyl(2,2,6,6-tetramethylpiperidin-4-yl)amino)pyridazin-3-yl)isoquinoline-1-carboxamide was subjected to methoxy deprotection conditions as described in GENERAL METHOD 2-1 followed by free basing via GENERAL METHOD 8-1 to afford the title compound (10.9 mg). LC/MS Rt=0.43. MS (M+1)=435.2 ¹H NMR (400 MHz, METHANOL-d4) δ ppm 8.90 (br. s., 1H), 8.04-8.20 (m, 2H), 7.48 (d, J=6.02 Hz, 1H), 7.29-7.44 (m, 1H), 7.18 (d, J=9.54 Hz, 1H), 7.00 (s, 1H), 5.06-5.35 (m, 1H), 3.02 (s, 3H), 1.65-1.76 (m, 2H), 1.49-1.62 (m, 2H), 1.39 (s, 6H), 1.23 (s, 6H).

Example 26-5: Synthesis of 7-hydroxy-6-(6-(methyl (2,2,6,6-tetramethylpiperidin-4-yl)amino)pyridazin-3-yl)quinoline-2-carboxamide

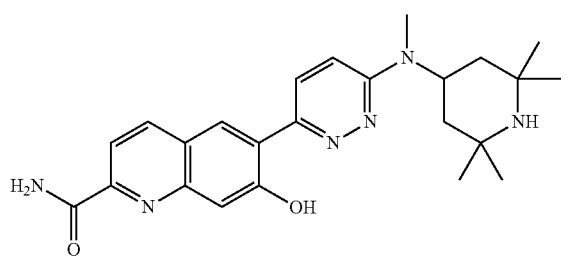 [SMILES: CN(c1ccc(-c2cc3ccc(C(N)=O)nc3cc2O)nn1)C1CC(C)(C)NC(C)(C)C1]

7-Hydroxy-6-(6-(methyl(2,2,6,6-tetramethylpiperidin-4-yl)amino)pyridazin-3-yl)quinoline-2-carboxamide was isolated as a by-product from the methoxy deprotection of 7-methoxy-6-(6-(methyl(2,2,6,6-tetramethylpiperidin-4-yl)amino)pyridazin-3-yl)quinoline-2-carbonitrile (Example 26-2) using GENERAL METHOD 2-1. LC/MS Rt=0.48. MS (M+1)=435.3 ¹H NMR (400 MHz, DMSO-d₆) δ 8.64 (s, 1H), 8.45 (d, J=8.4 Hz, 1H), 8.35 (d, J=9.9 Hz, 1H), 8.24 (d, J=2.9 Hz, 1H), 7.96 (d, J=8.4 Hz, 1H), 7.71 (d, J=2.8 Hz, 1H), 7.50-7.38 (m, 2H), 5.31-4.88 (m, 1H), 2.99 (s, 3H), 1.57 (s, 4H), 1.30 (s, 6H), 1.14 (s, 6H).

Example 26-6: Synthesis of 6-hydroxy-7-(6-(methyl (2,2,6,6-tetramethylpiperidin-4-yl)amino)pyridazin-3-yl)quinoline-2-carboxamide

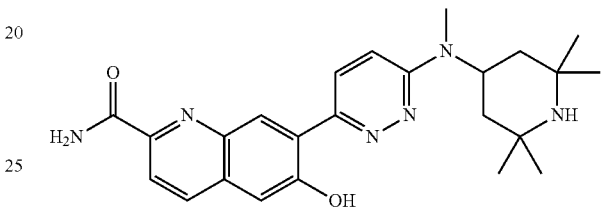

6-Hydroxy-7-(6-(methyl(2,2,6,6-tetramethylpiperidin-4-yl)amino)pyridazin-3-yl)quinoline-2-carboxamide was isolated as a by-product from the methoxy deprotection of 6-methoxy-7-(6-(methyl(2,2,6,6-tetramethylpiperidin-4-yl)amino)pyridazin-3-yl)quinoline-2-carbonitrile (Example 26-3) using GENERAL METHOD 2-1. LC/MS Rt=0.52. MS (M+1)=435.3 ¹H NMR (400 MHz, Methanol-d₄) δ 8.53 (s, 1H), 8.28 (d, J=9.9 Hz, 1H), 8.23 (s, 1H), 8.14 (d, J=8.5 Hz, 1H), 7.38 (s, 1H), 7.28 (d, J=9.8 Hz, 1H), 5.22 (m, 1H), 3.06 (s, 3H), 1.80 (dd, J=12.8, 3.4 Hz, 2H), 1.63 (t, J=12.0 Hz, 2H), 1.45 (s, 6H), 1.29 (s, 6H).

Example 26-7: Synthesis of methyl 6-hydroxy-7-(6-(methyl(2,2,6,6-tetramethylpiperidin-4-yl)amino) pyridazin-3-yl)quinoline-2-carboxylate

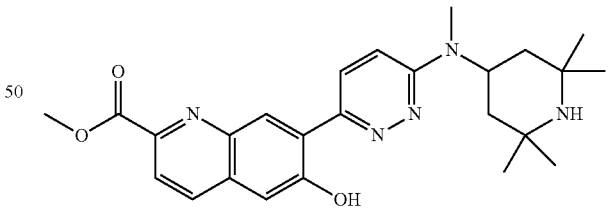

Methyl 6-hydroxy-7-(6-(methyl(2,2,6,6-tetramethylpiperidin-4-yl)amino)pyridazin-3-yl)quinoline-2-carboxylate was isolated as a by-product in the deprotection of 6-methoxy-7-(6-(methyl(2,2,6,6-tetramethylpiperidin-4-yl)amino)pyridazin-3-yl)quinoline-2-carbonitrile (Example 26-3) by GENERAL METHOD 2-1. LC/MS Rt=0.57. MS (M+1)=450.3 ¹H NMR (400 MHz, Methanol-d₄) δ 8.53 (s, 1H), 8.35-8.19 (m, 2H), 8.06 (dd, J=8.5, 1.5 Hz, 1H), 7.42-7.29 (m, 2H), 5.35-5.08 (m, 1H), 4.04 (d, J=1.5 Hz, 3H), 3.05 (s, 3H), 1.74 (dd, J=12.7, 3.6 Hz, 2H), 1.63 (t, J=12.5 Hz, 2H), 1.43 (s, 6H), 1.27 (s, 6H).

Example 27-1: Synthesis of 6-hydroxy-7-(6-(piper-azin-1-yl)pyridazin-3-yl)quinoline-2-carbonitrile

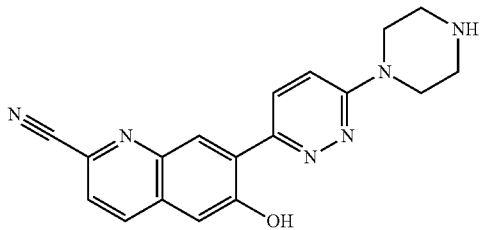 [SMILES: N#Cc1ccc2cc(O)c(-c3ccc(N4CCNCC4)nn3)cc2n1]

Step 1: tert-Butyl 4-(6-(2-cyano-6-methoxyquinolin-7-yl)pyridazin-3-yl)piperazine-1-carboxylate tert-Butyl 4-(6-(2-cyano-6-methoxyquinolin-7-yl)pyridazin-3-yl)piperazine-1-carboxylate was prepared from (2-cyano-6-methoxyquinolin-7-yl)boronic acid and tert-butyl 4-(6-chloropyridazin-3-yl)piperazine-1-carboxylate via Suzuki conditions described in GENERAL METHOD 1-1 (170 mg). MS (M+1)=447.3.

Step 2: 6-Hydroxy-7-(6-(piperazin-1-yl)pyridazin-3-yl)quinoline-2-carbonitrile tert-Butyl 4-(6-(2-cyano-6-methoxyquinolin-7-yl)pyridazin-3-yl)piperazine-1-carboxylate was subjected to Boc and methoxy deprotection conditions as described in GENERAL METHOD 2-1. The resulting solid was suspended in acetonitrile:$H_2O$ (3:1 mL). 1 M aqueous HCl (3 equivalents) was added and solvent was concentrated in vacuo to afford the title compound (8.6 mg). LC/MS Rt=0.48. MS (M+1)=333.1 $^1$H NMR (400 MHz, DMSO-$d_6$) δ 8.72 (s, 1H), 8.56 (d, J=9.8 Hz, 1H), 8.46 (d, J=8.5 Hz, 1H), 7.95 (d, J=8.5 Hz, 1H), 7.75 (d, J=9.8 Hz, 1H), 7.51 (s, 1H), 4.00 (m, 4H), 3.27 (bs, 4H).

Example 27-2: Synthesis of 7-hydroxy-6-(6-(piper-azin-1-yl)pyridazin-3-yl)quinoline-2-carbonitrile

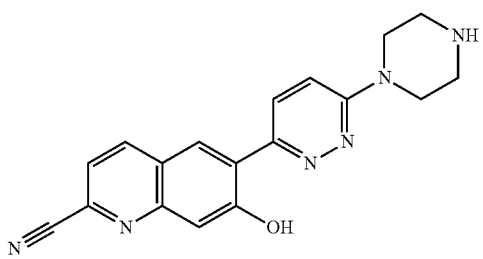 [SMILES: N#Cc1ccc2cc(-c3ccc(N4CCNCC4)nn3)c(O)cc2n1]

Step 1: tert-Butyl 4-(6-(2-cyano-7-methoxyquinolin-6-yl)pyridazin-3-yl) piperazine-1-carboxylate tert-Butyl 4-(6-(2-cyano-7-methoxyquinolin-6-yl)pyridazin-3-yl)piperazine-1-carboxylate was prepared from 7-methoxy-6-(4,4,5,5-tetramethyl-1,3,2-dioxaborolan-2-yl)quinoline-2-carbonitrile and tert-butyl 4-(6-chloropyridazin-3-yl)piperazine-1-carboxylate via Suzuki conditions described in GENERAL METHOD 1-1 (100 mg). MS (M+1)=447.4

Step 2: 7-Hydroxy-6-(6-(piperazin-1-yl)pyridazin-3-yl)quinoline-2-carbonitrile tert-butyl 4-(6-(2-cyano-7-methoxyquinolin-6-yl)pyridazin-3-yl)piperazine-1-carboxylate was subjected to Boc and methoxy deprotection conditions as described in GENERAL METHOD 2-1. Free basing via SCX, as described in GENERAL METHOD 3-1, afforded the title compound (1.9 mg). LC/MS Rt=0.45. MS (M+1)=333.1 $^1$H NMR (400 MHz, Methanol-$d_4$) δ 8.47-8.36 (m, 2H), 8.27 (d, J=9.9 Hz, 1H), 7.62 (d, J=8.3 Hz, 1H), 7.55 (s, 1H), 7.42 (d, J=9.8 Hz, 1H), 3.90-3.70 (m, 4H), 3.20-2.97 (m, 4H).

Example 27-3: Synthesis of 7-(6-(piperazin-1-yl)pyridazin-3-yl)isoquinolin-6-ol

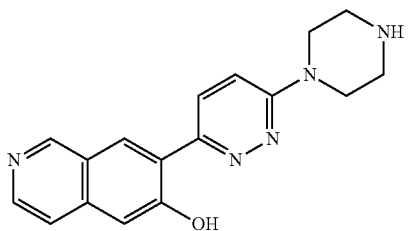 [SMILES: Oc1cc2ccncc2cc1-c1ccc(N2CCNCC2)nn1]

Step 1: tert-Butyl 4-(6-(6-methoxyisoquinolin-7-yl)pyridazin-3-yl)piperazine-1-carboxylate tert-Butyl 4-(6-(6-methoxyisoquinolin-7-yl)pyridazin-3-yl)piperazine-1-carboxylate was prepared from 6-methoxy-7-(4,4,5,5-tetramethyl-1,3,2-dioxaborolan-2-yl)isoquinoline-1-carbonitrile and tert-butyl 4-(6-chloropyridazin-3-yl)piperazine-1-carboxylate via Suzuki conditions described in GENERAL METHOD 1-1 (340 mg). MS (M+1)=422.6

Step 2: 7-(6-(Piperazin-1-yl)pyridazin-3-yl)isoquinolin-6-ol tert-Butyl 4-(6-(6-methoxyisoquinolin-7-yl)pyridazin-3-yl)piperazine-1-carboxylate was subjected to Boc and methoxy deprotection conditions as described in GENERAL METHOD 2-1 to afford the title compound (11.3 mg). LC/MS Rt=0.31. MS (M+1)=308.1 $^1$H NMR (400 MHz, DMSO-$d_6$) δ 9.17 (s, 1H), 8.76 (s, 1H), 8.41 (d, J=9.9 Hz, 1H), 8.35 (d, J=5.8 Hz, 1H), 7.68-7.57 (m, 2H), 7.29 (s, 1H), 3.74-3.55 (m, 4H), 2.94-2.73 (m, 4H).

Example 28-1: Synthesis of 7-(6-(1,2,3,6-tetrahy-dropyridin-4-yl)pyridazin-3-yl)quinolin-6-ol

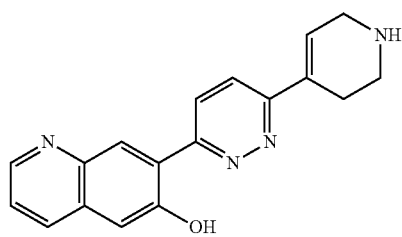 [SMILES: Oc1cc2cccnc2cc1-c1ccc(C2=CCNCC2)nn1]

Step 1: tert-Butyl 4-(6-chloropyridazin-3-yl)-5,6-dihydropyridine-1(2H)-carboxylate A mixture of 3,6-dichloropyridazine (265 mg, 1.78 mmol), tert-butyl 4-(4,4,5,5-tetramethyl-1,3,2-dioxaborolan-2-yl)-5,6-dihydropyridine-1(2H)-carboxylate (500 mg, 1.62 mmol), and Na$_2$CO$_3$ (514 mg, 4.85 mmol) in dioxane (3.1 mL) and water (0.5 mL) was degassed with a stream of dry nitrogen for 5 min. PdCl$_2$(dppf)-CH$_2$Cl$_2$ adduct (66 mg, 0.08 mmol) was added and the mixture was degassed for an addition 5 min with dry nitrogen and heated at 80° C. for 3 h. The reaction mixture was concentrated in vacuo, diluted with water and extracted with DCM. The organic exact was dried over Na$_2$SO$_4$ and concentrated in vacuo. The crude product was purified by silica gel chromatography (0-100% EtOAc/Hep) to afford tert-butyl 4-(6-chloropyridazin-3-yl)-5,6-dihydropyridine-1(2H)-carboxylate (192 mg). MS—tert-butyl (M+1)=240.4

Step 2: tert-Butyl 4-(6-(6-methoxyquinolin-7-yl)pyridazin-3-yl)-5,6-dihydropyridine-1(2H)-carboxylate tert-Butyl 4-(6-(6-methoxyquinolin-7-yl)pyridazin-3-yl)-5,6-dihydropyridine-1 (2H)-carboxylate was prepared from tert-butyl 4-(6-chloropyridazin-3-yl)-5,6-dihydropyridine-1 (2H)-carboxylate and 6-methoxy-7-(4,4,5,5-tetramethyl-1,3,2-dioxaborolan-2-yl)quinoline (prepared as in Example 6-1) via Suzuki conditions described in GENERAL METHOD 1-1 (175 mg). MS (M+1)=419.1

Step 3: 7-(6-(1,2,3,6-Tetrahydropyridin-4-yl)pyridazin-3-yl)quinolin-6-ol tert-Butyl 4-(6-(6-methoxyquinolin-7-yl)pyridazin-3-yl)-5,6-dihydropyridine-1 (2H)-carboxylate was subjected to Boc and methoxy deprotection conditions as described in GENERAL METHOD 2-3 to afford the title compound (2.0 mg). LC/MS Rt=0.40. MS (M+1)=305.1 1H NMR (400 MHz, Methanol-d4) δ 8.97 (d, J=4.7 Hz, 1H), 8.81 (d, J=8.4 Hz, 1H), 8.74 (s, 1H), 8.59 (d, J=9.0 Hz, 1H), 8.23 (d, J=8.9 Hz, 1H), 7.89 (dd, J=8.3, 4.7 Hz, 1H), 7.66 (s, 1H), 7.04-6.77 (m, 1H), 4.03 (d, J=3.5 Hz, 2H), 3.57 (t, J=6.0 Hz, 2H), 3.14 (d, J=6.3 Hz, 2H).

Example 29-1: Synthesis of 1-methyl-6-(6-(methyl(2,2,6,6-tetramethylpiperidin-4-yl)amino)pyridazin-3-yl)isoquinolin-7-ol

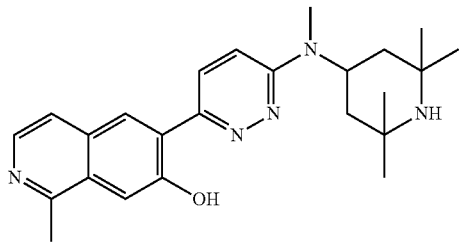

Step 1: 6-Bromo-7-methoxy-1-methylisoquinoline

To a mixture of 6-bromo-7-methoxyisoquinoline 2-oxide (160 mg, 0.630 mmol), prepared in the same manner as in Example 26-1, and THF (3.2 mL) cooled to 0° C. was added Bis(cyclopentadienyl)-µ-chloro(dimethylaluminum)-µ-methylenetitanium (Tebbe Reagent) (0.5 M in toluene, 1.4 mL, 0.693 mmol). The mixture was stirred at 00° C. for 1 h, quenched with 5.0 N aqueous NaOH, and extracted with DCM (3×). The combined organic exacts were dried over Na$_2$SO$_4$ and concentrated in vacuo. The crude product was purified by silica gel chromatography (0-5% MeOH/DCM) to afford 6-bromo-7-methoxy-1-methylisoquinoline (43 mg). MS (M+1)=254.3

Step 2: 7-Methoxy-1-methyl-6-(4,4,5,5-tetramethyl-1,3,2-dioxaborolan-2-yl)isoquinoline 7-Methoxy-1-methyl-6-(4,4,5,5-tetramethyl-1,3,2-dioxaborolan-2-yl)isoquinoline was prepared from 6-bromo-7-methoxy-1-methylisoquinoline via boronate ester formation as described in GENERAL METHOD 7-1 (132 mg). MS (M+1)=300.5

Step 3: 6-(7-Methoxy-1-methylisoquinolin-6-yl)-N-methyl-N-(2,2,6,6-tetramethylpiperidin-4-yl)pyridazin-3-amine 6-(7-methoxy-1-methylisoquinolin-6-yl)-N-methyl-N-(2,2,6,6-tetramethylpiperidin-4-yl)pyridazin-3-amine was prepared from 7-methoxy-1-methyl-6-(4,4,5,5-tetramethyl-1,3,2-dioxaborolan-2-yl)isoquinoline and 6-chloro-N-methyl-N-(2,2,6,6-tetramethylpiperidin-4-yl)pyridazin-3-amine (Intermediate 1) via Suzuki conditions described in GENERAL METHOD 1-1 (177 mg). MS (M+1)=420.6

Step 4: 1-Methyl-6-(6-(methyl(2,2,6,6-tetramethylpiperidin-4-yl)amino)pyridazin-3-yl)isoquinolin-7-ol 6-(7-Methoxy-1-methylisoquinolin-6-yl)-N-methyl-N-(2,2,6,6-tetramethylpiperidin-4-yl)pyridazin-3-amine was subjected to methoxy deprotection conditions as described in GENERAL METHOD 2-1 followed by free basing via GENERAL METHOD 8-1 to afford the title compound (8.0 mg). LC/MS Rt=0.42. MS (M+1)=406.3 $^1$H NMR (400 MHz, DMSO-d$_6$) δ 8.52 (s, 1H), 8.38 (d, J=9.9 Hz, 1H), 8.15 (d, J=5.7 Hz, 1H), 7.58 (d, J=5.7 Hz, 1H), 7.49 (s, 1H), 7.39 (d, J=9.9 Hz, 1H), 2.98 (s, 3H), 2.79 (s, 3H), 1.65-1.36 (m, 4H), 1.26 (s, 6H), 1.09 (s, 6H).

Example 29-2: Synthesis of 1-methyl-7-(6-(methyl(2,2,6,6-tetramethylpiperidin-4-yl)amino)pyridazin-3-yl)isoquinolin-6-ol

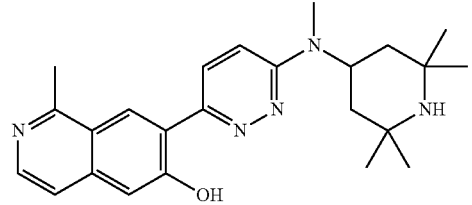 [SMILES: Cc1nccc2cc(O)c(-c3ccc(N(C)C4CC(C)(C)NC(C)(C)C4)nn3)cc12]

Step 1: N-(1-(3-Bromo-4-methoxyphenyl)ethyl)-2,2-dimethoxyethanamine

A mixture of 2,2-dimethoxyethanamine (2.5 g, 24.01 mmol) and 1-(3-bromo-4-methoxyphenyl)ethanone (5.0 g, 21.83 mmol) in toluene in a 250 mL flask equipped with a dean-stark adaptor and condenser was heated to 140° C. for 18 h. The reaction mixture was cooled to ambient temperature and concentrated in vacuo. To the resulting oil was added MeOH (112 mL) followed by NaBH₄ (1.6 g, 41.9 mmol). The mixture was stirred at room temperature for 3.5 h, cooled to 00° C. and acidified with 1N aqueous HCl then concentrated in vacuo to remove MeOH. The resulting aqueous mixture was washed with DCM, basified with 1N aqueous NaOH and extracted with DCM. The organic extract was dried over Na₂SO₄ and concentrated in vacuo to afford N-(1-(3-bromo-4-methoxyphenyl)ethyl)-2,2-dimethoxyethanamine (2.1 g). MS (M+1)=319.7.

Step 2: 7-Bromo-6-methoxy-1-methylisoquinoline

To a 2 mL microwave vial containing N-(1-(3-bromo-4-methoxyphenyl)ethyl)-2,2-dimethoxyethanamine (250 mg, 0.786 mmol) cooled to −78° C. was slowly added chlorosulfonic acid (0.53 mL, 7.86 mmol). The mixture was then allowed to stir at room temperature for 18 h, then added dropwise to ice water. The resulting aqeuous mixture was washed with diethyl ether, basified with saturated aqueous Na₂CO₃, and extracted with DCM (2×). The resulting organic extracts were dried over Na₂SO₄ and concentrated in vacuo to afford 7-bromo-6-methoxy-1-methylisoquinoline (86 mg). MS (M+1)=254.0.

Step 3: 6-Methoxy-1-methyl-7-(4,4,5,5-tetramethyl-1,3,2-dioxaborolan-2-yl)isoquinoline 6-Methoxy-1-methyl-7-(4,4,5,5-tetramethyl-1,3,2-dioxaborolan-2-yl)isoquinoline was prepared from 7-bromo-6-methoxy-1-methylisoquinoline via boronate ester formation as decribed in GENERAL METHOD 7-1. MS (M+1) =300.5.

Step 4: 6-(6-Methoxy-1-methylisoquinolin-7-yl)-N-methyl-N-(2,2,6,6-tetramethylpiperidin-4-yl) pyridazin-3-amine 6-(6-Methoxy-1-methylisoquinolin-7-yl)-N-methyl-N-(2,2,6,6-tetramethylpiperidin-4-yl)pyridazin-3-amine was prepared from 6-methoxy-1-methyl-7-(4,4,5,5-tetramethyl-1,3,2-dioxaborolan-2-yl)isoquinoline and 6-chloro-N-methyl-N-(2,2,6,6-tetramethylpiperidin-4-yl)pyridazin-3-amine (Intermediate I) via Suzuki conditions described in GENERAL METHOD 1-1 (156 mg). MS (M+1)=420.6.

Step 5: 1-Methyl-7-(6-(methyl(2,2,6,6-tetramethylpiperidin-4-yl)amino)pyridazin-3-yl)isoquinolin-6-ol 6-(6-Methoxy-1-methylisoquinolin-7-yl)-N-methyl-N-(2,2,6,6-tetramethylpiperidin-4-yl)pyridazin-3-amine was subjected to methoxy deprotection conditions as described in GENERAL METHOD 2-1 followed by free basing via GENERAL METHOD 8-1 to afford the title compound (6.0 mg). LC/MS Rt=0.41. MS (M+1)=404.1 ¹H NMR (400 MHz, Methanol-d₄) δ 8.95 (s, 1H), 8.55 (d, J=9.9 Hz, 1H), 8.21 (d, J=6.8 Hz, 1H), 8.03 (d, J=6.8 Hz, 1H), 7.68 (d, J=9.9 Hz, 1H), 7.58 (s, 1H), 5.55-5.23 (m, 1H), 3.22 (s, 3H), 3.14 (s, 3H), 2.07-1.98 (m, 4H), 1.66 (s, 6H), 1.54 (s, 6H).

Example 29-3: Synthesis of 1,3-dimethyl-7-(6-(methyl(2,2,6,6-tetramethylpiperidin-4-yl)amino) pyridazin-3-yl)isoquinolin-6-ol

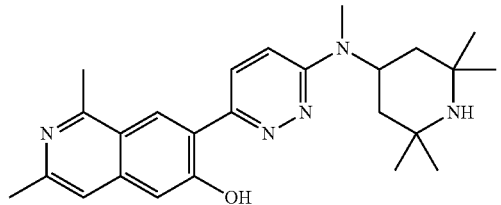

Step 1: N-(1,1-Dimethoxypropan-2-ylidene)-1-phenylmethanamine

A mixture of 1,1-dimethoxypropan-2-one (12.7 mL, 105 mmol), phenylmethanamine (10 mL, 91 mmol) and magnesium sulfate (11.0 g, 91 mmol) in DCM (91 mL) was stirred at room temperature for 18 h. The reaction mixture was filtered through celite and concentrated in vacuo to afford N-(1,1-dimethoxypropan-2-ylidene)-1-phenylmethanamine. ¹H NMR (400 MHz, Chloroform-d) δ 7.34 (d, J=5.0 Hz, 4H), 7.32-7.18 (m, 1H), 4.56 (d, J=1.6 Hz, 2H), 3.44 (s, 6H), 1.95 (s, 3H).

Step 2: N-Benzyl-1,1-dimethoxypropan-2-amine

To a mixture of N-(1,1-dimethoxypropan-2-ylidene)-1-phenylmethanamine (18.9 g, 91 mmol) in MeOH (101 ml) cooled to −78° C. was added NaBH₄ (4.0 g, 105 mmol) portionwise over 20 min. The resulting suspension was stirred at room temperature for 3 days and concentrated in vacuo. The resulting slurry was taken up in toluene, washed with water, saturated aqueous ammonium chloride, then dried over Na₂SO₄ and concentrated in vacuo to afford N-benzyl-1,1-dimethoxypropan-2-amine (19.0 g). MS (M+1)=210.0.

Step 3: 1,1-Dimethoxypropan-2-amine

A mixture of N-benzyl-1,1-dimethoxypropan-2-amine (19.0 g, 91 mmol) and 10% palladium on carbon (0.97 g, 0.910 mmol in MeOH (182 ml) was stirred at 50 psi under hydrogen for 18 h. The suspension was then filtered through celite and concentrated in vacuo to afford 1,1-dimethoxypropan-2-amine (10.8 g). ¹H NMR (400 MHz, Chloroform-d) δ 3.93 (d, J=5.9 Hz, 1H), 3.38 (s, 3H), 3.35 (s, 3H), 2.95 (p, J=6.4 Hz, 1H), 1.04 (d, J=6.5 Hz, 3H).

Step 4: N-(1-(3-Bromo-4-methoxyphenyl)ethyl)-1,1-dimethoxypropan-2-amine

A mixture of 1,1-dimethoxypropan-2-amine (0.5 g, 4.20 mmol), 1-(3-bromo-4-methoxyphenyl)ethanone (1.2 g, 5.0 mmol) and titanium(IV) isopropoxide (2.5 ml, 8.39 mmol) in THF (5 ml) was stirred at room temperature for 18 h. The mixture was then cooled to 0° C., NaBH₄ (0.48 g, 12.59 mmol) was added followed by EtOH (5 mL) and the mixture was stirred at room temperature 4 h. 1N aqueous ammonium hydroxide was added and the reaction was filtered through celite. The filtrate was extracted with ether and the organic extract was extracted with 1N aqueous HCl. The aqueous mixture was basified with 1N aqueous NaOH and extracted with ether (2×). The organic extracts were dried over Na$_2$SO$_4$ and concentrated in vacuo to afford N-(1-(3-bromo-4-methoxyphenyl)ethyl)-1,1-dimethoxypropan-2-amine (0.94 g). MS (M+1)=334.1.

Step 5: 7-Bromo-6-methoxy-1,3-dimethylisoquinoline

To a 5 mL microwave vial containing N-(1-(3-bromo-4-methoxyphenyl)ethyl)-1,1-dimethoxypropan-2-amine (1 g, 1.81 mmol) cooled to −78° C. was slowly added chlorosulfonic acid 2.2 mL, 32.5 mmol). The mixture was then allowed to stir at room temperature for 18 h, then added dropwise to ice water. The resulting aqueous material was washed with ether, basified with saturated aqueous Na$_2$CO$_3$, and extracted with DCM (2×). The resulting organic extracts were dried over Na$_2$SO$_4$ and concentrated in vacuo. The crude product was purified by silica gel chromatography (20-80% EtOAc/Hep) to afford 7-bromo-6-methoxy-1,3-dimethylisoquinoline (298 mg). MS (M+1)=268.0.

Step 6: 6-Methoxy-1,3-dimethyl-7-(4,4,5,5-tetramethyl-1,3,2-dioxaborolan-2-yl)isoquinoline 6-methoxy-1,3-dimethyl-7-(4,4,5,5-tetramethyl-1,3,2-dioxaborolan-2-yl)isoquinoline was prepared from 7-bromo-6-methoxy-1,3-dimethylisoquinoline via boronate ester formation as described in GENERAL METHOD 7-1 (135 mg). MS (M+1)=314.1.

Step 7: 6-(6-Methoxy-1,3-dimethylisoquinolin-7-yl)-N-methyl-N-(2,2,6,6-tetramethylpiperidin-4-yl)pyridazin-3-amine 6-(6-Methoxy-1,3-dimethylisoquinolin-7-yl)-N-methyl-N-(2,2,6,6-tetramethylpiperidin-4-yl)pyridazin-3-amine was prepared from 6-methoxy-1,3-dimethyl-7-(4,4,5,5-tetramethyl-1,3,2-dioxaborolan-2-yl)isoquinoline and 6-chloro-N-methyl-N-(2,2,6,6-tetramethylpiperidin-4-yl)pyridazin-3-amine (Intermediate 1) via Suzuki conditions described in GENERAL METHOD 1-1 (253 mg). MS (M+1)=434.2.

Step 8: 1,3-Dimethyl-7-(6-(methyl(2,2,6,6-tetramethylpiperidin-4-yl)amino)pyridazin-3-yl)isoquinolin-6-ol 6-(6-Methoxy-1,3-dimethylisoquinolin-7-yl)-N-methyl-N-(2,2,6,6-tetramethylpiperidin-4-yl)pyridazin-3-amine was subjected to methoxy deprotection conditions as described in GENERAL METHOD 2-1 followed by free basing via GENERAL METHOD 3-1 to afford the title compound (9.7 mg). LC/MS Rt=0.43. MS (M+1)=420.2 $^1$H NMR (400 MHz, DMSO-d$_6$) δ 8.58 (s, 1H), 8.48 (d, J=9.9 Hz, 1H), 7.38 (d, J=10.0 Hz, 1H), 7.27 (s, 1H), 7.16 (s, 1H), 5.21-4.85 (m, 1H), 3.33 (s, 3H), 2.99 (s, 3H), 2.88 (s, 3H), 1.63-1.37 (m, 4H), 1.28 (s, 6H), 1.11 (s, 6H).

Example 30-1: Synthesis of 7-hydroxy-3-methyl-6-(6-(methyl(2,2,6,6-tetramethylpiperidin-4-yl)amino)pyridazin-3-yl)isoquinoline-1-carbonitrile

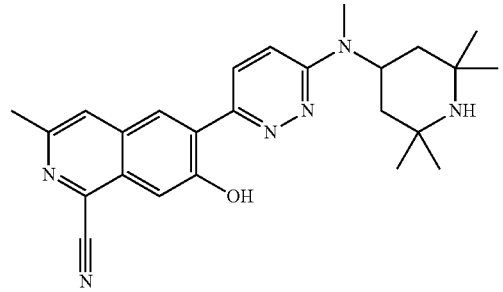

Step 1: N-(4-Bromo-3-methoxybenzyl)-1,1-dimethoxypropan-2-amine

To a mixture of 4-bromo-3-methoxybenzaldehyde (500 mg, 2.325 mmol) and 1,1-dimethoxypropan-2-amine (prepared as in Example 29-3) (610 mg, 5.12 mmol) in THF (4.7 mL) was added sodium triacetoxyborohydride (749 mg, 3.53 mmol). The reaction mixture was stirred at room temperature for 18 h, diluted with EtOAc, washed with saturated aqueous sodium bicarbonate, water, and brine, and dried over MgSO$_4$ to afford N-(4-bromo-3-methoxybenzyl)-1,1-dimethoxypropan-2-amine (700 mg). MS (M+1)=319.9

Step 2: 6-Bromo-7-methoxy-3-methylisoquinoline

To a 5 mL microwave vial containing N-(4-bromo-3-methoxybenzyl)-1,1-dimethoxypropan-2-amine (5.8 g, 18.26 mmol) cooled to −78° C. was slowly added chlorosulfonic acid (12.2 ml, 183 mmol). The mixture was then allowed to stir at room temperature for 18 h and added dropwise to ice water. The resulting aqeuous was washed with diethyl ether, basified with saturated aqueous Na$_2$CO$_3$, and extracted with DCM (2×). The resulting organic extracts were dried over Na$_2$SO$_4$ and concentrated in vacuo. The crude product was purified by silica gel chromatography (20-80% EtOAc/Hep) to afford 6-bromo-7-methoxy-3-methylisoquinoline (630 mg). MS (M+1)=254.0

Step 3: 6-Bromo-7-methoxy-3-methylisoquinoline 2-oxide

To mixture of 6-bromo-7-methoxy-3-methylisoquinoline (630 mg, 2.50 mmol) and MTO (24.9 mg, 0.100 mmol) in DCM (12.5 mL) cooled to 00° C. was added hydrogen peroxide (0.31 mL, 5.00 mmol). The resulting mixture was stirred at room temperature for 3 days. 5-10 mg of MnO$_2$ was added and the reaction mixture was stirred for 2 h. The suspension was filtered through celite and the filtrate was concentrated in vacuo to afford 6-bromo-7-methoxy-3-methylisoquinoline 2-oxide (610 mg). MS (M+1)=269.9

Step 4: 6-Bromo-7-methoxy-3-methylisoquinoline-1-carbonitrile

To a mixture of 6-bromo-7-methoxy-3-methylisoquinoline 2-oxide (585 mg, 2.18 mmol) and trimethylsilyl cyanide (351 mL, 2.62 mmol) in DCM (10.9 mL) was added dimethylcarbamoyl chloride (200 mL, 2.18 mmol). The reaction mixture was stirred at room temperature for 18 h, quenched with excess saturated aqueous $Na_2CO_3$ and extracted with DCM (2×). The organic extracts were washed with brine, dried over $Na_2SO_4$ and concentrated in vacuo to afford 6-bromo-7-methoxy-3-methylisoquinoline-1-carbonitrile (756 mg). MS (M+1)=279.0

Step 5: 7-Methoxy-3-methy-6-(4,4,5,5-tetramethyl-1,3,2-dioxaborolan-2-yl)isoquinoline-1-carbonitrile 7-Methoxy-3-methyl-6-(4,4,5,5-tetramethyl-1,3,2-dioxaborolan-2-yl)isoquinoline-1-carbonitrile was prepared from 6-bromo-7-methoxy-3-methylisoquinoline-1-carbonitrile via boronate ester formation as decribed in GENERAL METHOD 7-1 (702 mg). MS (M+1)=325.1.

Step 6: 7-Methoxy-3-methyl-6-(6-(methyl(2,2,6,6-tetramethylpiperidin-4-yl)amino)pyridazin-3-yl)isoquinoline-1-carbonitrile 7-Methoxy-3-methyl-6-(6-(methyl(2,2,6,6-tetramethylpiperidin-4-yl)amino)pyridazin-3-yl)isoquinoline-1-carbonitrile was prepared from 7-methoxy-3-methyl-6-(4,4,5,5-tetramethyl-1,3,2-dioxaborolan-2-yl)isoquinoline-1-carbonitrile and 6-chloro-N-methyl-N-(2,2,6,6-tetramethylpiperidin-4-yl)pyridazin-3-amine (Intermediate 1) via Suzuki conditions described in GENERAL METHOD 1-1 (960 mg). MS (M+1)=445.4.

Step 7: 7-Hydroxy-3-methyl-6-(6-(methyl(2,2,6,6-tetramethylpiperidin-4-yl)amino)pyridazin-3-yl)isoquinoline-1-carbonitrile 7-Methoxy-3-methyl-6-(6-(methyl(2,2,6,6-tetramethylpiperidin-4-yl)amino)pyridazin-3-yl)isoquinoline-1-carbonitrile was subjected to methoxy deprotection conditions as described in GENERAL METHOD 2-1 followed by free basing via GENERAL METHOD 3-1 to afford the title compound (11.6 mg). LC/MS Rt=0.46. MS (M+1)=431.4 $^1$H NMR (400 MHz, Methanol-$d_4$) δ 8.34 (s, 1H), 8.24 (d, J=9.8 Hz, 1H), 7.84 (s, 1H), 7.64 (s, 1H), 7.26 (d, J=9.8 Hz, 1H), 5.18 (d, J=12.0 Hz, 1H), 3.06 (s, 3H), 2.68 (s, 3H), 1.76 (dd, J=12.7, 3.4 Hz, 2H), 1.57 (t, J=12.6 Hz, 2H), 1.41 (s, 6H), 1.25 (s, 6H).

Example 31-1: Synthesis of 1-amino-7-(6-(methyl (2,2,6,6-tetramethylpiperidin-4-yl)amino)pyridazin-3-yl)isoquinolin-6-ol

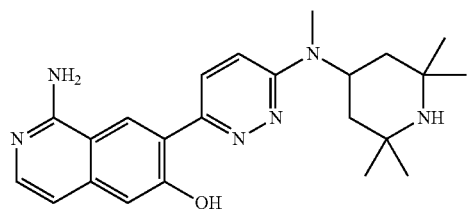 [SMILES: CN(c1ccc(-c2cc3c(N)nccc3cc2O)nn1)C1CC(C)(C)NC(C)(C)C1]

Step 1: 2-(7-Bromo-6-methoxyisoquinolin-1-yl) isoindoline-1,3-dione

To a mixture of 7-bromo-6-methoxyisoquinoline 2-oxide (prepared as described in in Example 3-7 (300 mg, 1.18 mmol), phthalimide (191 mg, 1.29 mmol) and tributylamine (0.6 mL, 2.48 mmol) in DCM (5.2 mL) was added benzoyl chloride (0.2 mL, 1.71 mmol) in DCM (0.74 mL). The reaction mixture was stirred at room temperature for 0.5 h, quenched with water and extracted with DCM. The organic extracts were washed with brine and concentrated in vacuo. The crude product was purified by silica gel chromatography (0-100% EtOAc/Hep) to afford 2-(7-bromo-6-methoxyisoquinolin-1-yl)isoindoline-1,3-dione (257 mg). MS (M+1)=385.0

Step 2: 2-(6-Methoxy-7-(4,4,5,5-tetramethyl-1,3,2-dioxaborolan-2-yl)isoquinolin-1-yl)isoindoline-1,3-dione 2-(6-Methoxy-7-(4,4,5,5-tetramethyl-1,3,2-dioxaborolan-2-yl)isoquinolin-1-yl)isoindoline-1,3-dione was prepared from 2-(7-bromo-6-methoxyisoquinolin-1-yl)isoindoline-1,3-dione via boronate ester formation as described in GENERAL METHOD 7-1. The resulting solid was stirred in diethyl ether and filtered, washing with diethyl ether to afford the product (110 mg). MS (M+1)=430.9

Step 3: 6-Methoxy-7-(6-(methyl(2,2,6,6-tetramethylpiperidin-4-yl)amino)pyridazin-3-yl)isoquinolin-1-amine A mixture of 2-(6-methoxy-7-(4,4,5,5-tetramethyl-1,3,2-dioxaborolan-2-yl)isoquinolin-1-yl)isoindoline-1,3-dione (110 mg, 0.256 mmol), 6-chloro-N-methyl-N-(2,2,6,6-tetramethylpiperidin-4-yl)pyridazin-3-amine (108 mg, 0.383 mmol), potassium acetate (271 mg, 1.28 mmol) and Xphos precatalyst (20.1 mg, 0.026 mmol) in DMF (1.3 mL) was stirred at room temperature for 18 h. The mixture was diluted with excess MeOH, filtered through celite and concentrated in vacuo. To the crude material was added hydrazine (35% aq, 68.8 µL, 0.767 mmol) and MeOH (2 mL). The mixture was heated at 60° C. for 48 h and purified via preparative reverse-phase HPLC (acetonitrile in water, 5 mM ammonium hydroxide modifier) to afford 6-methoxy-7-(6-(methyl(2,2,6,6-tetramethylpiperidin-4-yl)amino) pyridazin-3-yl)isoquinolin-1-amine (15 mg). MS (M+1)=421.3

Step 4: 1-Amino-7-(6-(methyl(2,2,6,6-tetramethylpiperidin-4-yl)amino)pyridazin-3-yl)isoquinolin-6-ol 6-Methoxy-7-(6-(methyl(2,2,6,6-tetramethylpiperidin-4-yl)amino)pyridazin-3-yl)isoquinolin-1-amine was subjected to methoxy deprotection conditions as described in GENERAL METHOD 2-1 followed by free basing via GENERAL METHOD 3-1 to afford the title compound (5.1 mg). LC/MS Rt=0.43. MS (M+1)=405.3 $^1$H NMR (400 MHz, Methanol-$d_4$) δ 8.55 (s, 1H), 8.32 (d, J=10.0 Hz, 1H), 7.61 (d, J=6.1 Hz, 1H), 7.31 (d, J=9.9 Hz, 1H), 7.07 (s, 1H), 6.81 (d, J=6.1 Hz, 1H), 5.28-5.04 (m, 1H), 3.01 (s, 3H), 1.78-1.50 (m, 4H), 1.41 (s, 6H), 1.25 (s, 6H).

Example 32-1: Synthesis of 7-hydroxy-1,3-dimethyl-6-(6-(methyl(2,2,6,6-tetramethylpiperidin-4-yl)amino)pyridazin-3-yl)quinazoline-2,4(1H,3H)-dione

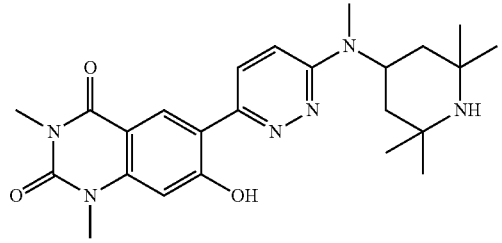

Step 1: 7-(Benzyloxy)-6-bromoquinazoline-2,4(1H,3H)-dione

A mixture of 2-amino-4-(benzyloxy)-5-bromobenzoic acid (500 mg, 1.55 mmol) and urea (3.7 g, 62.1 mmol) was heated at 150° C. for 48 h. The reaction was then cooled to 100° C., excess water was added and the mixture was stirred for 5 min, then cooled to room temperature. The product precipitated and was filtered to afford 7-(benzyloxy)-6-bromoquinazoline-2,4(1H,3H)-dione (341 mg). MS (M+1)=348.9.

Step 2: 7-(Benzyloxy)-6-bromo-1,3-dimethylquinazoline-2,4(1H,3H)-dione

A mixture of 7-(benzyloxy)-6-bromoquinazoline-2,4(1H, 3H)-dione (292 mg, 0.841 mmol), $K_2CO_3$ (581 mg, 4.21 mmol) and MeI (0.174 mL, 2.78 mmol) in DMF (4.2 mL) was stirred at room temperature for 3 h. The mixture was diluted with water and the resulting precipitate was filtered and washed with ether to afford 7-(benzyloxy)-6-bromo-1,3-dimethylquinazoline-2,4(1H, 3H)-dione (207 mg). MS (M+1)=377.0.

Step 3: 7-(Benzyloxy)-1,3-dimethyl-6-(4,4,5,5-tetramethyl-1,3,2-dioxaborolan-2-yl)quinazoline-2,4(1H,3H)-dione 7-(Benzyloxy)-1,3-dimethyl-6-(4,4,5,5-tetramethyl-1,3,2-dioxaborolan-2-yl)quinazoline-2,4(1H, 3H)-dione was prepared from 7-(benzyloxy)-6-bromo-1,3-dimethylquinazoline-2,4(1H, 3H)-dione via boronate ester formation as decribed in GENERAL METHOD 7-1 (115 mg). MS (M+1)=423.2.

Step 4: 7-(Benzyloxy)-1,3-dimethyl-6-(6-(methyl(2,2,6,6-tetramethylpiperidin-4-yl)amino)pyridazin-3-yl) quinazoline-2,4(1H,3H)-dione 7-(Benzyloxy)-1,3-dimethyl-6-(6-(methyl(2,2,6,6-tetramethylpiperidin-4-yl)amino)pyridazin-3-yl)quinazoline-2,4(1H, 3H)-dione was prepared from 7-(benzyloxy)-1,3-dimethyl-6-(4,4,5,5-tetramethyl-1,3,2-dioxaborolan-2-yl)quinazoline-2,4(1H,3H)-dione and 6-chloro-N-methyl-N-(2,2,6,6-tetramethylpiperidin-4-yl)pyridazin-3-amine (Intermediate 1) via Suzuki conditions described in GENERAL METHOD 1-2 (129 mg). MS (M+1)=543.2.

Step 5: 7-Hydroxy-1,3-dimethyl-6-(6-(methyl(2,2,6,6-tetramethylpiperidin-4-yl)amino)pyridazin-3-yl)quinazoline-2,4(1H,3H)-dione To a 50 mL flask containing 7-(benzyloxy)-1,3-dimethyl-6-(6-(methyl(2,2,6,6-tetramethylpiperidin-4-yl)amino)pyridazin-3-yl)quinazoline-2,4(1H, 3H)-dione (93 mg, 0.171 mmol) was added HBr (33% in AcOH, 1.4 mL, 8.57 mmol). The resulting suspension was stirred at room temperature for 1 h, quenched with excess water and purified by SCX via GENERAL METHOD 3-1 to afford the title compound (16.8 mg). LC/MS Rt=0.51. MS (M+1)=453.2 $^1$H NMR (400 MHz, DMSO-$d_6$) δ 8.45 (s, 1H), 8.28 (d, J=9.9 Hz, 1H), 7.35 (d, J=9.8 Hz, 1H), 6.85 (s, 1H), 4.99 (m, 1H), 3.49 (s, 3H), 3.30 (s, 3H), 2.95 (s, 3H), 1.59-1.37 (m, 4H), 1.27 (s, 6H), 1.11 (s, 6H).

Example 33-1: Synthesis of 6-hydroxy-5-(6-(methyl(2,2,6,6-tetramethylpiperidin-4-yl)amino)pyridazin-3-yl)benzo[d]oxazol-2(3H)-one

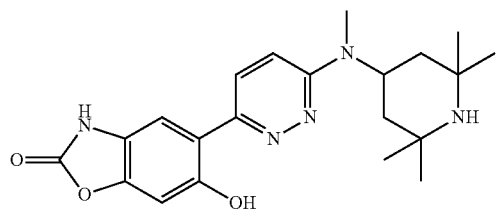 [SMILES: CN(c1ccc(-c2cc3[nH]c(=O)oc3cc2O)nn1)C1CC(C)(C)NC(C)(C)C1]

Step 1: 5-Bromo-6-methoxybenzo[d]oxazol-2(3H)-one

A mixture of 6-methoxybenzo[d]oxazol-2(3H)-one (400 mg, 2.422 mmol) and bromine (0.19 mL, 3.63 mmol) in water (1.3 mL, 72.7 mmol) and AcOH (1.4 mL, 24.22 mmol) was stirred at room temperature for 18 h. The reaction mixture was diluted with water and the product was filtered to afford 5-bromo-6-methoxybenzo[d]oxazol-2(3H)-one (535 mg) as a white precipitate. MS (M+1)=243.9.

Step 2: 6-Methoxy-5-(4,4,5,5-tetramethyl-1,3,2-dioxaborolan-2-yl)benzo[d]oxazol-2(3H)-one 6-Methoxy-5-(4,4,5,5-tetramethyl-1,3,2-dioxaborolan-2-yl)benzo[d]oxazol-2(3H)-one was prepared from 5-bromo-6-methoxybenzo[d]oxazol-2(3H)-one via boronate ester formation as described in GENERAL METHOD 7-1 (400 mg). MS (M+1)=292.1.

Step 3: 6-Methoxy-5-(6-(methyl(2,2,6,6-tetramethylpiperidin-4-yl)amino)pyridazin-3-yl)benzo[d]oxazol-2(3H)-one 6-Methoxy-5-(6-(methyl(2,2,6,6-tetramethylpiperidin-4-yl)amino)pyridazin-3-yl)benzo[d]oxazol-2(3H)-one was prepared from 6-methoxy-5-(4,4,5,5-tetramethyl-1,3,2-dioxaborolan-2-yl)benzo[d]oxazol-2(3H)-one and 6-chloro-N-methyl-N-(2,2,6,6-tetramethylpiperidin-4-yl)pyridazin-3-amine (Intermediate 1) via Suzuki conditions described in GENERAL METHOD 1-2 (77 mg). MS (M+1)=412.2.

Step 4: 6-hydroxy-5-(6-(methyl(2,2,6,6-tetramethylpiperidin-4-yl)amino)pyridazin-3-yl)benzo[d]oxazol-2(3H)-one 6-Methoxy-5-(6-(methyl(2,2,6,6-tetramethylpiperidin-4-yl)amino)pyridazin-3-yl)benzo[d]oxazol-2(3H)-one was subjected to methoxy deprotection conditions as described in GENERAL METHOD 2-3 to afford the title compound (3.3 mg). LC/MS Rt=0.46. MS (M+1)=398.2 $^1$H NMR (400 MHz, Methanol-$d_4$) δ 7.92 (d, J=9.9 Hz, 1H), 7.35 (s, 1H), 7.18 (d, J=9.9 Hz, 1H), 6.86 (s, 1H), 5.04 (t, J=12.5 Hz, 1H), 3.00 (s, 3H), 1.73 (dd, J=12.8, 3.4 Hz, 2H), 1.53 (t, J=12.4 Hz, 2H), 1.39 (s, 6H), 1.23 (s, 6H).

Example 34-1: Synthesis of 2-methyl-5-(6-(methyl(2,2,6,6-tetramethylpiperidin-4-yl)amino)pyridazin-3-yl)-2H-indazol-6-ol

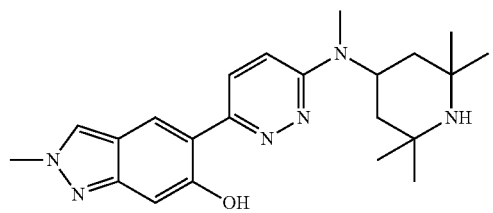

Step 1: 5-Bromo-6-methoxy-1-methyl-1H-indazole and 5-bromo-6-methoxy-2-methyl-2H-indazole To a suspension of NaH (85 mg, 2.11 mmol) in DMF (4 mL) at 0° C. was added 1H-indazol-6-ol (400 mg, 1.76 mmol) in DMF (4 mL). The mixture was stirred at room temperature for 20 min, cooled to 00° C. and MeI (0.17 mL, 2.64 mmol) was added. The reaction mixture was stirred at room temperature for 2 h, quenched with excess saturated aqeuous NH$_4$Cl and extracted with EtOAc. The organic exact was dried over Na$_2$SO$_4$ and concentrated in vacuo. The crude product was purified by silica gel chromatography (0-100% EtOAc/Hep) to afford 5-bromo-6-methoxy-1-methyl-1H-indazole (276 mg). MS (M+1)=243.0 and 5-bromo-6-methoxy-2-methyl-2H-indazole (76 mg). MS (M+1)=243.0.

Step 2: 6-Methoxy-2-methyl-5-(4,4,5,5-tetramethyl-1,3,2-dioxaborolan-2-yl)-2H-indazole 6-Methoxy-2-methyl-5-(4,4,5,5-tetramethyl-1,3,2-dioxaborolan-2-yl)-2H-indazole was prepared from 5-bromo-6-methoxy-2-methyl-2H-indazole via boronate ester formation as described in GENERAL METHOD 7-1 (88 mg). MS (M+1)=289.1.

Step 3: 6-(6-Methoxy-2-methyl-2H-indazol-5-yl)-N-methyl-N-(2,2,6,6-tetramethylpiperidin-4-yl)pyridazin-3-amine 6-(6-Methoxy-2-methyl-2H-indazol-5-yl)-N-methyl-N-(2,2,6,6-tetramethylpiperidin-4-yl)pyridazin-3-amine was prepared 6-methoxy-2-methyl-5-(4,4,5,5-tetramethyl-1,3,2-dioxaborolan-2-yl)-2H-indazole and 6-chloro-N-methyl-N-(2,2,6,6-tetramethylpiperidin-4-yl)pyridazin-3-amine (Intermediate 1) via Suzuki conditions described in GENERAL METHOD 1-2 (101 mg). MS (M+1)=409.3.

Step 4: 2-Methyl-5-(6-(methyl(2,2,6,6-tetramethylpiperidin-4-yl)amino)pyridazin-3-yl)-2H-indazol-6-ol 6-(6-Methoxy-2-methyl-2H-indazol-5-yl)-N-methyl-N-(2,2,6,6-tetramethylpiperidin-4-yl)pyridazin-3-amine was subjected to methoxy deprotection conditions as described in GENERAL METHOD 2-3 to afford the title compound (12.5 mg). LC/MS Rt=0.43. MS (M+1)=395.2. $^1$H NMR (400 MHz, Methanol-$d_4$) δ 8.19-8.06 (m, 3H), 7.30 (d, J=9.9 Hz, 1H), 6.94 (s, 1H), 5.08 (t, J=12.5 Hz, 1H), 4.14 (s, 3H), 3.01 (s, 3H), 1.69 (dd, J=12.7, 3.6 Hz, 2H), 1.58 (t, J=12.5 Hz, 2H), 1.39 (s, 6H), 1.23 (s, 6H).

Example 34-2: Synthesis of 1-methyl-5-(6-(methyl(2,2,6,6-tetramethylpiperidin-4-yl)amino)pyridazin-3-yl)-1H-indazol-6-ol

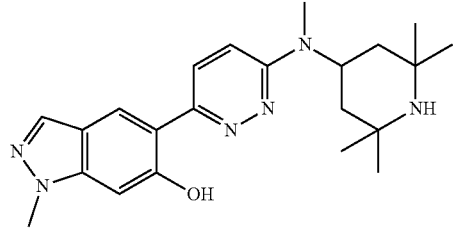 [SMILES: CN(c1ccc(-c2cc3cnn(C)c3cc2O)nn1)C1CC(C)(C)NC(C)(C)C1]

1-Methyl-5-(6-(methyl(2,2,6,6-tetramethylpiperidin-4-yl)amino)pyridazin-3-yl)-1H-indazol-6-ol was prepared in the same manner as Example 34-1 (9.4 mg). LC/MS Rt=0.48. MS (M+1)=395.3. $^1$H NMR (400 MHz, Methanol-$d_4$) δ 8.24-8.12 (m, 2H), 7.95 (d, J=1.0 Hz, 1H), 7.32 (d, J=9.9 Hz, 1H), 6.93 (d, J=0.9 Hz, 1H), 5.14-4.99 (m, 1H), 3.97 (s, 3H), 3.01 (s, 3H), 1.69 (dd, J=12.7, 3.6 Hz, 2H), 1.57 (t, J=12.4 Hz, 2H), 1.38 (s, 6H), 1.23 (s, 6H).

Example 35-1: Synthesis of 6-hydroxy-2-methyl-7-(6-(methyl(2,2,6,6-tetramethylpiperidin-4-yl)amino)pyridazin-3-yl)isoquinolin-1(2H)-one hydrochloride salt

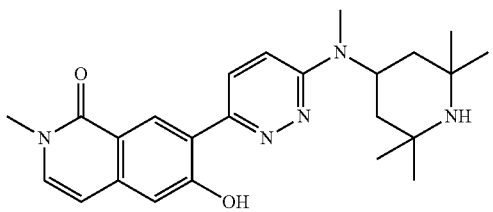

Step 1: 7-Bromo-6-methoxy-2-methylisoquinolin-1(2H)-one

In a 100 mL flask, KHMDS (3.31 mL, 1.653 mmol) was added to Intermediate 14 (210 mg, 0.827 mmol) in dioxane (12 mL) at 0° C., and stirred for 0.5 hr. Methyl iodide (0.078 mL, 1.240 mmol) was added, and the mixture was allowed to stir at room temperature overnight. Water (50 mL) was added to quench the reaction, then the reaction mixture was diluted with EtOAc (100 mL). The layers were separated, and the aqueous layer was extracted with EtOAc (2×). The combined organic layers were washed with brine, dried over MgSO$_4$, filtered, and concentrated in vacuo. The crude residue was purified by silica gel chromatography (20-60% EtOAc/Hep, 24 g Isco column) to provide 7-bromo-6-methoxy-2-methylisoquinolin-1(2H)-one as a yellowish solid, (112 mg, 0.409 mmol, 49.5% yield). MS (M+1)=270.1. $^1$H NMR (400 MHz, CHLOROFORM-d) δ 8.61 (s, 1H), 7.08 (d, J=7.53 Hz, 1H), 6.86 (s, 1H), 6.40 (d, J=7.28 Hz, 1H), 3.99 (s, 3H), 3.59 (s, 3H).

Step 2: (6-Methoxy-2-methyl-1-oxo-1,2-dihydroisoquinolin-7-yl)boronic acid

The title compound (product not isolated) was prepared following GENERAL METHOD 7-1 for boronate ester formation from 7-bromo-6-methoxy-2-methylisoquinolin-1(2H)-one. MS (M+1)=234.2 (boronic acid), 316.2 (boronic ester).

Step 3: 6-Methoxy-2-methyl-7-(6-(methyl(2,2,6,6-tetramethylpiperidin-4-yl)amino)pyridazin-3-yl)isoquinolin-1(2H)-one The title compound (product not isolated) was prepared following GENERAL METHOD 1-1 for Suzuki reaction of Intermediate 1 (70 mg, 0.25 mmol) and (6-methoxy-2-methyl-1-oxo-1,2-dihydroisoquinolin-7-yl)boronic acid (100 mg, 0.43 mmol). MS (M+1)=436.6.

Step 4: 6-Hydroxy-2-methyl-7-(6-(methyl(2,2,6,6-tetramethylpiperidin-4-yl)amino)pyridazin-3-yl)isoquinolin-1 (2H)-one The title compound (48 mg, 0.103 mmol, 49.7% yield) was prepared from 6-methoxy-2-methyl-7-(6-(methyl(2,2,6,6-tetramethylpiperidin-4-yl)amino)pyridazin-3-yl)isoquinolin-1(2H)-one (90 mg, 0.207 mmol) following GENERAL METHOD 2-3 for demethylation using boron tribromide. The crude residue was purified by preparative reverse-phase HPLC (10-30% MeCN/Water, 0.01% TFA modifier). LC/MS Rt=0.50 min. MS (M+1)=422.2. $^1$H NMR (400 MHz, METHANOL-d$_4$) δ 8.59 (s, 1H), 8.48 (d, J=10.04 Hz, 1H), 8.06 (d, J=10.04 Hz, 1H), 7.45 (d, J=7.28 Hz, 1H), 7.10-7.19 (m, 1H), 6.61 (d, J=7.28 Hz, 1H), 5.02 (br. s., 1H), 3.60 (s, 3H), 3.20 (s, 3H), 1.99-2.15 (m, 4H), 1.65 (s, 6H), 1.58 (s, 6H).

Example 35-2: Synthesis of 2-ethyl-6-hydroxy-7-(6-((2,2,6,6-tetramethylpiperidin-4-yl)oxy)pyridazin-3-yl)isoquinolin-1(2H)-one

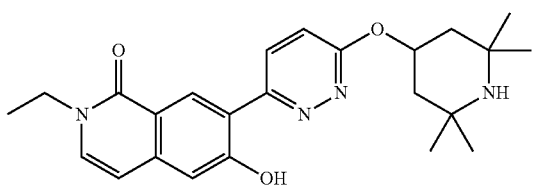 [SMILES: CCn1ccc2cc(O)c(-c3ccc(OC4CC(C)(C)NC(C)(C)C4)nn3)cc2c1=O]

Step 1:
7-Bromo-2-ethyl-6-methoxyisoquinolin-1(2H)-one

In a 30 mL vial, LiHMDS (2.4 mL, 1.2 mmol) was added to Intermediate 14 (75 mg, 0.295 mmol) in dioxane (1.5 mL) at RT, and stirred for 0.5 hr. Then ethyl iodide (70 μl, 0.885 mmol) was added, and the mixture was stirred overnight at 80° C., and allowed to stir overnight. The reaction was cooled to room temperature and water (10 mL) was added to quench reaction, and the reaction mixture was diluted with EtOAc (15 mL). The layers were separated and the aqueous layers extracted with EtOAc (2×). The combined organic layers were washed with brine, dried over MgSO$_4$, filtered, and concentrated in vacuo. The crude residue was purified by silica gel chromatography (20-60% EtoAc/Hep, 12 g Isco column, elutes at 40% EtOAc) to provide the title compound as a yellowish solid (62 mg, 0.220 mmol). MS (M+1)=283.9. $^1$H NMR (400 MHz, DMSO-d$_6$) δ 8.30 (s, 1H), 7.51 (d, J=7.33 Hz, 1H), 7.29 (s, 1H), 6.60 (d, J=7.33 Hz, 1H), 3.90-4.01 (m, 5H), 1.23 (t, J=7.07 Hz, 3H).

Step: 2-Ethyl-6-methoxy-7-(4,4,5,5-tetramethyl-1,3,2-dioxaborolan-2-yl)isoquinolin-1(2H)-one The title compound (product not isolated) was prepared following GENERAL METHOD 7-1 for boronate ester formation from 7-bromo-2-ethyl-6-methoxyisoquinolin-1(2H)-one. The crude product was used without further purification. MS (M+1)=248.1 (boronic acid), 330.1 (boronic ester).

Step 3: 2-Ethyl-6-methoxy-7-(6-((2,2,6,6-tetramethylpiperidin-4-yl)oxy)pyridazin-3-yl)isoquinolin-1 (2H)-one The title compound (product not isolated) was prepared following GENERAL METHOD 1-1 for Suzuki reaction of Intermediate 3 (50 mg, 0.185 mmol) and 2-ethyl-6-methoxy-7-(4,4,5,5-tetramethyl-1,3,2-dioxaborolan-2-yl)isoquinolin-1(2H)-one (68.7 mg, 0.278 mmol). MS (M+1)=437.2.

Step 4: 2-Ethyl-6-hydroxy-7-(6-((2,2,6,6-tetramethylpiperidin-4-yl)oxy)pyridazin-3-yl)isoquinolin-1 (2H)-one The title compound (9 mg, 0.019 mmol, 13.18% yield) was prepared from 2-ethyl-6-methoxy-7-(6-((2,2,6,6-tetramethylpiperidin-4-yl)oxy)pyridazin-3-yl)isoquinolin-1 (2H)-one (63 mg, 0.144 mmol) following GENERAL METHOD 2-3 for demethylation using boron tribromide. The crude residue was purified by preparative reverse-phase HPLC (10-30% ACN/Water, 0.01% TFA modifier). LC/MS Rt=0.53 min. MS (M+1)=423.2. $^1$H NMR (400 MHz, METHANOL-d$_4$) δ 8.75 (d, J=9.35 Hz, 1H), 8.70 (s, 1H), 7.97-8.05 (m, 3H), 7.51 (d, J=7.33 Hz, 1H), 7.20 (s, 1H), 6.66 (d, J=7.33 Hz, 1H), 5.69-5.84 (m, 1H), 4.10 (q, J=7.07 Hz, 2H), 2.53 (dd, J=3.79, 13.64 Hz, 2H), 1.99 (m, 2H), 1.66 (s, 6H), 1.62 (s, 6H), 1.38 (t, J=7.07 Hz, 3H).

Example 35-3: Synthesis of 1-ethoxy-7-(6-(methyl (2,2,6,6-tetramethylpiperidin-4-yl)amino)pyridazin-3-yl)isoquinolin-6-ol

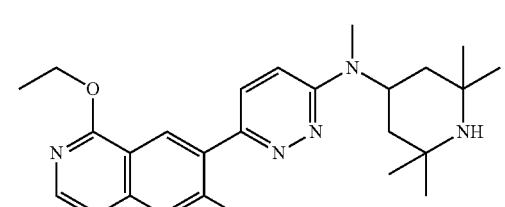

Step 1: 7-Bromo-1-ethoxy-6-methoxyisoquinoline

In a 30 mL vial, 7-bromo-1-chloro-6-methoxyisoquinoline (200 mg, 0.734 mmol) was partially dissolved in 2 mL sodium ethoxide 3 M solution (2 mL, 6.00 mmol), and stirred at 80° C. overnight. The mixture was concentrated in vacuo. The crude residue was purified by silica gel chromatography (12 g Isco column, 5-30% EtOAc/Hep) to provide the title compound (157 mg, 0.556 mmol, 76% yield). MS (M+1)=284.0. 1H NMR (400 MHz, Chloroform-d) δ 8.46 (s, 1H), 7.95 (d, J=5.8 Hz, 1H), 7.09 (d, J=6.0 Hz, 1H), 7.03 (s, 1H), 4.53 (q, J=7.1 Hz, 2H), 4.02 (s, 3H), 1.50 (t, J=7.0 Hz, 3H).

Step 2: 1-Ethoxy-6-methoxy-7-(4,4,5,5-tetramethyl-1,3,2-dioxaborolan-2-yl)isoquinoline The title compound (product not isolated) was prepared following GENERAL METHOD 7-1 for boronate ester formation from 7-bromo-2-ethyl-6-methoxyisoquinolin-1(2H)-one. MS (M+1)=248.1 (boronic acid), 330.1 (boronic ester).

Step 3: 6-(1-Ethoxy-6-methoxyisoquinolin-7-yl)-N-methyl-N-(2,2,6,6-tetramethylpiperidin-4-yl)pyridazin-3-amine The title compound (product not isolated) was prepared following GENERAL METHOD 1-1 for Suzuki reaction of Intermediate 1 (100 mg, 0.354 mmol) and 1-ethoxy-6-methoxy-7-(4,4,5,5-tetramethyl-1,3,2-dioxaborolan-2-yl)isoquinoline (150 mg, 0.607 mmol). MS (M+1)=450.1.

Step 4: 1-Ethoxy-7-(6-(methyl(2,2,6,6-tetramethylpiperidin-4-yl)amino)pyridazin-3-yl)isoquinolin-6-ol The title compound (10 mg, 0.022 mmol, 10% yield) was prepared from 6-(1-ethoxy-6-methoxyisoquinolin-7-yl)-N-methyl-N-(2,2,6,6-tetramethylpiperidin-4-yl)pyridazin-3-amine (100 mg, 0.222 mmol) following GENERAL METHOD 2-3 for demethylation using boron tribromide. The crude residue was purified by preparative reverse-phase HPLC (10-30% MeCN/Water, 0.01% TFA modifier). LC/MS Rt=0.56 min. MS (M+1)=436.3. ¹H NMR (400 MHz, METHANOL-d₄) δ 8.64 (s, 1H), 8.24 (d, J=10.04 Hz, 1H), 7.81 (d, J=6.02 Hz, 1H), 7.36 (d, J=10.04 Hz, 1H), 7.19 (s, 1H), 7.12 (d, J=6.02 Hz, 1H), 5.29 (br. s., 1H), 4.54 (q, J=7.03 Hz, 2H), 3.05 (s, 3H), 1.69-1.87 (m, 4H), 1.48-1.56 (m, 9H), 1.36 (s, 6H).

Example 35-4: Synthesis of 7-(6-((2,2,6,6-tetramethylpiperidin-4-yl)oxy)pyridazin-3-yl)isoquinoline-1,6-diol

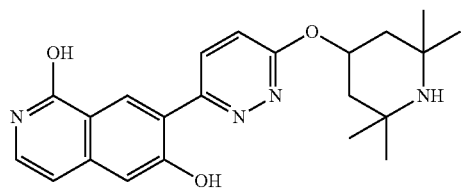 [SMILES: CC1(C)CC(Oc2ccc(-c3cc4c(O)nccc4cc3O)nn2)CC(C)(C)N1]

Step 1: 1-Ethoxy-6-methoxy-7-(6-((2,2,6,6-tetramethylpiperidin-4-yl)oxy)pyridazin-3-yl)isoquinoline The title compound (product not isolated) was prepared following GENERAL METHOD 1-1 for Suzuki reaction of Intermediate 3 (30 mg, 0.111 mmol) and 1-ethoxy-6-methoxy-7-(4,4,5,5-tetramethyl-1,3,2-dioxaborolan-2-yl)isoquinoline (50 mg, 0.151 mmol). MS (M+1)=437.6.

Step 2: 5-Bromo-7-(6-((2,2,6,6-tetramethylpiperidin-4-yl)oxy)pyridazin-3-yl)isoquinoline-1,6-diol The title compound (product not isolated) was prepared from 1-ethoxy-6-methoxy-7-(6-((2,2,6,6-tetramethylpiperidin-4-yl)oxy)pyridazin-3-yl)isoquinoline (45 mg, 0.103 mmol) following GENERAL METHOD 2-3 for demethylation using boron tribromide. The crude residue was purified by preparative reverse-phase HPLC (15-40% ACN/Water, 5 mM NH₄OH modifier). MS (M+1)=475.0.

Step 3. 7-(6-((2,2,6,6-Tetramethylpiperidin-4-yl)oxy)pyridazin-3-yl)isoquinoline-1,6-diol In a 30 mL vial, 5-bromo-7-(6-((2,2,6,6-tetramethylpiperidin-4-yl)oxy)pyridazin-3-yl)isoquinoline-1,6-diol (5 mg, 10.56 μmol), and Pd—C (11.24 mg, 10.56 μmol) were combined in ethanol (Volume: 1500 μl) with a few drops of 1N HCl. The vial was purged with H₂ for 5 min, and stirred overnight under an H₂ balloon at room temperature. The crude residue was purified by preparative reverse-phase HPLC (10-30% MeCN/Water, 0.01% TFA modifier) to provide the title compound (1 mg, 0.002 mmol, 23% yield). LC/MS Rt=0.49 min. MS (M+1)=395.1. ¹H NMR (400 MHz, METHANOL-d₄) δ 8.72 (s, 1H), 8.36 (d, J=9.54 Hz, 1H), 7.30 (d, J=9.54 Hz, 1H), 7.08 (d, J=7.28 Hz, 1H), 7.04 (s, 1H), 6.49 (d, J=7.28 Hz, 1H), 5.75 (t, J=4.14 Hz, 1H), 2.42 (dd, J=4.02, 13.80 Hz, 2H), 1.68-1.80 (m, 2H), 1.54 (s, 6H), 1.45 (s, 6H).

Example 36-1 to 36-6

The following compounds were prepared from triflate Intermediate 16 or Intermediate 17, and an alkyne, according to GENERAL METHOD 10-2 for Sonogashira reaction, followed by amine cyclization according to GENERAL METHOD 10-3, and then methoxy deprotection as outlined in GENERAL METHOD 2-1. The products were purified by preparative reverse-phase HPLC (10-30% MeCN/Water, 0.01% TFA modifier).

TABLE

Examples 36-1 to 36-6:

| Example | Alkyne | Compound | MS (M + 1), LC/MS Rt | ¹H NMR 400 MHz |
|---|---|---|---|---|
| 36-1 | phenylacetylene | 7-(6-(methyl(2,2,6,6-tetramethyl-piperidin-4-yl)amino)-pyridazin-3-yl)-3-phenylisoquinolin-6-ol | 468.3, 0.55 min | METHANOL-d4 δ 9.66 (s, 1H), 8.97 (s, 1H), 8.47-8.56 (m, 2H), 7.92-8.04 (m, 3H), 7.66-7.76 (m, 4H), 5.14 (br. s., 1H), 3.24 (s, 3H), 2.03-2.22 (m, 4H), 1.69 (s, 6H), 1.60 (s, 6H) |
| 36-2 | propyne | 3-methyl-7-(6-(methyl(2,2,6,6-tetramethylpiperidin-4-yl)amino)-pyridazin-3-yl)isoquinolin-6-ol | 406.2, 0.42 min | METHANOL-d4 δ 9.03 (s, 1H), 8.52 (s, 1H), 8.33 (d, J = 10.11 Hz, 1H), 7.45 (s, 1H), 7.38 (d, J = 9.85 Hz, 1H), 7.19 (s, 1H), 5.26 (t, J = 12.13 Hz, 1H), 3.06 (s, 3H), 2.62 (s, 3H), 1.66-1.85 (m, 4H), 1.50 (s, 6H), 1.34 (s, 6H) |
| 36-3 | cyclopropylacetylene | 3-cyclopropyl-7-(6-(methyl(2,2,6,6-tetramethyl-piperidin-4-yl)amino)pyridazin-3-yl)isoquinolin-6-ol | 432.3, 0.45 min | Methanol-d4 δ 8.91 (s, 1H), 8.37 (s, 1H), 8.21 (d, J = 9.9 Hz, 1H), 7.32 (s, 1H), 7.27 (d, J = 9.9 Hz, 1H), 7.10 (s, 1H), 5.16-5.05 (m, 1H), 2.99 (s, 3H), 2.14 (tt, J = 8.0, 5.3 Hz, 1H), 1.67 (dd, J = 12.7, 3.6 Hz, 2H), 1.56 (t, J = 12.4 Hz, 2H), 1.38 (s, 6H), 1.23 (s, 6H), 1.07-0.94 (m, 4H) |
| 36-4 | 3-methyl-1-butyne | 3-isopropyl-7-(6-(methyl(2,2,6,6-tetramethyl-piperidin-4-yl)amino)pyridazin-3-yl)isoquinolin-6-ol | 434.3, 0.46 min | Methanol-d4 δ 9.01 (s, 1H), 8.44 (s, 1H), 8.25 (d, J = 9.7 Hz, 1H), 7.40 (s, 1H), 7.29 (d, J = 9.8 Hz, 1H), 7.17 (s, 1H), 5.12 (t, J = 12.2 Hz, 1H), 3.18-3.06 (m, 1H), 2.99 (s, 3H), 1.68 (dd, J = 12.7, 3.6 Hz, 2H), 1.57 (t, J = 12.4 Hz, 2H), 1.41-1.29 (m, 12H), 1.23 (s, 6H) |
| 36-5 | 1-pentyne | 3-propyl-7-(6-((2,2,6,6-tetramethylpiperidin-4-yl)oxy)-pyridazin-3-yl)isoquinolin-6-ol | 421.2, 0.48 min | METHANOL-d4 δ 9.04 (br. s., 1H), 8.53 (s, 1H), 8.44 (d, J = 9.60 Hz, 1H), 7.41 (s, 1H), 7.29 (d, J = 9.35 Hz, 1H), 7.19 (s, 1H), 5.73-5.86 (m, 1H), 2.84 (t, J = 7.45 Hz, 2H), 2.27 (dd, J = 3.92, 12.51 Hz, 2H), 1.82 (sxt, J = 7.43 Hz, 2H), 1.47 (t, J = 11.75 Hz, 2H), 1.40 (s, 6H), 1.28 (s, 6H), 1.02 (t, J = 7.45 Hz, 3H) |

TABLE-continued

Examples 36-1 to 36-6:

| Example | Alkyne | Compound | MS (M + 1), LC/MS Rt | ¹H NMR 400 MHz |
|---|---|---|---|---|
| 36-6 | | | 421.1, 0.46 min | METHANOL-d4 δ 9.04 (s, 1H), 8.52 (s, 1H), 8.44 (d, J = 9.35 Hz, 1H), 7.43 (s, 1H), 7.28 (d, J = 9.35 Hz, 1H), 7.21 (s, 1H), 5.79 (m, 1H), 3.14 (m J = 6.88 Hz, 1H), 2.26 (dd, J = 4.04, 12.63 Hz, 2H), 1.45 (t, J = 11.87 Hz, 2H), 1.39 (m, J = 3.41 Hz, 12H), 1.28 (s, 6H) |
| | | 3-isopropyl-7-(6-((2,2,6,6-tetramethylpiperidin-4-yl)oxy)-pyridazin-3-yl)isoquinolin-6-ol | | |

Example 37-1: Synthesis of 3-methyl-7-(6-(piperazin-1-yl)pyridazin-3-yl)isoquinolin-6-ol

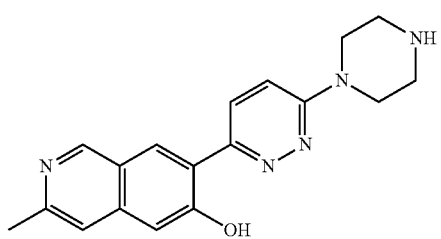 [SMILES: Cc1cc2cc(O)c(-c3ccc(N4CCNCC4)nn3)cc2cn1]

Step 1: tert-Butyl 4-(6-(5-formyl-4-hydroxy-2-methoxyphenyl)pyridazin-3-yl)piperazine-1-carboxylate The title compound (107 mg, 0.258 mmol, 21.43% yield) was prepared following GENERAL METHOD 9-1 for Suzuki reaction of tert-butyl 4-(6-chloropyridazin-3-yl)piperazine-1-carboxylate (4.7 g, 16.62 mmol) and Intermediate 15 (500 mg, 1.8 mmol). Dioxane was removed in vacuo and EtOAc/DCM and water were added. The layers were separated and the aqueous layer was washed with DCM. The combined organics were dried over MgSO4, filtered, and concentrated in vacuo. The crude residue was purified by silica gel chromatography (5-80% EtOAc/Hep). MS (M+1)=415.5. ¹H NMR (400 MHz, Chloroform-d) δ 11.57-11.51 (m, 1H), 9.85-9.79 (m, 1H), 8.26-8.20 (m, 1H), 7.82-7.73 (m, 1H), 6.97-6.89 (m, 1H), 6.58-6.52 (m, 1H), 3.96-3.90 (m, 3H), 3.70 (s, 4H), 3.65-3.56 (m, 4H), 1.53-1.47 (m, 9H).

Step 2: tert-Butyl 4-(6-(5-formyl-2-methoxy-4-(((trifluoromethyl)sulfonyl)oxy)-phenyl)pyridazin-3-yl)piperazine-1-carboxylate In a 20 mL vial, tert-butyl 4-(6-(5-formyl-4-hydroxy-2-methoxyphenyl)pyridazin-3-yl)piperazine-1-carboxylate (100 mg, 0.241 mmol) and N-phenyltrifluoromethane sulfonimide (172 mg, 0.483 mmol) were dissolved in DCM (1.21 mL) under N₂. TEA (135 µl, 0.965 mmol) was added, and the heterogenous mixture stirred for several hours at room temperature until complete dissolution was seen. The reaction was stirred overnight, then taken up in minimum amount of DCM and purified by silica gel chromatography (10-80% EtOAc/Hep, column pretreated with TEA). The collected fractions were concentrated, and placed under high vacuum for several days to provide the title compound, (125 mg, 0.229 mmol, 95% yield). MS (M+1)=547.3. ¹H NMR (400 MHz, CHLOROFORM-d) δ 10.14 (s, 1H), 8.57 (s, 1H), 7.77 (d, J=9.54 Hz, 1H), 6.92-6.98 (m, 2H), 3.98 (s, 3H), 3.57-3.82 (m, 8H), 1.50 (s, 9H).

Step 3: tert-Butyl 4-(6-(5-formyl-2-methoxy-4-(prop-1-yn-1-yl)phenyl)pyridazin-3-yl)piperazine-1-carboxylate The title compound (product not isolated) was prepared following GENERAL METHOD 10-1 for Sonogashira reaction of tert-butyl 4-(6-(5-formyl-2-methoxy-4-(((trifluoromethyl)sulfonyl)-oxy)phenyl)pyridazin-3-yl)piperazine-1-carboxylate (50 mg, 0.091 mmol) and prop-1-yne (18 mg, 0.457 mmol). MS (M+1)=437.6.

Step 4: tert-Butyl 4-(6-(6-methoxy-3-methylisoquinolin-7-yl)pyridazin-3-yl)piperazine-1-carboxylate The title compound (product not isolated) was prepared following GENERAL METHOD 11-1 for aldehyde cyclization from tert-butyl 4-(6-(5-formyl-2-methoxy-4-(prop-1-yn-1-yl)phenyl)pyridazin-3-yl)piperazine-1-carboxylate (39 mg, 0.089 mmol). MS (M+1)=436.5.

Step 5: 3-Methyl-7-(6-(piperazin-1-yl)pyridazin-3-yl)isoquinolin-6-ol

The title compound (5 mg, 0.015 mmol, 16.85% yield) was prepared from tert-butyl 4-(6-(6-methoxy-3-methylisoquinolin-7-yl)pyridazin-3-yl)piperazine-1-carboxylate (39 mg, 0.090 mmol) following GENERAL METHOD 2-1 for demethylation using pyridine hydrochloride. The crude residue was purified by preparative reverse-phase HPLC (10-30% ACN/Water, 0.01% TFA modifier). LC/MS Rt=0.35 min. MS (M+1)=322.01. ¹H NMR (400 MHz, METHANOL-d₄) δ 8.89 (s, 1H), 8.39 (s, 1H), 8.19 (d, J=9.85 Hz, 1H), 7.38 (d, J=9.85 Hz, 1H), 7.31 (s, 1H), 7.06 (s, 1H), 3.55-3.68 (m, 4H), 2.85-2.94 (m, 4H), 2.50 (s, 3H).

LC/MS Conditions
Column: Waters Acquity UPLC BEH C18 1.7 um, 2.1×30 mm (Part #: 186002349)
 Flow rate: 1 mL/min
 Temperature: 55° C. (column temp)
 Mobile phase compositions:
 A. 0.05% formic acid in water.
 B. 0.04% formic acid in methanol
 Gradient:

| Time (min) | Flow (mL/min) | % A | % B |
| --- | --- | --- | --- |
| 0 | 1.000 | 95.0 | 5.0 |
| 0.10 | 1.000 | 95.0 | 5.0 |
| 0.50 | 1.000 | 20.0 | 80.0 |
| 0.60 | 1.000 | 5.0 | 95.0 |
| 0.80 | 1.000 | 5.0 | 95.0 |
| 0.90 | 1.000 | 95.0 | 5.0 |
| 1.15 | 1.000 | 95.0 | 5.0 |

Abbreviations $2^{nd}$ Generation Xphos Precatalyst: chloro(2-dicyclohexylphosphino-2',4',6'-triisopropyl-1,1'-biphenyl)[2-(2'-amino-1,1'-biphenyl)]palladium(II)

ACN: acetonitrile
BOC: tertiary butyl carboxy
Bn: benzyl
BSA: Bovine Serum Albumin
$CH_3CN$: acetonitrile
d: doublet
DCM: dichloromethane
DIEA: N,N-diisopropylethylamine
DMA: dimethylacetamide
DMSO: dimethylsulfoxide
$EC_{50}$: half maximal effective concentration
Et: ethyl
$Et_2O$: diethyl ether
g: gram
h: hour(s)

HPLC: High Pressure Liquid Chromatography
Hz: Hertz
L: liter
LC/MS: liquid chromatography and mass spectrometry
m: multiplet
M, as in M + 1: Molecular Mass
mAB: monoclonal antibody
MeOH: methanol
MHz: mega Hertz
mm: millimeter
mL: milliliter
N: normal
NMP: N-methylpyrrolidone PBST: Phosphate buffered saline with Tween
PhSH: thiophenol
ppm: parts per million
q: quartet
RIPA: radio-immunoprecipitation assay
RT: room temperature
s: singlet
SCX: Strong Cation Exchange
SPhos: 2-Dicyclohexylphosphino-2',6'-dimethoxybiphenyl t: triplet
TBSCl: tert-butyldimethylsilyl chloride
TEA: triethylamine
THF: tetrahydrofuran
TMB: tertramethylbenzidine uL: microliter
UV: ultraviolet
wt: weight
XPhos: 2-Dicyclohexylphosphino-2',4',6'-triisopropylbiphenyl aq: aqueous
$BOC_2O$: tertiary butylcarboxyanhydride
br s: broad singlet CHN: C, H, N elemental analysis
dd: doublet of doublets
DIBAL: diisobutylaluminium hydride
DIPEA: N,N-diisopropylethylamine
DMF: N,N-dimethylformamide
dppf: 1,1'-bis(diphenylphosphino)ferrocene
ELISA: enzyme-linked immunosorbent assay
EtOAc: ethyl acetate
EtOH: ethanol HATU: O-(7-azobenzotriazol-1-yl)-1,1,3,3-tetramethyluroniumhexafluorophosphate
HRP: horse radish peroxidase LC: liquid chromatography M: Molar
mM: millimolar
Me: methyl
mg: milligram
min: minute(s)
mmol: millimole
MS: mass spectrometry
nM: nanomolar
NMR: Nuclear Magnetic Resonance Spectroscopy
Ph: phenyl
pM: picomolar Rt: retention time sat: saturated
SFC: Supercritical Fluid Chromatography TBAF: tetra-butylammonium fluoride
tBu: tert-butyl
Tf: triflate
TLC: thin layer chromatography
TMSOTf: trimethylsilyl trifluoromethanesulfonate
umol: micromol XPhos Precatalyst: Chloro(2-dicyclohexylphosphino-2',4',6'-triisopropyl-1,1'-biphenyl)[2-(2-aminoethyl)phenyl)]palladium(II)

Xphos Precatalyst, 2$^{nd}$ Generation: chloro(2-dicyclohexylphosphino-2',4',6'-triisopropyl-1,1'-biphenyl)[2-(2'-amino-1,1'-biphenyl)]palladium(II)

Biological Example 1

A cellular SMN ELISA was used to measure the effects of low molecular weight compounds on SMN protein elevation. Cells from a myoblast cell line derived from the SMNdelta7 mouse model (kind gift from Steve Burden, NYU) were seeded into a 384-well plate at a density of 3000 cells/well and treated with compounds for 24 hours. ELISA capture plates were prepared by coating 384-well plates (Immulon 4HBX) with 0.5 ug/mL of anti-SMN mAb (BD Science, Catalog number 610647) at 4° C. overnight. The plates were washed 5 times with 110 uL of PBS-Tween (0.05% Tween-20, PBST), blocked with 100 uL of 1% BSA in PBST for 2 hours and washed (5 times) with 100 uL of PBST. After 24 hours of compound treatment cells were lysed in a modified RIPA-buffer, on ice for 1 hour. 20 uL of lysate and 20 uL of 1% BSA were then added to the ELISA capture plates and incubated at 4° C. overnight. Plates were washed (5 times) with PBST and then incubated with 1:100 dilution of primary rabbit anti-SMN polyclonal antibody (Santa cruz, Catalog number SC-15320) at room temperature for 1 hour and subsequently washed (5 times) with 110 uL of PBST. This was followed by addition of 1:100 Goat anti-Rabbit IgG-HRP linked (Cell Signaling, Catalog number 7074) secondary antibody for 1 hour. Plates were then washed with PBST and incubated with 40 uL TMB substrate (Cell Signaling, Catalog number 7004 L) at room temperature for 1-10 minutes with shaking. The reaction was stopped by addition of 40 uL of stop solution (Cell signaling, Catalog number 7002 L) and absorption was measured at 450 nm. Data was reported as fold activation over DMSO control, and $EC_{50}$.

ELISA assay condition 1: compound concentration range 20 nM-10 uM; ELISA assay condition 2: compound concentration 100 pM-10 uM. Data generated in Biological Example 1 using ELISA conditions 1 or 2.

Biological Example 2

SMN2 Full Reporter Construct:

pSMN2 Splicing Luciferase reporter was constructed according to Zhang et al., (An in vivo reporter system for measuring increased inclusion of exon 7 in SMN2 mRNA: potential therapy of SMA. Gene Ther. 2001 October; 8(20): 1532-8) via overlapping PCR. The final PCR fragment containing Exon6-Intron6-Exon7 (with a C insertion before 49T)-Intron7-Exon8-Luciferase was inserted to BamHI and NotI site of pCAG-IRESblast expression vector (Chen et al., Establishment and Maintenance of Genomic Methylation Patterns in Mouse Embryonic Stem Cells by Dnmt3a and Dnmt3b. Mol Cell Biol. 2003 August; 23(16):5594-605).

Human SMN2 exon1-exon6 cDNA were amplified by PCR (Forward primer: ACGGATCCATGGCGAT-GAGCAGCGG; reverse primer: GCCAGTATGATAGC-CACTCATGTACC), and Exon6-Intron6 (Forward primer: ATAATTCCCCCACCACCTCCC; reverse primer: CAT-TCCCTACAATCAATTTCAAATCAGAG) were fused by overlap PCR to create Exon1-Intron6 fragment, and was inserted into pSMN2 splicing Luciferase reporter via BamHI and HindIII sites to create pSMN2 exon1-6 splicing reporter. SMN2 promoter 5.1 kb fragment was amplified from human genomic DNA by PCR (Forward primer: CAGCTAGCACGCGTAAGCTCTGATTGGTGAGC-GATGGTGG; reverse primer: CACTCGAGAGCAAACCCGCGGGTGCGCAGCG), and inserted between MluI site and BamHI site (Blunted using DNA blunting kit, Takara, Cat #6025) of pSMN2 exon1-6 splicing reporter to replace chicken β-actin promoter and the human cytomegalovirus immediate early enhancer, to finalize the pSMN2-Full-reporter.

SMN2 Full Reporter Stable Clone in NSC34 Cells:

pSMN2-Full reporter was stably transfected into NSC34 cells using Lipofectamine 2000, which were subsequently selected in blasticidin-containing medium for two weeks. Blasticidin-resistant colonies were screened by Luciferase signal and response to SAHA as well as by RT-PCR for alternative splicing of Exon7.

Reporter Gene Assay:

NSC34 SMN2 Full reporter stable line was cultured in DMEM (Invitrogen, Cat:11965)+10% FBS+7 µg/ml Blasticidin. Cells in culture media without Blasticidin were seeded into a 384-well plate at a density of 6000 cells/well and treated with compounds for 24 hours. Luciferase signal was assessed by BrightGlo assay. Eequal volume of BrightGlo reagent (Promega, Cat #E2620) was added to the cells and incubated for 10 minutes at room temperature. Luminescent signal was read in either BioTek or Envision plate reader.

Reporter gene assay conditions: compound concentration range 3 nM-10 uM.

Activity Table: Data generated in Biological Example 3 were generated using methods described in Biological example 1 or Biological example 2.

| Example | Biological Example number | SMN Activity | Compound name |
|---|---|---|---|
| Preparation 11 | 1 | 280 nM, 2.6 fold | 4-chloro-2-methyl-6-(6-(methyl(2,2,6,6-tetramethylpiperidin-4-yl)amino)pyridazin-3-yl)quinolin-7-ol |
| Preparation 12 | 1 | 30 nM, 2.6 fold | 4-chloro-6-(6-(methyl(2,2,6,6-tetramethylpiperidin-4-yl)amino)pyridazin-3-yl)quinolin-7-ol |

-continued

Activity Table: Data generated in Biological Example 3 were generated using methods described in Biological example 1 or Biological example 2.

| Example | Biological Example number | SMN Activity | Compound name |
| --- | --- | --- | --- |
| Preparation 13 | 1 | 7 nM, 2.6 fold | 4-chloro-7-(6-(methyl(2,2,6,6-tetramethylpiperidin-4-yl)amino)pyridazin-3-yl)quinolin-6-ol |
| 1-1 | 1 | 20 nM, 2.9 fold | 6-(6-(methyl(2,2,6,6-tetramethylpiperidin-4-yl)amino)pyridazin-3-yl)quinolin-7-ol |
| 1-2 | 1 | 340 nM, 2.4 fold | 6-(6-(methyl(1,2,2,6,6-pentamethylpiperidin-4-yl)amino)pyridazin-3-yl)quinolin-7-ol |
| 1-3 | 1 | 255 nM, 2.5 fold | 6-(6-((3aR,6aS)-5-methylhexahydropyrrolo[3,4-c]pyrrol-2(1H)-yl)pyridazin-3-yl)quinolin-7-ol |
| 2-1 | 1 | 20 nM, 3.0 fold | 2-methyl-6-(6-(methyl(2,2,6,6-tetramethylpiperidin-4-yl)amino)pyridazin-3-yl)quinolin-7-ol |
| 3-1 | 1 | 70 nM, 3.1 fold | 7-(6-(methyl(1,2,2,6,6-pentamethylpiperidin-4-yl)amino)pyridazin-3-yl)isoquinolin-6-ol |
| 3-2 | 1 | 5 nM, 2.75 fold | 7-(6-(methyl(2,2,6,6-tetramethylpiperidin-4-yl)amino)pyridazin-3-yl)isoquinolin-6-ol |
| 3-3 | 1 | 83 nM, 2.5 fold | 7-(6-((2,2,6,6-tetramethylpiperidin-4-yl)oxy)pyridazin-3-yl)isoquinolin-6-ol |
| 3-4 | 1 | 60 nM, 2.3 fold | 7-(6-((3aR,6aS)-5-methylhexahydropyrrolo[3,4-c]pyrrol-2(1H)-yl)pyridazin-3-yl)isoquinolin-6-ol |
| 3-5 | 1 | 14 nM, 2.54 fold | 1-cyclopropyl-7-(6-(methyl(2,2,6,6-tetramethylpiperidin-4-yl)amino)pyridazin-3-yl)isoquinolin-6-ol |
| 3-6 | 1 | 8 nM, 2.43 fold | 7-(6-(methyl(2,2,6,6-tetramethylpiperidin-4-yl)amino)pyridazin-3-yl)isoquinoline-1,6-diol |
| 3-7 | 1 | 2 nM, 2.9 fold | 6-hydroxy-7-(6-(methyl(2,2,6,6-tetramethylpiperidin-4-yl)amino)pyridazin-3-yl)isoquinoline-1-carbonitrile |
| 4-1 | 1 | 6 nM, 2.6 fold | 6-(6-(methyl(2,2,6,6-tetramethylpiperidin-4-yl)amino)pyridazin-3-yl)isoquinolin-7-ol |
| 5-1 | 1 | 300 nM, 2.6 fold | 8-(6-(methyl(2,2,6,6-tetramethylpiperidin-4-yl)amino)pyridazin-3-yl)quinolin-7-ol |
| 6-1 | 1 | 7 nM, 2.82 fold | 7-(6-(methyl(2,2,6,6-tetramethylpiperidin-4-yl)amino)pyridazin-3-yl)quinolin-6-ol |
| 6-2 | 1 | 4 nM, 3.2 fold | 2-methyl-7-(6-(methyl(2,2,6,6-tetramethylpiperidin-4-yl)amino)pyridazin-3-yl)quinolin-6-ol |
| 7-1 | 1 | 14 nM, 2.8 fold | 3-chloro-6-(6-(methyl(2,2,6,6-tetramethylpiperidin-4-yl)amino)pyridazin-3-yl)quinolin-7-ol |
| 7-2 | 1 | 8 nM, 2.6 fold | 3-bromo-6-(6-(methyl(2,2,6,6-tetramethylpiperidin-4-yl)amino)pyridazin-3-yl)quinolin-7-ol |
| 7-3 | 1 | 8 nM, 3.1 fold | 7-hydroxy-6-(6-(methyl(2,2,6,6-tetramethylpiperidin-4-yl)amino)pyridazin-3-yl)quinoline-3-carbonitrile |
| 7-4 | 1 | 200 nM, 2.2 fold | 6-(6-(methyl(2,2,6,6-tetramethylpiperidin-4-yl)amino)pyridazin-3-yl)-3-(1-methyl-1H-imidazol-4-yl)quinolin-7-ol |
| 7-5 | 1 | 50 nM, 2.5 fold | 3-(1H-imidazol-1-yl)-6-(6-(methyl(2,2,6,6-tetramethylpiperidin-4-yl)amino)pyridazin-3-yl)quinolin-7-ol |
| 7-6 | 1 | 300 nM, 2.9 fold | 6-(6-(methyl(2,2,6,6-tetramethylpiperidin-4-yl)amino)pyridazin-3-yl)quinoline-3,7-diol |

-continued

Activity Table: Data generated in Biological Example 3 were generated using methods described in Biological example 1 or Biological example 2.

| Example | Biological Example number | SMN Activity | Compound name |
|---|---|---|---|
| 8-1 | 1 | 86 nM, 2.9 fold | 3-ethyl-6-(6-(methyl(2,2,6,6-tetramethylpiperidin-4-yl)amino)pyridazin-3-yl)quinolin-7-ol |
| 8-2 | 1 | 190 nM, 2.50 fold | 3-isopropyl-6-(6-(methyl(2,2,6,6-tetramethylpiperidin-4-yl)amino)pyridazin-3-yl)quinolin-7-ol |
| 9-1 | 1 | 30 nM, 2.25 fold | 7-hydroxy-6-(6-(methyl(2,2,6,6-tetramethylpiperidin-4-yl)amino)pyridazin-3-yl)quinolin-2(1H)-one |
| 9-2 | 1 | 7 nM, 2.25 fold | 7-hydroxy-1-methyl-6-(6-(methyl(2,2,6,6-tetramethylpiperidin-4-yl)amino)pyridazin-3-yl)quinolin-2(1H)-one |
| 10-1 | 1 | 10 nM, 3.3 fold | 4-methoxy-2-methyl-6-(6-(methyl(2,2,6,6-tetramethylpiperidin-4-yl)amino)pyridazin-3-yl)quinolin-7-ol |
| 10-2 | 1 | 65 nM, 2.6 fold | 2-methyl-6-(6-(methyl(2,2,6,6-tetramethylpiperidin-4-yl)amino)pyridazin-3-yl)-4-(pyrrolidin-1-yl)quinolin-7-ol |
| 10-3 | 1 | 110 nM, 2.6 fold | 2-methyl-6-(6-(methyl(2,2,6,6-tetramethylpiperidin-4-yl)amino)pyridazin-3-yl)-4-morpholinoquinolin-7-ol |
| 10-4 | 1 | 12 nM, 2.7 fold | 4-(dimethylamino)-2-methyl-6-(6-(methyl(2,2,6,6-tetramethylpiperidin-4-yl)amino)pyridazin-3-yl)quinolin-7-ol |
| 10-5 | 1 | 20 nM, 3.3 fold | 4-ethoxy-2-methyl-6-(6-(methyl(2,2,6,6-tetramethylpiperidin-4-yl)amino)pyridazin-3-yl)quinolin-7-ol |
| 11-1 | 1 | 60 nM, 2.6 fold | 2-methyl-6-(6-(methyl(2,2,6,6-tetramethylpiperidin-4-yl)amino)pyridazin-3-yl)-4-(1-methyl-1H-pyrazol-4-yl)quinolin-7-ol |
| 12-1 | 1 | 3 nM, 2.4 fold | 4-methoxy-7-(6-(methyl(2,2,6,6-tetramethylpiperidin-4-yl)amino)pyridazin-3-yl)quinolin-6-ol |
| 13-1 | 1 | 9 nM, 2.7 fold | 7-(6-(methyl(2,2,6,6-tetramethylpiperidin-4-yl)amino)pyridazin-3-yl)quinoxalin-6-ol |
| 14-1 | 1 | 63 nM, 2.91 fold | 6-(6-(methyl(2,2,6,6-tetramethylpiperidin-4-yl)amino)pyridazin-3-yl)-3-(tetrahydro-2H-pyran-4-yl)quinolin-7-ol |
| 15-1 | 1 | 16 nM, 2.68 fold | 3-chloro-7-(6-(methyl(2,2,6,6-tetramethylpiperidin-4-yl)amino)pyridazin-3-yl)quinolin-6-ol |
| 15-2 | 1 | 19 nM, 2.52 fold | 3-bromo-7-(6-(methyl(2,2,6,6-tetramethylpiperidin-4-yl)amino)pyridazin-3-yl)quinolin-6-ol |
| 15-3 | 1 | 7 nM, 3.28 fold | 3-methyl-7-(6-(methyl(2,2,6,6-tetramethylpiperidin-4-yl)amino)pyridazin-3-yl)quinolin-6-ol |
| 16-1 | 1 | 258 nM, 2.44 fold | 5-bromo-3-methyl-7-(6-(methyl(2,2,6,6-tetramethylpiperidin-4-yl)amino)pyridazin-3-yl)quinolin-6-ol |
| 17-1 | 1 | 685 nM, 2.56 fold | 6-hydroxy-1-methyl-7-(6-(methyl(2,2,6,6-tetramethylpiperidin-4-yl)amino)pyridazin-3-yl)quinolin-4(1H)-one |
| 18-1 | 1 | 15 nM, 3.24 fold | 2,3-dimethyl-7-(6-(methyl(2,2,6,6-tetramethylpiperidin-4-yl)amino)pyridazin-3-yl)quinoxalin-6-ol |
| 18-2 | 1 | 9 nM, 3.31 fold | 2-methyl-7-(6-(methyl(2,2,6,6-tetramethylpiperidin-4-yl)amino)pyridazin-3-yl)quinoxalin-6-ol |
| 18-3 | 1 | 16 nM, 2.72 fold | 3-methyl-7-(6-(methyl(2,2,6,6-tetramethylpiperidin-4-yl)amino)pyridazin-3-yl)quinoxalin-6-ol |

-continued

Activity Table: Data generated in Biological Example 3 were generated using methods described in Biological example 1 or Biological example 2.

| Example | Biological Example number | SMN Activity | Compound name |
|---|---|---|---|
| 19-1 | 1 | 10 nM, 2.65 fold | 4-methoxy-6-(6-(methyl(2,2,6,6-tetramethylpiperidin-4-yl)amino)pyridazin-3-yl)quinolin-7-ol |
| 20-1 | 1 | 84 nM, 2.86 fold | 4-(azetidin-1-yl)-2-methyl-6-(6-(methyl(2,2,6,6-tetramethylpiperidin-4-yl)amino)pyridazin-3-yl)quinolin-7-ol |
| 20-2 | 1 | 48 nM, 2.68 fold | 7-hydroxy-2-methyl-6-(6-(methyl(2,2,6,6-tetramethylpiperidin-4-yl)amino)pyridazin-3-yl)quinoline-4-carbonitrile |
| 20-3 | 1 | 65 nM, 2.72 fold | 4-cyclopropyl-2-methyl-6-(6-(methyl(2,2,6,6-tetramethylpiperidin-4-yl)amino)pyridazin-3-yl)quinolin-7-ol |
| 20-4 | 1 | 166 nM, 2.72 fold | 4-(3,6-dihydro-2H-pyran-4-yl)-2-methyl-6-(6-(methyl(2,2,6,6-tetramethylpiperidin-4-yl)amino)pyridazin-3-yl)quinolin-7-ol |
| 20-5 | 1 | 286 nM, 2.69 fold | 2-methyl-6-(6-(methyl(2,2,6,6-tetramethylpiperidin-4-yl)amino)pyridazin-3-yl)-4-(tetrahydro-2H-pyran-4-yl)quinolin-7-ol formate salt |
| 20-6 | 1 | 165 nM, 3.18 fold | 2-methyl-6-(6-(methyl(2,2,6,6-tetramethylpiperidin-4-yl)amino)pyridazin-3-yl)-4-(oxetan-3-yl)quinolin-7-ol |
| 21-1 | 1 | 60 nM, 3.01 fold | 4-(dimethylamino)-6-(6-(methyl(2,2,6,6-tetramethylpiperidin-4-yl)amino)pyridazin-3-yl)quinolin-7-ol di-formate salt |
| 22-1 | 1 | 110 nM, 2.58 fold | 7-hydroxy-6-(6-(methyl(2,2,6,6-tetramethylpiperidin-4-yl)amino)pyridazin-3-yl)quinazolin-4(1H)-one |
| 23-1 | 1 | 41 nM, 3.6 fold | 6-(6-(methyl(2,2,6,6-tetramethylpiperidin-4-yl)amino)pyridazin-3-yl)quinazolin-7-ol |
| 24-1 | 1 | 71 nM, 1.74 fold | 7-hydroxy-1-methyl-6-(6-(methyl(2,2,6,6-tetramethylpiperidin-4-yl)amino)pyridazin-3-yl)-3,4-dihydroquinolin-2(1H)-one |
| 25-1 | 1 | 23 nM, 2.72 fold | 7-hydroxy-1-methyl-6-(6-(methyl(2,2,6,6-tetramethylpiperidin-4-yl)amino)pyridazin-3-yl)-3,4-dihydroquinolin-2(1H)-one |
| 26-1 | 1 | 16 nM, 2.58 fold | 7-hydroxy-6-(6-(methyl(2,2,6,6-tetramethylpiperidin-4-yl)amino)pyridazin-3-yl)isoquinoline-1-carbonitrile |
| 26-2 | 1 | 7 nM, 3.14 fold | 7-hydroxy-6-(6-(methyl(2,2,6,6-tetramethylpiperidin-4-yl)amino)pyridazin-3-yl)quinoline-2-carbonitrile |
| 26-3 | 1 | 6 nM, 3.47 fold | 6-hydroxy-7-(6-(methyl(2,2,6,6-tetramethylpiperidin-4-yl)amino)pyridazin-3-yl)quinoline-2-carbonitrile |
| 26-4 | 1 | 7 nM, 2.57 fold | 6-hydroxy-7-(6-(methyl(2,2,6,6-tetramethylpiperidin-4-yl)amino)pyridazin-3-yl)isoquinoline-1-carboxamide |
| 26-5 | 1 | 1 nM, 2.16 fold | 7-hydroxy-6-(6-(methyl(2,2,6,6-tetramethylpiperidin-4-yl)amino)pyridazin-3-yl)quinoline-2-carboxamide |
| 26-6 | 1 | 7 nM, 2.6 fold | 6-hydroxy-7-(6-(methyl(2,2,6,6-tetramethylpiperidin-4-yl)amino)pyridazin-3-yl)quinoline-2-carboxamide |
| 26-7 | 1 | 17 nM, 2.64 fold | methyl 6-hydroxy-7-(6-(methyl(2,2,6,6-tetramethylpiperidin-4-yl)amino)pyridazin-3-yl)quinoline-2-carboxylate |

-continued

Activity Table: Data generated in Biological Example 3 were generated using methods described in Biological example 1 or Biological example 2.

| Example | Biological Example number | SMN Activity | Compound name |
| --- | --- | --- | --- |
| 27-1 | 1 | 46 nM, 2.49 fold | 6-hydroxy-7-(6-(piperazin-1-yl)pyridazin-3-yl)quinoline-2-carbonitrile |
| 27-2 | 1 | 395 nM, 2.42 fold | 7-hydroxy-6-(6-(piperazin-1-yl)pyridazin-3-yl)quinoline-2-carbonitrile |
| 27-3 | 1 | 199 nM, 2.74 fold | 7-(6-(piperazin-1-yl)pyridazin-3-yl)isoquinolin-6-ol |
| 28-1 | 1 | 155 nM, 1.9 fold | 7-(6-(1,2,3,6-tetrahydropyridin-4-yl)pyridazin-3-yl)quinolin-6-ol |
| 29-1 | 1 | 14 nM, 2.96 fold | 1-methyl-6-(6-(methyl(2,2,6,6-tetramethylpiperidin-4-yl)amino)pyridazin-3-yl)isoquinolin-7-ol |
| 29-2 | 1 | 9 nM, 2.53 fold | 1-methyl-7-(6-(methyl(2,2,6,6-tetramethylpiperidin-4-yl)amino)pyridazin-3-yl)isoquinolin-6-ol |
| 29-3 | 2 | 40 nM, Amax 2453 | 1,3-dimethyl-7-(6-(methyl(2,2,6,6-tetramethylpiperidin-4-yl)amino)pyridazin-3-yl)isoquinolin-6-ol |
| 30-1 | 2 | 30 nM, Amax 2008 | 7-hydroxy-3-methyl-6-(6-(methyl(2,2,6,6-tetramethylpiperidin-4-yl)amino)pyridazin-3-yl)isoquinoline-1-carbonitrile |
| 31-1 | 2 | 25 nM, Amax 3014 | 1-amino-7-(6-(methyl(2,2,6,6-tetramethylpiperidin-4-yl)amino)pyridazin-3-yl)isoquinolin-6-ol |
| 32-1 | 2 | 133 nM, Amax 3313 | 7-hydroxy-1,3-dimethyl-6-(6-(methyl(2,2,6,6-tetramethylpiperidin-4-yl)amino)pyridazin-3-yl)quinazoline-2,4(1H,3H)-dione |
| 33-1 | 2 | 3 uM, Amax 2396 | 6-hydroxy-5-(6-(methyl(2,2,6,6-tetramethylpiperidin-4-yl)amino)pyridazin-3-yl)benzo[d]oxazol-2(3H)-one |
| 34-1 | 2 | 150 nM, Amax 3448 | 2-methyl-5-(6-(methyl(2,2,6,6-tetramethylpiperidin-4-yl)amino)pyridazin-3-yl)-2H-indazol-6-ol |
| 34-2 | 2 | 220 nM, Amax 3534 | 1-methyl-5-(6-(methyl(2,2,6,6-tetramethylpiperidin-4-yl)amino)pyridazin-3-yl)-1H-indazol-6-ol |
| 35-1 | 1 | 3 nM, 2.43 fold | 6-hydroxy-2-methyl-7-(6-(methyl(2,2,6,6-tetramethylpiperidin-4-yl)amino)pyridazin-3-yl)isoquinolin-1(2H)-one hydrochloride salt |
| 35-2 | 2 | 363 nM, Amax 4321 | 2-ethyl-6-hydroxy-7-(6-((2,2,6,6-tetramethylpiperidin-4-yl)oxy)pyridazin-3-yl)isoquinolin-1(2H)-one |
| 35-3 | 1 | 13 nM, 2.26 fold | 1-ethoxy-7-(6-(methyl(2,2,6,6-tetramethylpiperidin-4-yl)amino)pyridazin-3-yl)isoquinolin-6-ol |
| 35-4 | 1 | 96 nM, 3.26 fold | 7-(6-((2,2,6,6-tetramethylpiperidin-4-yl)oxy)pyridazin-3-yl)isoquinoline-1,6-diol |
| 36-1 | 1 | 282 nM, 2.32 fold | 7-(6-(methyl(2,2,6,6-tetramethyl-piperidin-4-yl)amino)-pyridazin-3-yl)-3-phenylisoquinolin-6-ol |
| 36-2 | 1 | 9 nM, 2.64 fold | 3-methyl-7-(6-(methyl(2,2,6,6-tetramethylpiperidin-4-yl)amino)-pyridazin-3-yl)isoquinolin-6-ol |
| 36-3 | 2 | 30 nM, Amax 2690 | 3-cyclopropyl-7-(6-(methyl(2,2,6,6-tetramethyl-piperidin-4-yl)amino)pyridazin-3-yl)isoquinolin-6-ol |
| 36-4 | 2 | 190 nM, Amax 1956 | 3-isopropyl-7-(6-(methyl(2,2,6,6-tetramethyl-piperidin-4-yl)amino)pyridazin-3-yl)isoquinolin-6-ol |
| 36-5 | 2 | 580 nM, Amax 1603 | 3-propyl-7-(6-((2,2,6,6-tetramethylpiperidin-4-yl)oxy)-pyridazin-3-yl)isoquinolin-6-ol |

| Example | Biological Example number | SMN Activity | Compound name |
|---|---|---|---|
| 36-6 | 2 | 640 nM, Amax 1298 | 3-isopropyl-7-(6-((2,2,6,6-tetramethylpiperidin-4-yl)oxy)-pyridazin-3-yl)isoquinolin-6-ol |
| 37-1 | 1 | 124 nM, 2.33 fold | 3-methyl-7-(6-(piperazin-1-yl)pyridazin-3-yl)isoquinolin-6-ol |

Comparison of the SMN ELISA (as described in Biological Example 1) potency and fold activation for unsubstituted, ortho-hydroxy and ortho-alkoxy 6,6-heterocyclic substituted pyridazines:

| Structure | Substitution | Example | SMN ELISA EC50 | Fold activation |
|---|---|---|---|---|
| quinoline | R = H | | 0.66 | 2.2 |
| | R = OH | 1-1 | 0.020 | 2.9 |
| quinoline | R = H | | 0.37 | 2.5 |
| | R = OH | 6-1 | 0.007 | 2.8 |
| | R = OMe | | 1.17 | 1.7 |
| isoquinoline | R = H | | 0.25 | 2.7 |
| | R = OH | 3-2 | 0.005 | 2.8 |
| isoquinoline | R = H | | 0.32 | 2.7 |
| | R = OH | 4-1 | 0.006 | 2.6 |
| quinoxaline | R = OH | 13-1 | 0.009 | 2.7 |
| | R = OEt | | Inactive | — |

What is claimed is:

1. A compound according to Formula (IA), or salt thereof (IA)

wherein A is selected from the group consisting of:

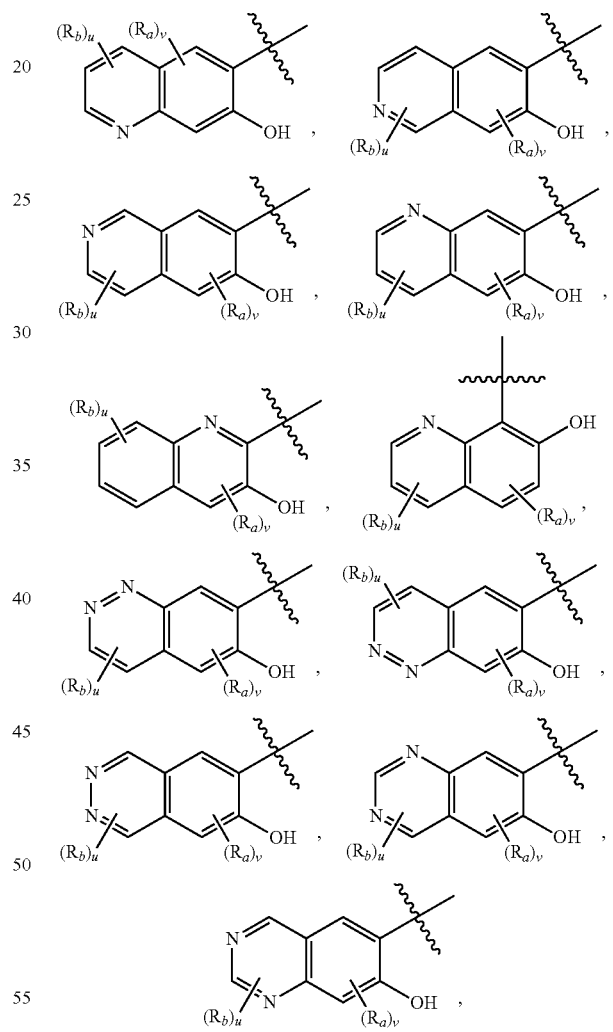

and

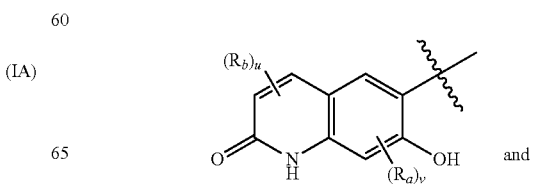

-continued

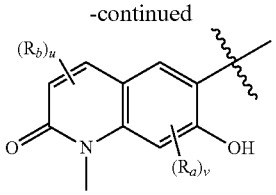

wherein
u and v are each, independently, 0, 1, 2 or 3; and
each $R_a$ and $R_b$, are, independently, selected from cyano, halogen, hydroxy, $C_1$-$C_4$ alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, and $C_1$-$C_4$alkoxy substituted with hydroxy, $C_1$-$C_4$ alkoxy, amino and mono-and di-$C_1$-$C_4$alkylamino; and
B is selected from the group consisting of:

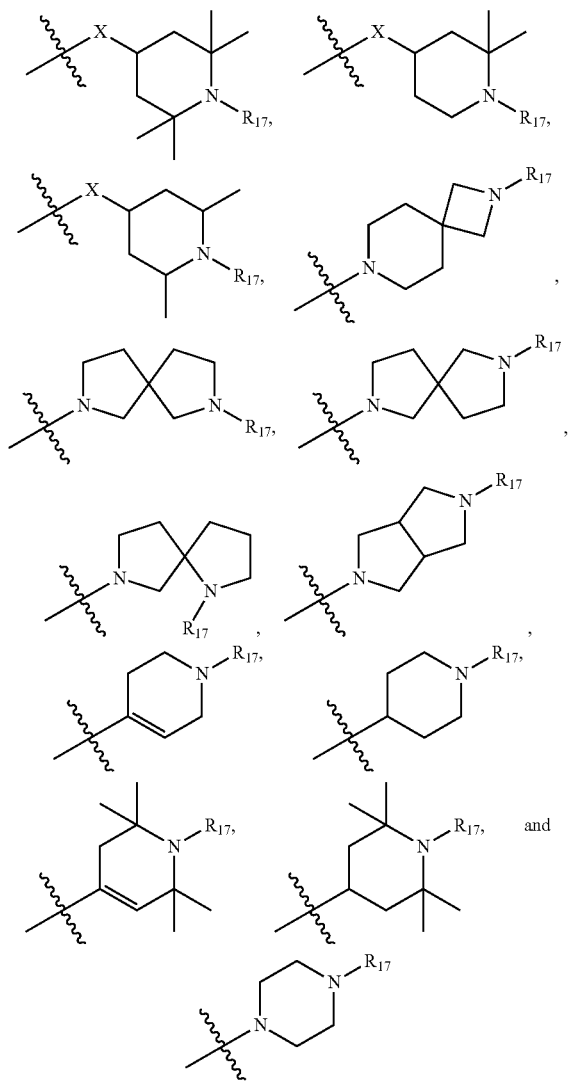

wherein X is O or N(Me) or NH; and
$R_{17}$ is hydrogen or methyl.

2. A compound, according to claim 1, or salt thereof, wherein the compound is of formula II:

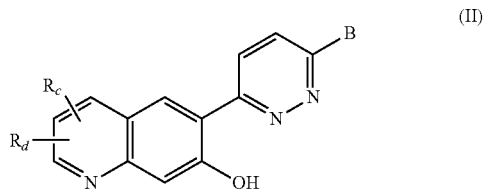

wherein
$R_c$, and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono-and di-$C_1$-$C_4$alkylamino.

3. A compound, or salt thereof, according to claim 1, wherein the compound is of formula III:

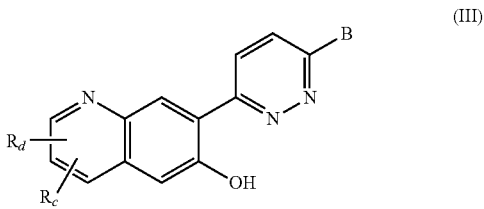

wherein
$R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono-and di-$C_1$-$C_4$alkylamino.

4. A compound, according to claim 1, or salt thereof, wherein the compound is of formula IV:

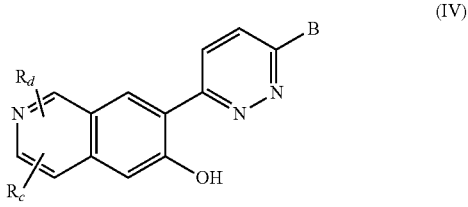

wherein
$R_c$, and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono-and di-$C_1$-$C_4$alkylamino.

5. A compound, according to claim 1, or salt thereof, wherein the compound is of formula V:

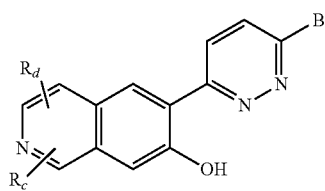

(V)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono-and di-$C_1$-$C_4$alkylamino.

6. A compound, according to claim 1, or salt thereof, wherein the compound is of formula VI:

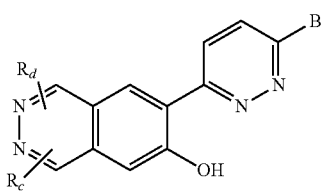

(VI)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono-and di-$C_1$-$C_4$alkylamino.

7. A compound, according to claim 1, or salt thereof, wherein the compound is of formula VIII:

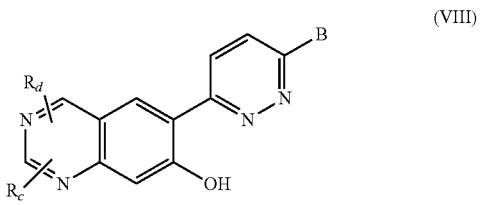

(VIII)

wherein $R_c$ and $R_d$ are each, independently, selected from hydrogen, cyano, halogen, hydroxy, $C_1$-$C_4$alkyl, $C_2$-$C_4$alkenyl, $C_2$-$C_4$alkynyl, $C_1$-$C_4$alkoxy, $C_3$-$C_7$cycloalkyl, heterocyclyl, heteroaryl, heterocyclyl $C_1$-$C_4$alkyl, $C_1$-$C_4$alkyl aryl, $C_1$-$C_4$alkyl heterocyclyl, $C_1$-$C_4$alkyl heteroaryl, $C_1$-$C_4$alkoxy aryl, $C_1$-$C_4$alkoxy heterocyclyl, $C_1$-$C_4$alkoxy heteroaryl, $C_1$-$C_4$alkoxy substituted with hydroxy, $C_1$-$C_4$alkoxy, amino and mono-and di-$C_1$-$C_4$alkylamino.

8. A pharmaceutical composition comprising a therapeutically effective amount of a compound according to claim 1, or a pharmaceutically acceptable salt thereof and one or more pharmaceutically acceptable carriers.

9. A combination comprising a therapeutically effective amount of a compound according to claim 1, or a pharmaceutically acceptable salt thereof and one or more therapeutically active co-agents.

\* \* \* \* \*